US008575145B2

(12) United States Patent
Allen et al.

(10) Patent No.: US 8,575,145 B2
(45) Date of Patent: Nov. 5, 2013

(54) TRIAZOLOPYRIDINE COMPOUNDS AS PIM KINASE INHIBITORS

(75) Inventors: Shelley Allen, Boulder, CO (US); Laura L. Celeste, Gaithersburg, MD (US); T. Gregg Davis, Boulder, CO (US); Robert Kirk DeLisle, Boulder, CO (US); Julie Marie Greschuk, Boulder, CO (US); Stefan D. Gross, Superior, CO (US); Erik James Hicken, Boulder, CO (US); Leila J. Jackson, Boulder, CO (US); Nicholas C. Kallan, Boulder, CO (US); Joseph P. Lyssikatos, Piedmont, CO (US); Fredrik P. Marmsater, Boulder, CO (US); Mark C. Munson, Boulder, CO (US); Jed Pheneger, Boulder, CO (US); Bryson Rast, Westminster, CO (US); John E. Robinson, Boulder, CO (US); Stephen T. Schlachter, Boulder, CO (US); George T. Topalov, Boulder, CO (US); A. Dale Wright, Boulder, CO (US); Qian Zhao, Boulder, CO (US)

(73) Assignee: Array BioPharma Inc., Boulder, CO (US)

( * ) Notice: Subject to any disclaimer, the term of this patent is extended or adjusted under 35 U.S.C. 154(b) by 327 days.

(21) Appl. No.: 13/059,902

(22) PCT Filed: Aug. 18, 2009

(86) PCT No.: PCT/US2009/054193
§ 371 (c)(1),
(2), (4) Date: Feb. 18, 2011

(87) PCT Pub. No.: WO2010/022076
PCT Pub. Date: Feb. 25, 2010

(65) Prior Publication Data
US 2011/0144085 A1    Jun. 16, 2011

Related U.S. Application Data

(60) Provisional application No. 61/089,952, filed on Aug. 19, 2008, provisional application No. 61/175,277, filed on May 4, 2009.

(51) Int. Cl.
| | | |
|---|---|---|
| A61K 31/55 | (2006.01) | |
| A61K 31/437 | (2006.01) | |
| A61K 31/513 | (2006.01) | |
| A61K 31/5377 | (2006.01) | |
| C07D 471/04 | (2006.01) | |
| A61P 35/00 | (2006.01) | |
| A61P 25/00 | (2006.01) | |
| A61P 29/00 | (2006.01) | |

(52) U.S. Cl.
USPC .............. 514/210.21; 514/303; 514/217.07; 514/272; 514/233.2; 546/119; 544/331; 544/127; 540/597

(58) Field of Classification Search
USPC ............ 514/210.21, 217.07, 272, 233.2, 303; 546/119; 544/331, 127; 540/597
See application file for complete search history.

(56) References Cited

U.S. PATENT DOCUMENTS

| | | |
|---|---|---|
| 2005/0256309 A1 | 11/2005 | Altenbach et al. |
| 2007/0154919 A1 | 7/2007 | Korn et al. |
| 2007/0173508 A1 | 7/2007 | Hutchinson et al. |
| 2008/0027063 A1 | 1/2008 | Zhao et al. |
| 2008/0261988 A1 | 10/2008 | Bearss et al. |
| 2009/0042918 A1 | 2/2009 | Kearney et al. |

FOREIGN PATENT DOCUMENTS

| | | |
|---|---|---|
| EP | 1277754 A1 | 1/2003 |
| WO | 01/34603 A2 | 5/2001 |
| WO | 02/12236 A1 | 9/2002 |
| WO | 02/72579 A1 | 9/2002 |
| WO | 2004/058749 A1 | 7/2004 |
| WO | 2004/058769 A2 | 7/2004 |
| WO | 2005/028624 A2 | 3/2005 |
| WO | 2006/018727 A2 | 2/2006 |
| WO | 2006/058752 A1 | 6/2006 |
| WO | 2007/044724 A2 | 4/2007 |
| WO | 2008/082839 A2 | 7/2008 |
| WO | 2008/121687 A2 | 10/2008 |

OTHER PUBLICATIONS

Chen et al., Blood, (2008), vol. 111, No. 3, pp. 1677-1685.*
International Search Report corresponding to PCT Application No. PCT/US2009/054193, (Nov. 24, 2009).
Chemcats Accession No. 205019468, Chembridge Screening Library, (Jun. 8, 2009).
Bullock, Alex N. et al., "Structural Basis of Inhibitor Specificity of the Human Protooncogene Proviral Insertion Site in Moloney Murine Leukemia Virus (PIM-1) Kinase", J. Med. Chem, 2005, 48, 7604-7614.
Pierce, Albert C., et al., "Docking Study Yields Four Novel Inhibitors of the Protooncogene Pim-1 Kinase", J. Med. Chem, 2008, 51, 1972-1975.

\* cited by examiner (Continued)

*Primary Examiner* — Niloofar Rahmani
(74) *Attorney, Agent, or Firm* — Viksnins Harris & Padys PLLP; Sarah Smith Mastous

(57) ABSTRACT

Compounds of Formula (I), in which A, B, $R^1$, $R^{1a}$, $R^2$, $R^3$, $R^4$, $R^5$, $R^6$, and $R^7$ have the meanings given in the specification, are receptor tyrosine inhibitors useful in the treatment of immune cell-associated diseases and disorders, such as inflammatory and autoimmune diseases.

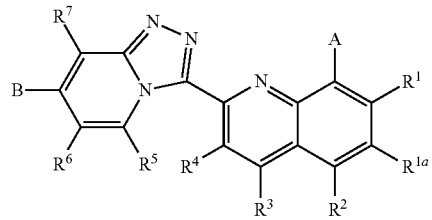

29 Claims, 9 Drawing Sheets

TRIAZOLOPYRIDINE COMPOUNDS AS PIM KINASE INHIBITORS

The present invention relates to novel compounds, to pharmaceutical compositions comprising the compounds, to a process for making the compounds and to the use of the compounds in therapy. More particularly, it relates to certain triazolopyridine compounds useful in the treatment and prevention of diseases which can be treated with a PIM kinase inhibitor, including diseases mediated by PIM kinases. Particular compounds of this invention have been found to be inhibitors of PIM-1 and/or PIM-2 and/or PIM-3.

Protein kinases constitute a family of structurally related enzymes that are responsible for the control of a vast array of cellular processes.

The PIM kinase sub-family consists of three distinct serine/threonine protein kinase isoforms (PIM-1, -2 and -3) belonging to the calmodulin-dependent protein kinase-related (CAMK) group. PIM-2 and PIM-3 are respectively 58% and 69% identical to PIM-1 at the amino acid level.

The over-expression of PIM-1 has been reported in various human lymphomas and acute leukemias (Amson, R. et al., Proc. Natl. Acad. Sci. U.S.A., 1989, 86: 8857-8861). PIM-1 has been shown to synergize with c-Myc to drive lymphomagenesis (Breuer M., et. al., Nature, 1989, 340; 61-63), and plays an important role in cytokine signaling in T-cell development (Schmidt, T., et. al., EMBO J, 1998, 17:5349-5359). In addition, there is evidence that PIM-1 is over-expressed in prostatic neoplasia and human prostate cancer (Valdman, A. et al., The Prostate, 2004, 60: 367-371; Cibull, T. L. et al., J. Clin. Pathol., 2006, 59: 285-288) and may serve as a useful biomarker in identification of prostate cancer (Dhanasekaran, S. M. et al, Nature, 2001, 412(13): 822-826). PIM-1 has been shown to be critical for IL-6 mediated proliferation of hematopoietic cells (Hirano, T., et. al. Oncogene 2000, 19: 2548-2556), as well as STAT3 mediated cell cycle progression (Shirogane, T., et al., Immunity 1999, 11:709).

Recently, it has been discovered that PIM-1 is up-regulated by Flt-3 and may play an important role in Flt-3 mediated cell survival (Kim, K. T. et al., Neoplasia, 2005, 105(4): 1759-1767). Since Flt-3 itself is implicated in leukemias like AML, additional knockdown of PIM-1 may be a useful approach to treating leukemias driven by Flt-3 or various mutations. Accordingly, PIM-1 inhibitors may be useful as therapeutic agents for a variety of cancers such as hematological cancers.

PIM-2 is a highly conserved serine/threonine kinase involved in cell proliferation and the prevention of apoptosis (Baytel et al., Biochim. Biophys. Acta Gene Struct. Expr. 1442: 274 (1998)). PIM-2 is upregulated in AML, CLL, and possibly in prostate cancer.

PIM-3 is a proto-oncogene identified in pancreatic liver and colon cancers, and is an apoptotic regulator (Popivanova, B., et al., Cancer Sci., 98(3): 321 (2007)).

Based upon the direct involvement of the Pim kinases in a wide variety of cancers downstream of STAT3/5 activation, it is expected that inhibition of the Pim kinases will result in inhibition of proliferation and survival of multiple cancer cell types. This would then be expected to provide a therapeutic benefit to cancer patients with a variety of cancers (both in solid tumor and hematologic settings), as well as other conditions that are mediated by Pim kinase signaling.

In addition to the malignant cells detailed above, PIM kinases are also expressed in hematopoietically-derived cell lines and hematopoietically-derived primary cells including cells of the immune system such as B cells, T cells, monocytes, macrophages, eosinophils, basophils, and dendritic cells. Expression of PIM kinases is induced by cytokines which utilize Jak/Stat signaling, such as IL-2, IL-3,IL-4, IL-5, IL-6, IL-7, IL-9, IL-12, IL-15, GM-CSF, IFNα, IFNγ, erythropoietin, thrombopoietin, and prolactin, and the generation, differentiation, maintenance and activation of hematopoietically-derived cells is dependent on these cytokines. Moreover, PIM proteins have been shown to be required for the efficient proliferation of peripheral T cells mediated by T-cell receptor and IL-2 signaling (Mikkers, et al., Mol. Cell. Biol., 2004, 6104). Although the exact mechanism of action of PIM kinases in an immunological setting has yet to be fully defined, they have been reported to phosphorylate a number of substrates involved in cellular proliferation, differentiation, and survival (Bullock et al., J. Biol. Chem., 2005 280: 41675; Chen et al., PNAS 2002 99:2175; Dautry et al., J. Biol. Chem. 1998 263:17615).

Chronic and acute inflammatory and autoimmune diseases are associated with the overproduction of pro-inflammatory cytokines and activation of immune cells against the body's own tissues. However, many of these diseases are not adequately treated by current therapies and/or these therapies have significant side effects/risks.

A particular example of an autoimmune disease is multiple sclerosis (MS). MS is a progressive central nervous system (CNS) inflammatory autoimmune disease wherein the immune system mounts responses against CNS components. The resulting damage to axons and nerves leads to progressive neurological impairment and significant disability. MS affects over 2.5 million people worldwide (www.nationalmssociety.org); however many current therapies are only moderately effective and have questionable risk factors A need therefore remains for compounds and methods for treating autoimmune and inflammatory diseases.

International patent application, publication number WO 2004/058769 discloses, inter alia, certain 3-aryl and 3-N-arylamino-substituted [1,2,4]triazolo[4,3-b]pyridazines purported to inhibit several protein kinases, including PIM-1.

International patent application, publication number WO 2008/022164 discloses phenyl- and pyridyl-substituted pyrazines and pyridines as PIM-2 inhibitors said to be useful in the treatment of cancer and inflammation.

International patent application, publication number WO 2008/106692, published 4 Sep. 2008 after the first priority date for the present invention, discloses carboxamide-substituted pyridines and 2-oxopyrimidines which are inhibitors of PIM-1, PIM-2 and PIM-3.

It has now been found that certain [1,2,4]triazole[4,3-a] pyridine compounds bearing a quinolinyl group at the 3 position of the triazolopyridine ring are inhibitors of PIM kinases, in particular PIM-1, PIM-2 and/or PIM-3 kinases, which are useful for treating diseases such as cancers and inflammatory diseases. In addition, compounds of the invention may be useful for treating immune cell-associated diseases and disorders, such as inflammatory and autoimmune diseases.

Accordingly, provided is a compound of general Formula I:

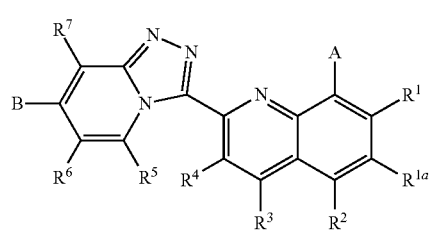

or a pharmaceutically acceptable salt thereof, wherein:

A is $OR^{10}$ or $NR^{11}R^{12}$;

B is H, F, Cl, $OR^a$, (1-6C alkyl)$NR^bR^g$, (1-6C alkyl)OH, $CH(OH)CH_2OH$, or (1-4C alkyl);

$R^1$ is H, F, Cl, Br, Me, cyclopropyl or CN;

$R^{1a}$, $R^2$, $R^3$ and $R^4$ are independently H, F, Cl, Br, Me or CN;

$R^5$ and $R^7$ are independently H, F, Me or CN;

$R^6$ is H, F, Me, Br, CN, cyclopropyl, phenyl, MeO— or $MeOCH_2CH_2O$—;

$R^{10}$ is H, hetCyc$^1$, -(1-3C alkyl)hetCyc$^{1a}$, hetCyc$^2$, $(CR^{17}R^{18})_p(CR^{13}R^{14})CH_2NR^{15}R^{16}$, —$(CR^{17}R^{18})_p(CR^{13}R^{14})CH_2OH$, (1-6C alkyl), hetAr$^1$, (1-3C alkyl)hetAr$^{1a}$, or (3-7C)cycloalkyl substituted with $NH_2$, NH(1-6C alkyl) or N(1-6C alkyl)$_2$;

$R^{11}$ is H or (1-6C)alkyl;

$R^{12}$ is hetCyc$^3$, (1-6C alkyl)$NR^{15}R^{16}$, C(O)(1-6C alkyl)$NR^{15}R^{16}$, (1-6C alkyl)NHC(O)O(1-6C alkyl), or (4-7C)cycloalkyl optionally substituted with OH, $NH_2$, NH(1-6C alkyl) or N(1-6C alkyl)$_2$;

$R^{13}$ is H, (1-6C)alkyl, F or OH, and $R^{14}$ is H, (1-6C)alkyl or F, or $R^{13}$ and $R^{14}$ together with the carbon atom to which they are attached form a 3-6 membered carbocyclic ring;

each $R^{15}$, $R^{16}$, $R^{17}$ and $R^{18}$ is independently H or (1-6C)alkyl, or each $R^{15}$, $R^{17}$ and $R^{18}$ is independently H or (1-6C)alkyl and $R^{16}$ is H, (1-6C)alkyl, C(=O)$CH_2F$, $CH_2CHF_2$ or $CH_2CF_3$;

or $NR^{15}R^{16}$ forms a 5-6 membered heterocyclic ring having a first ring heteroatom which is N and optionally having a second ring heteroatom selected from N and O;

hetCyc$^1$, hetCyc$^{1a}$, and hetCyc$^3$ are independently a 4-7 membered heterocycle having a ring nitrogen atom and optionally substituted with one or more $R^9$ groups, or hetCyc$^1$ and hetCyc$^3$ are independently a 4-7 membered heterocycle having a ring nitrogen atom and optionally substituted with one or more $R^9$ groups, and hetCyc$^{1a}$ is selected from a morpholinyl and 4-7 membered azacyclic ring optionally substituted with one or more $R^9$ groups;

each $R^9$ is independently selected from halogen, (1-6C) alkyl, cyclopropylmethyl, benzyl, $NR^fR^g$, -(1-6C alkyl)N-$R^hR^i$, $OR^j$, (1-6C alkyl)$OR^k$, (1-6C)fluoroalkyl, C(O)$NR^mR^n$, (1-6C alkyl)C(O)$NR^pR^q$, and C(O)O(1-6C alkyl);

hetCyc$^2$ is an 8-membered bridged heterocycle having a ring nitrogen atom;

hetAr$^1$ and hetAr$^{1a}$ are independently a 5 or 6 membered heteroaryl having 1-2 ring nitrogen atoms and optionally substituted with one or more substituents independently selected from F, Cl, Br, Me, cyclopropyl, CN, $NH_2$, NH(1-6C alkyl) and N(1-6C alkyl)$_2$;

$R^a$ is H, (1-6C alkyl), -(1-6C alkyl)-O-(1-6C alkyl) or -(1-6C alkyl)-O-(3-6C cycloalkyl);

each $R^b$, $R^f$, $R^g$, $R^h$, $R^i$, $R^k$, $R^m$, $R^p$ and $R^q$ is independently selected from H and (1-6C alkyl);

$R^j$ is H, (1-6C alkyl) or cyclopropyl;

$R^n$ is H, (1-6C alkyl), —O(1-6C alkyl) or —O(3-6C cycloalkyl); and p is 0, 1 or 2.

Also provided is a compound of general Formula I:

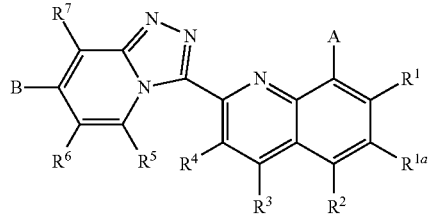

or a pharmaceutically acceptable salt thereof, wherein:

A is $OR^{10}$ or $NR^{11}R^{12}$;

B is H, F, $OR^a$, (1-6C alkyl)$NR^bR^c$, (1-6C alkyl)OH, $CH(OH)CH_2OH$, or (1-4C alkyl);

$R^1$ is H, F, Cl, Br, Me, cyclopropyl or CN;

$R^{1a}$, $R^2$, $R^3$ and $R^4$ are independently H, F, Cl, Br, Me or CN;

$R^5$ and $R^7$ are independently H, F, Me or CN;

$R^6$ is H, F, Me, Br, CN, cyclopropyl or phenyl;

$R^{10}$ is H, hetCyc$^1$, -(1-3C alkyl)hetCyc$^{1a}$, hetCyc$^2$, $(CR^{17}R^{18})_p(CR^{13}R^{14})CH_2NR^{15}R^{16}$, —$(CR^{17}R^{18})_p(CR^{13}R^{14})CH_2OH$, (1-6C alkyl), hetAr$^1$, (1-3C alkyl)hetAr$^{1a}$, or (3-7C)cycloalkyl substituted with $NH_2$, NH(1-6C alkyl) or N(1-6C alkyl)$_2$;

$R^{11}$ is H or (1-6C)alkyl;

$R^{12}$ is hetCyc$^3$, (1-6C alkyl)$NR^{15}R^{16}$, C(O)(1-6C alkyl)$NR^{15}R^{16}$, (1-6C alkyl)NHC(O)O(1-6C alkyl), or (4-7C)cycloalkyl optionally substituted with OH, $NH_2$, NH(1-6C alkyl) or N(1-6C alkyl)$_2$;

$R^{13}$ is H, (1-6C)alkyl, F or OH, and $R^{11}$ is H, (1-6C)alkyl or F, or $R^{13}$ and $R^{14}$ together with the carbon atom to which they are attached form a 3-6 membered carbocyclic ring;

each $R^{15}$, $R^{16}$, $R^{17}$ and $R^{18}$ is independently H or (1-6C)alkyl, or $NR^{15}R^{16}$ forms a 5-6 membered heterocyclic ring having a first ring heteroatom which is N and optionally having a second ring heteroatom selected from N and O;

hetCyc$^1$, hetCyc$^{1a}$, and hetCyc$^3$ are independently a 4-7 membered heterocycle having a ring nitrogen atom and optionally substituted with one or more $R^9$ groups;

each $R^9$ is independently selected from halogen, (1-6C) alkyl, cyclopropylmethyl, benzyl, $NR^fR^g$, -(1-6C alkyl)N-$R^hR^i$, $OR^k$, (1-6C alkyl)$OR^k$, (1-6C)fluoroalkyl, C(O)$NR^mR^n$, (1-6C alkyl)C(O)$NR^pR^q$, and C(O)O(1-6C alkyl);

hetCyc$^2$ is an 8-membered bridged heterocycle having a ring nitrogen atom;

hetAr$^1$ and hetAr$^{1a}$ are independently a 5 or 6 membered heteroaryl having 1-2 ring nitrogen atoms and optionally substituted with one or more substituents independently selected from F, Cl, Br, Me, cyclopropyl, CN, $NH_2$, NH(1-6C alkyl) and N(1-6C alkyl)$_2$;

$R^a$ is H, (1-6C alkyl), -(1-6C alkyl)-O-(1-6C alkyl) or -(1-6C alkyl)-O-(3-6C cycloalkyl);

each $R^b$, $R^f$, $R^g$, $R^h$, $R^i$, $R^k$, $R^m$, $R^p$ and $R^q$ is independently selected from H and (1-6C alkyl);

$R^j$ is H, (1-6C alkyl) or cyclopropyl;

$R^n$ is H, (1-6C alkyl), -0(1-6C alkyl) or —O(3-6C cycloalkyl); and p is 0, 1 or 2.

In certain embodiments, B is selected from any of the values described above, other than (1-4C alkyl).

The term "$C_1$-$C_6$ alkyl" as used herein refers to saturated linear or branched-chain monovalent hydrocarbon radicals of one to six carbon atoms, respectively. Examples include, but are not limited to, methyl, ethyl, 1-propyl, 2-propyl, 1-butyl, 2-methyl-1-propyl, 2-butyl, 2-methyl-2-propyl, 2,2-dimethylpropyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

In certain embodiments, $R^1$ is H, F or Cl. In certain embodiments, $R^1$ is H. In certain embodiments, $R^1$ is F. In certain embodiments, $R^1$ is Br.

In certain embodiments, $R^{1a}$ is H or F. In certain embodiments, $R^{1a}$ is H.

In certain embodiments, $R^2$ is H.
In certain embodiments, $R^3$ is H.
In certain embodiments, $R^4$ is H.
In certain embodiments, $R^5$ is H.
In certain embodiments, $R^6$ is H, F, or Br.
In certain embodiments, $R^6$ is CN or Me.
In certain embodiments, $R^6$ is phenyl or cyclopropyl.
In certain embodiments, $R^6$ is MeO— or MeOCH$_2$CH$_2$O—.
In certain embodiments, $R^6$ is H.
In certain embodiments, $R^7$ is H.
In certain embodiments, each of $R^2$, $R^3$, $R^4$, $R^5$ and $R^7$ is H.
In certain embodiments, each of $R^1$, $R^{1a}$, $R^2$, $R^3$, $R^4$, $R^5$, $R^6$ and $R^7$ is H.

In certain embodiments, A is $OR^{10}$.

In certain embodiments, A is $OR^{10}$ where $R^{10}$ is represented by the formula hetCyc$^1$ or (1-3C alkyl)hetCyc$^{1a}$. Particular examples of hetCyc$^1$ and hetCyc$^{1a}$ rings include piperidinyl, pyrrolidinyl and azepanyl rings. In certain embodiments, hetCyc$^1$ and hetCyc$^{1a}$ are substituted with one or more $R^9$ groups.

Examples of $R^9$ groups when represented by halogen include F, Cl and Br.

In certain embodiments, $R^9$ is cyclopropylmethyl.
In certain embodiments, $R^9$ is benzyl.
Examples of $R^9$ groups represented by the formula -(1-6C) alkyl include methyl, ethyl, propyl and isopropyl.

Examples of $R^9$ groups represented by the formula $NR^fR^g$ include groups where $R^f$ is H or Me and $R^g$ is H, methyl, ethyl, propyl, isopropyl, butyl, or isobutyl. Particular values of $R^9$ when represented by $NR^fR^g$ include NH$_2$ and NHMe.

Examples of $R^9$ groups represented by the formula -(1-6C alkyl)$NR^hR^i$, include groups where $R^h$ is H and $R^i$ is H or (1-6C)alkyl. Particular values of $R^9$ when represented by -(1-6C alkyl)$NR^hR^i$ include CH$_2$NR$^h$R$^i$, for example CH$_2$NH$_2$ and CH$_2$NHMe.

Examples of $R^9$ groups having the formula $OR^j$ include groups where $R^j$ is H, (1-6C) alkyl [for example methyl, ethyl, or isopropyl] or cylcopropyl. Particular examples of $R^9$ when represented by $OR^j$ include OH, OMe and —O-cyclopropyl.

Examples of $R^9$ groups represented by the formula (1-6C alkyl)$OR^k$ include groups where $R^k$ is H or Me. Particular values of such substituents include CH$_2$OH, CH$_2$CH$_2$OH and CH$_2$OMe.

An example of $R^9$ groups represented by the formula (1-6C)fluoroalkyl includes CH$_2$CH$_2$F.

Examples of $R^9$ groups having the formula $C(O)NR^mR^n$ include groups where $R^m$ is H or (1-6C) alkyl (for example H or methyl). In certain embodiments, $R^{11}$ is H, (1-6C) alkyl or O-(1-6C alkyl), (for example H, methyl or OMe. Particular values of $R^9$ include C(O)NH$_2$ and C(O)NMe(OMe).

Examples of $R^9$ groups having the formula (1-6C alkyl)C(O)$NR^pR^q$ include groups where both $R^p$ and $R^q$ are hydrogen. In other embodiments, one of $R^p$ and $R^q$ is hydrogen and the other is (1-6C alkyl). In other embodiments, both $R^p$ and $R^q$ are independently selected from (1-6C alkyl), for example methyl or ethyl. Particular values of $R^9$ include CH$_2$C(=O)NH$_2$, CH$_2$CH$_2$C(=O)NH$_2$, CH$_2$C(=O)NHMe and CH$_2$C(=O)NMe$_2$.

Examples of $R^9$ groups having the formula C(O)O(1-6C alkyl) include CO$_2$Me and CO$_2$C(CH$_3$)$_3$.

In particular embodiments, hetCyc$^1$ and hetCyc$^{1a}$ are unsubstituted or substituted with one or more $R^9$ groups independently selected from F, (1-6C)alkyl, cyclopropylmethyl, benzyl, C(O)O(1-6C)alkyl, (1-6C alkyl)$OR^k$, C(O)$NR^mR^n$, (1-6C alkyl)C(O)$NR^pR^q$, OR and (1-6C)fluoroalkyl.

In particular embodiments, hetCyc$^1$ and hetCyc$^{1a}$ are unsubstituted or substituted with one or more $R^9$ groups independently selected from F, (1-6C)alkyl, cyclopropylmethyl, benzyl, C(O)O(1-6C)alkyl, (1-6C alkyl)$OR^k$, C(O)$NR^mR^n$, (1-6C alkyl)C(O)$NR^pR^q$ and $OR^j$.

In certain embodiments, hetCyc$^1$ and hetCyc$^{1a}$ are optionally substituted with one or more substituents independently selected from F, methyl, ethyl, isopropyl, CO$_2$Me, CO$_2$C(CH$_3$)$_3$, C(O)NH$_2$, C(O)N(Me)OMe, CH$_2$C(=O)NH$_2$, cyclopropylmethyl, benzyl, CH$_2$OH, CH$_2$CH$_2$OH, OH, OMe, and CH$_2$CH$_2$F.

In particular embodiments, hetCyc$^1$ and hetCyc$^{1a}$ are optionally substituted with one or more substituents independently selected from F, methyl, ethyl, isopropyl, CO$_2$Me, CO$_2$C(CH$_3$)$_3$, C(O)NH$_2$, C(O)N(Me)OMe, CH$_2$C(=O)NH$_2$, cyclopropylmethyl, benzyl, CH$_2$OH, CH$_2$CH$_2$OH, OH, and OMe.

In certain embodiments, each hetCyc$^1$ and hetCyc$^{1a}$ is independently and optionally substituted with one or two $R^9$ groups.

In another embodiment, A is $OR^{10}$ where $R^{10}$ is represented by the formula (1-3C alkyl)hetCyc$^{1a}$ and hetCyc$^{1a}$ is morpholinyl.

Particular embodiments of $OR^{10}$ when $R^{10}$ is hetCyc$^1$ or (1-3C alkyl)hetCyc$^{1a}$ include the structures:

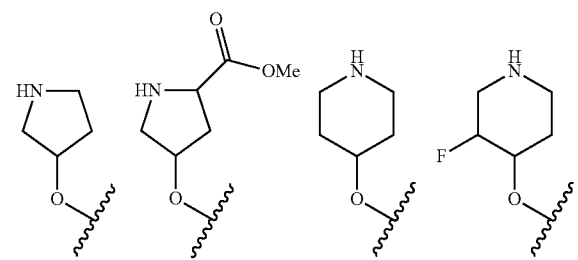

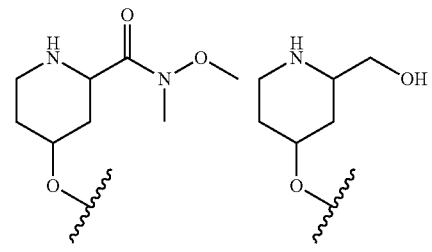

-continued

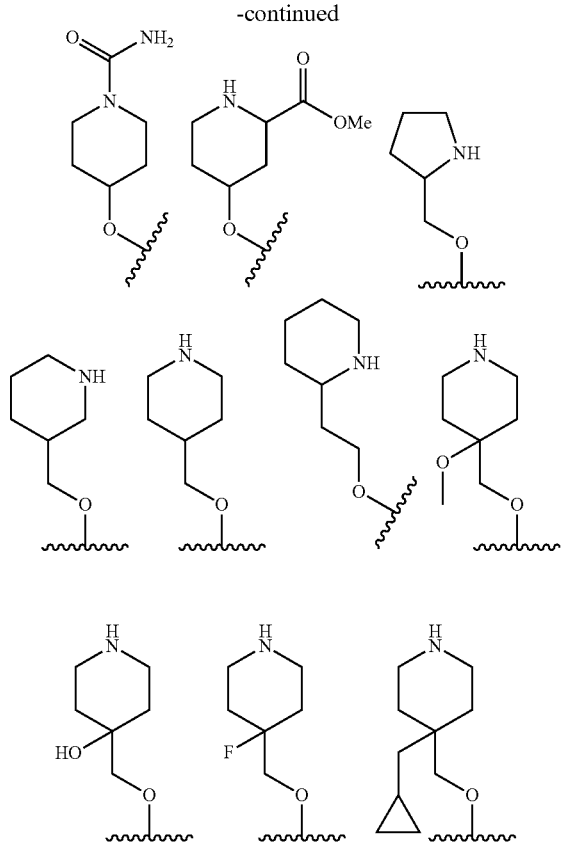

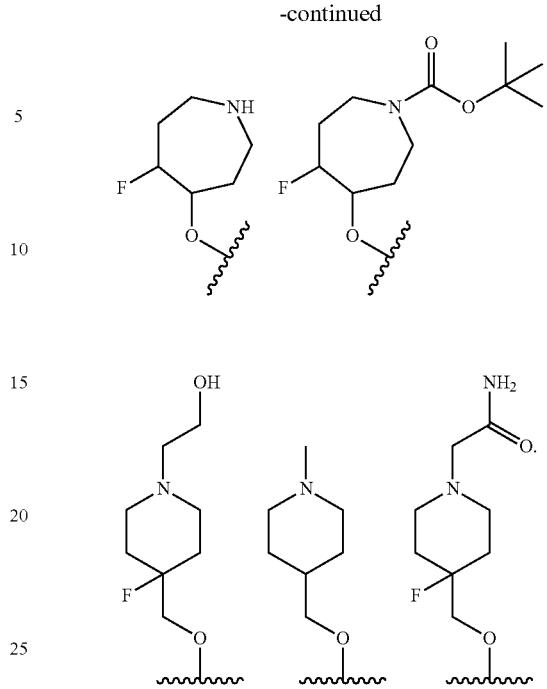

Additional examples of $OR^{10}$ when $R^{10}$ is hetCyc$^1$ or (1-3C alkyl)hetCyc$^{1a}$ include the structures:

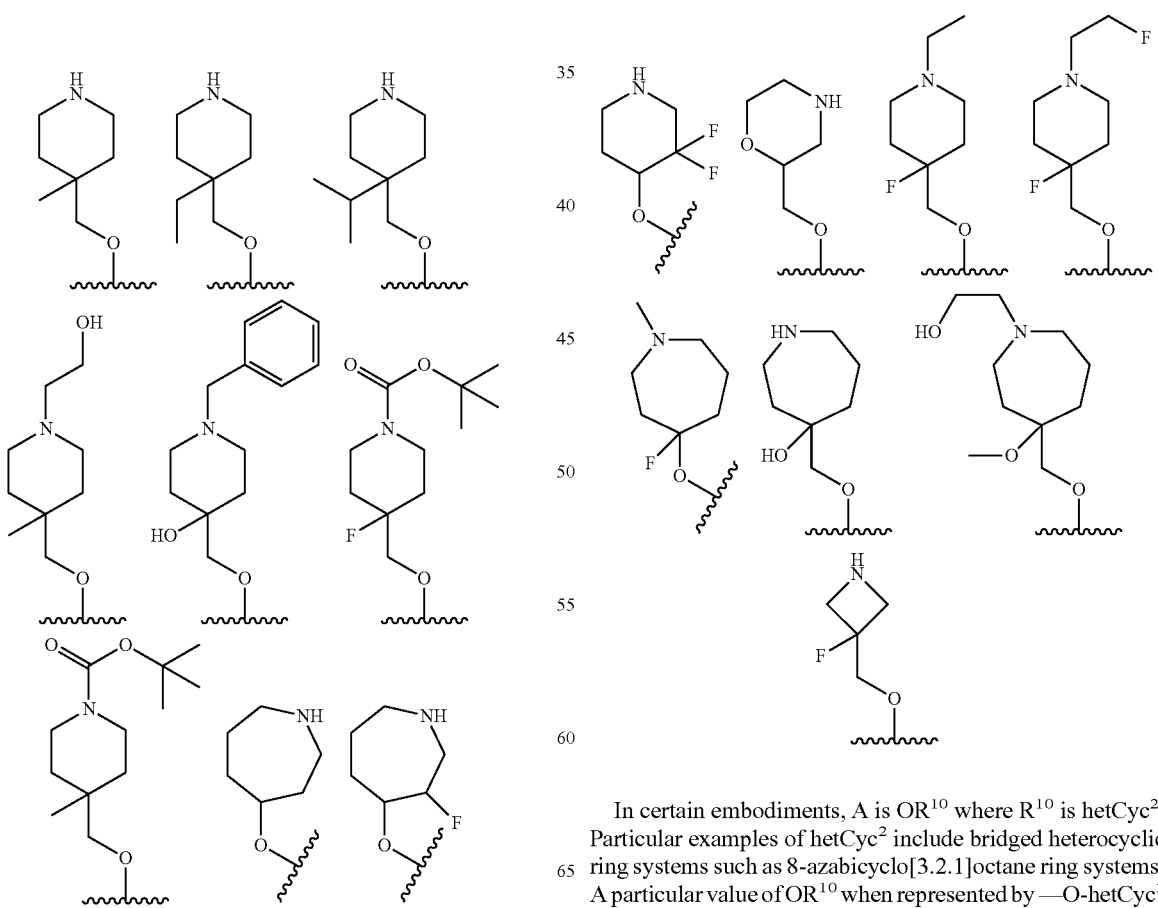

In certain embodiments, A is $OR^{10}$ where $R^{10}$ is hetCyc$^2$. Particular examples of hetCyc$^2$ include bridged heterocyclic ring systems such as 8-azabicyclo[3.2.1]octane ring systems. A particular value of $OR^{10}$ when represented by —O-hetCyc$^2$ includes the structure:

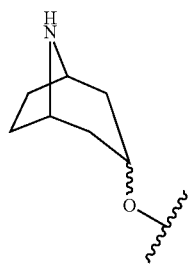 [SMILES: *OC1CC2CCC(C1)N2]

In certain embodiments, A is OR$^{10}$ where R$^{10}$ is represented by the formula $(CR^{17}R^{18})_p(CR^{13}R^{14})CH_2NR^{15}R^{16}$. In certain embodiments, p is 0. In other embodiments, p is 1 or 2. In certain embodiments, R$^{17}$ and R$^{18}$ are both H. In certain embodiments, R$^{17}$ and R$^{18}$ are both independently selected from a (1-6C alkyl) group, for example methyl, ethyl, propyl and isopropyl. In certain embodiments, one of R$^{17}$ and R$^{18}$ is H and the other is (1-6C alkyl). In certain embodiments, R$^{13}$ and R$^{14}$ are each H. In certain embodiments, R$^{13}$ and R$^{14}$ are each F. In other embodiments, R$^{13}$ and R$^{14}$ are independently H or (1-6C) alkyl, for example methyl, ethyl, propyl or isopropyl. In other embodiments, R$^{13}$ and R$^{14}$ together with the carbon atom to which they are attached form a cyclopropyl ring. In certain embodiments, R$^{15}$ and R$^{16}$ are each H. In other embodiments, R$^{15}$ and R$^{16}$ are independently H or (1-6C) alkyl, for example methyl, ethyl, propyl or isopropyl. In certain embodiments, R$^{17}$ is H. In other embodiments, R$^{17}$ is (1-6C alkyl), for example methyl, ethyl, propyl or isopropyl. Particular embodiments of OR$^{10}$ when represented by —O—$(CR^{17}R^{18})_p(CR^{13}R^{13})CH_2NR^{15}R^{16}$ include the structures:

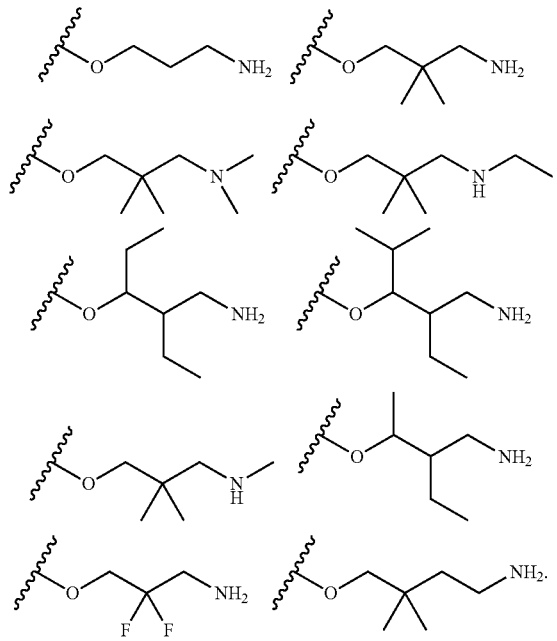

In certain embodiments, A is OR$^{10}$ where R$^{10}$ is represented by the formula $(CR^{17}R^{18})_p(CR^{13}T^{14})CH_2NR^{15}R^{16}$ and R$^{13}$ and R$^{14}$ together with the carbon atom to which they are attached form a cyclopentyl ring. A particular example is the structure:

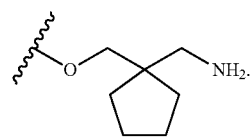 [SMILES: *OCC1(CN)CCCC1]

In certain embodiments, A is OR$^{10}$ where R$^{10}$ is represented by the formula $(CR^{17}R^{18})_p(CR^{13}R^{14})CH_2NR^{15}R^{16}$, where each R$^{15}$, R$^{17}$ and R$^{18}$ is independently H or (1-6C) alkyl and R$^{16}$ is H, (1-6C)alkyl, C(=O)CH$_2$F, CH$_2$CHF$_2$ or CH$_2$CF$_3$. In certain embodiments, R$^{15}$, R$^{17}$ and R$^{18}$ are H and R$^{16}$ is C(=O)CH$_2$F, CH$_2$CHF$_2$ or CH$_2$CF$_3$. Particular examples include the structures:

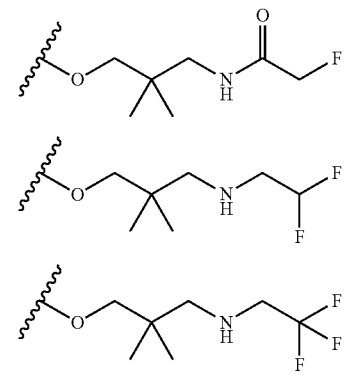

In certain embodiments, A is OR$^{10}$ where R$^{10}$ is represented by the formula —$(CR^{17}R^{18})_p(CR^{13}R^{14})CH_2OH$. In certain embodiments, p is 0. In other embodiments, p is 1 or 2. In certain embodiments, R$^{17}$ and R$^{18}$ are both hydrogen. In certain embodiments, R$^{17}$ and R$^{18}$ are both independently selected from (1-6C alkyl), for example independently selected from methyl, ethyl and propyl. In certain embodiments, one of R$^{17}$ and R$^{18}$ is hydrogen and the other is selected from (1-6C alkyl). In certain embodiments, R$^{13}$ and R$^{14}$ are each H. In certain embodiments, R$^{13}$ and R$^{14}$ are each independently selected from a (1-6C)alkyl group, such as methyl, ethyl, propyl or isopropyl. In other embodiments, R$^{13}$ is OH, and R$^{14}$ is H. In other embodiments, R$^{13}$ and R$^{14}$ together with the atom to which they are attached form a 3-6 membered carbocycle, for example a cyclopropyl, cyclobutyl, cyclopentyl or cyclohexyl ring. Particular embodiments of OR$^{10}$ when represented by —O—$(CR^{17}R^{18})_p(CR^{13}R^{14})CH_2OH$ include the structures:

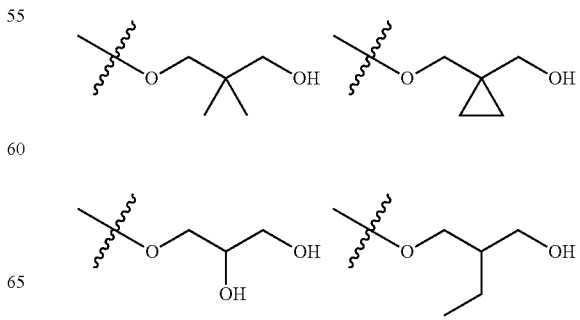

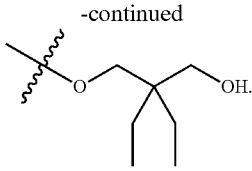

In certain embodiments, A is OR$^{10}$ where R$^{10}$ is (1-6C alkyl). Particular examples of OR$^{10}$ include the structures:

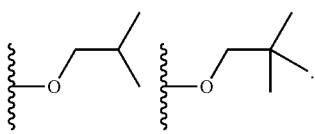

In certain embodiments, A is OR$^{10}$ where R$^{10}$ is (3-7C) cycloalkyl substituted with a substituent selected from NH$_2$, NH(1-6C alkyl) or N(1-6C alkyl)$_2$, for example NH$_2$, NHMe or NMe$_2$. A particular value of OR$^{10}$ when R$^{10}$ is (3-6C) cycloalkyl includes the structure:

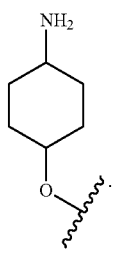 [SMILES: *OC1CCC(N)CC1]

In certain embodiments, A is OR$^{10}$ where R$^{10}$ is hetAr$^1$ or (1-3Calkyl)hetAr$^{1a}$. Examples of hetAr$^1$ and hetAr$^{1a}$ include pyridyl and pyrimidyl rings optionally substituted with C$_1$ or NH$_2$. Particular values of OR$^{10}$ when R$^{10}$ is hetAr$^1$ or (1-3Calkyl)hetAr$^{1a}$ include the structures:

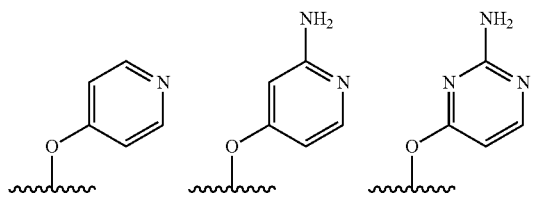

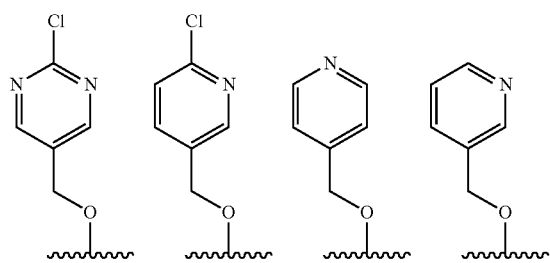

In certain embodiments, A is OH.
In certain embodiments, A is NR$^{11}$R$^{12}$.

In certain embodiments, A is NR$^{11}$R$^{12}$, wherein R$^{12}$ is hetCyc$^3$ optionally substituted with one or more R$^9$ groups described hereinabove. Particular examples of hetCyc$^3$ include piperidinyl and pyrrolidinyl rings. In certain embodiments, hetCyc$^3$ is substituted with one or more R$^9$ groups independently selected from (1-6C) alkyl. In certain embodiments, R$^{11}$ is H. Particular examples of NR$^{11}$R$^{12}$ when R$^{12}$ is hetCyc$^3$ include the structures:

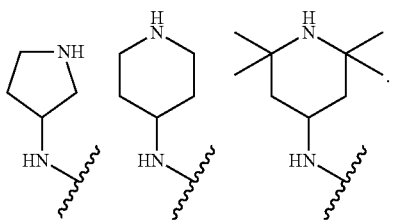

In certain embodiments, A is NR$^{11}$R$^{12}$ and R$^{12}$ is (1-6C alkyl)NR$^{15}$R$^{16}$. In certain embodiments, R$^{11}$ is H. In certain embodiments, R$^{15}$ and R$^{16}$ are each H. In certain embodiments, R$^{15}$ is H and R$^{16}$ is (1-6C)alkyl, for example methyl, ethyl, propyl or isopropyl. In certain embodiments, NR$^{15}$R$^{16}$ forms a 5-6 membered heterocyclic ring having a first ring heteroatom which is N and optionally having a second ring heteroatom selected from N and O. Examples of heterocyclic rings include pyrrolidinyl, piperidinyl, piperazinyl and morpholinyl. Particular embodiments of NR$^{11}$R$^{12}$ include the structures:

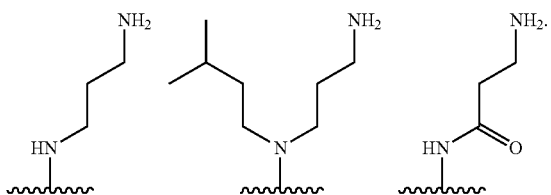

In certain embodiments, A is NR$^{11}$R$^{12}$, wherein R$^{12}$ is C(O)(1-6C alkyl)NR$^{15}$R$^{16}$. In certain embodiments, R$^{11}$ is H. In certain embodiments, R$^{15}$ and R$^{16}$ are each H. In certain embodiments, R$^{15}$ is H and R$^{16}$ is (1-6C)alkyl, for example methyl, ethyl, propyl or isopropyl. In certain embodiments, NR$^{15}$R$^{16}$ forms a 5-6 membered heterocyclic ring having a first ring heteroatom which is N and optionally having a second ring heteroatom selected from N and O. Examples of heterocyclic rings include pyrrolidinyl, piperidinyl, piperazinyl and morpholinyl. A particular value of NR$^{11}$R$^{12}$ is NHC(O)CH$_2$CH$_2$NH$_2$.

In certain embodiments, A is NR$^{11}$R$^{12}$, wherein R$^{12}$ is (1-6 C alkyl)NHC(O)O(1-6C alkyl), for example (1-6 C alkyl) NHC(O)OC(CH$_3$)$_3$. In certain embodiments, R$^{11}$ is H. A particular value of NR$^{11}$R$^{12}$ is (CH$_2$)$_3$NHCO$_2$C(CH$_3$)$_3$.

In certain embodiments, A is NR$^{11}$R$^{12}$, wherein R$^{12}$ is (4-7C)cycloalkyl substituted with a substituent selected from OH, NH$_2$, NH(1-6C alkyl) or N(1-6C alkyl)$_2$. In certain embodiments, R$^{11}$ is H. A particular example of A is the structure:

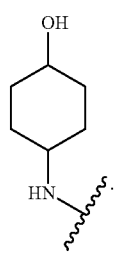 [SMILES: *NC1CCC(O)CC1]

In certain embodiments, B is H.
In certain embodiments, B is F.
In certain embodiments, B is OR$^a$.

Examples of OR$^a$ when R$^a$ is represented by (1-6C)alkyl include OMe, OEt and O-(isobutyl). A particular value of B when represented by OR$^a$ is OMe.

Examples of OR$^a$ when R$^a$ is represented by -(1-6C alkyl)-O-(1-6C alkyl) include —OCH$_2$CH$_2$OMe and —OCH$_2$CH$_2$CH$_2$OMe. A particular value of B when represented by OR$^a$ is —OCH$_2$CH$_2$OMe.

In certain embodiments, B is (1-6C alkyl)NR$^b$R$^c$. In certain embodiments, R$^b$ is H and R$^c$ is H or (1-6C)alkyl. Particular values of B include groups having the formula CH$_2$NR$^b$R$^c$, for example CH$_2$NHEt and CH$_2$NH$_2$.

In certain embodiments, B is (1-6C alkyl)OH. A particular value of B is CH$_2$OH.

In certain embodiments, B is CH(OH)CH$_2$OH.

In certain embodiments, B is (1-4C alkyl). A particular example is methyl.

It will be appreciated that certain compounds according to the invention may contain one or more centers of asymmetry and may therefore be prepared and isolated in a mixture of isomers such as a racemic mixture, or in an enantiomerically pure form.

It will further be appreciated that the compounds of Formula I or their salts may be isolated in the form of solvates, and accordingly that any such solvate is included within the scope of the present invention.

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I.

Examples of salts of Formula I include acid addition salts, including salts of inorganic and organic acids. Particular mention is made of hydrochloride and trifluoroacetate salts of Formula I.

According to another aspect, the present invention provides a process for the preparation a compound of Formula I or a salt thereof as defined herein which comprises:

(a) for a compound of Formula I wherein A is NR$^{11}$R$^{12}$, coupling a corresponding compound having the formula II

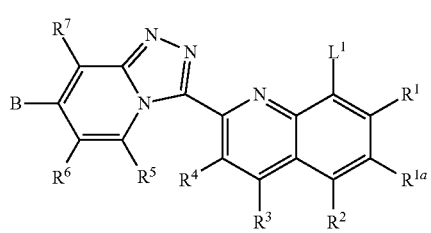

wherein L$^1$ represents a leaving atom or group, with a compound having the formula HNR$^{11}$R$^{12}$, using a palladium (II) catalyst and a ligand in the presence of a base; or (b) reacting a compound of Formula III

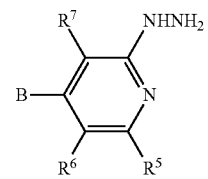

with a compound having the Formula IV

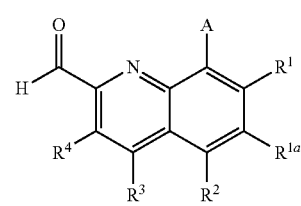

in the presence of an organo hypervalent iodine reagent; or (c) for a compound of Formula I wherein A is OR$^{10}$, coupling a corresponding compound having the Formula V

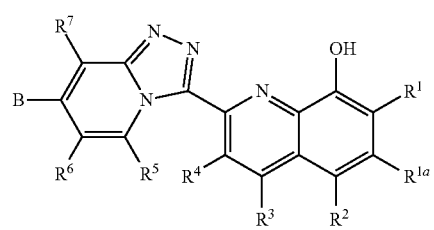

with a compound having the formula HO—R$^{10}$ in the presence of a coupling agent and triphenylphosphine in a suitable solvent; or (d) for a compound of Formula I wherein B is (CH$_2$)NR$^b$R$^c$, reacting a corresponding compound having the Formula VI

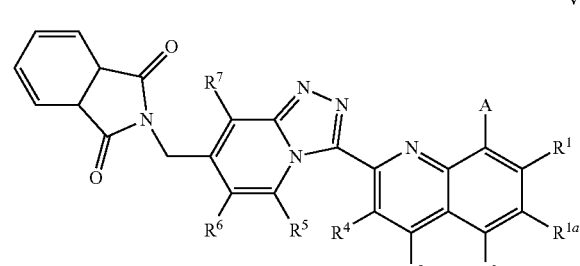

with hydrazine; or (e) for a compound of Formula I where B is OR$^a$, reacting a corresponding compound having the Formula VII

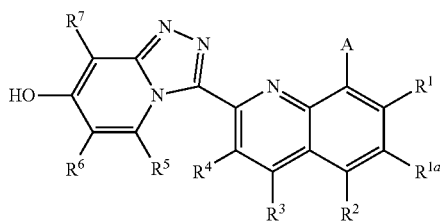

VII with a compound of the formula $R^a$-$L^2$, wherein $L^2$ represents a leaving atom or group, in the presence of a base; and removing any protecting group or groups and, if desired, forming a salt.

Referring to method (a), the leaving atom $L^1$ may be, for example a halogen atom such as Br or I. Alternatively, $L^1$ can be a leaving group, such as a hydrocarbylsulfonyloxy group, for example, a triflate group, or an arylsulfonyloxy group or an alkylsulfonyloxy group, such as a mesylate or a tosylate group. Suitable palladium catalysts include $Pd_2(dba)_3$ and $Pd(OAc)_2$. Suitable ligands include rac-BINAP or DIPHOS. The base may be, for example, an alkali metal carbonate or alkoxide, such as for example cesium carbonate or sodium tert-butoxide. Convenient solvents include aprotic solvents such as ethers (for example tetrahydrofuran or p-dioxane) or toluene. Alternatively, the reaction can be performed in the absence of a solvent. The coupling of a compound of formula (II) with $HNR^{11}R^{12}$ can be conveniently performed at a temperature between 0° C. and reflux, and more particularly at reflux, for example at 100° C.

Referring to method (b), the organo hypervalent iodine reagent refers to any hypervalent iodine reagent suitable for forming heterocyclic rings. Examples include iodobenzene diacetate (IBD) and [hydroxy(tosyloxy)iodo]benzene (HTIB), which can be prepared by treating IBD with p-toluenesulfonic acid monohydrate in acetonitrile. Suitable solvent systems when using IBD include methanolic potassium hydroxide. Suitable solvent systems when using HT1B include neutral solvents, for example acetonitrile or dioxane. The reaction can be performed at a temperature ranging from 80 to 110° C.

Referring to method (c), the coupling reagent may be any suitable reagent(s) known to those skilled in the art, for example, DEAD and $PPh_3$. Convenient solvents include aprotic solvents such as ethers (for example tetrahydrofuran). The reaction can be conveniently performed at a temperature ranging from −78 to 100° C.

Referring to method (d), the reaction is conveniently performed at ambient temperature. Suitable solvents include alcohols such as methanol.

Referring to method (e), the leaving atom $L^2$ may be, for example a halogen atom such as Br, Cl or I. Alternatively, $L^2$ can be a leaving group, for example an arylsulfonyloxy group or an alkylsulfonyloxy group, such as a mesylate or a tosylate group. The base may be, for example, an alkali metal hydride or carbonate, such as sodium hydride, potassium hydride, sodium carbonate, potassium carbonate or cesium carbonate. Convenient solvents include aprotic solvents such as ethers (for example tetrahydrofuran or p-dioxane), DMF, or acetone. The reaction can be conveniently performed at a temperature ranging from −78 to 100° C.

A compound of Formula II

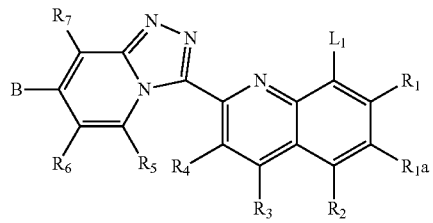

II can be prepared by cyclizing a corresponding compound having the formula VIII

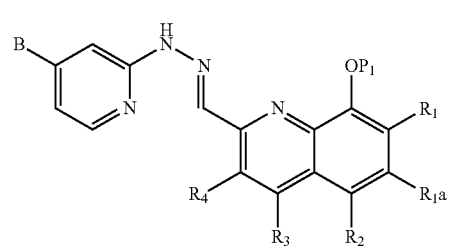

VIII where $P^1$ is an alcohol protecting group, in the presence of an organo hypervalent iodine reagent as described above, followed by deprotection of the alcohol group and conversion of the alcohol group to an alkylsulfonyloxy group, such as a mesylate or a tosylate group.

A compound of Formula VI can be prepared by reducing a corresponding aldehyde having the formula IX

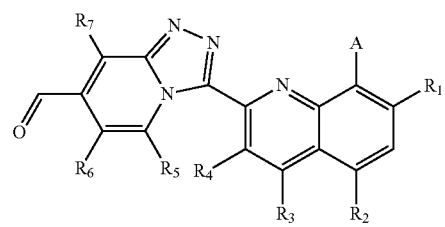

IX to the corresponding alcohol, followed by reacting the alcohol with isoindoline-1,3-dione in the presence of triphenylphosphine.

The compounds of the formulas (II), (V), (VI), (VIII) and (IX) are believed to be novel and are provided as further aspects of the invention.

The compounds of Formula I include compounds of Formula Ia

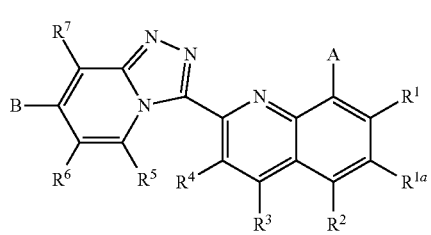

Ia and pharmaceutically acceptable salts thereof, wherein:
A is $OR^{10}$;
B is H, —$CH_2NH_2$, —OMe, —$OCH_2CH_2OMe$, F, Cl or Me;
$R^1$ is H, F, Cl, Br, Me, cyclopropyl or CN;
$R^{1a}$, $R^2$, $R^3$ and $R^4$ are independently H, F, Cl, Br, Me or CN;
$R^5$ and $R^7$ are independently H, F, Me or CN;
$R^6$ is H, F, Me, Br, CN, cyclopropyl, phenyl, —OMe, or —$OCH_2CH_2OMe$;
$R^{10}$ is $hetCyc^1$, -(1-3C alkyl)$hetCyc^{1a}$ or $hetCyc^2$;
$hetCyc^1$ is a 4-7 membered heterocycle having a ring nitrogen atom and optionally substituted with one or more $R^9$ groups;
$hetCyc^{1a}$ is selected from a morpholinyl and 4-7 membered azacyclic ring optionally substituted with one or more $R^9$ groups;
each $R^9$ is independently selected from halogen, (1-6C) alkyl, cyclopropylmethyl, $OR^j$, (1-6C alkyl)$OR^k$, (1-6C)fluoroalkyl, C(O)$NR^mR^n$, (1-6C alkyl)C(O)$NR^pR^q$, and C(O)O (1-6C alkyl);
$hetCyc^2$ is an 8-membered bridged heterocycle having a ring nitrogen atom;
each $R^k$, $R^m$, $R^p$ and $R^q$ is independently selected from H and (1-6C alkyl);
$R^j$ is H, (1-6C alkyl) or cyclopropyl;
$R^n$ is H, (1-6C alkyl), —O(1-6C alkyl) or —O(3-6C cycloalkyl); and
p is 0, 1 or 2.

In certain embodiments of Formula Ia, each of $R^1$, $R^2$, $R^3$, $R^5$ and $R^7$ is hydrogen.

In certain embodiments of Formula Ia, B is hydrogen.

In certain embodiments of Formula Ia, $R^{10}$ is $hetCyc^1$ or -(1-3C alkyl)$hetCyc^{1a}$.

In certain embodiments of Formula Ia, $hetCyc^1$ and -(1-3C alkyl)$hetCyc^{1a}$ are optionally substituted with one or two $R^9$ groups independently selected from Me, Et, isopropyl, cyclopropylmethyl, F, OH, OMe, $CH_2OH$, $CH_2CH_2OH$, $CH_2CH_2F$, $CH_2OMe$, C(=O)OMe, C(=O)$NH_2$ and $CH_2C$(=O)$NH_2$.

The compounds of Formula I include compounds of Formula Ib

Ib and pharmaceutically acceptable salts thereof, wherein:
A is $OR^{10}$;
B is H, —$CH_2NH_2$, —OMe, —$OCH_2CH_2OMe$, F, Cl or Me;
$R^1$ is H, F, Cl, Br, Me, cyclopropyl or CN;
$R^{1a}$, $R^2$, $R^3$ and $R^4$ are independently H, F, Cl, Br, Me or CN;
$R^5$ and $R^7$ are independently H, F, Me or CN;
$R^6$ is H, F, Me, Br, CN, cyclopropyl or phenyl;
$R^{10}$ is H, $(CR^{17}R^{18})_p(CR^{13}R^{14})CH_2NR^{15}R^{16}$, —$(CR^{17}R^{18})_p(CR^{13}R^{14})CH_2OH$, (1-6C alkyl), or a (3-7C) cycloalkyl ring substituted with $NH_2$, NH(1-6C alkyl) or N(1-6C alkyl)$_2$;

$R^{13}$ is H, (1-6C)alkyl, F or OH, and
$R^{14}$ is H, (1-6C)alkyl or F, or
$R^{13}$ and $R^{14}$ together with the carbon atom to which they are attached form a 3-6 membered carbocyclic ring;
each $R^{15}$, $R^{17}$ and $R^{18}$ is independently H or (1-6C)alkyl;
$R^{16}$ is H, (1-6C)alkyl, C(=O)$CH_2F$, $CH_2CHF_2$ or $CH_2CF_3$; and
p is 0, 1 or 2.

In certain embodiments of Formula Ib, each of $R^1$, $R^2$, $R^3$, $R^5$ and $R^7$ is hydrogen.

In certain embodiments of Formula Ib, B is hydrogen.

The compounds of Formula I include compounds of Formula Ic

Ic and pharmaceutically acceptable salts thereof, wherein:
A is $NR^{11}R^{12}$;
B is H, —$CH_2NH_2$, —OMe, —$OCH_2CH_2OMe$, F, Cl or Me;
$R^1$ is H, F, Cl, Br, Me, cyclopropyl or CN;
$R^{1a}$, $R^2$, $R^3$ and $R^4$ are independently H, F, Cl, Br, Me or CN;
$R^5$ and $R^7$ are independently H, F, Me or CN;
$R^6$ is H, F, Me, Br, CN, cyclopropyl, phenyl, MeO— or $MeOCH_2CH_2O$—;
$R^{11}$ is H or (1-6C)alkyl;
$R^{12}$ is $hetCyc^3$;
$hetCyc^3$ is a 4-7 membered heterocycle having a ring nitrogen atom and optionally substituted with one or more $R^9$ groups;
each $R^9$ is independently selected from (1-6C)alkyl; and
p is 0, 1 or 2.

In certain embodiments of Formula Ic, each of $R^1$, $R^2$, $R^3$, $R^5$ and $R^7$ is hydrogen.

In certain embodiments of Formula Ic, B is hydrogen.

The compounds of Formula I include compounds of Formula Id

Id and pharmaceutically acceptable salts thereof, wherein:
A is $NR^{11}R^{12}$;
B is H, —$CH_2NH_2$, —OMe, —$OCH_2CH_2OMe$, F, Cl or Me;
$R^1$ is H, F, Cl, Br, Me, cyclopropyl or CN;
$R^{1a}$, $R^2$, $R^3$ and $R^4$ are independently H, F, Cl, Br, Me or CN;

$R^5$ and $R^7$ are independently H, F, Me or CN;

$R^6$ is H, F, Me, Br, CN, cyclopropyl, phenyl, MeO— or MeOCH$_2$CH$_2$O—;

$R^{11}$ is H or (1-6C)alkyl;

$R^{12}$ is (1-6C alkyl)NR$^{15}$R$^{16}$, C(O)(1-6C alkyl)NR$^{15}$R$^{16}$, (1-6C alkyl)NHC(O)O(1-6C alkyl), or (4-7C)cycloalkyl optionally substituted with OH, NH$_2$, NH(1-6C alkyl) or N(1-6C alkyl)$_2$; and each $R^{15}$, $R^{17}$ $R^{16}$ and $R^{18}$ is independently H or (1-6C) alkyl.

In certain embodiments of Formula Ic, each of $R^1$, $R^2$, $R^3$, $R^5$ and $R^7$ is hydrogen.

In certain embodiments of Formula Ic, B is hydrogen.

The ability of test compounds to act as PIM-1, PIM-2 and/or PIM-3 inhibitors may be demonstrated by the assay described in Examples A, B, and C, respectively.

Compounds of Formula I have been found to be inhibitors of PIM-1 and/or PIM-2 and/or PIM-3, and are useful for treating diseases and disorders which can be treated with a Pim-1 and/or Pim-2 and/or Pim-3 kinase inhibitor, including diseases mediated by Pim-1 and/or Pim-2 and/or Pim-3 kinases. Particular compounds of this invention are inhibitors of Pim-1 and therefore are useful in treating diseases and disorders mediated by Pim-1, such as cancers, such as hematological cancers and solid tumors (e.g., breast cancer, colon cancer, gliomas).

Examples of hematological cancers include, for instance, leukemias, lymphomas (non-Hodgkin's lymphoma), Hodgkin's disease (also called Hodgkin's lymphoma), and myeloma, for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), promyelocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma. Additional examples of hematological cancers include myeloproliferative disorders (MPD) such as polycythemia vera (PV), essential thrombocytopenia (ET) and idiopathic primary myelofibrosis (IMF/IPF/PMF). Certain cancers which can be treated with compounds of Formula I are cancers which are derived from T cells or B cells.

A further embodiment of this invention provides a compound of Formula I or a pharmaceutically acceptable salt thereof, for use in the treatment of cancer.

Accordingly, a further embodiment of this invention provides a method of treating cancer in a mammal in need thereof, comprising administering to said mammal a compound of Formula I or a pharmaceutically acceptable salt thereof. In one embodiment, the cancer is a hematological cancer. In one embodiment, the cancer derives from T cells. In one embodiment, the cancer derives from B cells.

A further embodiment of this invention provides a compound of Formula I or a pharmaceutically acceptable salt thereof, for use in the treatment of cancer. In one embodiment, the cancer is a hematological cancer. In one embodiment, the cancer derives from T cells. In one embodiment, the cancer derives from B cells.

Expression of PIM kinases in immune cells is induced by cytokines present during immune responses. Immune cells are critically dependent on cytokines for differentiation and development of effector functions during normal and pathogenic immune responses. Thus, compounds of the invention may be useful for treating diseases and disorders characterized by aberrant cytokine production and responses and/or aberrant immune cell activation.

Accordingly, another embodiment of the invention provides a method of treating diseases and disorders characterized by aberrant cytokine production and responses and/or aberrant immune cell activation in a mammal in need thereof, comprising administering to the mammal a compound of Formula I or a pharmaceutically acceptable salt thereof. Examples of such diseases and disorders include autoimmune and inflammatory diseases.

Another embodiment provides a compound of Formula I or a pharmaceutically acceptable salt thereof for use in the treatment of diseases and disorders characterized by aberrant cytokine production and responses and/or aberrant immune cell activation in a mammal. Examples of such diseases and disorders include autoimmune and inflammatory diseases.

Particular examples of diseases and disorders which can be treated using a compound of Formula I include transplant rejection and autoimmune diseases and disorders. Examples of autoimmune diseases and disorders include multiple sclerosis, systemic lupus erythematosis, inflammatory bowel disease (IBD), Crohn's disease, irritable bowel syndrome, pancreatitis, ulcerative colitis, diverticulosis, Grave's disease, arthritis (including rheumatoid arthritis, juvenile rheumatoid arthritis, osteoarthritis, psoriatic arthritis and ankylosing spondylitis), myasthenia gravis, vasculitis, autoimmune thyroiditis, dermatitis (including atopic dermatitis and eczematous dermatitis), psoriasis, scleroderma, asthma, allergy, systemic sclerosis, vitiligo, grave vs. host disease (GVHD), Sjogren's syndrome, glomerulonephritis, IgA nephoropathy, and diabetes mellitus (type I).

As described in further detail in Example E, compounds of Formula I were found to be effective in inhibiting the proliferation of T cells, as well as inhibiting cytokine production by T cells stimulated through T cell receptors and by cytokines in vitro. The effect of these compounds on IL-4 production and IL-22 production supports the utility of compounds of Formula I in treating diseases where these cytokines have been shown to play a role. Particular examples of such diseases include asthma, MS and inflammatory bowel disease (IBD), lupus, psoriasis and rheumatoid arthritis.

As an extension of the in vitro data, a compound of Formula I was found to be effective at inhibiting the generation of T cells responses to antigen in vivo as assessed by proliferation and cytokine production ex vivo (Example F). Since T cell activation or proliferation and cytokine production are often key components of autoimmune diseases, the data provided in Example F supports the utility of compounds of Formula I in treating diseases associated with T cell proliferation and cytokine production, including autoimmune diseases such as those described herein.

B cells are also critically dependent on cytokines for production of particular types of immunoglobulins, called antibody (Ab) isotypes, in a process referred to as isotype switching. Over time, isotype switching can be observed in mice which have been immunized with proteins to produce antibodies, which can then be quantified (Shi et al, 1999 Immunity 10:197-206). As demonstrated in Example G, a compound of Formula I was found to be effective at inhibiting the production of cytokine-stimulated Ab isotypes in response to protein immunization. This suggests that compounds of Formula I affect B cells and supports their use in treating autoimmune and inflammatory diseases, including diseases thought to be associated in part by pathogenic B cell and Ab responses. Examples of such diseases include lupus, multiple sclerosis and rheumatoid arthritis.

As demonstrated in Example H, a compound of Formula I was found to be effective in a T cell-mediated murine model of experimental autoimmune encephalomyelitis (EAE). Furthermore, as shown in Example I, a compound of Formula I was found to be effective in a second EAE model in which the disease is caused by generating an immune response to a central nervous system (CNS) protein. EAE mimics many of the pathological features of multiple sclerosis (MS), and these models are widely used to model human disease and its treatment.

T cells also play in role in the inflammatory bowel disease (IBD), which is an autoimmune disease. As demonstrated in Example J, a compound of Formula I was shown to be effective in a T cell-mediated model of this disease.

Lupus is an autoimmune disease characterized by aberrant T and B cell responses. In particular, lupus patients can exhibit elevated cytokine levels and increased amounts of anti-nuclear antibodies (Abs). In lupus, Abs can deposit in the kidneys and mediate tissue damage resulting in nephritis. In the MRL/lpr mouse, a murine model of lupus, a compound of Formula I was shown to decrease the production of anti-DNA Abs as well as decrease proteinuria, a measure of kidney damage (Example K).

Taken together, these examples show that a compound of Formula I is effective at preventing T cell responses both in vitro and in vivo and B cell responses in vivo. Further, this concept is put into practice by showing efficacy of a compound of Formula I in animal models of multiple sclerosis, inflammatory bowel disease and lupus, diseases thought to be associated in part with aberrant immune cell responses. These data support the utility of compounds of Formula I in treating diseases associated with immune cells, such as autoimmune and inflammatory conditions.

Accordingly, certain compounds according to the present invention may be useful for the treatment of inflammatory disorders mediated by T and B cells function, such as rheumatoid arthritis, lupus, multiple sclerosis, and inflammatory bowel disease.

Another embodiment of this invention provides a method of treating or preventing inflammatory and autoimmune diseases, comprising administering to a mammal in need thereof an effective amount of a compound of Formula I. Examples of diseases which can be treated include inflammatory or autoimmune diseases. In one embodiment, the disease is multiple sclerosis. In another embodiment, the disease is lupus. In another embodiment, the disease is inflammatory bowel disease.

A further embodiment of this invention provides a compound of Formula I for use in treating an inflammatory or autoimmune disease. In one embodiment, the disease is multiple sclerosis. In another embodiment, the disease is lupus. In another embodiment, the disease is inflammatory bowel disease.

A subset of the triazolopyridine compounds disclosed herein was found to have $IC_{50}$ values for Pim-1 that are at least 10 fold less than the $IC_{50}$ values for Pim-2. As a further example, particular triazolopyridine compounds disclosed herein were found to have $IC_{50}$ values for Pim-1 that are at least 100 fold less than the $IC_{50}$ for Pim-2. Accordingly, also provided are triazolopyridine compounds which are highly potent Pim-1 inhibitors and are highly selective for Pim-1 relative to Pim-2.

A subset of the triazolopyridine compounds disclosed herein were found to have an $IC_{50}$ values for Pim-1 that are at least 10 fold less than the $IC_{50}$ values for Pim-2 and $IC_{50}$ values for Pim-3 approximately equivalent to that observed for Pim-1. As a further example, particular triazolopyridine compounds disclosed herein were found to have $IC_{50}$ values for Pim-1 that are at least 100 fold less than the $IC_{50}$ values for Pim-2, and $IC_{50}$ values for Pim-3 approximately equivalent to that observed for Pim-1. Accordingly, also provided are triazolopyridine compounds which are highly potent Pim-1/Pim-3 dual inhibitors and are highly selective for Pim-1 and Pim-3 relative to Pim-2.

As used herein, the term treatment includes prophylaxis as well as treatment of an existing condition.

Accordingly, another aspect of this invention provides a method of treating diseases or medical conditions in a mammal mediated by a Pim-1 and/or Pim-2 and/or Pim-3 kinase, comprising administering to said mammal one or more compounds of Formula I or a pharmaceutically acceptable salt or prodrug thereof in an amount effective to treat or prevent said disorder.

Compounds of Formula I may also be useful as adjuvants to cancer treatment, that is, they can be used in combination with one or more additional drugs, for example a chemotherapeutic that works by the same or by a different mechanism of action.

Compounds of the present invention may also be used in combination with one or more additional drugs, for example an anti-inflammatory compound, an immunosuppressive compound or an immunodepleting agent that works by the same or a different mechanism of action.

The phrase "effective amount" means an amount of compound that, when administered to a mammal in need of such treatment, is sufficient to (i) treat or prevent a particular disease, condition, or disorder mediated by a Pim-1 and/or Pim-2 and/or Pim-3 kinase, (ii) attenuate, ameliorate, or eliminate one or more symptoms of the particular disease, condition, or disorder, or (iii) prevent or delay the onset of one or more symptoms of the particular disease, condition, or disorder described herein.

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

Compounds of the invention may be administered by any convenient route, e.g. into the gastrointestinal tract (e.g. rectally or orally), the nose, lungs, musculature or vasculature, or transdermally or dermally. Compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

According to another aspect, the present invention provides a pharmaceutical composition, which comprises a compound of Formula I or a pharmaceutically acceptable salt thereof, as defined hereinabove. In one embodiment, the pharmaceutical composition includes the compound of Formula I together with a pharmaceutically acceptable diluent or carrier.

According to another aspect, the present invention provides a compound of Formula I or a pharmaceutically acceptable salt thereof, for use in therapy, such as the treatment of a Pim-1 and/or Pim-2 and/or Pim-3 kinase-mediated condition.

According to a further aspect, the present invention provides the use of a compound of Formula I, or a pharmaceutically acceptable salt thereof, for use in the treatment of a Pim-1 and/or Pim-2 and/or Pim-3 kinase-mediated condition, as defined hereinabove.

Particular compounds of the invention include:

2-([1,2,4]Triazolo[4,3-a]pyridin-3-yl)-N-(piperidin-4-yl)quinolin-8-amine di-trifloroacetate;
2-([1,2,4]Triazolo[4,3-a]pyridin-3-yl)-N-(2,2,6,6-tetramethylpiperidin-4-yl)quinolin amine;
(trans)-4-(2-([1,2,4]Triazolo[4,3-a]pyridin-3-yl)quinolin-8-ylamino)cyclohexanol;
(S)-2-([1,2,4]Triazolo[4,3-a]pyridin-3-yl)-N-(pyrrolidin-3-yl)quinolin-8-amine;
(R)-2-([1,2,4]Triazolo[4,3-a]pyridin-3-yl)-N-(pyrrolidin-3-yl)quinolin-8-amine;
tert-Butyl 3-(2-([1,2,4]Triazolo[4,3-a]pyridin-3-yl)quinolin-8-ylamino)propylcarbamate;
N1-(2-([1,2,4]Triazolo[4,3-a]pyridin-3-yl)quinolin-8-yl)propane-1,3-diamine;
N1-(2-([1,2,4]Triazolo[4,3-a]pyridin-3-yl)quinolin-8-yl)-N1-isopentylpropane-1,3-diamine;
2-([1,2,4]triazolo[4,3-a]pyridin-3-yl)-8-(piperidin-4-yloxy)quinoline;
3-(2-([1,2,4]Triazolo[4,3-a]pyridin-3-yl)quinolin-8-yloxy)propan-1-amine;
(R)-2-([1,2,4]Triazolo[4,3-a]pyridin-3-yl)-8-(pyrrolidin-3-yloxy)quinoline;
(S)-2-([1,2,4]Triazolo[4,3-a]pyridin-3-yl)-8-(pyrrolidin-3-yloxy)quinoline;
(2S,4S)-Methyl 4-(2-([1,2,4]triazolo[4,3-a]pyridin-3-yl)quinolin-8-yloxy)piperidine-2-carboxylate;
2-([1,2,4]Triazolo[4,3-a]pyridin-3-yl)-8-(piperidin-4-ylmethoxy)quinoline;
2-([1,2,4]Triazolo[4,3-a]pyridin-3-yl)-8-(2-(piperidin-2-yl)ethoxy)quinoline;
2-([1,2,4]Triazolo[4,3-a]pyridin-3-yl)-8-(piperidin-3-ylmethoxy)quinoline;
(trans)-4-(2-([1,2,4]Triazolo[4,3-a]pyridin-3-yl)quinolin-8-yloxy)cyclohexanamine;
3-(2-([1,2,4]Triazolo[4,3-a]pyridin-3-yl)quinolin-8-yloxy)-2,2-dimethylpropan-1-amine;
3-(2-(7-(aminomethyl)-[1,2,4]triazolo[4,3-a]pyridin-3-yl)quinolin-8-yloxy)-2,2-dimethylpropan-1-ol;
(3-(8-isobutoxyquinolin-2-yl)-[1,2,4]triazolo[4,3-a]pyridin-7-yl)methanamine;
3-(2-([1,2,4]triazolo[4,3-a]pyridin-3-yl)quinolin-8-yloxy)-N,N,2,2-tetramethylpropan-1-amine;
(1-((2-([1,2,4]triazolo[4,3-a]pyridin-3-yl)quinolin-8-yloxy)methyl)cyclopropyl)methanol;
2-([1,2,4]triazolo[4,3-a]pyridin-3-yl)-8-(neopentyloxy)quinoline;
3-(2-([1,2,4]triazolo[4,3-a]pyridin-3-yl)quinolin-8-yloxy)-2,2-dimethylpropan-1-ol;
2-([1,2,4]triazolo[4,3-a]pyridin-3-yl)-8-((trans)-3-fluoropiperidin-4-yloxy)quinoline;
2-([1,2,4]triazolo[4,3-a]pyridin-3-yl)-8-((cis)-3-fluoropiperidin-4-yloxy)quinoline;
3-(2-([1,2,4]triazolo[4,3-a]pyridin-3-yl)quinolin-8-yloxy)-N-ethyl-2,2-dimethylpropan-1-amine;
3-(2-([1,2,4]triazolo[4,3-a]pyridin-3-yl)quinolin-8-yloxy)-N,2,2-trimethylpropan-1-amine;
8-(8-azabicyclo[3.2.1]octan-3-yloxy)-2-([1,2,4]triazolo[4,3-a]pyridin-3-yl)quinoline;
(2S)-3-(2-([1,2,4]triazolo[4,3-a]pyridin-3-yl)quinolin-8-yloxy)-2-ethylpentan-1-amine;
(2R)-3-(2-([1,2,4]triazolo[4,3-a]pyridin-3-yl)quinolin-8-yloxy)-2-ethylpentan-1-amine;
(2S)-3-(2-([1,2,4]triazolo[4,3-a]pyridin-3-yl)quinolin-8-yloxy)-2-ethylbutan-1-amine;
(2R)-3-(2-([1,2,4]triazolo[4,3-a]pyridin-3-yl)quinolin-8-yloxy)-2-ethylbutan-1-amine;
(2S)-3-(2-([1,2,4]triazolo[4,3-a]pyridin-3-yl)quinolin-8-yloxy)-2-ethylhexan-1-amine;
(2R)-3-(2-([1,2,4]triazolo[4,3-a]pyridin-3-yl)quinolin-8-yloxy)-2-ethylhexan-1-amine;
(2S,4R)-methyl 4-(2-([1,2,4]triazolo[4,3-a]pyridin-3-yl)quinolin-8-yloxy)pyrrolidine-2-carboxylate;
2-(7-(2-methoxyethoxy)-[1,2,4]triazolo[4,3-a]pyridin-3-yl)quinolin-8-ol;
2-(7-methoxy-[1,2,4]triazolo[4,3-a]pyridin-3-yl)quinolin-8-ol;
3-(2-([1,2,4]triazolo[4,3-a]pyridin-3-yl)-6-fluoroquinolin-8-yloxy)-2,2-dimethylpropan-1-amine;
4-(2-([1,2,4]triazolo[4,3-a]pyridin-3-yl)quinolin-8-yloxy)piperidine-1-carboxamide;
3-(2-([1,2,4]triazolo[4,3-a]pyridin-3-yl)quinolin-8-yloxy)-2,2-difluoropropan-1-amine;
(cis)-4-(2-([1,2,4]triazolo[4,3-a]pyridin-3-yl)quinolin-8-yloxy)cyclohexanamine;
3-(2-([1,2,4]triazolo[4,3-a]pyridin-3-yl)-5-fluoroquinolin-8-yloxy)-2,2-dimethylpropan-1-amine;
2-([1,2,4]triazolo[4,3-a]pyridin-3-yl)-8-(pyridin-3-ylmethoxy)quinoline;
2-([1,2,4]triazolo[4,3-a]pyridin-3-yl)-8-(pyridin-4-ylmethoxy)quinoline;
2-([1,2,4]triazolo[4,3-a]pyridin-3-yl)-8-(5-fluoroazepan-4-yloxy)quinoline;
Stereoisomer #1 of 2-([1,2,4]triazolo[4,3-a]pyridin-3-yl)-8-(–5-fluoroazepan-4-yloxy)quinoline;
Stereoisomer #2 of 2-([1,2,4]triazolo[4,3-a]pyridin-3-yl)-8-(5-fluoroazepan-4-yloxy)quinoline;
Stereoisomer #3 of 2-([1,2,4]triazolo[4,3-a]pyridin-3-yl)-8-(5-fluoroazepan-4-yloxy)quinoline;
Stereoisomer #4 of 2-([1,2,4]triazolo[4,3-a]pyridin-3-yl)-8-(5-fluoroazepan-4-yloxy)quinoline;
2-([1,2,4]triazolo[4,3-a]pyridin-3-yl)-8-(-3-fluoroazepan-4-yloxy)quinoline;
2-([1,2,4]triazolo[4,3-a]pyridin-3-yl)-8-(azepan-4-yloxy)quinoline;
(2S,4S)-4-(2-([1,2,4]triazolo[4,3-a]pyridin-3-yl)quinolin-8-yloxy)-1-(tert-butoxycarbonyl)piperidine-2-carboxylic acid;
(2S,4S)-4-(2-([1,2,4]triazolo[4,3-a]pyridin-3-yl)quinolin-8-yloxy)-N,N-dimethylpiperidine-2-carboxamide;
(2S,4S)-4-(2-([1,2,4]triazolo[4,3-a]pyridin-3-yl)quinolin-8-yloxy)-N-methoxy-N-methylpiperidine-2-carboxamide;
((2S,4S)-4-(2-([1,2,4]triazolo[4,3-a]pyridin-3-yl)quinolin-8-yloxy)piperidin-2-yl)methanol;
2-([1,2,4]triazolo[4,3-a]pyridin-3-yl)-842S,4S)-2-(methoxymethyl)piperidin-4-yloxy)quinoline;
3-(2-([1,2,4]triazolo[4,3-a]pyridin-3-yl)-7-bromoquinolin-8-yloxy)-2,2-dimethylpropan-1-amine;
2-(6-fluoro-[1,2,4]triazolo[4,3-a]pyridin-3-yl)-8-((cis)-3-fluoropiperidin-4-yloxy)quinoline;
cis-2-(7-fluoro-[1,2,4]triazolo[4,3-a]pyridin-3-yl)-8-3-fluoropiperidin-4-yloxy)quinoline;
(S)-2-([1,2,4]triazolo[4,3-a]pyridin-3-yl)-8-(pyrrolidin-2-ylmethoxy)quinoline;

3-(2-([1,2,4]triazolo[4,3-a]pyridin-3-yl)quinolin-8-yloxy) propane-1,2-diol;
3-(2-(6-bromo-[1,2,4]triazolo[4,3-a]pyridin-3-yl)quinolin-8-yloxy)-2,2-dimethylpropan-1-amine;
3-(2-(6-cyclopropyl-[1,2,4]triazolo[4,3-a]pyridin-3-yl) quinolin-8-yloxy)-2,2-dimethylpropan-1-amine;
2,2-Dimethyl-3-(2-(6-phenyl-[1,2,4]triazolo[4,3-a]pyridin-3-yl)quinolin-8-yloxy)propan-1-amine;
2-([1,2,4]triazolo[4,3-a]pyridin-3-yl)-8-((4-fluoropiperidin-4-yl)methoxy)quinoline;
2-([1,2,4]triazolo[4,3-a]pyridin-3-yl)-8-((4-methylpiperidin-4-yl)methoxy)quinoline;
2-([1,2,4]triazolo[4,3-a]pyridin-3-yl)-8-((4-ethylpiperidin-4-yl)methoxy)quinoline;
2-([1,2,4]triazolo[4,3-a]pyridin-3-yl)-8-((4-(cyclopropylmethyl)piperidin-4-yl)methoxy)quinoline;
2-([1,2,4]triazolo[4,3-a]pyridin-3-yl)-8-((4-isopropylpiperidin-4-yl)methoxy)quinoline;
4-((2-([1,2,4]triazolo[4,3-a]pyridin-3-yl)quinolin-8-yloxy) methyl)-1-benzylpiperidin-4-ol;
4-((2-([1,2,4]triazolo[4,3-a]pyridin-3-yl)quinolin-8-yloxy) methyl)piperidin-4-ol;
2-([1,2,4]triazolo[4,3-a]pyridin-3-yl)-8-((4-methoxypiperidin-4-yl)methoxy)quinoline;
2-([1,2,4]triazolo[4,3-a]pyridin-3-yl)-8-(pyridin-4-yloxy) quinoline;
4-(2-([1,2,4]triazolo[4,3-a]pyridin-3-yl)quinolin-8-yloxy) pyridin-2-amine;
4-(2-([1,2,4]triazolo[4,3-a]pyridin-3-yl)quinolin-8-yloxy) pyrimidin-2-amine;
2-(6-bromo-[1,2,4]triazolo[4,3-a]pyridin-3-yl)-8-((4-fluoropiperidin-4-yl)methoxy)-quinoline;
2-(6-bromo-[1,2,4]triazolo[4,3-a]pyridin-3-yl)-8-((cis)-3-fluoropiperidin-4-yloxy)quinoline;
2-(6-cyclopropyl-[1,2,4]triazolo[4,3-a]pyridin-3-yl)-8-((4-fluoropiperidin-4-yl)methoxy)quinoline;
2-(6-cyclopropyl-[1,2,4]triazolo[4,3-a]pyridin-3-yl)-8-((cis)-3-fluoropiperidin-4-yloxy)quinoline;
8-((4-fluoropiperidin-4-yl)methoxy)-2-(6-phenyl-[1,2,4] triazolo[4,3-a]pyridin-3-yl)quinoline;
8-((cis)-3-fluoropiperidin-4-yloxy)-2-(6-phenyl-[1,2,4]triazolo[4,3-a]pyridin-3-yl)quinoline;
2-(4-((2-([1,2,4]triazolo[4,3-a]pyridin-3-yl)quinolin-8-yloxy)methyl)-4-fluoropiperidin-1-yl)acetamide;
2-([1,2,4]triazolo[4,3-a]pyridin-3-yl)-8-((4-fluoro-1-methylpiperidin-4-yl)methoxy)quinoline;
2-(4-((2-([1,2,4]triazolo[4,3-a]pyridin-3-yl)quinolin-8-yloxy)methyl)-4-fluoropiperidin-1-yl)ethanol;
2-(4-((2-([1,2,4]triazolo[4,3-a]pyridin-3-yl)quinolin-8-yloxy)methyl)-4-fluoropiperidin-1-yl)ethanol;
(2S,4S)-methyl 4-(2-([1,2,4]triazolo[4,3-a]pyridin-3-yl) quinolin-8-yloxy)pyrrolidine-2-carboxylate;
2-([1,2,4]triazolo[4,3-a]pyridin-3-yl)-6-fluoro-8-((cis)-3-fluoropiperidin-4-yloxy)quinoline;
(S)-2-([1,2,4]triazolo[4,3-a]pyridin-3-yl)-6-fluoro-8-(piperidin-3-ylmethoxy)quinoline;
Enantiomer 1 of cis-2-([1,2,4]triazolo[4,3-a]pyridin-3-yl)-6-fluoro-8-5-fluoroazepan-4-yloxy)quinoline;
Enantiomer 2 of trans-2-([1,2,4]triazolo[4,3-a]pyridin-3-yl)-6-fluoro-8-5-fluoroazepan-4-yloxy)quinoline;
Enantiomer 1 of cis-8-5-fluoroazepan-4-yloxy)-2-(7-methyl-[1,2,4]triazolo[4,3-a]pyridin-3-yl)quinoline;
2-([1,2,4]triazolo[4,3-a]pyridin-3-yl)-8-(3,3-difluoropiperidin-4-yloxy)-6-fluoroquinoline;
Enantiomer 1 of 2-([1,2,4]triazolo[4,3-a]pyridin-3-yl)-8-((cis)-3-fluoropiperidin-4-yloxy)quinoline;
Enantiomer 2 of 2-([1,2,4]triazolo[4,3-a]pyridin-3-yl)-8-((cis)-3-fluoropiperidin-4-yloxy)quinoline;
Enantiomer 1 of 2-([1,2,4]triazolo[4,3-a]pyridin-3-yl)-8-((trans)-3-fluoropiperidin-4-yloxy)quinoline;
Enantiomer 2 of 2-([1,2,4]triazolo[4,3-a]pyridin-3-yl)-8-((trans)-3-fluoropiperidin-4-yloxy)quinoline;
2-(6-cyclopropyl-[1,2,4]triazolo[4,3-a]pyridin-3-yl)-8-((trans)-5-fluoroazepan-4-yloxy)quinoline;
Enantiomer 1 of 8-((trans)-5-fluoroazepan-4-yloxy)-2-(6-methyl-[1,2,4]triazolo[4,3-a]pyridin-3-yl)quinoline;
Enantiomer 2 of 8-((trans)-5-fluoroazepan-4-yloxy)-2-(6-methyl-[1,2,4]triazolo[4,3-a]pyridin-3-yl)quinoline;
3-(8-((trans)-5-fluoroazepan-4-yloxy)quinolin-2-yl)-[1,2,4] triazolo[4,3-a]pyridine-6-carbonitrile;
2-(6-fluoro-[1,2,4]triazolo[4,3-a]pyridin-3-yl)-8-((trans)-5-fluoroazepan-4-yloxy)quinoline;
2-(6-fluoro-[1,2,4]triazolo[4,3-a]pyridin-3-yl)-8-((4-fluoropiperidin-4-yl)methoxy)quinoline;
2-([1,2,4]triazolo[4,3-a]pyridin-3-yl)-84(1-ethyl-4-fluoropiperidin-4-yl)methoxy)quinoline;
2-([1,2,4]triazolo[4,3-a]pyridin-3-yl)-84(4-fluoro-1-(2-fluoroethyl)piperidin-4-yl)methoxy)quinoline;
2-([1,2,4]triazolo[4,3-a]pyridin-3-yl)-6-fluoro-8-((4-fluoropiperidin-4-yl)methoxy)quinoline;
2-([1,2,4]triazolo[4,3-a]pyridin-3-yl)-8-((3-fluoroazetidin-3-yl)methoxy)quinoline;
2-([1,2,4]triazolo[4,3-a]pyridin-3-yl)-6-fluoro-8-((3-fluoroazetidin-3-yl)methoxy)quinoline;
8-((4-fluoropiperidin-4-yl)methoxy)-2-(6-methoxy-[1,2,4] triazolo[4,3-a]pyridin-3-yl)quinoline;
6-fluoro-8-((4-fluoropiperidin-4-yl)methoxy)-2-(6-methoxy-[1,2,4]triazolo[4,3-a]pyridin-3-yl)quinoline;
8-((4-fluoropiperidin-4-yl)methoxy)-2-(7-(2-methoxyethoxy)-[1,2,4]triazolo[4,3-a]pyridin-3-yl)quinoline;
(R)-4-(2-([1,2,4]triazolo[4,3-a]pyridin-3-yl)-6-fluoroquinolin-8-yloxy)-3,3-dimethylbutane-1,2-diol;
(R)-4-(2-([1,2,4]triazolo[4,3-a]pyridin-3-yl)quinolin-8-yloxy)-3,3-dimethylbutane-1,2-diol;
2-([1,2,4]triazolo[4,3-a]pyridin-3-yl)-6-fluoro-8-((4-methoxyazepan-4-yl)methoxy)quinoline;
2-(4-((2-([1,2,4]triazolo[4,3-a]pyridin-3-yl)-6-fluoroquinolin-8-yloxy)methyl)-4-methoxyazepan-1-yl)ethanol;
4-((2-([1,2,4]triazolo[4,3-a]pyridin-3-yl)quinolin-8-yloxy) methyl)azepan-4-ol;
2-([1,2,4]triazolo[4,3-a]pyridin-3-yl)-8-((4-methoxyazepan-4-yl)methoxy)quinoline;
Stereoisomer 1 of 2-([1,2,4]triazolo[4,3-a]pyridin-3-yl)-8-((trans)-5-fluoro-1-methylazepan-4-yloxy)quinoline;
Stereoisomer 2 of 2-([1,2,4]triazolo[4,3-a]pyridin-3-yl)-8-((trans)-5-fluoro-1-methylazepan-4-yloxy)quinoline;
Stereoisomer 3 of 2-([1,2,4]triazolo[4,3-a]pyridin-3-yl)-8-((trans)-5-fluoro-1-methylazepan-4-yloxy)quinoline;
Stereoisomer 4 of 2-([1,2,4]triazolo[4,3-a]pyridin-3-yl)-8-((trans)-5-fluoro-1-methylazepan-4-yloxy)quinoline;
Enantiomer 2 of 2-([1,2,4]triazolo[4,3-a]pyridin-3-yl)-6-fluoro-8-((cis)-5-fluoroazepan-4-yloxy)quinoline;
2-([1,2,4]triazolo[4,3-a]pyridin-3-yl)-6-fluoro-8-(trans-5-fluoroazepan-4-yloxy)quinoline;
8-((cis-4,5)-5-fluoroazepan-4-yloxy)-2-(7-methyl-[1,2,4] triazolo[4,3-a]pyridin-3-yl)quinoline;
2,2-dimethyl-3-(2-(7-methyl-[1,2,4]triazolo[4,3-a]pyridin-3-yl)quinolin-8-yloxy)propan-1-amine;
2-(7-chloro-[1,2,4]triazolo[4,3-a]pyridin-3-yl)-8-((3R,4S)-3-fluoropiperidin-4-yloxy)quinoline;
8-((4-methoxypiperidin-4-yl)methoxy)-2-(7-methyl-[1,2,4] triazolo[4,3-a]pyridin-3-yl)quinoline;

2-((2-([1,2,4]triazolo[4,3-a]pyridin-3-yl)quinolin-8-yloxy)methyl)morpholine;
Enantiomer 1 of 2-([1,2,4]triazolo[4,3-a]pyridin-3-yl)-8-(azepan-4-yloxy)quinoline;
Enantiomer 2 of 2-([1,2,4]triazolo[4,3-a]pyridin-3-yl)-8-(azepan-4-yloxy)quinoline;
(1-((2-([1,2,4]triazolo[4,3-a]pyridin-3-yl)quinolin-8-yloxy)methyl)cyclopentyl)methanamine;
2-((2-([1,2,4]triazolo[4,3-a]pyridin-3-yl)quinolin-8-yloxy)methyl)butan-1-ol;
2-((2-([1,2,4]triazolo[4,3-a]pyridin-3-yl)quinolin-8-yloxy)methyl)-2-ethylbutan-1-ol;
4-(2-([1,2,4]triazolo[4,3-a]pyridin-3-yl)quinolin-8-yloxy)-3,3-dimethylbutan-1-amine;
2-([1,2,4]triazolo[4,3-a]pyridin-3-yl)-8-((3-fluoropiperidin-3-yl)methoxy)quinoline;
N-(3-(2-([1,2,4]triazolo[4,3-a]pyridin-3-yl)quinolin-8-yloxy)-2,2-dimethylpropyl)-2-fluoroacetamide;
3-(2-([1,2,4]triazolo[4,3-a]pyridin-3-yl)quinolin-8-yloxy)-N-(2,2-difluoroethyl)-2,2-dimethylpropan-1-amine;
3-(2-([1,2,4]triazolo[4,3-a]pyridin-3-yl)quinolin-8-yloxy)-2,2-dimethyl-N-(2,2,2-trifluoroethyl)propan-1-amine;
and pharmaceutically acceptable salts thereof. Particular mention is made of hydrochloride salts (including dihydrochloride and trihydrochloride salts) and trifluoroacetate salts (including bis-trifluoroacetate salts) of the aforementioned compounds.

EXAMPLES

The following examples illustrate the invention. In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), dichloromethane (DCM, methylene chloride), toluene, and dioxane were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents by syringe. Glassware was oven dried and/or heat dried.

Example A

PIM-1 Enzyme Assay

Figure 1:
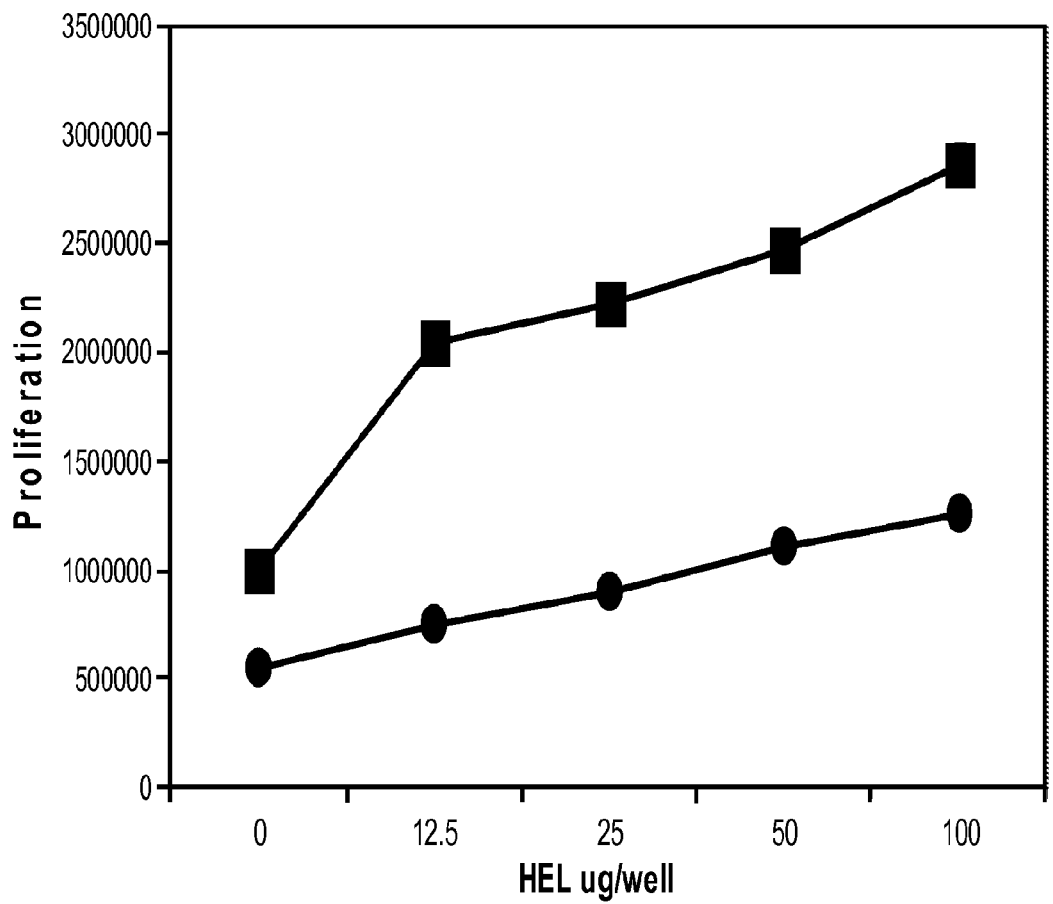
FIG. 1 shows the amount of ex vivo proliferation in response to the indicated HEL protein concentrations in cells harvested from mice following in vivo priming with HEL protein and 7 days of treatment with the compound of Example 26 (circles) or vehicle control animals (squares).

The assay for the determination of PIM activity is based on the incorporation of [$^{33}$P]PO$_4$ from [γ-$^{33}$P]ATP into PIM2tide substrate and capture of the radiolabeled peptide onto a Whatman P81 (phosphocellulose) filter plate. The amount of radiolabeled product is then measured by liquid scintillation counting. The final buffer conditions were as follows: 20 mM K$^+$MOPS, pH 7.4, 10 mM MgCl$_2$, 0.005% Tween-20, 1 mM DTT. Assay mixtures contained 35 μM [γ-$^{33}$P]ATP (20 μCi/mL), 7.5 μM PIM2tide and 0.25 nM PIM-1 in a total volume of 50 pt. Incubations were carried out for 60 min at 22° C. and quenched with 75 μL of 200 mM H$_3$PO$_4$, filtered through a Whatman P81 plate and washed (1×200 μL and 5×100 μL) with 200 mM H$_3$PO$_4$. Liquid scintillation cocktail (50 μL) was then added per well, and the plate was counted for 30 s/well using a TopCount NXT.

IC$_{50}$ Determinations

Compounds were prepared at 50× the final concentration in DMSO by conducting 3-fold serial dilutions from a 500-μM intermediate dilution to give a 10-point dosing curve having a high dose of 10 μM. One-μL aliquots of these were then transferred to the assay mixtures above to give a final concentration of DMSO of 2%. A standard or reference compound was typically included on each assay plate to validate that plate. For each plate, percent of control (POC) values were calculated for each well. IC$_{50}$'s were estimated from the POC's using a standard 4-parameter logistic model. The IC$_{50}$ is defined as the concentration of inhibitor at which the POC equals 50 for the fitted curve. Compounds of Formula I were found to have an average $IC_{50}$ below 10 μM when tested in this assay. Specific $IC_{50}$ values are provided in Table 2.

Example B

PIM-2 Enzyme Assay

Assay was performed as described in Example A, using 4 μM [γ-$^{33}$P]ATP (20 μCi/mL), 1.0 μM PIM2tide and 1.5 nM GST-tagged recombinant full-length human PIM-2 in place of PIM-1. Compounds of Formula I were found to have an average $IC_{50}$ below 10 μM when tested in this assay. Specific $IC_{50}$ values are provided in Table 2.

Example C

PIM-3 Enzyme Assay

Assay was performed as described in Example A, using 30 μM [γ-$^{33}$P]ATP (20 μCi/mL), 3.75 μM PIM2tide and 0.5 nM recombinant rat PIM-3 in place of PIM-1. Compounds of Formula I were found to have an average $IC_{50}$ below 10 μM when tested in this assay. Specific $IC_{50}$ values are provided in Table 2.

Example D

Cellular Proliferation Assay

The assay for determination of the antiproliferative activity of multiple Pim inhibitors in the JAK2-driven cell lines was conducted as follows. Cells were plated out to 96-well plates at an initial density of 10,000 cells/well in 95 pt. Compounds were prepared at 20× the final concentration in DMSO by conducting 3-fold serial dilutions to give a 10-point dosing curve having a high dose of 1000 μM. Aliquots (5 μt) of these dilutions were then transferred to the appropriate wells of the 96-well plates containing cells to yield a final DMSO concentration of 0.5%. The cells were then incubated with compound for 72 hours at 37° C., 5% $CO_2$. CelltiterBlue reagent (Promega, Catalog #: G8080) was then added (20 μL/well) and incubated at 37° C., 5% $CO_2$ for 1-8 hours depending on the cell line being analyzed. The plate was then quantified employing a fluorescence plate reader (Model: Gemini [Molecular Devices]; Settings: 560 nm (Ex)/590 nm (Em) 570 nm (cut-off) [CellTiter Blue Assay].

The values for each well were then converted to a percent of untreated control (POC). These POC values were then plotted as a function of compound concentration. A 4-parameter curve-fit analysis was performed for each compound dilution and an $IC_{50}$ value was calculated from this curve.

Table 1 provides $IC_{50}$ values for certain compound of this invention when tested in this assay cell lines A-E listed below (Note: all are commercially available from ATCC®).

Cell lines
A: PC3 (Androgen independent prostate cancer)
B: K562 (Ph+chronic myelogenous leukemia)
C: MV4-11 (Acute myelogenous leukemia)
D: BxPC3 (Pancreatic Cancer)
E: HepG2 (Hepatocellular Carcinoma)
F: BaF3 (Mouse pro-B-cell line)
G: BaF3 TEL-JAK2 (Mouse pro-B-cell transformed with TEL-JAK2 fusion)
H: BaF2 BCR-Ab1 (Mouse pro-B-cell transformed with BCR-Ab1 fusion)

The symbols in Table 1 are relative indicators of the inherent potencies (antiproliferative effect) of compounds of Examples 1, 16, 17, 18 and 26 against multiple cell lines, tested according to the general experimental procedure outlined in Example D. The definitions of the symbols are as follows:

ND data not determined
(−) $IC_{50}$ is >10 uM
(+) $IC_{50}$ is <10 uM
(++) $IC_{50}$ is <5 uM
(+++) $IC_{50}$ is <2 uM

TABLE 1

| Example # | Cell Line | | | | | | | |
|---|---|---|---|---|---|---|---|---|
| | A | B | C | D | E | F | G | H |
| 1  | +   | −  | ND  | ND | ND | +++ | +++ | +   |
| 16 | ++  | +  | ND  | −  | −  | +++ | +++ | ++  |
| 17 | +++ | +  | ND  | +  | +  | +++ | +++ | +++ |
| 18 | +++ | ++ | +++ | +  | +  | +++ | +++ | +++ |
| 26 | ++  | +  | +++ | ND | ND | +++ | +++ | +++ |

Table 2 provides $IC_{50}$ values for compounds of the invention when tested in the assays of Examples A, B and/or C.

TABLE 2

| Example No. | PIM-1 $IC_{50}$ (nM) | PIM-2 $IC_{50}$ (nM) | PIM-3 $IC_{50}$ (nM) |
|---|---|---|---|
| 1  | 1.6   | 1107  | 4.4 |
| 2  | 95    | 10000 | 448 |
| 3  | 3     | 807   | 25  |
| 4  | 22    | 6025  | 105 |
| 5  | 5     | 2021  | 20  |
| 6  | 32    | 10000 | 155 |
| 7  | 5     | 1045  | 35  |
| 8  | 16    | 5573  | 93  |
| 9  | 4     | 570   | 17  |
| 10 | 3     | 514   | 13  |
| 11 | 23    | 2470  | 33  |
| 12 | 30    | 4910  | 77  |
| 13 | ND    | 189   | 9   |
| 14 | 2     | 562   | 11  |
| 15 | 16    | 4219  | 102 |
| 16 | 1     | 169   | 4   |
| 17 | 0.65  | 134   | 3   |
| 18 | 1.5   | 49    | 2   |
| 19 | 0.70  | 17    | 2   |
| 20 | 2     | 51    | 5   |
| 21 | 4     | 1354  | ND  |
| 22 | 5     | 501   | 25  |
| 23 | 2     | 144   | 6   |
| 24 | 0.8   | 77    | 4   |
| 25 | 4     | 686   | 20  |
| 26 | 3     | 137   | 9   |
| 27 | 3     | 323   | 13  |
| 28 | 2     | 143   | 4   |
| 29 | 5     | 585   | 30  |
| 30 | 3     | 318   | 13  |
| 31 | 4     | 413   | 19  |
| 32 | 4     | 399   | 17  |
| 33 | 5     | 279   | 19  |
| 34 | 13    | 1346  | 51  |
| 35 | 10    | 1359  | 48  |
| 36 | ND    | ND    | ND  |
| 37 | ND    | ND    | ND  |
| 38 | ND    | ND    | ND  |
| 39 | 0.55  | 26    | ND  |
| 40 | 12    | 1277  | 46  |
| 41 | 4     | 182   | ND  |
| 42 | 0.75  | 22    | ND  |
| 43 | 139   | 10000 | ND  |
| 44 | 63    | 7473  | ND  |
| 45 | 26.9  | 1734  | ND  |
| 46 | 1     | 96    | ND  |
| 47 | 32    | 1174  | 41  |
| 48 | 0.70  | 147   | 4   |

TABLE 2-continued

| Example No. | PIM-1 IC$_{50}$ (nM) | PIM-2 IC$_{50}$ (nM) | PIM-3 IC$_{50}$ (nM) |
|---|---|---|---|
| 49 | 0.92 | 100 | 2 |
| 50 | 12 | 290 | 8 |
| 51 | 3 | 406 | 10 |
| 52 | 2 | 110 | 4 |
| 53 | NA | NA | NA |
| 54 | 178 | 10000 | 465 |
| 55 | 70 | 10000 | 222 |
| 56 | 9 | 427 | 24 |
| 57 | 4 | 484 | NA |
| 58 | 10 | 204 | NA |
| 59 | 55 | 2866 | 98 |
| 60 | 26 | 1760 | NA |
| 61 | 132 | 10000 | 728 |
| 62 | 34 | 1721 | 262 |
| 63 | 0.65 | 101 | NA |
| 64 | 0.64 | 323 | 5 |
| 65 | 0.8 | 174 | NA |
| 66 | 0.8 | 52 | 3 |
| 67 | 0.95 | 69 | 3 |
| 68 | 1.3 | 126 | 10 |
| 69 | 1.6 | 95 | ND |
| 70 | 0.75 | 67 | ND |
| 71 | 16 | 10000 | 112 |
| 72 | 5.3 | 588 | ND |
| 73 | 0.96 | 79 | 5 |
| 74 | 151 | 1994 | ND |
| 75 | 263 | 8935 | ND |
| 76 | 648 | 10000 | ND |
| 77 | 17 | 1389 | ND |
| 78 | 8 | 1278 | ND |
| 79 | 0.2 | 55 | ND |
| 80 | 2 | 1163 | ND |
| 81 | 0.45 | 142 | ND |
| 82 | 3 | 1035 | ND |
| 83 | 4 | 193 | ND |
| 84 | 2 | 73 | ND |
| 85 | 2 | 105 | ND |
| 86 | 3 | 142 | 10 |
| 87 | 167 | ND | 248 |
| 88 | 8 | 502 | 24 |
| 89 | ND | ND | ND |
| 90 | 0.4 | 131 | 2 |
| 91 | 0.8 | 39 | 0.9 |
| 92 | 1 | 244 | 3 |
| 93 | 4.4 | 506 | ND |
| 94 | 19.4 | 1000 | ND |
| 95 | 9.8 | 481.8 | ND |
| 96 | 10.8 | 1000 | ND |
| 97 | 49 | 1000 | ND |
| 98 | 0.7 | 661.3 | ND |
| 99 | 17.4 | 1000 | 39.7 |
| 100 | 1.5 | 351.9 | 2 |
| 101 | 13 | 1000 | ND |
| 102 | 4.9 | 439.6 | ND |
| 103 | 1.4 | 65.6 | ND |
| 104 | 3.9 | 191.2 | ND |
| 105 | 8.7 | 409 | ND |
| 106 | 0.5 | 25.4 | ND |
| 107 | 9.4 | 1000 | ND |
| 108 | 7.3 | 489.2 | ND |
| 109 | 4.7 | 384.1 | ND |
| 110 | 1.9 | 163.4 | ND |
| 111 | 8.3 | 1000 | ND |
| 112 | 3.3 | 299.9 | 10.1 |
| 113 | 2.2 | 166.9 | 8.8 |
| 114 | 0.7 | 86 | ND |
| 115 | 1.4 | 222.4 | ND |
| 116 | 11.8 | 1000 | ND |
| 117 | 1 | 91.5 | ND |
| 118 | 3 | 330 | ND |
| 119 | 1.3 | 573.8 | ND |
| 120 Enantiomer 2 | 11 | 958.6 | 10.9 |
| 121 Enantiomer 1 | 30.5 | 520.2 | 16.1 |
| 122 Enantiomer 2 | 17.5 | 1000 | 23.5 |
| 123 | 0.9 | 156 | ND |
| 124 | 31 | 1000 | ND |
| 125 | 1 | 429.1 | ND |
| 126 | 14.2 | 353.7 | ND |
| 127 | 4.8 | 437.7 | 6.8 |
| 128 | 19.1 | 1000 | 79.4 |
| 129 | 4.9 | 1000 | ND |
| 130 | 5.8 | 1000 | ND |
| 131 | 2.3 | 1000 | ND |
| 132 | 1 | 76.5 | ND |
| 133 | 1.6 | 141.6 | ND |
| 134 | 10.1 | 951.8 | ND |
| 135 | 12.6 | 506.2 | ND |
| 136 | 5.5 | 361.9 | ND |

ND: Not determined

Example E

T Cell in vitro Functional Assays

The in vitro assays to assess the effects of the compounds of Examples 16, 18 and 26 on T cells were conducted as described in assays A, B, C and D below. CD4+ T cells were isolated from red blood cell-depleted splenocytes of C57B1/6J mice (Jackson Laboratories, catalog #000664) using CD4+ T cell isolation kit (Miltenyi, catalog #130-090-860).

In assay (A), purified CD4+ T cells were plated in 96 well plates at 90000 cells/well in 90 µL. A dilution series of the compounds of Examples 16, 18 and 26 were prepared at 100× the final concentration in DMSO and then diluted 10-fold into complete media (10× stocks). 10 µL of 10×compound stocks were added to appropriate wells of 96 well plates containing cells and incubated for 1 hour at 37° C., 5% CO$_2$. The cell/compound mixtures were then transferred to a 96 well plate coated with anti-CD3 mAb (1 µg/mL; BD Pharmingen, catalog #553057) and soluble anti-CD28 mAb (1 µg/mL; BD Pharmingen, catalog #553294) was added. Plates were cultured at 37° C., 5% CO$_2$ for 40 hours. 20 µL of the culture were removed for determination of proliferation using the CellTitre-Glo™ luminescent assay (Promega, Catalog #G7571) according to the manufacturer's protocol. The plate was quantified on a Packard TopCount instrument using luminescence protocol and data was analyzed using Prism software.

In assay (B), purified CD4+ cells were treated with compound and stimulated as described for assay (A). After 40 hours, supernatants were assayed for IL-2 using R&D duo set ELISA kits (catalog #DY402). ELISA plates were quantified relative to a standard curve using Molecular Devices Versamax Reader at 450 nM and Softmax Pro software.

In assay (C), 1000000 cells/mL of purified CD4+ T cells were mixed with 1 µg/mL anti-CD28, 10 ng/mL IL-4 (R&D Systems cat #404-ML-010/CF) and 2 µg/mL anti-IFNγ (R&D Systems cat #AB-485-NA) and placed into plates coated with 1 µg/mL anti-CD3. After 5 days, cells were harvested, washed and incubated overnight at 37° 5% CO$_2$. The following day, 50,000 cells were plated into each well of a 96 well plate. A dilution series of compounds were prepared at 200× the final concentration in DMSO, then 10×stocks were prepared by dilution in cell culture media. 10 µL of 10× stocks were added to the cells in the 96 well plate and incubated for 2 hours at 37° C., 5% CO2. Cell/compound mixtures were then transferred to well coated with 0.1 µg anti-CD3 and incubated at 37° C., 5% CO$_2$. Culture supernatants were removed 18 hours later and tested for IL-4 levels by ELISA (R&D Systems catalog #DY404). ELISA plates were quantified relative to a standard curve using Molecular Devices Versamax Reader at 450 nM and Softmax Pro software.

In assay (D), 1,000,000 cells/mL of purified CD4+ T cells were mixed with 1 µg/mL anti-CD28, 50 ng/mL IL-6 (R&D Systems cat #406-ML-025/CF), 1 ng/mL TGFβ (R&D Systems cat #303-B2-002), 2 µg/mL anti-IL-4 (R&D Systems cat #AB-404-NA), 2 µg/mL anti-IFNγ (R&D Systems cat #AB-485-NA) and placed into plates coated with 1 µg/mL anti-CD3. After 4 days, cells were harvested, washed and 100,000 cells were plated into 96 well plate. A dilution series of compounds were prepared at 200× the final concentration in DMSO, then 10× stocks were prepared by dilution in cell culture media. 10 µL of 10× stocks were added to the cells in the 96 well plate. After 2 hours, 50 ng IL-23 (R&D Systems catalog #1887-ML-010/CF) was added to each well and 18 hours later supernatants were removed and tested for IL-22 levels by ELISA (R&D Systems catalog #M2200). ELISA plates were quantified relative to a standard curve using Molecular Devices Versamax Reader at 450 nM and Softmax Pro software.

For each of assays A, B, C and D, the values for each well were converted to a percent of vehicle-treated (DMSO) control (POC). These POC values were plotted as a function of compound concentration and an $IC_{50}$ calculated using a 4-parameter curve-fit analysis program. Table 3 provides relative indicators of the inherent potencies of the compounds of Examples 16, 18 and 26 in assays A, B, C and D.

TABLE 3

| Compound of Example # | Proliferation (Assay A) | IL-2 Production (Assay B) | IL-4 Production (Assay C) | IL-22 Production (Assay D) |
|---|---|---|---|---|
| 16 | +++ | +++ | +++ | +++ |
| 18 | +++ | +++ | +++ | +++ |
| 26 | ++ | ++ | ++ | ++ |

(−) $IC_{50}$ is ≥ 10 uM
(+) $IC_{50}$ is ≤ 10 uM
(++) $IC_{50}$ is ≤ 5 uM
(+++) $IC_{50}$ is ≤ 1 uM

The data shown in Table 3 indicate the compounds of Examples 16, 18 and 26 decrease proliferation and cytokine production by T cells. These data support the utility of compounds of Formula I in diseases associated with T cells or the soluble factors (including IL-2, IL-4, IL-22) secreted by these cells.

Example F

T Cell In Vivo Functional Assay

To determine the effect of compounds of Formula I on T cell responses, the following experiment was conducted. On Day O, C57BL/6 (Jackson Laboratories #000664, 6-8 weeks of age) were immunized at the base of the tail with 100 µg of hen egg lysozyme (HEL; Sigma #L7773) with complete Freund's adjuvant (CFA; Sigma #F5881). Starting on Day 0 and continuing until Day 7, mice were dosed twice a day by oral administration with vehicle (water) or the compound of Example 26 (200 mg/kg). On Day 7, opopiteal lymph nodes were removed, single cell suspensions were prepared and 500,000 cells in 200 µL were activated in 96 well plates with the indicated dose of HEL peptide. Following incubation for 72 hours at 37° C., 5% $CO_2$, supernatants were harvested for IFNγ ELISA (R&D Systems catalog #MIF00) and proliferation was assessed using the CellTitre-Glo™ luminescent assay (Promega, Catalog #G7571) with both assays performed according to the manufacturer's protocol. ELISA plates were quantified relative to a standard curve using Molecular Devices Versamax Reader at 450 nM and Softmax Pro software; proliferation was quantitated on a Packard Top-Count instrument using luminescence protocol and data was analyzed using excel software.

Figure 2:
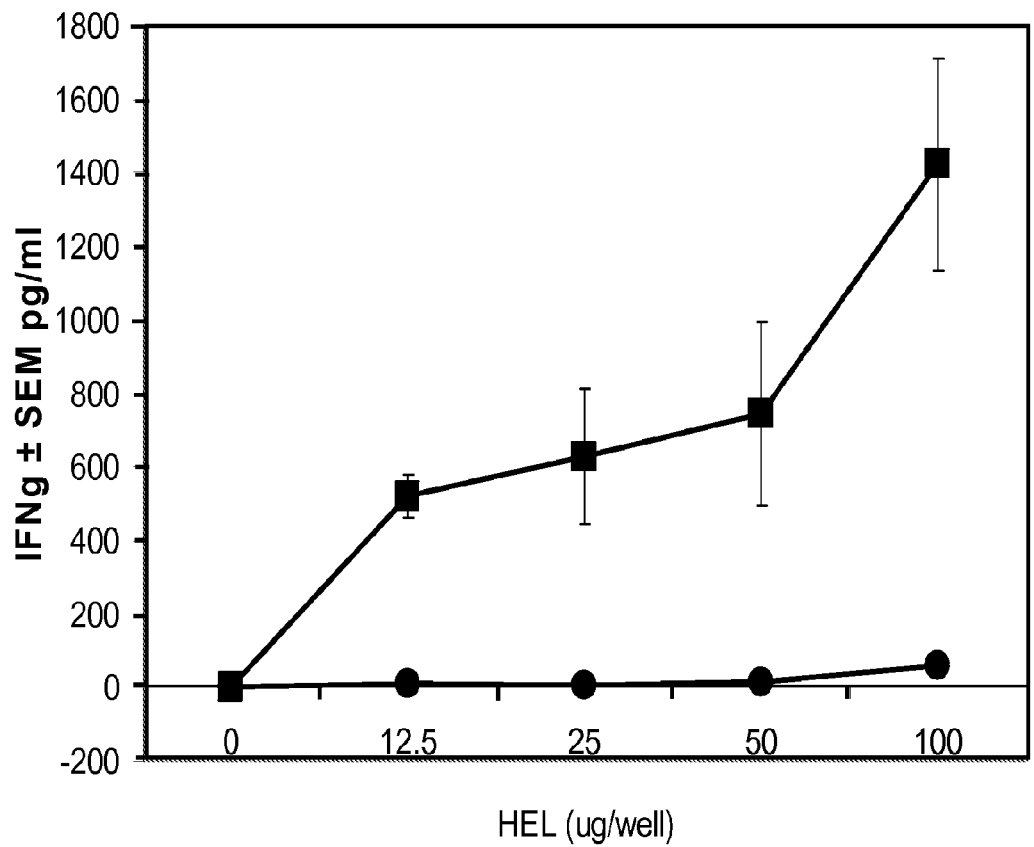
FIG. 2 shows the amount of ex vivo IFNγ production in response to the indicated HEL protein concentrations in cells harvested from mice following in vivo priming with HEL protein and 7 days of treatment with the compound of Example 26 (circles) or vehicle control (squares).

FIG. 1 shows the ex vivo HEL-specific proliferation following 7 days of in vivo treatment with vehicle (squares) or the compound of Example 26 (circles). FIG. 2 shows amount of IFNγ production following 7 days of in vivo treatment with vehicle (squares) or the compound of Example 26 (circles). Both HEL-specific proliferation and IFNγ production are decreased relative to vehicle following dosing with a compound of Formula I.

The data shown in FIGS. 1 and 2 demonstrate that immunization in the presence of a compound of Formula I impairs the ability to generate a T cell-mediated immune response, and support the utility of compounds of Formula I in treating diseases associated with the immune system.

Example G

B Cell in vivo Functional Assay

To determine the effect of a compound of Formula I on B cell responses, the following experiment was conducted. On Day O, C57BL/6J mice (Jackson Laboratories #000664, 6-8 weeks of age) were immunized at the base of the tail with 20 µg of hen egg lysozyme (HEL; Sigma #L7773) with complete Freund's adjuvant (CFA; Sigma #F5881). Mice were re-immunized on day 7 with 20 µg HEL in alum (Pierce catalog #77161). Starting on Day 0 and continuing through Day 28, mice were dosed once a day by oral administration with vehicle (water) or the compound of Example 26 (200 mg/kg). Serum was collected on days 0, 7, 14, 21, and 28 and analyzed for HEL-specific total IgG, IgG1, IgG2a, IgG2b, and IgG3 antibody production by capture ELISA (antibodies purchased from Invitrogen, catalog #M30007, #M32107, #M32307, #M32507, #M32607). ELISA plates were quantitated using Molecular Devices Versamax reader at 450 nM. The group mean titer of each antibody analyte was converted to percent of vehicle control (=100%).

Figure 3:
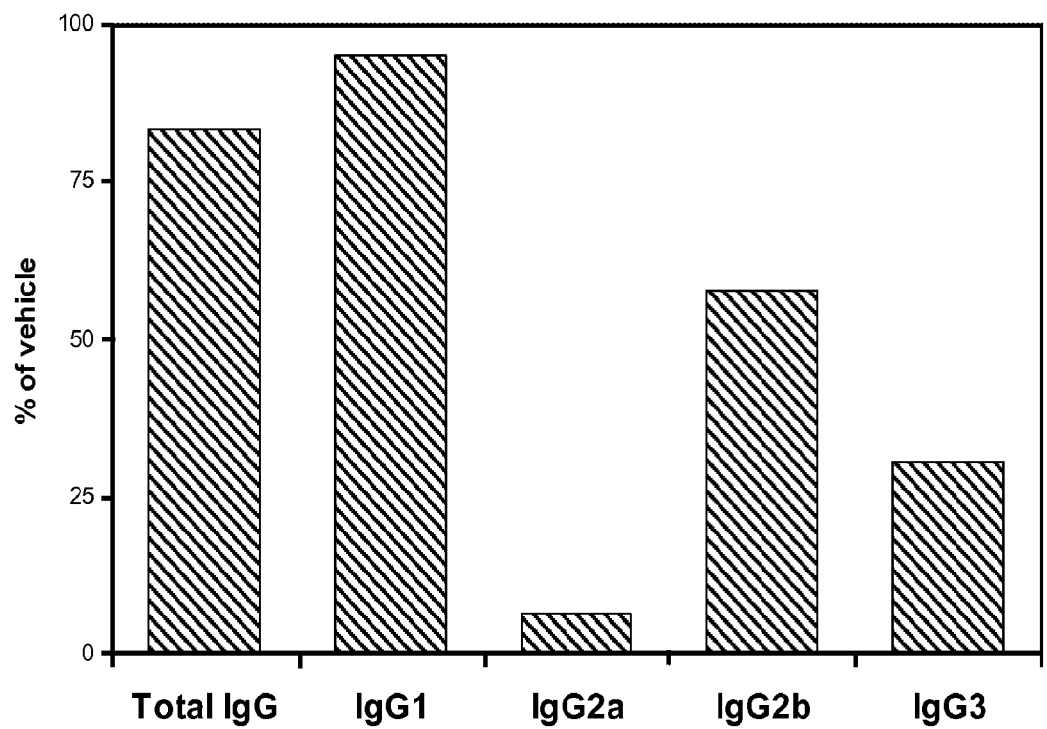
FIG. 3 shows the levels of HEL antigen-specific IgG, IgG1, IgG2a, IgG2b, and IgG3 antibodies present in mouse serum relative to vehicle control (defined as 100%) following 2 immunizations with protein antigen and 21 days of in vivo treatment with the compound of Example 26.

FIG. 3 shows the percent of vehicle control of HEL-specific total IgG, IgG1, IgG2a, IgG2b, and IgG3 antibodies on Day 21. Mice treated with the compound of Example 26 (hatched bars) have decreased titers of IgG2a, IgG2b and IgG3.

These data demonstrate that a compound of Formula I can alter the nature of the B-cell antibody response resulting in a different profile of antibody isotypes being produced. Isotypes of antibodies have differential functions. These data therefore support the utility of compounds of Formula I in treating diseases associated with B cells and characterized by pathogenic antibodies.

Example H

Adoptive Transfer Experimental Autoimmune Encephalomyelitis

Having observed that compounds of Formula I inhibit T cell activation in vitro and in vivo, the effect of a compound of Formula I on an autoimmune disease induced by T cells was determined using an adoptive transfer EAE model, an animal model of human multiple sclerosis (Brain (2006), 129, 1953-

Figure 4:
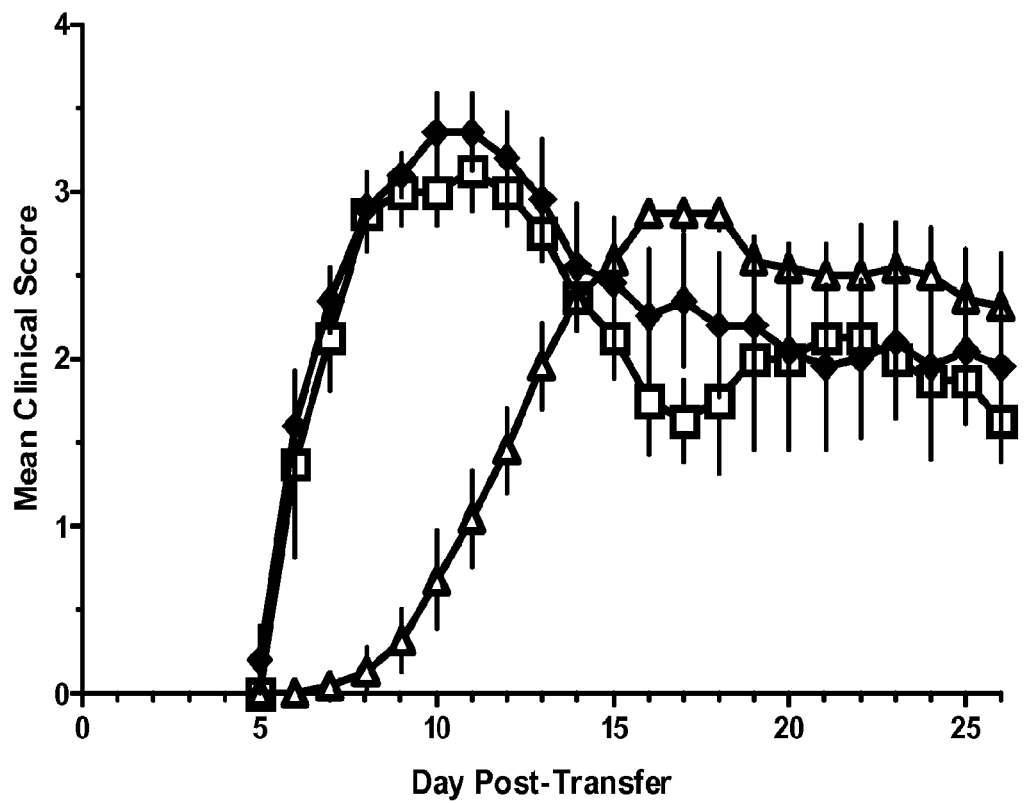
FIG. 4 shows the mean clinical score over time in experimental autoimmune encephalomyelitis (EAE) disease-induced in mice by adoptive transfer of encephalogenic cells in the absence of further treatment (open squares), in vehicle-treated animals from day 0 to day 26 (solid diamonds), and in animals treated with the compound of Example 26 administered from day 0 to day 26 (open triangles).

1971). This model relies on the injection of T cells from animals with EAE into disease-free host animals. This injection of cells is known to those skilled in the art as adoptive transfer. By injecting the animals with activated, encephalogenic T cells, this model is focused on the pathogenic stage of EAE autoimmune disease. On Day-14, C57BL/6 mice (Taconic Farms; 10 weeks old) were immunized with a disease-causing protein, MOG(35-55) peptide in complete Freund's adjuvant (Hooke Laboratories, catalog #EK-0113). On Day -3, spleens were harvested, single cell suspensions were prepared and then 5,000,000 cells/mL were stimulated with 20 µg/mL MOG(33-55) peptide (Open Biosystems), 30 ng/mL IL-12 (R&D Systems catalog #419-ML-010), 10 µg/mL anti-IFNγ antibody (BD Biosciences catalog #554408) at 37° C., 5% $CO_2$. On Day 0, 1,500,000 of these cells were injected intravenously into the tail veins of C57BL/6 recipient mice. The recipient mice were divided into treatment groups for vehicle (distilled water; 10 mL/kg) or the compound of Example 26 (200 mg/kg), both administered by oral gavage twice daily for 26 days. The recipient mice were scored daily days 0 through 26 using the following clinical scoring system:

0.0—no symptoms
1.0—limp tail
2.0—limp tail and weakness of hind legs
3.0—limp tail and complete hind limb paralysis, or partial front and hind limb paralysis, or severe head tilting combined with pushing against cage wall and spinning when picked up by tail
4.0—limp tail, complete hind limb paralysis and partial front limb paralysis
5.0—Full body paralysis, or spontaneous rolling or found dead due to paralysis FIG. 4 shows the group mean+/−SEM (standard error of the mean) of clinical score for the duration of the adoptive transfer experiment for the vehicle-treated animals (solid diamonds) and animals treated with the compound of Example 26 (open triangles), relative to untreated animals (open squares). As shown, treatment with the compound of Example 26 resulted in significant delay in disease onset in this model (where "disease onset" is defined by the first of 2 consecutive days with a clinical score greater than or equal to 1). Median day of onset of the untreated and vehicle groups was day 6 while treatment with the compound of Example 26 extended the median day of onset to 11 days. These results support the utility of compounds of Formula I in the treatment of multiple sclerosis.

Example I

MOG(35-55)-induced Experimental Autoimmune Encephalomyelitis

To further determine the effect of compounds of Formula I on an autoimmune disease associated with T cells and cytokines, a MOG-induced experimental autoimmune encephalomyelitis (EAE) experiment was performed. MOG-induced EAE is an animal model of human multiple sclerosis (Brain (2006), 129, 1953-1971).

On Day 0, C57BL/6J mice (Jackson Laboratories #000664, 6-8 weeks of age) were injected subcutaneously with 100 µL of complete Freund's adjuvant (CFA) prepared as a 1:1 emulsion of (a) incomplete Freund's adjuvant (Difco, catalog #263910) containing 8 mg/mL *m. tuberculosis* H37RA (Difco, catalog #231141) and (b) phosphate buffered saline (PBS) containing 1 mg/mL MOG(35-55) peptide (California Peptide Research Inc). On the day 0 and 2, mice were injected intravenously with 200 ng of pertussis toxin (List Biological Laboratories, catalog #181). On day 7, the mice were randomized into treatment groups which received vehicle (distilled water) or the compound of Example 26 (200 mg/kg) administered by oral gavage twice daily from days 7 through 27.

Figure 5:
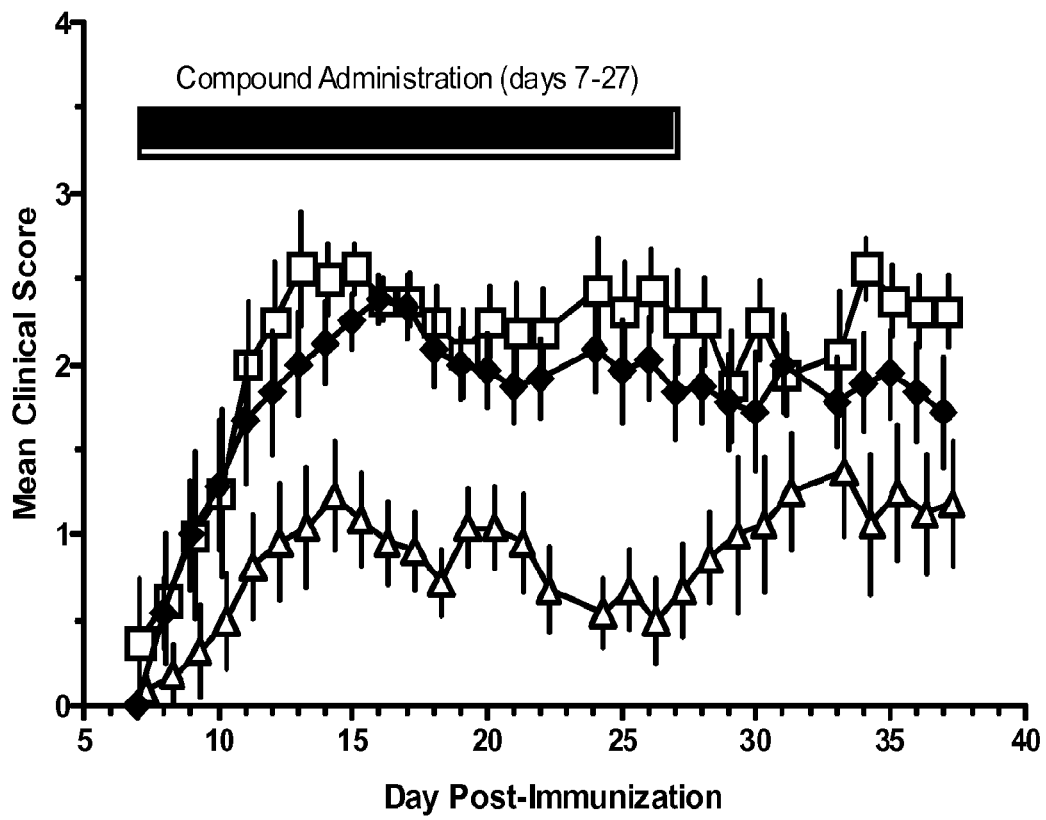
FIG. 5 shows the mean clinical EAE disease score versus days post MOG(33-55) peptide immunization for mice treated from day 7 to day 27 with vehicle (solid diamonds) or the compound of Example 26 (open triangles) and for untreated animals (open squares).

The mice were scored daily on days 7 through 37 using the following clinical scoring system:

0.0—no symptoms
0.5—tail weakness
1.0—limp tail
1.5—unsteady gait, mild hind limb ataxia
2.0—partial hind limb paralysis (hind limbs carrying weight)
2.5—partial hind limb paralysis (hind limbs not carrying weight)
3.0—full hind limb paralysis
3.5—full hind limb paralysis and partial front limb paralysis
4.0—full body paralysis FIG. 5 shows daily clinical scores over time as mean+/−SEM for each treatment group. Vehicle-treated mice (filled diamonds) and untreated mice (open squares) developed severe EAE, with median maximal scores reaching 3.0 for both groups. Mice treated with the compound of Example 26 (open triangles) had reduced paralysis with a median maximal score of 1.5.

These results further demonstrate that treatment with a compound of Formula I is efficacious in decreasing the severity of symptoms in EAE, and further support the utility of compounds of Formula I for the treatment of diseases associated with pathogenic T cell responses, including multiple sclerosis.

Example J

CD4+CD45RBhi Adoptive Transfer Inflammatory Bowel Disease

An adoptive transfer model of inflammatory bowel disease (IBD) was performed to determine the effect of compounds of Formula I on IBD, which is an autoimmune disease associated with T cells and cytokines On Day 0, CD4+ T cells were isolated from the spleens of female Balb/cAnNCrl mice (Charles River Laboratories; 12 weeks old) as described in Example E. The resulting cells were labeled with fluorescent antibodies against CD4 and CD45 markers and were sorted by flow cytometry for CD4+ CD45RBhi cells based on fluorescence. 400,000 CD4+ CD45RBhi cells were then injected intraperitoneally into C.B17/Icr-Prkdc$^{scid}$/IcrIcoCrl mice (Charles River Laboratories strain code 236; 12 weeks old). This injection of cells is known to those skilled in the art as adoptive transfer. On Day 21, mice were randomized into groups for oral gavage treatment with vehicle (1% carboxymethylcellulose sodium (CMC)/0.5% Tween 80 once daily; CMC, Sigma catalog #C9481, Tween 80 Sigma catalog #P1754) or the compound of Example 26 (200 mg/kg; twice daily). Treatments continued through Day 42.

At the conclusion of the study, mice were sacrificed and the distal half of their colons were placed in 10% neutral buffered formalin (Richard Allen Scientific catalog #53120-1) and paraffin embedded, sectioned into 4 µm slices and stained with hematoxylin and eosin (H&E) for analysis by a board certified veterinary pathologist.

For each H&E stained section, submucosal edema was quantitated by measuring the distance from the muscularis mucosa to the internal border of the outer muscle layer in a non-tangential area thought to most representative the severity of this change. Mucosal thickness was also measured in a non-tangential area of the section that best represented the overall mucosal thickness. This parameter is indicative of gland elongation and mucosal hyperplasia. The extent of inflammation (macrophage, lymphocyte and polymorphonuclear leukocyte (PMN) infiltrate) was assigned severity scores according to the following criteria:

Normal=0
Minimal=1 (generally focal affecting 1-10% of mucosa or if diffuse then minimal)
Mild=2 (generally focal affecting 11-25% of mucosa or if diffuse then mild)
Moderate=3 (26-50% of mucosa affected with areas of gland loss replaced by inflammatory cell infiltrate, milder in remaining areas of mucosa)
Marked=4 (51-75% of mucosa affected with areas of gland loss replaced by inflammatory cell infiltrate, milder in remaining areas of mucosa)
Severe=5 (76-100% of mucosa affected with areas of gland loss replaced by inflammatory cell infiltrate, milder in remaining areas of mucosa)

The parameters reflecting epithelial cell loss/damage were scored individually using a % area involved scoring method:
None=0
1-10% of the mucosa affected=1
11-25% of the mucosa affected=2
26-50% of the mucosa affected=3
51-75% of the mucosa affected=4
76-100% of the mucosa affected=5

Parameters that were scored using % involvement included: colon glandular epithelial loss (this includes crypt epithelial as well as remaining gland epithelial loss), and colon erosion (this reflects loss of surface epithelium and generally is associated with mucosal hemorrhage (reflective of the bleeding seen clinically and at necropsy).

The three scored parameters (inflammation, glandular epithelial loss, and erosion) were ultimately summed to arrive at a sum of histopathology scores, which indicates the overall damage and would have a maximum score of 15.

Figure 6:
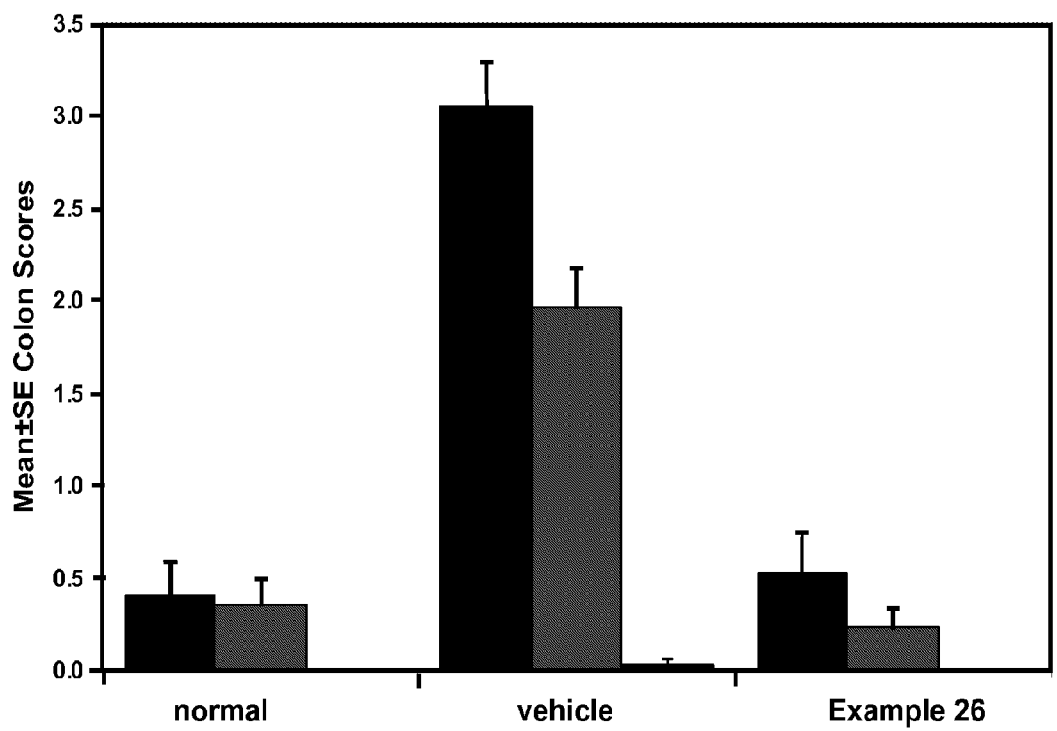
FIG. 6 shows the histological score for inflammation (solid bars), gland loss (hatched bars) and erosion (bricked bars) in the colon of normal mice or mice following 21 days of treatment with vehicle or the compound of Example 26 compared to normal mice as indicated in the murine CD4+CD45RBhi adoptive transfer model of inflammatory bowel disease.
Figure 7:
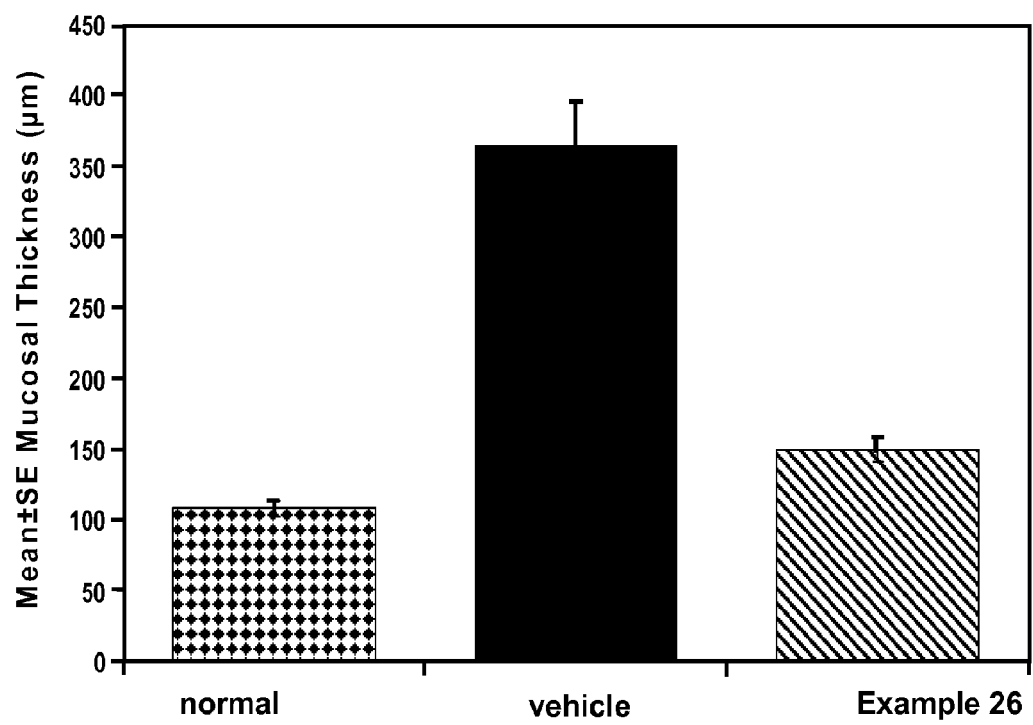
FIG. 7 shows the histological score for mucosal thickening in a murine CD4+CD45RBhi adoptive transfer model of inflammatory bowel disease following 21 days of treatment with vehicle (solid bar) or the compound of Example 26 (hatched bar) compared to normal animals (diamond-speckled bars).

FIG. 6 shows the group mean+/−SEM colon histopathology scores for inflammation (solid bars), gland loss (hatched bars) and erosion (brick bars) in mice that were untreated (left bars), or treated with vehicle (middle bars) or the compound of Example 26 (right bars) following 21 days of treatment. Treatment with the compound of Example 26 resulted in reduced severity of disease as assessed by these histologic endpoints. FIG. 7 shows the group mean+/−SEM for histological assessment of colon mucosal thickness for untreated animals (diamond-speckled bars) and for animals treated with vehicle (solid black bars) or the compound of Example 26 (hatched bars). Treatment with the compound of Example 26 resulted in an 84% decrease in mucosal thickening (a sign of tissue injury), relative to vehicle treated animals.

These results show that treatment with a compound of Formula I is efficacious in decreasing the severity of colon damage in a model of IBD and support the utility of compounds of Formula I for treatment diseases associated with pathogenic T cell responses, including IBD.

Example K

MRL/lpr Lupus Model

MRL/lpr is considered to be an animal model of systemic lupus erythematosus (SLE), an autoimmune disease (Cohen and Maldonado 2003, Current Protocols in Immunology Chapter 15, Unit 15.20). MRL/lpr mice have a defect in the apoptosis of activated lymphocytes and over time develop a spontaneous and severe lymphoproliferative disorder characterized by enlarged lymphoid organs, auto-antibody production and kidney disease resulting in proteinuria. SLE patients also exhibit auto-antibodies, and some patients develop kidney disease. To determine the effect of compounds of Formula I in this model of SLE, the following experiment was conducted.

MRL/MpJ-Fas<lpr>and age-matched MRL/MpJ control mice (Jackson Laboratories, catalog #000485 and #000486, respectively) were treated once daily with vehicle (1% CMC/ 0.5% Tween 80) or twice daily with the compound of Example 26 (200 mg/kg) for 10 weeks. Body weights, lymphadenopathy and urine protein levels were monitored weekly. Urine protein levels were determined with Bayer Albustix dipsticks (Bayer catalog #2191) and scored according to the following scale:

0=none detected
0.5=trace amounts
1=30 mg/dL
2=100 mg/dL
3=300 mg/dL
4=2000 mg/dL Serum levels of anti-ds-DNA antibody were measured by ELISA (Alpha Diagnostic, catalog #5120) on Day 28 and upon study termination. ELISA plates were quantitated using a Molecular Devices Versamax plate reader at 450 nM and titers calculated relative using to a standard curve using a 4-parameter curve fit with Softmax Pro software.

Figure 8:
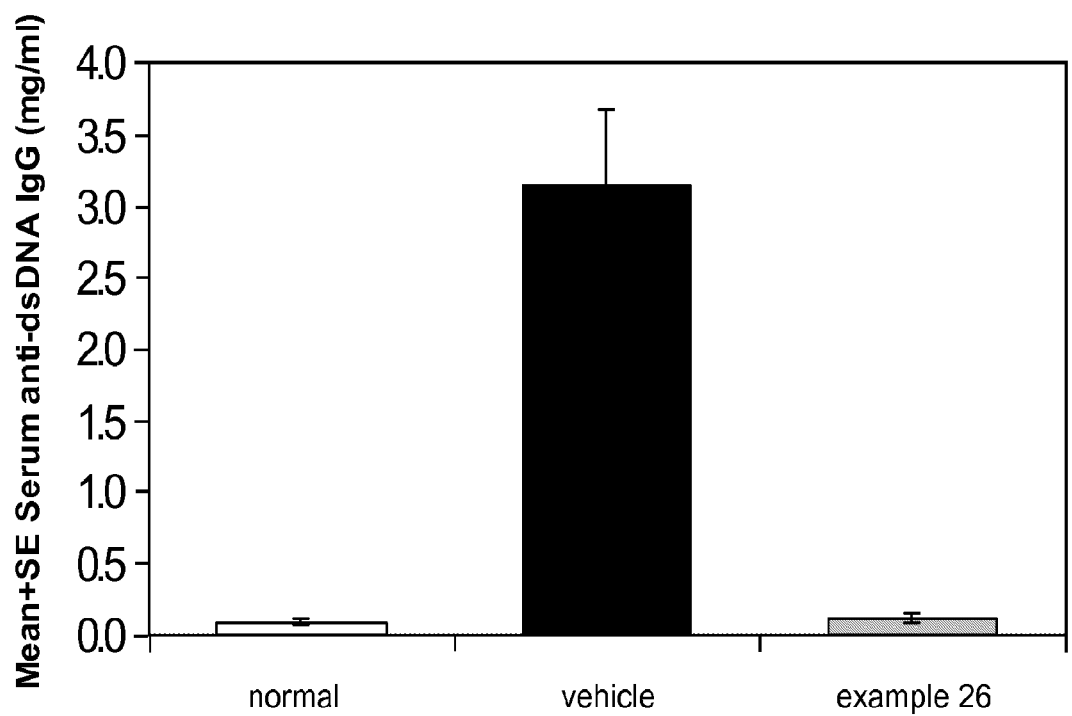
FIG. 8 shows the titer of anti-dsDNA auto-antibodies in serum of mice after 79 days of treatment with vehicle (solid black bars) or with the compound of Example 26 (hatched bars) in the MRL/lpr model of lupus versus the titer in normal mice (speckled bar).

Treatment with the compound of Example 26 for 28 days resulted in a 74% decrease in serum anti-dsDNA relative to vehicle control animals (data not shown). FIG. 8 shows the group mean+/−SEM of anti-dsDNA levels at the termination of the study (79 days of dosing) for untreated animals (speckled bar) and animals treated with vehicle (solid black bar) or the compound of Example 26 (hatched bar). Treatment with compound of Example 26 resulted in a 99% decrease in serum anti-dsDNA antibodies relative to vehicle control animals.

Figure 9:
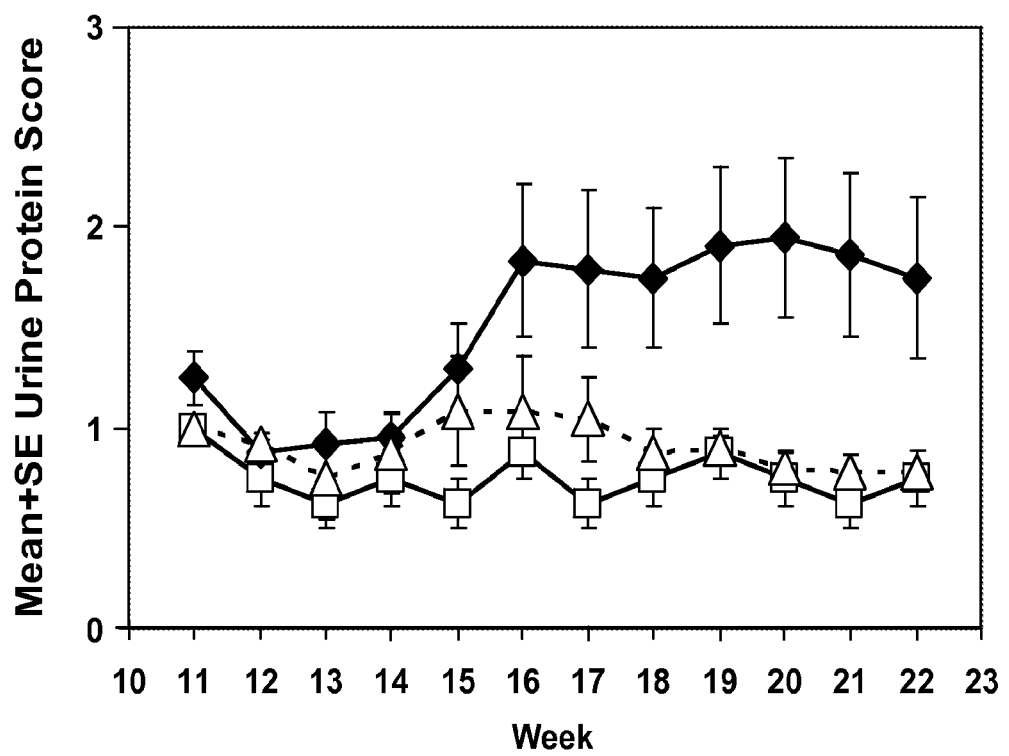
FIG. 9 shows the scored levels of proteinuria present in mice over the time course of the experiment in the MRL/lpr model of lupus after treatment with vehicle (filled diamonds) or the compound of Example 26 (open triangles), relative to normal animals (open squares).

FIG. 9 shows the group mean+/−SEM proteinuria over time for normal animals (open squares) and animals treated with vehicle (filled diamonds) or the compound of Example 26 (open triangles) and demonstrates that treatment with the compound of Example 26 prevents the development of proteinuria relative to vehicle control.

The results shown in FIGS. 8 and 9 support the utility of compounds of Formula I in treating some aspects of lupus.

Preparative Examples

Example 1

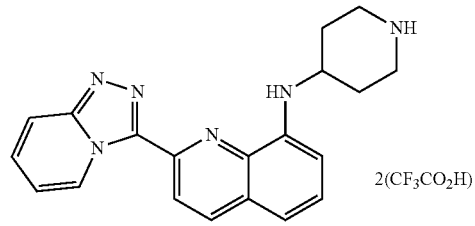 [SMILES: c1cc(NC2CCNCC2)c2nc(-c3nnc4ccccn34)ccc2c1]

2-([1,2,4]Triazolo[4,3-a]pyridin-3-yl)-N-(piperidin-4-yl)quinolin-8-amine di-trifloroacetate Step A: Preparation of 8-(tert-butyldimethylsilyloxy) quinoline-2-carbaldehyde: To a solution of 8-hydroxyquinoline-2-carbaldehyde (15.0 g, 86.62 mmol) and imidazole (12.97 g, 190.6 mmol) in anhydrous CH₂Cl₂ (250 mL) at 0° C. was added tert-butylchlorodimethylsilane (14.36 g, 95.28 mmol). The mixture was allowed to warm slowly to ambient temperature over 16 hours and then partitioned between CH₂Cl₂ and water. The aqueous phase was extracted with CH₂Cl₂ and the combined organic phases were washed successively with saturated NaHCO₃, water and brine, dried over Na₂SO₄, filtered and concentrated under reduced pressure. The residue was purified by silica gel pad filtration eluting with hexanes followed by 19:1 ethyl acetate/hexanes to provide 23.69 g (95%) of desired product as a dark yellow oil.

Step B: Preparation of (E/Z)-8-(tert-butyldimethylsilyloxy)-2-((2-(pyridin-2-yl)hydrazono)methyl)quinoline: A solution of 8-(tert-butyldimethylsilyloxy)quinoline-2-carbaldehyde (23.40 g, 81.41 mmol) and 2-hydrazinylpyridine (8.88 g, 81.41 mmol) in ethanol (500 mL) was stirred at ambient temperature for 16 hours. The resulting precipitate was filtered, washed with cold ethanol and dried in vacuo to provide 30.82 g (82%) of desired product as a beige-colored solid.

Step C: Preparation of 2-([1,2,4]triazolo[4,3-a]pyridin-3-yl)-8-(tert-butyldimethylsilyloxy)quinoline: To a suspension of (E/Z)-8-(tert-butyldimethylsilyloxy)-2-((2-(pyridin-2-yl)hydrazono)methyl)quinoline (25.40 g, 67.10 mmol) in anhydrous CH₂Cl₂ (400 mL) was added iodosobenzene diacetate (23.77 g, 73.81 mmol). The mixture was stirred at ambient temperature for 64 hours after which the solution was partitioned between CH₂Cl₂ and saturated Na₂S₂O₃. The aqueous phase was extracted with CH₂Cl₂ and the combined organic phases were washed with brine, dried over Na₂SO₄, filtered and concentrated under reduced pressure. The residue was triturated with diethyl ether, filtered and dried in vacuo to provide 18.92 g (75%) of desired product as a beige powder.

Step D: Preparation of 2-([1,2,4]triazolo[4,3-a]pyridin-3-yl)quinolin-8-ol: To a solution of 2-([1,2,4]triazolo[4,3-a]pyridin-3-yl)-8-(tert-butyldimethylsilyloxy) quinoline (18.92 g, 50.25 mmol) in anhydrous THF (400 mL) at 0° C. was added tetrabutylammonium fluoride (75.4 mL, 1.0 M/THF, 75.4 mmol). After stirring for 1 hour at this temperature the mixture was partitioned between saturated NaHCO₃ and EtOAc. The aqueous phase was extracted with EtOAc and the combined organic phases were washed with brine, dried over Na₂SO₄, filtered and concentrated under reduced pressure. The residue was triturated with CH₂Cl₂, filtered and dried in vacuo to provide 11.91 g (90%) of desired product as a beige solid.

Step E: Preparation of 2-([1,2,4]triazolo[4,3-a]pyridin-3-yl)quinolin-8-yl trifluoromethanesulfonate: To a suspension of 2-([1,2,4]triazolo[4,3-a]pyridin-3-yl)quinolin-8-ol (0.485 g, 1.85 mmol) in a mixture of THF (5 mL) and DMF (2 mL) was added triethylamine (0.57 mL, 4.07 mmol) followed by N-phenyltriflimide (0.727 g, 2.03 mmol). The mixture was stirred at ambient temperature for 16 hours then treated with water (50 mL). The resulting precipitate was filtered, washed successively with water and ether and dried in vacuo to provide 0.569 g (78%) of desired product as a light grey solid.

Step F: Preparation of tert-butyl 4-(2-([1,2,4]triazolo[4,3-a]pyridin-3-yl)quinolin-8-ylamino)piperidine-1-carboxylate: 2-([1,2,4]triazolo[4,3-a]pyridin-3-yl)quinolin-8-yl trifluoromethanesulfonate (0.100 g, 0.25 mmol), tert-butyl 4-aminopiperidine-1-carboxylate (0.102 g, 0.51 mmol), Pd₂dba₃ (0.023 g, 0.025 mmol), BINAP (0.032 g, 0.05 mmol) and cesium carbonate (0.124 g, 0.38 mmol) were combined in a capped vial and stirred at 100° C. for 16 hours. The cooled mixture was filtered through GF paper and the filtrate partitioned between saturated NaHCO₃ and EtOAc. The aqueous phase was extracted with EtOAc and the combined organic phases were washed with brine, dried over Na₂SO₄, filtered and concentrated under reduced pressure. The residue was purified by flash column chromatography (CH₂Cl₂ followed by 1% MeOH/CH₂Cl₂) to provide 0.107 g (95%) of desired product as an orange foam.

Step G: Preparation of 2-([1,2,4]triazolo[4,3-a]pyridin-3-yl)-N-(piperidin-4-yl)quinolin-8-amine di-trifloroacetate: To a solution of tert-butyl 4-(2-([1,2,4]triazolo[4,3-a]pyridin-3-yl)quinolin-8-ylamino)piperidine-1-carboxylate (0.107 g, 0.241 mmol) in CH₂Cl₂ (4 mL) was added TFA (1 mL). The solution was stirred at ambient temperature for 1 hour then concentrated under reduced pressure. The residue was triturated with ether, filtered and dried in vacuo to provide 0.110 g (80%) of desired product as the di-TFA salt. MS ESI (+) m/z 345 (M+1) detected.

Example 2

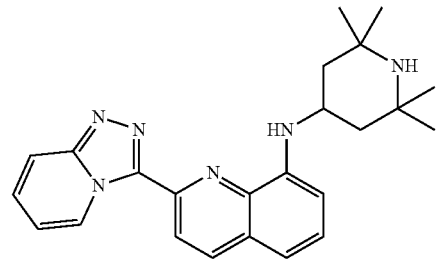 [SMILES: CC1(C)CC(Nc2cccc3ccc(-c4nnc5ccccn45)nc23)CC(C)(C)N1]

2-([1,2,4]Triazolo[4,3-a]pyridin-3-yl)-N-(2,2,6,6-tetramethylpiperidin-4-yl)quinolin amine Prepared as described in Example 1 using tert-butyl 4-amino-2,2,6,6-tetramethylpiperidine-1-carboxylate in place of tert-butyl 4-aminopiperidine-1-carboxylate in step F. MS ESI (+) m/z 401 (M+1) detected.

Example 3

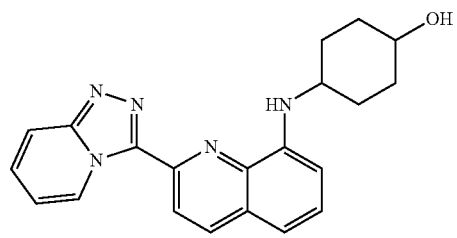 [SMILES: OC1CCC(Nc2cccc3ccc(-c4nnc5ccccn45)nc23)CC1]

(trans)-4-(2-([1,2,4]Triazolo[4,3-a]pyridin-3-yl) quinolin-8-ylamino)cyclohexanol Prepared as described in Example 1 using trans-(1,4)-4-aminocyclohexanol in place of tert-butyl 4-aminopiperidine-1-carboxylate in step F. MS APCI (+) m/z 360 (M+1) detected.

Example 4

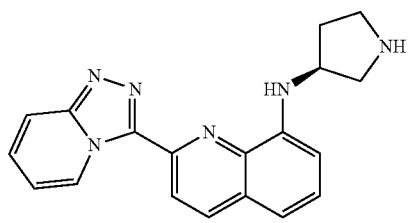 [SMILES: c1cc(N[C@H]2CCNC2)c2nc(-c3nnc4ccccn34)ccc2c1]

(S)-2-([1,2,4]Triazolo[4,3-a]pyridin-3-yl)-N-(pyrrolidin-3-yl)quinolin-8-amine

Prepared as described in Example 1 using (S)-tert-butyl 3-aminopyrrolidine-1-carboxylate in place of tert-butyl 4-aminopiperidine-1-carboxylate in step F. MS ESI (+) m/z 331 (M+1) detected.

Example 5

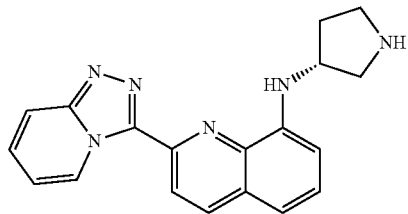 [SMILES: c1cc(N[C@@H]2CCNC2)c2nc(-c3nnc4ccccn34)ccc2c1]

(R)-2-([1,2,4]Triazolo[4,3-a]pyridin-3-yl)-N-(pyrrolidin-3-yl)quinolin-8-amine

Prepared as described in Example 1 using (R)-tert-butyl 3-aminopyrrolidine-1-carboxylate in place of tert-butyl 4-aminopiperidine-1-carboxylate in step F. MS ESI (+) m/z 331 (M+1) detected.

Example 6

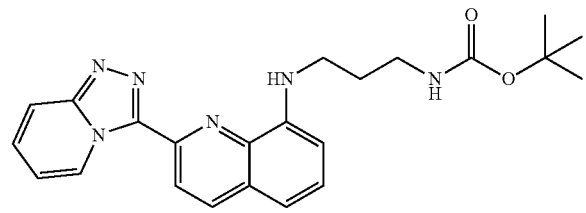 [SMILES: CC(C)(C)OC(=O)NCCCNc1cccc2ccc(-c3nnc4ccccn34)nc12]

tert-Butyl 3-(2-([1,2,4]triazolo[4,3-a]pyridin-3-yl)quinolin-8-ylamino)propylcarbamate Prepared as described in Example 1 using tert-butyl 3-aminopropylcarbamate in place of tert-butyl 4-aminopiperidine-1-carboxylate in step F. MS ESI (+) m/z 419 (M+1) detected.

Example 7

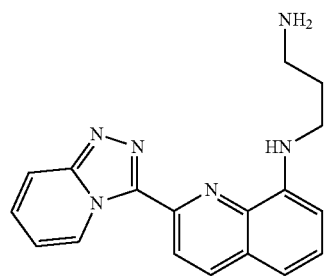 [SMILES: NCCCNc1cccc2ccc(-c3nnc4ccccn34)nc12]

N1-(2-([1,2,4]Triazolo[4,3-a]pyridin-3-yl)quinolin-8-yl)propane-1,3-diamine

Prepared as described in Example 1 using tert-butyl 3-(2-([1,2,4]triazolo[4,3-a]pyridin-3-yl)quinolin-8-ylamino)propylcarbamate (Example 6). MS ESI (+) m/z 319 (M+1) detected.

Example 8

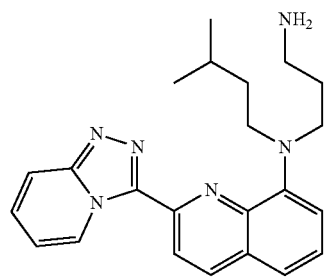 [SMILES: CC(C)CCN(CCCN)c1cccc2ccc(-c3nnc4ccccn34)nc12]

N1-(2-([1,2,4]Triazolo[4,3-a]pyridin-3-yl)quinolin-8-yl)-N1-isopentylpropane-1,3-diamine Prepared as described in Example 1 using tert-butyl 3-(isopentylamino)propylcarbamate in place of tert-butyl 4-aminopiperidine-1-carboxylate in step F. MS ESI (+) m/z 389 (M+1) detected.

Example 9

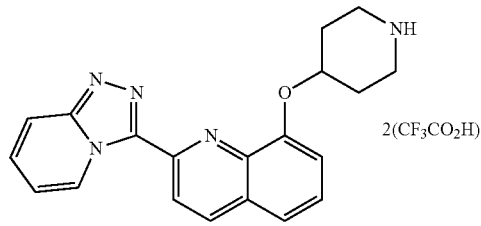 [SMILES: c1cc(OC2CCNCC2)c2nc(-c3nnc4ccccn34)ccc2c1]

2-([1,2,4]triazolo[4,3-a]pyridin-3-yl)-8-(piperidin-4-yloxy)quinoline di-trifluoroacetate Step A: Preparation of tert-butyl 4-(2-([1,2,4]triazolo[4,3-a]pyridin-3-yl)quinolin-8-yloxy)piperidine-1-carboxylate:

To a suspension of 2-([1,2,4]triazolo[4,3-a]pyridin-3-yl)quinolin-8-ol (prepared according to Example 1; 112 mg, 0.427 mmol) in anhydrous THF (5 mL) at ambient temperature were added tert-butyl 4-hydroxypiperidine-1-carboxylate (95 mg, 0.47 mmol), PPh$_3$ (168 mg, 0.64 mmol), and DEAD (101 µL, 0.64 mmol). The resulting yellow solution was stirred for 72 hours and then partitioned between saturated NaHCO$_3$ and ethyl acetate (20 mL). The phases were separated and the aqueous layer was extracted with ethyl acetate. The combined organics were dried over Na$_2$SO$_4$, filtered and concentrated under reduced pressure to afford a yellow oil. The oil was purified by flash column chromatography using gradient elution (CH$_2$Cl$_2$ to 1% MeOH/CH$_2$Cl$_2$) to provide the Boc-protected product (90 mg, 47%) as a white foam.

Step B: Preparation of 2-([1,2,4]triazolo[4,3-a]pyridin-3-yl)-8-(piperidin-4-yloxy)quinoline di-trifluoroacetate: The product from Step A was dissolved in CH$_2$Cl$_2$ (4 mL) and treated with TFA (1 mL). After stirring for 2 hours, the reaction mixture was concentrated to afford a yellow solid. This was triturated with ether, filtered and dried in vacuo to afford the desired product as the di-TFA salt, as a white solid. MS ESI (+) m/z 346 (M+1) detected.

Example 10

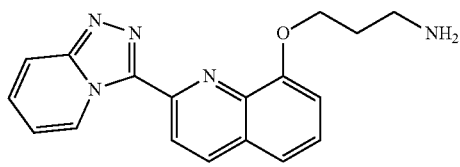 [SMILES: NCCCOc1cccc2ccc(-c3nnc4ccccn34)nc12]

3-(2-([1,2,4]Triazolo[4,3-a]pyridin-3-yl)quinolin-8-yloxy)propan-1-amine

Prepared as described in Example 9 using tert-butyl 3-hydroxypropylcarbamate in place of tert-butyl 4-hydroxypiperidine-1-carboxylate in step A. MS ESI (+) m/z 320 (M+1) detected.

Example 11

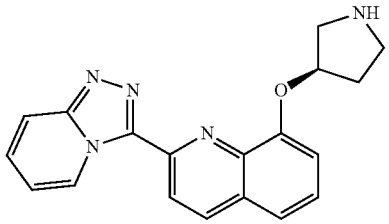 [SMILES: c1cc(O[C@@H]2CCNC2)c2nc(-c3nnc4ccccn34)ccc2c1]

(R)-2-([1,2,4]Triazolo[4,3-a]pyridin-3-yl)-8-(pyrrolidin-3-yloxy)quinoline

Prepared as described in Example 9 using (S)-tert-butyl 3-hydroxypyrrolidine-1-carboxylate in place of tert-butyl 4-hydroxypiperidine-1-carboxylate in step A. MS ESI (+) m/z 332 (M+1) detected.

Example 12

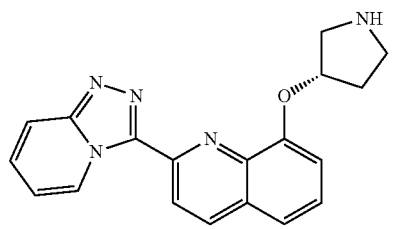 [SMILES: c1cc(O[C@H]2CCNC2)c2nc(-c3nnc4ccccn34)ccc2c1]

(S)-2-([1,2,4]Triazolo[4,3-a]pyridin-3-yl)-8-(pyrrolidin-3-yloxy)quinoline

Prepared as described in Example 9 using (R)-tert-butyl 3-hydroxypyrrolidine-1-carboxylate in place of tert-butyl 4-hydroxypiperidine-1-carboxylate in step A. MS ESI (+) m/z 332 (M+1) detected.

Example 13

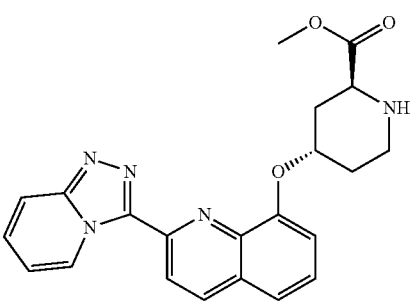 [SMILES: COC(=O)[C@@H]1C[C@@H](Oc2cccc3ccc(-c4nnc5ccccn45)nc23)CCN1]

(2S,4S)-Methyl 4-(2-([1,2,4]triazolo[4,3-a]pyridin-3-yl)quinolin-8-yloxy)piperidine-2-carboxylate Prepared as described in Example 9 using (2S,4R)-1-tert-butyl 2-methyl 4-hydroxypiperidine-1,2-dicarboxylate in place of tert-butyl 4-hydroxypiperidine-1-carboxylate in step A. MS ESI (+) m/z 404 (M+1) detected.

Example 14

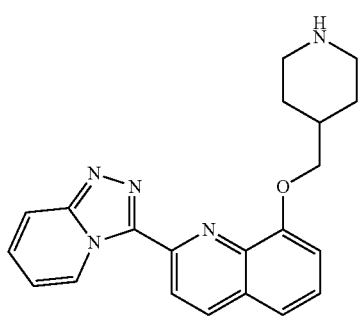 [SMILES: c1cc(OCC2CCNCC2)c2nc(-c3nnc4ccccn34)ccc2c1]

2-([1,2,4]Triazolo[4,3-a]pyridin-3-yl)-8-(piperidin-4-ylmethoxy)quinoline

Prepared as described in Example 9 using tert-butyl 4-(hydroxymethyl)piperidine-1-carboxylate in place of tert-butyl 4-hydroxypiperidine-1-carboxylate in step A. MS ESI (+) m/z 360 (M+1) detected.

Example 15

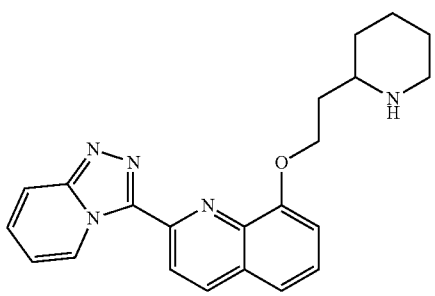 [SMILES: c1cc(OCCC2CCCCN2)c2nc(-c3nnc4ccccn34)ccc2c1]

2-([1,2,4]Triazolo[4,3-a]pyridin-3-yl)-8-(2-(piperidin-2-yl)ethoxy)quinoline

Prepared as described in Example 9 using tert-butyl 2-2-(hydroxyethyl)piperidine-1-carboxylate in place of tert-butyl 4-hydroxypiperidine-1-carboxylate in step A. MS ESI (+) m/z 374 (M+1) detected.

Example 16

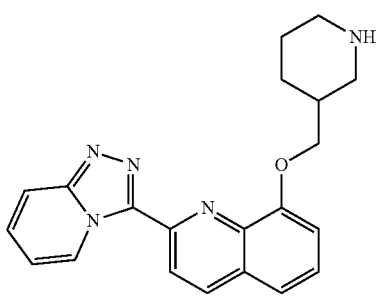 [SMILES: c1cc(OCC2CCCNC2)c2nc(-c3nnc4ccccn34)ccc2c1]

2-([1,2,4]Triazolo[4,3-a]pyridin-3-yl)-8-(piperidin-3-ylmethoxy)quinoline

Prepared as described in Example 9 using tert-butyl 3-(hydroxymethyl)piperidine-1-carboxylate in place of tert-butyl 4-hydroxypiperidine-1-carboxylate in step A. MS ESI (+) m/z 360 (M+1) detected.

Example 17

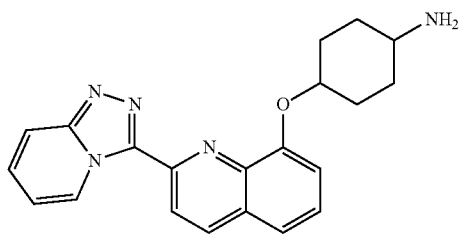 [SMILES: NC1CCC(Oc2cccc3ccc(-c4nnc5ccccn45)nc23)CC1]

(trans)-4-(2-([1,2,4]Triazolo[4,3-a]pyridin-3-yl)quinolin-8-yloxy)cyclohexanamine Prepared as described in Example 9 using cis-tert-butyl-(1,4)-4-hydroxycyclohexylcarbamate in place of tert-butyl 4-hydroxypiperidine-1-carboxylate in step A. MS ESI (+) m/z 360 (M+1) detected.

Example 18

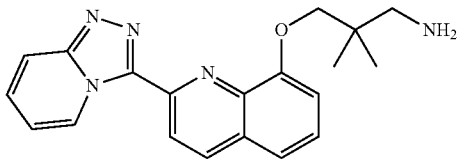

3-(2-([1,2,4]Triazolo[4,3-a]pyridin-3-yl)quinolin-8-yloxy)-2,2-dimethylpropan-1-amine Prepared as described in Example 9 using tert-butyl 3-hydroxy-2,2-dimethylpropylcarbamate as a replacement for tert-butyl 4-hydroxypiperidine-1-carboxylate in step A. MS ESI (+) m/z 348 (M+1) detected.

Example 19

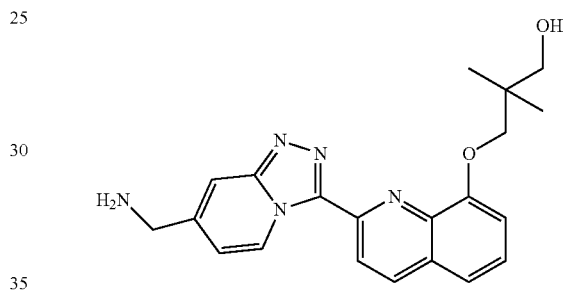

3-(2-(7-(aminomethyl)-[1,2,4]triazolo[4,3-a]pyridin-3-yl)quinolin-8-yloxy)-2,2-dimethylpropan-1-ol Step A: Preparation of 8-(tert-butyldimethylsilyloxy)-2-((E)-((Z)-(4-iodopyridin-2(1H)-ylidene)hydrazono)methyl)quinoline: To 8-(tert-butyldimethylsilyloxy)quinoline-2-carbaldehyde (3.21 g, 11.2 mmol) in DCM (30 mL) was added (Z)-1-(4-iodopyridin-2(1H)-ylidene)hydrazine (3.15 g, 13.4 mmol). The reaction was stirred for 1 hour, affording a yellow precipitate, which was collected by filtration and used without further purification in the next step.

Step B: Preparation of 8-(tert-butyldimethylsilyloxy)-2-(7-iodo-[1,2,4]triazolo[4,3-a]pyridin-3-yl)quinoline: 8-(tert-butyldimethylsilyloxy)-2-((E)-((Z)-(4-iodopyridin-2(1H)-ylidene)hydrazono)methyl)quinoline was weighed into a 1 neck flask and dissolved in THF. Iodobenzene diacetate (IBD) (4.199 g) was added portionwise, and the reaction was stirred for 5 minutes. The reaction was quenched with saturated $Na_2S_2O_3$ (20 mL). The phases were separated, followed by extraction of the aqueous phase with DCM. The combined organics were dried over $Na_2SO_4$ and concentrated in vacuo. The crude material was purified by flash column chromatography (eluting with a 2:1 mixture of Hexanes/ethyl acetate), affording the desired product.

Step C: Preparation of 8-(tert-butyldimethylsilyloxy)-2-(7-vinyl-[1,2,4]triazolo[4,3-a]pyridin-3-yl)quinoline: To 8-(tert-butyldimethylsilyloxy)-2-(7-iodo-[1,2,4]triazolo[4,3-a]pyridin-3-yl)quinoline (2.011 g, 4.003 mmol) in NMP/THF (10 mL/10 mL) was added tributyl(vinyl)stannane (1.523 g, 4.803 mmol), trifuran-2-ylphosphine (0.0929 g, 0.400 mmol), Pd₂dba₃ (0.367 g, 0.4003 mmol) and triethylamine (0.405 g, 4.00 mmol). The reaction was degassed with N₂ and heated to 60° C. for 1 hour. The crude mixture was diluted with ethyl acetate and the organic layer was washed with H₂O. The combined organics fractions were dried over Na₂SO₄ and concentrated in vacuo. The crude material was purified by flash column chromatography (eluting with a 5:1 mixture of Hexanes/ethyl acetate), affording the desired product.

Step D: Preparation 1-(3-(8-(tert-butyldimethylsilyloxy)quinolin-2-yl)-[1,2,4]triazolo[4,3-a]pyridin-7-yl)ethane-1,2-diol: To 8-(tert-butyldimethylsilyloxy)-2-(7-vinyl-[1,2,4]triazolo[4,3-a]pyridin-3-yl)quinoline (1.321 g, 3.281 mmol) in acetone (10 mL) was added NMO (0.577 g, 4.93 mmol) and OsO₄ (0.5 mL, 3.28 mmol) (0.025% in tBuOH). The reaction was stirred for 4 hours, quenched with saturated Na₂S₂O₃ and concentrated in vacuo. DCM was added to the crude slurry, and the aqueous layer was separated. The organics were dried over Na₂SO₄ and concentrated to provide the crude product.

Step E: Preparation of 3-(8-(tert-butyldimethylsilyloxy)quinolin-2-yl)-[1,2,4]triazolo[4,3-a]pyridine-7-carbaldehyde: Sodium periodate (6.060 mL, 3.939 mmol) was added to silica gel (6 g) in DCM (10 mL), affording a slurry. 1-(3-(8-(tert-butyldimethylsilyloxy)quinolin-2-yl)-[1,2,4]triazolo[4,3-a]pyridin-7-yl)ethane-1,2-diol (1.433 g, 3.282 mmol) in DCM (10 mL) was added to the slurry and the reaction was stirred for 1 hour. The silica gel was removed by filtration and washed with DCM. The filtrate was concentrated in vacuo to provide the crude product.

Step F: Preparation of (3-(8-(tert-butyldimethylsilyloxy)quinolin-2-yl)-[1,2,4]triazolo[4,3-a]pyridin-7-yl)methanol: NaBH₄ (0.124 g, 3.28 mmol was added to a solution of 3-(8-(tert-butyldimethylsilyloxy)quinolin-2-yl)-[1,2,4]triazolo[4,3-a]pyridine-7-carbaldehyde (1.328 g, 3.283 mmol) in MeOH (20 mL) at 0° C. The cold bath was removed and the reaction allowed to warm to ambient temperature over 1 hour. HCl was added and the solution was concentrated. The residue was triturated with DCM. The resulting solid was filtered and concentrated to provide the crude product.

Step G: Preparation of 2-((3-(8-(tert-butyldimethylsilyloxy)quinolin-2-yl)-[1,2,4]triazolo[4,3-a]pyridin-7-yl)methyl)isoindoline-1,3-dione: DEAD (0.6524 mL, 4.143 mmol) was added to a solution of (3-(8-(tert-butyldimethylsilyloxy)quinolin-2-yl)-[1,2,4]triazolo[4,3-a]pyridin-7-yl)methanol (1.123 g, 2.762 mmol), isoindoline-1,3-dione (0.6096 g, 4.143 mmol) and triphenylphosphine (1.087 g, 4.143 mmol) in THF (20 mL) at 0° C. Following addition, the cold bath was removed and the reaction stirred at ambient temperature for 3 hours. The crude reaction was concentrated and the residue was purified by flash column chromatography (eluting with at 1:4 mixture of ethyl acetate/Hexanes) to afford the desired product mixed with triphenylphosphine oxide.

Step H: Preparation of 243-(8-hydroxyquinolin-2-yl)-[1,2,4]triazolo[4,3-a]pyridin-7-yl)methyl)isoindoline-1,3-dione: To a solution of 2-((3-(8-(tert-butyldimethylsilyloxy)quinolin-2-yl)-[1,2,4]triazolo[4,3-a]pyridin-7-yl)methyl)isoindoline-1,3-dione (1.012 g, 1.889 mmol) and silica gel (3 g) in THF (20 mL) was added TBAF (2.267 mL, 2.267 mmol) (1M in THF). The reaction was stirred for 20 minutes, then filtered and washed with DCM/MeOH (10:1). The combined organics were concentrated in vacuo to afford the desired crude product.

Step I: Preparation of 2-((3-(8-(3-hydroxy-2,2-dimethylpropoxy)quinolin-2-yl)-[1,2,4]triazolo[4,3-a]pyridin-7-yl)methyl)isoindoline-1,3-dione: Cs₂CO₃ (0.513 g, 1.57 mmol) was added to a solution of 2-43-(8-hydroxyquinolin-2-yl)-[1,2,4]triazolo[4,3-a]pyridin-7-yl)methyl)isoindoline-1,3-dione (0.221 g, 0.524 mmol) and 3-bromo-2,2-dimethylpropan-1-ol (0.350 g, 2.10 mmol) in DMA (2 mL). The reaction was sealed and heated at 100° C. and stirred for 30 minutes. The reaction was cooled to ambient temperature and diluted with EtOAc/H₂O (2:1). The phases were separated and the aqueous layer was extracted with ethyl acetate. The combined organics were dried over Na₂SO₄ and concentrated in vacuo. The crude material was purified by flash column chromatography (eluting with a 20:1 mixture of DCM/MeOH), to afford the desired product.

Step J: Preparation of 3-(2-(7-(aminomethyl)-[1,2,4]triazolo[4,3-a]pyridin-3-yl)quinolin-8-yloxy)-2,2-dimethylpropan-1-ol: To a solution of 2-43-(8-(3-hydroxy-2,2-dimethylpropoxy)quinolin-2-yl)-[1,2,4]triazolo[4,3-a]pyridin-7-yl)methyl)isoindoline-1,3-dione (0.056 g, 0.11 mmol) in EtOH (2 mL) was added hydrazine (0.018 g, 0.55 mmol), and the reaction was stirred for 30 minutes. The reaction was concentrated, and the crude material was purified by flash column chromatography (eluting with a 20:1:0.1 mixture of DCM/MeOH/NH₄OH) to afford the desired product (4 mg). MS ESI (+) m/z 378 (M+1) detected.

Example 20

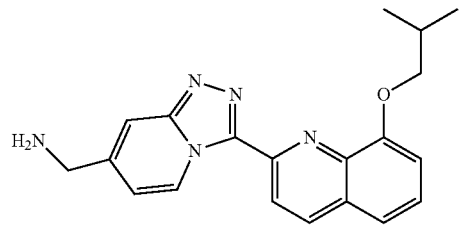 [SMILES: CC(C)COc1cccc2ccc(-c3nnc4cc(CN)ccn34)nc12]

(3-(8-isobutoxyquinolin-2-yl)-[1,2,4]triazolo[4,3-a]pyridin-7-yl)methanamine

Prepared as described in Example 19, using 2-methylpropan-1-ol in place of 3-bromo-2,2-dimethylpropan-1-ol in step 1. MS ESI (+) m/z 348 (M+1) detected.

Example 21

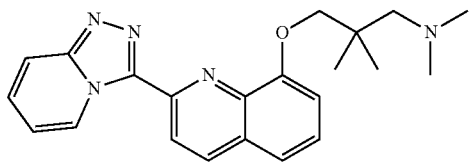 [SMILES: CN(C)CC(C)(C)COc1cccc2ccc(-c3nnc4ccccn34)nc12]

3-(2-([1,2,4]triazolo[4,3-a]pyridin-3-yl)quinolin-8-yloxy)-N,N,2,2-tetramethylpropan-1-amine Prepared as described in Example 9, using 3-(dimethylamino)-2,2-dimethylpropan-1-ol in place of tert-butyl 4-hydroxypiperidine-1-carboxylate in step A. MS ESI (+) m/z 376.2 (M+1) detected.

Example 22

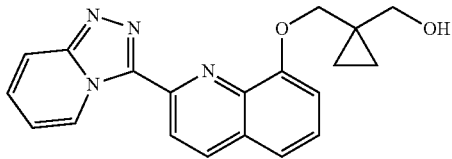 [SMILES: OCC1(COc2cccc3ccc(-c4nnc5ccccn45)nc23)CC1]

(1-((2-([1,2,4]triazolo[4,3-a]pyridin-3-yl)quinolin-8-yloxy)methyl)cyclopropyl)methanol Prepared as described in Example 9, using 1,1-bis(hydroxymethyl)cyclopropane in place of tert-butyl 4-hydroxypiperidine-1-carboxylate in step A. MS ESI (+) m/z 347.1 (M+1) detected.

Example 23

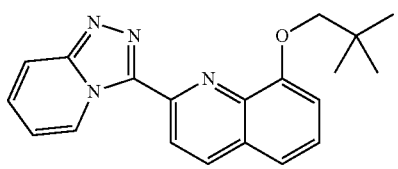 [SMILES: CC(C)(C)COc1cccc2ccc(-c3nnc4ccccn34)nc12]

2-([1,2,4]triazolo[4,3-a]pyridin-3-yl)-8-(neopentyloxy)quinoline

To a solution of 2-([1,2,4]triazolo[4,3-a]pyridin-3-yl)quinolin-8-ol (100 mg, 0.38 mmol), Example 1, Step D, in anhydrous DMA (2 mL) was added cesium carbonate (373 mg, 1.14 mmol) followed by neopentyl iodide (101 µL, 0.76 mmol). The heterogeneous mixture was stirred at ambient temperature for 2 hours then at 100° C. for 16 hours. The cooled mixture was treated with water (30 mL) and extracted with EtOAc (3×20 mL). The combined organic phases were washed with water and brine, dried over Na$_2$SO$_4$ and concentrated to afford a cream-colored solid. This was triturated with ether and the resulting solid collected by filtration and dried in vacuo to provide desired product (62 mg, 49%) as a white powder. MS ESI (+) m/z 333.3 (M+1) detected.

Example 24

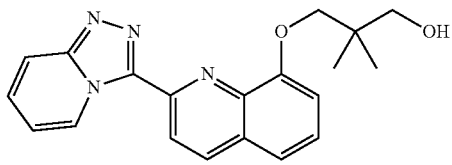 [SMILES: CC(C)(CO)COc1cccc2ccc(-c3nnc4ccccn34)nc12]

3-(2-([1,2,4]triazolo[4,3-a]pyridin-3-yl)quinolin-8-yloxy)-2,2-dimethylpropan-1-ol Prepared as described in Example 23 using 3-bromo-2,2-dimethylpropan-1-ol in place of neopentyl iodide. MS ESI (+) m/z 349.2 (M+1) detected.

Example 25

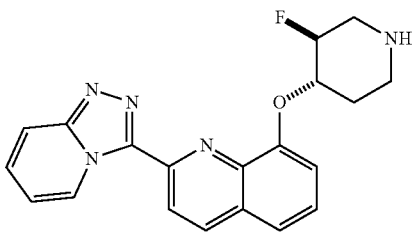

2-([1,2,4]triazolo[4,3-a]pyridin-3-yl)-8-((trans)-3-fluoropiperidin-4-yloxy)quinoline Prepared as described in Example 23 using (cis)-tert-butyl-3-fluoro-4-(methylsulfonyloxy)piperidine-1-carboxylate in place of neopentyl iodide. Boc deprotection was achieved as described in Example 9, Step B. MS ESI (+) m/z 364.1 (M+1) detected.

Example 26

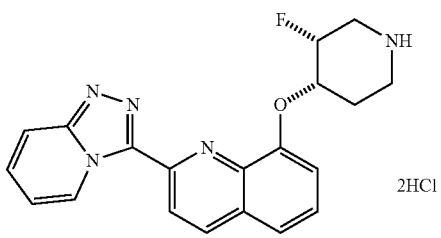

2-([1,2,4]triazolo[4,3-a]pyridin-3-yl)-8-((cis)-3-fluoropiperidin-4-yloxy)quinoline dihydrochloride Prepared as described in Example 23, using (trans)-tert-butyl-3-fluoro-4-(methylsulfonyloxy)piperidine-1-carboxylate in place of (cis)-tert-butyl-3-fluoro-4-(methylsulfonyloxy)piperidine-1-carboxylate. MS ESI (+) m/z 364.1 (M+1) detected.

A more detailed description of the synthesis is described in Steps A and B below.

Step A: Preparation of cis-(3,4)-tert-butyl 4-(2-([1,2,4]triazolo[4,3-a]pyridin-3-yl)quinolin-8-yloxy)-3-fluoropiperidine-1-carboxylate: 2-([1,2,4]triazolo[4,3-a]pyridin-3-yl)quinolin-8-ol (5.1 g, 19 mmol), trans-(3,4)-tert-butyl 3-fluoro-4-(methylsulfonyloxy)piperidine-1-carboxylate (5.8 g, 19 mmol) and cesium carbonate (19 g, 58 mmol) were combined in a round bottom flask and dissolved in 120 mL of DMA and heated at 100° C. overnight, after which the reaction was complete by TLC. The reaction was filtered and the mother liquor concentrated in vacuo. The residue was purified by flash column chromatography, gradient elution 1-10%

MeOH/DCM, affording the desired product as a yellow solid containing the starting marterial 2-([1,2,4]triazolo[4,3-a]pyridin-3-yl)quinolin-8-ol as an impurity. MS ESI (+) m/z 464.0 (M+1) detected.

Step B: Preparation of 2-([1,2,4]triazolo[4,3-a]pyridin-3-yl)-8-(cis-(3,4)-3-fluoropiperidin-4-yloxy)quinoline dihydrochloride: cis-(3,4)-tert-butyl 4-(2-([1,2,4]triazolo[4,3-a]pyridin-3-yl)quinolin-8-yloxy)-3-fluoropiperidine-1-carboxylate (9.0 g, 19 mmol) was weighed into a round bottom flask and dissolved in 300 mL of chloroform. HCl (49 mL, 194 mmol) was added dropwise, followed by stirring for 1 hour at ambient temperature, at which time the reaction was complete by LC/TLC. The crude product was collected by filtration, wash with 3×100 mL of DCM and then Et$_2$O, affording the desired product (4.7 g, 13 mmol, 67% yield) as an off white powder.

Example 27

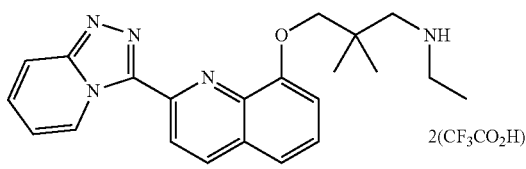 [SMILES: CCNCC(C)(C)COc1cccc2ccc(-c3nnc4ccccn34)nc12]

3-(2-([1,2,4]triazolo[4,3-a]pyridin-3-yl)quinolin-8-yloxy)-N-ethyl-2,2-dimethylpropan-1-amine di-trifluoroacetate Step A: Preparation of tert-butyl 3-(2-([1,2,4]triazolo[4,3-a]pyridin-3-yl)quinolin-8-yloxy)-2,2-dimethylpropyl(ethyl)carbamate: To a solution of tert-butyl 3-(2-([1,2,4]triazolo[4,3-a]pyridin-3-yl)quinolin-8-yloxy)-2,2-dimethylpropylcarbamate (50 mg, 0.11 mmol) in anhydrous DMF (2 mL) was added NaH (7 mg, 60%, 0.17 mmol). After stirring at ambient temperature for 20 min, ethyl iodide (27 μL, 0.34 mmol) was added and the mixture stirred for a further 5 hrs. The mixture was treated with saturated NH$_4$Cl (20 mL) and extracted with EtOAc (3×10 mL). The combined organic phases were washed with water and brine and concentrated to afford a yellow gum. The residue was purified by flash column chromatography using gradient elution (CH$_2$Cl$_2$ to 1% MeOH/CH$_2$Cl$_2$ to 2% MeOH/CH$_2$Cl$_2$) to afford desired product (45 mg, 85%) as a colorless gum.

Step B: Preparation of 3-(2-([1,2,4]triazolo[4,3-a]pyridin-3-yl)quinolin-8-yloxy)-N-ethyl-2,2-dimethylpropan-1-amine di-trifluoroacetate: To a solution of tert-butyl 3-(2-([1,2,4]triazolo[4,3-a]pyridin-3-yl)quinolin-8-yloxy)-2,2-dimethylpropyl(ethyl)carbamate (45 mg, 0.09 mmol) in CH$_2$Cl$_2$ (4 mL) was added TFA (1 mL). The yellow/brown solution was stirred at ambient temperature for 2 hours then concentrated and dried in vacuo. The residue was triturated with ether, filtered and dried in vacuo to afford desired product (44 mg, 76%) as the di-TFA salt as a white solid. MS APCI (+) m/z 376.2 (M+1) detected.

Example 28

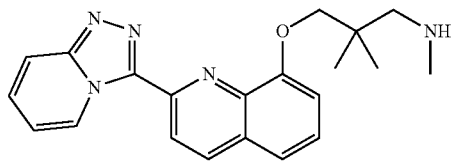 [SMILES: CNCC(C)(C)COc1cccc2ccc(-c3nnc4ccccn34)nc12]

3-(2-([1,2,4]triazolo[4,3-a]pyridin-3-yl)quinolin-8-yloxy)-N,2,2-trimethylpropan-1-amine Prepared as described in Example 27, using methyl iodide in place of ethyl iodide in Step A. MS APCI (+) m/z 362.2 (M+1) detected.

Example 29

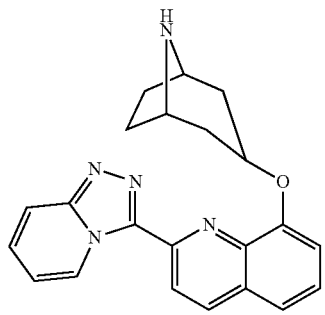 [SMILES: c1cc(OC2CC3CCC(C2)N3)c2nc(-c3nnc4ccccn34)ccc2c1]

8-(8-azabicyclo[3.2.1]octan-3-yloxy)-2-([1,2,4]triazolo[4,3-a]pyridin-3-yl)quinoline Prepared as described in Example 9, using tert-butyl 3-hydroxy-8-azabicyclo[3.2.1]octane-8-carboxylate in place of tert-butyl 4-hydroxypiperidine-1-carboxylate in step A. MS ESI (+) m/z 372.2 (M+1) detected.

Example 30

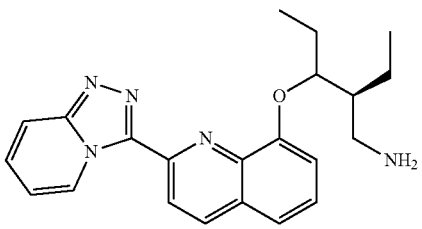 [SMILES: CCC(Oc1cccc2ccc(-c3nnc4ccccn34)nc12)[C@@H](CC)CN]

(2S)-3-(2([1,2,4]triazolo[4,3-a]pyridin-3-yl)quinolin-8-yloxy)-2-ethylpentan-1-amine Step A: Preparation of tert-butyl (2S )-3-(2-([1,2,4]triazolo[4,3-a]pyridin-3-yl)quinolin-8-yloxy)-2-ethylpentylcarbamate: 2-([1,2,4]Triazolo[4,3-a]pyridin-3-yl)quinolin-8-ol (101 mg, 0.385 mmol), tert-butyl (2S )-2-ethyl-3-hydroxypentylcarbamate (89 mg, 0.385 mmol), PPh₃ (151 mg, 0.577 mmol) and DEAD (90.9 µL, 0.577 mmol) were combined at ambient temperature in 5 mL anhydrous THF. The reaction mixture was heated at reflux for 6 hours. The crude mixture was cooled to ambient temperature and diluted with water and ethyl acetate. The crude mixture was extracted with ethyl acetate, and the combined organic layers were dried over Na₂SO₄ and concentrated in vacuo to provide the desired product.

Step B: Preparation of (2S)-3-(2-([1,2,4]triazolo[4,3-a]pyridin-3-yl)quinolin-8-yloxy)-2-ethylpentan-1-amine: tert-Butyl (2S)-3-(2-([1,2,4]triazolo[4,3-a]pyridin-3-yl)quinolin-8-yloxy)-2-ethylpentylcarbamate was dissolved in 5 mL DCM and cooled to 0° C. TFA (5 mL) was added and the mixture was allowed to warm to ambient temperature over 1 hour. The reaction mixture was evaporated to dryness, and the residue was dissolved in 30 mL DCM and washed with 1N NaOH. The combined organic layers were dried over Na₂SO₄, filtered, and concentrated under vacuum. The residue was purified by silica gel chromatography followed by preparative TLC to give the desired product (42.5 mg, 29%). MS ESI (+) m/z 376.1 (M+1) detected.

Example 31

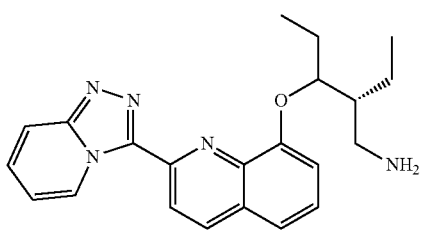 [SMILES: CCC(Oc1cccc2ccc(-c3nnc4ccccn34)nc12)[C@H](CC)CN]

(2R)-3-(2-([1,2,4]triazolo[4,3-a]pyridin-3-yl)quinolin-8-yloxy)-2-ethylpentan-1-amine Prepared as described in Example 30, using tert-butyl (2R)-2-ethyl-3-hydroxypentylcarbamate in place of tert-butyl (2S)-2-ethyl-3-hydroxypentylcarbamate in step A. MS ESI (+) m/z 376.1 (M+1) detected.

Example 32

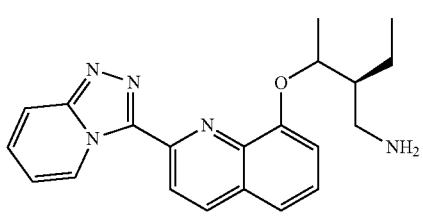 [SMILES: CC[C@@H](CN)C(C)Oc1cccc2ccc(-c3nnc4ccccn34)nc12]

(2S)-3-(2-([1,2,4]triazolo[4,3-a]pyridin-3-yl)quinolin-8-yloxy)-2-ethylbutan-1-amine Prepared as described in Example 30, using tert-butyl (2S)-2-ethyl-3-hydroxybutylcarbamate in place of tert-butyl (2S)-2-ethyl-3-hydroxypentylcarbamate in step A. MS ESI (+) m/z 362.1 (M+1) detected.

Example 33

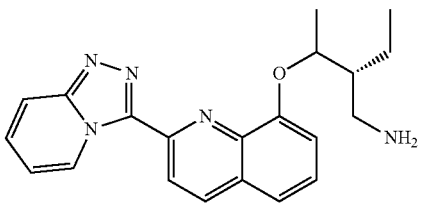 [SMILES: CC[C@H](CN)C(C)Oc1cccc2ccc(-c3nnc4ccccn34)nc12]

(2R)-3-(2-([1,2,4]triazolo[4,3-a]pyridin-3-yl)quinolin-8-yloxy)-2-ethylbutan-1-amine Prepared as described in Example 30, using tert-butyl (2R)-2-ethyl-3-hydroxybutylcarbamate in place of tert-butyl (2S)-2-ethyl-3-hydroxypentylcarbamate in step A. MS ESI (+) m/z 362.2 (M+1) detected.

Example 34

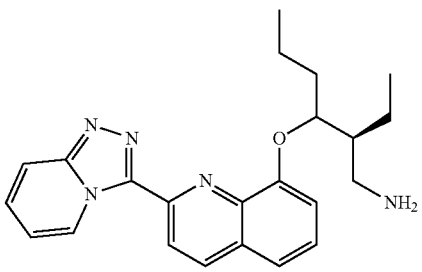 [SMILES: CCCC(Oc1cccc2ccc(-c3nnc4ccccn34)nc12)[C@@H](CC)CN]

(2S)-3-(2-([1,2,4]triazolo[4,3-a]pyridin-3-yl)quinolin-8-yloxy)-2-ethylhexan-1-amine Prepared as described in Example 30, using tert-butyl (2S)-2-ethyl-3-hydroxyhexylcarbamate in place of tert-butyl (2S)-2-ethyl-3-hydroxypentylcarbamate in step A. MS ESI (+) m/z 390.2 (M+1) detected.

Example 35

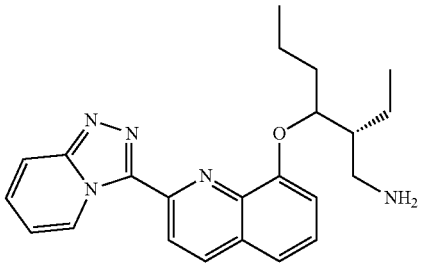 [SMILES: CCCC(Oc1cccc2ccc(-c3nnc4ccccn34)nc12)[C@H](CC)CN]

(2R)-3-(2-([1,2,4]triazolo[4,3-a]pyridin-3-yl)quinolin-8-yloxy)-2-ethylhexan-1-amine Prepared as described in Example 30 using tert-butyl (2R)-2-ethyl-3-hydroxyhexylcarbamate in place of tert-butyl (2S)-2-ethyl-3-hydroxypentylcarbamate in step A. MS ESI (+) m/z 390.2 (M+1) detected.

Example 36

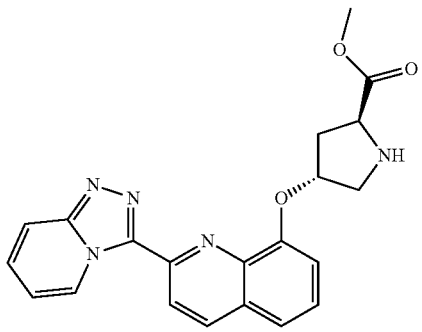 [SMILES: COC(=O)[C@@H]1C[C@@H](Oc2cccc3ccc(-c4nnc5ccccn45)nc23)CN1]

(2S,4R)-methyl 4-(2-([1,2,4]triazolo[4,3-a]pyridin-3-yl)quinolin-8-yloxy)pyrrolidine-2-carboxylate Prepared as described in Example 13, using (2S,4S)-1-tert-butyl 2-methyl 4-hydroxypyrrolidine-1,2-dicarboxylate in place (2S,4R)-1-tert-butyl 2-methyl 4-hydroxypiperidine-1,2-dicarboxylate. MS ESI (+) m/z 390.2 (M+1) detected.

Example 37

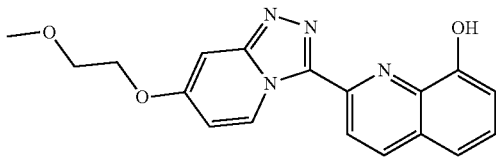 [SMILES: COCCOc1ccn2c(-c3ccc4cccc(O)c4n3)nnc2c1]

2-(7-(2-methoxyethoxy)-[1,2,4]triazolo[4,3-a]pyridin-3-yl)quinolin-8-ol

Step A: Preparation of 2-chloro-4-(2-methoxyethoxy)pyridine: Potassium 2-methylpropan-2-olate (4.214 g, 35.68 mmol) was slowly added to a solution of 2-chloro-4-nitropyridine (5.142 g, 32.434 mmol) in 2-methoxyethanol (40.0 mL, 506.74 mmol). The reaction was stirred at ambient temperature for 2 hours, then concentrated under reduced pressure. The resulting oil was diluted with water (200 mL) and extracted with Ethyl acetate (2×100 mL). The combined organic phases were dried over $Na_2SO_4$, filtered and concentrated under reduced pressure to give 5.36 g (88%) of the desired product as a colorless oil.

Step B: Preparation of 2-hydrazinyl-4-(2-methoxyethoxy)pyridine: Hydrazine (10 mL, 318.6 mmol) was added to a solution of 2-chloro-4-(2-methoxyethoxy)pyridine (1.00 g, 5.330 mmol) in pyridine (25 mL), then heated to reflux. After 18 hours the reaction mixture was partitioned between $H_2O$ and DCM and the aqueous phase was extracted with DCM. The combined organic extracts were dried over $Na_2SO_4$, filtered and concentrated under reduced pressure. The residue was purified by flash column chromatography (40:1 DCM/MeOH followed by 20:1 DCM/MeOH) to provide 320 mg (33%) of desired product as a white solid.

Step C: Preparation of 8-(tert-butyldimethylsilyloxy)quinoline-2-carbaldehyde: 8-Hydroxyquinoline-2-carbaldehyde (5.00 g, 28.9 mmol) and imidazole (4.32 g, 63.5 mmol) were dissolved in DCM (50 mL) under $N_2$. The reaction mixture was cooled to 0° C., followed by addition of tert-butylchlorodimethylsilane (4.94 g, 31.8 mmol). After stirring for 16 hours at ambient temperature the reaction mixture was partitioned between DCM and $H_2O$. The organic layer was washed with $H_2O$ and aqueous saturated $NaHCO_3$, dried over $Na_2SO_4$, filtered and concentrated under reduced pressure to afford an orange oil. The residue was purified by flash column chromatography (10:1 Hexanes/EtOAc) to provide 6.85 g (83%) of desired product as a yellow/orange oil.

Step D: Preparation of 8-(tert-butyldimethylsilyloxy)-2-((2-(4-(2-methoxyethoxy)pyridin-2-yl)hydrazono)methyl)quinoline: 2-Hydrazinyl-4-(2-methoxyethoxy)pyridine (0.076 g, 0.415 mmol) and 8-(tert-butyldimethylsilyloxy)quinoline-2-carbaldehyde (0.119 g, 0.415 mmol) were heated to reflux in EtOH (2 mL) for 16 hours. After cooling to ambient temperature the reaction mixture was filtered and washed with EtOH to provide 105 mg (56%) of desired product as an orange solid.

Step E: Preparation of 8-(tert-butyldimethylsilyloxy)-2-(7-(2-methoxyethoxy)-[1,2,4]triazolo[4,3-a]pyridin-3-yl)quinoline: To a solution of 8-(tert-butyldimethylsilyloxy)-2-((2-(4-(2-methoxyethoxy)pyridin-2-yl)hydrazono)methyl)quinoline (0.101 g, 0.223 mmol) in DCM (1.0 mL) was added iodosobenzene diacetate (0.0719 g, 0.223 mmol). After stirring at ambient temperature for 5 hours the reaction mixture was partitioned between DCM and aqueous saturated $Na_2S_2O_3$. The organic layer was washed with brine, dried over $Na_2SO_4$, filtered and concentrated under reduced pressure. The residue was purified by flash column chromatography (40:1 DCM/MeOH) to provide 70 mg (70%) of desired product.

Step F: Preparation of 2-(7-(2-methoxyethoxy)-[1,2,4]triazolo[4,3-a]pyridin-3-yl)quinolin-8-ol: To a solution of 8-(tert-butyldimethylsilyloxy)-2-(7-(2-methoxyethoxy)-[1,2,4]triazolo[4,3-a]pyridin-3-yl)quinoline (0.070 g, 0.155 mmol) in THF (8 mL) was added 1M HCl (1.5 mL, 1.50 mmol). After stirring at ambient temperature for 2 hours, 1 M HCl (5 mL) was added and the reaction mixture stirred for an additional 16 hours. The mixture was neutralized with 1M NaOH and diluted with EtOAc. The organic layer was washed with brine, dried over $Na_2SO_4$, filtered and concentrated under reduced pressure to give 40 mg (77%) of desired product. MS APCI (+) m/z 337.3 (M+1) detected.

Example 38

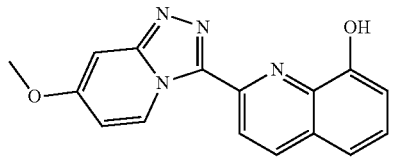 [SMILES: COc1ccn2c(-c3ccc4cccc(O)c4n3)nnc2c1]

2-(7-methoxy-[1,2,4]triazolo[4,3-a]pyridin-3-yl)quinolin-8-ol

Prepared as described in Example 37 using the 4-methoxy-2-chloropyridine in place of 2-chloro-4-(2-methoxyethoxy)pyridine. MS APCI (+) m/z 293.5 (M+1) detected.

Example 39

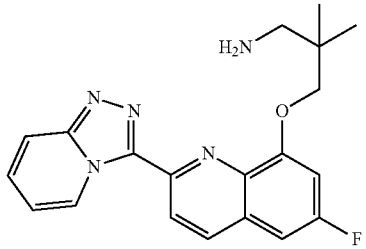 [SMILES: CC(C)(CN)COc1cc(F)cc2ccc(-c3nnc4ccccn34)nc12]

3-(2-([1,2,4]triazolo[4,3-a]pyridin-3-yl)-6-fluoro-quinolin-8-yloxy)-2,2-dimethylpropan-1-amine Step A: Preparation of 6-fluoro-2-methylquinolin-8-ol: 2-amino-5-fluorophenol (13.0 g, 102 mmol) was dissolved in 6N HCl (78 mL) and heated to reflux. The solution was treated with (E)-but-2-enal (8.8 mL, 107 mmol) in 1 mL portions over 1 hour. The reaction was heated at reflux for 13 hours. The reaction mixture was cooled and adjusted to pH 8 with concentrated NH₄OH. The reaction was diluted with ethyl acetate, stirred for 30 minutes then filtered through a nylon membrane (0.45 µM). The filtrate was separated and the aqueous was washed with ethyl acetate then the combined organics were washed with saturated NaHCO₃, saturated NaCl, dried over Na₂SO₄ and concentrated in vacuo to provide the product as a thick dark oil (19 g). MS APCI (+) m/z 178.1 (M+1) detected.

Step B: Preparation of 6-fluoro-2-methyl-8-(triisopropylsilyloxy)quinoline: 6-fluoro-2-methylquinolin-8-ol (19.0 g, 107 mmol) was dissolved in methylene chloride (300 mL) and treated with 1H-imidazole (10.9 g, 160 mmol) and triisopropylsilyl trifluoromethanesulfonate (33.1 mL, 123 mmol). The reaction was stirred at ambient temperature for 13 hours. The reaction mixture was quenched with saturated NH₄Cl and separated. The organic layer was washed twice with saturated NH₄Cl, dried over Na₂SO₄ and concentrated in vacuo to provide the desired product (35 g).

Step C: Preparation of 6-fluoro-8-(triisopropylsilyloxy)quinoline-2-carbaldehyde: 6-fluoro-2-methyl-8-(triisopropylsilyloxy)quinoline (1.76 g, 5.29 mmol) was dissolved in dioxane (58 mL) and water (0.49 mL). The reaction was treated with selenium dioxide (0.76 g, 6.8 mmol) and the mixture was heated to reflux for 13 hours. The mixture was cooled and filtered through GF/F paper. The filtered solids were washed with Et₂O and all the filtrates were concentrated in vacuo. The crude mixture was chromatographed on SiO₂ eluting with a gradient of 1-5% Et₂O/hexanes to provide the desired product (0.515 g).

Step D: Preparation of 6-fluoro-2-((2-(pyridin-2-yl)hydrazono)methyl)-8-(triisopropylsilyloxy)quinoline: 6-Fluoro-8-(triisopropylsilyloxy)quinoline-2-carbaldehyde (15.0 g, 43.2 mmol) and 2-hydrazinylpyridine (4.71 g, 43.2 mmol) were combined in 100 mL of anhydrous EtOH, and stirred at ambient temperature over night. Following over night stirring, the desired product was collected by filtration (washing with cold EtOH), affording 6-fluoro-2-((2-(pyridin-2-yl)hydrazono)methyl)-8-(triisopropylsilyloxy)quinoline (14.0 g, 31.9 mmol, 74% yield) as a yellow-white powder.

Step E: Preparation of 2-([1,2,4]triazolo[4,3-a]pyridin-3-yl)-6-fluoro-8-(triisopropylsilyloxy)quinoline: 6-Fluoro-2-((2-(pyridin-2-yl)hydrazono)methyl)-8-(triisopropylsily-loxy)quinoline (10 g, 23 mmol) was weighed into a 1000 mL 1 neck round bottom flask, followed by addition of iodo benzene diacetate (8.1 g, 25 mmol) and 400 mL of dichloromethane. The mixture was stirred at ambient temperature for 24 hours, at which time the reaction was complete. The crude mixture was partitioned with Na₂S₂O₃, back extracted with DCM, and the combined organics were washed with brine and dried over sodium sulfate, then concentrated in vacuo. The crude product was the purified by flash column chromatography (SP1 Biotage Horizon, 1-15% MeOH/DCM gradient elution), affording the desired product (9.4 g, 94% yield) as a white powder.

Step F: Preparation of 2-([1,2,4]triazolo[4,3-a]pyridin-3-yl)-6-fluoroquinolin-8-ol: 2-([1,2,4]triazolo[4,3-a]pyridin-3-yl)-6-fluoro-8-(triisopropylsilyloxy)quinoline (5.00 g, 11.5 mmol) was dissolved in 250 mL of anhydrous THF, followed by cooling to 0° C., then addition of TBAF (4.49 g, 17.2 mmol). Following 1 hour, the reaction was complete by TLC, and the crude reaction partitioned between water and ethyl acetate. The crude work-up was then filtered through standard filter paper with ethyl acetate wash, affording the desired product 2-([1,2,4]triazolo[4,3-a]pyridin-3-yl)-6-fluoro-quinolin-8-ol (2.8 g, 9.99 mmol, 87% yield) as a white solid.

Step G: Preparation of: 3-(2-([1,2,4]triazolo[4,3-a]pyridin-3-yl)-6-fluoroquinolin-8-yloxy)-2,2-dimethylpropan-1-amine: The desired product was prepared as described in Example 25 using 3-(tert-butoxycarbonylamino)-2,2-dimethylpropyl methanesulfonate in place of (cis)-tert-butyl-3-fluoro-4-(methylsulfonyloxy)piperidine-1-carboxylate, and 2-([1,2,4]triazolo[4,3-a]pyridin-3-yl)-6-fluoroquinolin-8-ol in place of 2-([1,2,4]triazolo[4,3-a]pyridin-3-yl)quinolin-8-ol. MS ESI (+) m/z 366 (M+1) detected.

Example 40

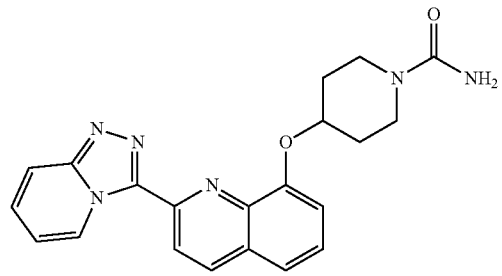 [SMILES: NC(=O)N1CCC(Oc2cccc3ccc(-c4nnc5ccccn45)nc23)CC1]

4-(2-([1,2,4]triazolo[4,3-a]pyridin-3-yl)quinolin-8-yloxy)piperidine-1-carboxamide To a solution of 2-([1,2,4]triazolo[4,3-a]pyridin-3-yl)-8-(piperidin-4-yloxy)quinoline (prepared as described in Example 9, 46 mg, 0.133 mmol) in CH₂Cl₂ (5 mL) were added DIEA (116 µL, 0.67 mmol), DMAP (2 mg, 0.01 mmol), and TMS-isocyanate (104 µL, 0.67 mmol). The reaction mixture was stirred at ambient temperature for 16 hours then partitioned between saturated NaHCO₃ and CH₂Cl₂. The aqueous layer was extracted with CH₂Cl₂ and the combined organic phases were washed with brine, dried over Na₂SO₄, filtered and concentrated. The residue was purified by flash column chromatography with gradient elution (CH₂Cl₂ to 1% MeOH/CH₂Cl₂ to 3% MeOH/CH₂Cl₂) to afford desired product (33 mg, 64%) as a colorless glass. MS ESI (+) m/z 411.2 (M+Na⁺) detected.

Example 41

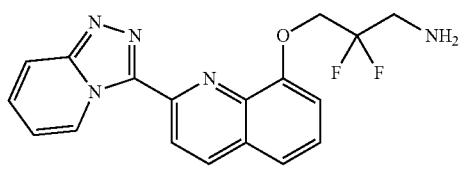 [SMILES: NCC(F)(F)COc1cccc2ccc(-c3nnc4ccccn34)nc12]

3-(2-([1,2,4]triazolo[4,3-a]pyridin-3-yl)quinolin-8-yloxy)-2,2-difluoropropan-1-amine Prepared as described in Example 23 using 3-(tert-butoxycarbonylamino)-2,2-difluoropropyl methanesulfonate in place of neopentyl iodide. Boc deprotection was achieved as described in Example 9, Step B. MS ESI (+) m/z 356.2 (M+1) detected.

Example 42

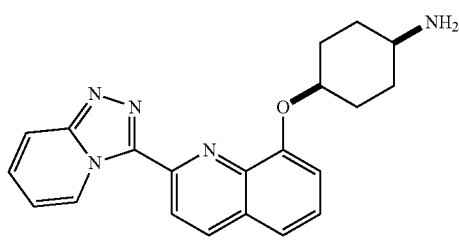

(cis)-4-(2-([1,2,4]triazolo[4,3-a]pyridin-3-yl)quinolin-8-yloxy)cyclohexanamine

Prepared as described in Example 9, using tert-butyl (trans)-4-hydroxycyclohexylcarbamate in place of tert-butyl 4-hydroxypiperidine-1-carboxylate. MS ESI (+) m/z 360.5 (M+1) detected.

Example 43

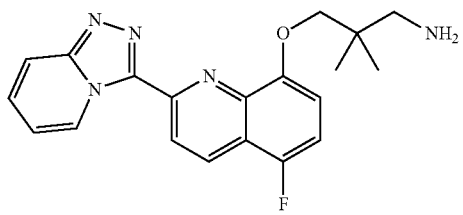 [SMILES: CC(C)(CN)COc1ccc(F)c2ccc(-c3nnc4ccccn34)nc12]

3-(2-([1,2,4]triazolo[4,3-a]pyridin-3-yl)-5-fluoroquinolin-8-yloxy)-2,2-dimethylpropan-1-amine Prepared as described in Example 39 using 2-([1,2,4]triazolo[4,3-a]pyridin-3-yl)-5-fluoroquinolin-8-ol (which was prepared from 2-amino-4-fluorophenol in place of 2-amino-5-fluorophenol in Step A) as a replacement for, 2-([1,2,4]triazolo[4,3-a]pyridin-3-yl)-6-fluoroquinolin-8-ol. MS ESI (+) m/z 366.2 (M+1) detected.

Example 44

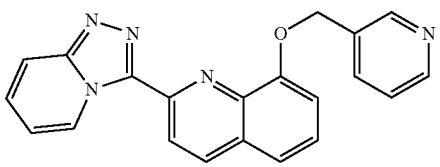 [SMILES: c1cncc(COc2cccc3ccc(-c4nnc5ccccn45)nc23)c1]

2-([1,2,4]triazolo[4,3-a]pyridin-3-yl)-8-(pyridin-3-ylmethoxy)quinoline

Prepared as described in Example 23 using 3-(iodomethyl)pyridine in place of neopentyl iodide and DMF in place of DMA. MS ESI (+) m/z 354.2 (M+1) detected.

Example 45

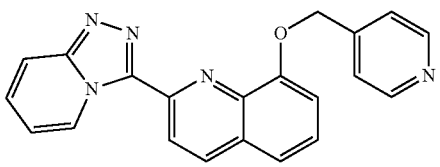 [SMILES: c1cc(OCc2ccncc2)c2nc(-c3nnc4ccccn34)ccc2c1]

2-([1,2,4]triazolo[4,3-a]pyridin-3-yl)-8-(pyridin-4-ylmethoxy)quinoline

Prepared as described in Example 23 using 4-(bromomethyl)pyridine in place of neopentyl iodide and DMF in place of DMA. MS ESI (+) m/z 354.1 (M+1) detected.

Example 46

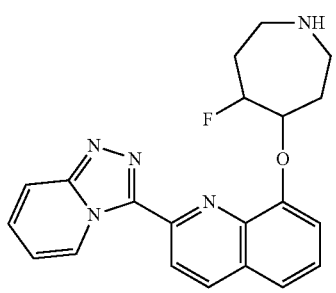 [SMILES: FC1CCNCCC1Oc1cccc2ccc(-c3nnc4ccccn34)nc12]

2-([1,2,4]triazolo[4,3-a]pyridin-3-yl)-8-(5-fluoroazepan-4-yloxy)quinoline

Step A: Preparation of 1-tert-butyl 4-ethyl 4-fluoro-5-oxoazepane-1,4-dicarboxylate: NaH (2.66 g, 105 mmol) was suspended in THF (300 mL) and cooled to 0° C., and 1-tert-butyl 4-ethyl 5-oxoazepane-1,4-dicarboxylate (30 g, 105 mmol) was added as THF solution (550 mL) using an addition funnel over 30 minutes. The mixture was stirred for 30 minutes and then diluted with DMF (200 mL). Selectfluor (41.0 g, 116 mmol) was added as a DMF solution (200 mL). The mixture was warmed to ambient temperature and stirred for 2 hours. The mixture was then concentrated to remove THF and diluted with 1N $KHSO_4$ (300 mL), water (300 mL) and EtOAc (750 mL). The organic layer was washed with brine (2×250 mL). The combined aqueous layers were washed with EtOAc (200 mL) and this organic layer was washed with brine (200 mL). The combined organic layers were then dried over $Na_2SO_4$, filtered and concentrated. The crude product was passed through a silica gel plug (1 kg, 20 to 40% EtOAc/hexanes) to provide 23.6 g (74%) of the product as a colorless oil.

Step B: Preparation of tert-butyl 4-fluoro-5-oxoazepane-1-carboxylate: To a 500 mL flask containing the product from Step A (23.5 g, 77.5 mmol) was added DMSO (160 mL) followed by $H_2O$ (6.98 mL, 387 mmol) and then LiCl (16.4 g, 387 mmol). The mixture was warmed to 125° C. and stirred for 5 hours. The resulting dark mixture was then cooled to ambient temperature and diluted with EtOAc (500 mL) and washed with a saturated aqueous $NaHCO_3$:water (1:1, 3×250 mL). The combined aqueous phase was washed with EtOAc (100 mL) and the combined organic phases were washed with brine and dried over $Na_2SO_4$, filtered and concentrated. The crude oil was purified by column chromatography (10 to 30% EtOAc/hexanes) to provide 10.0 g (56%) of the desired product as a light golden oil.

Step C: Preparation of tert-butyl 4-fluoro-5-hydroxyazepane-1-carboxylate: To a 50 mL flask containing the product from Step B (1.0 g, 4.32 mmol) was added MeOH (20 mL), and the resulting solution was cooled to 0° C. $NaBH_4$ (0.409 g, 10.8 mmol) was carefully added and the mixture stirred at 0° C. for 3.0 hours. The mixture was concentrated to remove the solvent and the residue was taken up in EtOAc (50 mL) and a saturated aqueous $NH_4Cl$ solution (20 mL) was added followed by water (20 mL). The layers were mixed and separated and the aqueous phase extracted with EtOAc (2×20 mL). The combined organic extracts were washed with brine and dried over $Na_2SO_4$, then filtered and concentrated. The crude product was purified by column chromatography (10% to 60% EtOAc/hexanes gradient) to provide 0.980 g (97%) of the product as a thick colorless oil that solidified to a white solid while standing overnight. The product contained of a mixture of cis and trans isomers.

Step D: Preparation of tert-butyl 4-(2-([1,2,4]triazolo[4,3-a]pyridin-3-yl)quinolin-8-yloxy)-5-fluoroazepane-1-carboxylate: Prepared as described in Example 9 using the product of Step C in place of tert-butyl 4-hydroxypiperidine-1-carboxylate in Step A and substituting THF:Toluene (1:1) for THF. MS ESI (+) m/z 478.1 (M+1) detected.

Step E: Preparation of 2-([1,2,4]triazolo[4,3-a]pyridin-3-yl)-8-((5-fluoroazepan-4-yloxy)quinoline: To a solution of tert-butyl 4-(2-[1,2,4]triazolo[4,3-a]pyridin-3-yl)quinolin-8-yloxy)-5-fluoroazepane-1-carboxylate (0.157 g, 0.329 mmol) in $CHCl_3$ (3.2 mL) was added HCl (3.29 mL, 13.2 mmol, 4.0 M in dioxane). The mixture was stirred at ambient temperature for 5 hours and was then filtered directly. The solid was washed with $CH_2Cl_2$ (5 mL) and $Et_2O$ (5 mL) and carefully dried in vacuo to afford the desired product as an off-white solid. The salt was purified directly by column chromatography (10% $MeOH/CH_2Cl_2$ with 1% $NH_3$) to provide the free amine product as an off-white solid. MS ESI (+) m/z 378.1 (M+1) detected.

Example 47

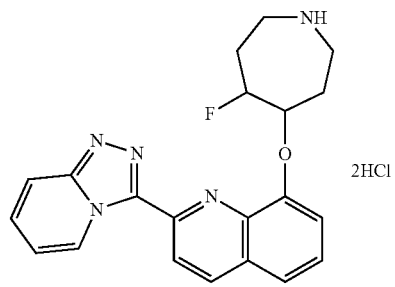 [SMILES: FC1CCNCCC1Oc1cccc2ccc(-c3nnc4ccccn34)nc12]

Stereoisomer #1 of 2-([1,2,4]triazolo[4,3-a]pyridin-3-yl)-8-(-5-fluoroazepan-4-yloxy)quinoline dihydrochloride Step A: Preparation of Stereoisomer #1 of tert-butyl 4-(2-([1,2,4]triazolo[4,3-a]pyridin-3-yl)quinolin-8-yloxy)-5-fluoroazepane-1-carboxylate: The racemic material from Example 46 (Step D) was purified by Chiral HPLC OJ-H 85% MeOH/15% EtOH, to provide the first eluting peak as a single stereoisomer (99% ee, 99% de), designated stereoisomer #1.

Step B: Preparation of Stereoisomer #1 of 2-([1,2,4]triazolo[4,3-a]pyridin-3-yl)-8-(-5-fluoroazepan-4-yloxy)quinoline dihydrochloride: To a 10 mL flask containing the product from Step A (0.138 g, 0.289 mmol) was added $CHCl_3$ (3.0 mL). To this stirring solution was added HCl (2.89 mL, 11.6 mmol, in dioxane). The mixture was stirred at ambient temperature for 3.0 hours and then filtered directly and washed with $CH_2Cl_2$ and $Et_2O$ and dried carefully in vacuo. This provided 0.120 g (92%) of the desired product as an off-white solid. MS ESI (+) m/z 378.1 (M+1) detected.

Example 48

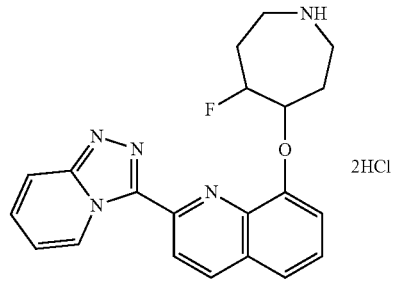 [SMILES: FC1CCNCCC1Oc1cccc2ccc(-c3nnc4ccccn34)nc12]

Stereoisomer #2 of 2-([1,2,4]triazolo[4,3-a]pyridin-3-yl)-8-(5-fluoroazepan-4-yloxy)quinoline dihydrochloride Step A: Preparation of Stereoisomer #2 of tert-butyl 4-(2-([1,2,4]triazolo[4,3-a]pyridin-3-yl)quinolin-8-yloxy)-5-fluoroazepane-1-carboxylate: The racemic material from Example 46 (Step D) was purified by Chiral HPLC OJ-H 85%

MeOH/15% EtOH, to provide the second eluting peak as a single stereoisomer (99% ee, 99% de), designated as stereoisomer #2.

Step B: Preparation of Stereoisomer #2 of 2-([1,2,4]triazolo[4,3-a]pyridin-3-yl)-8-(5-fluoroazepan-4-yloxy)quinoline dihydrochloride: Deprotection was performed as described in Example 47, step B. MS ESI (+) m/z 378.1 (M+1) detected. Specific rotation: $[\alpha]^{25}_D = -66°$ (c=0.5, MeOH).

Example 49

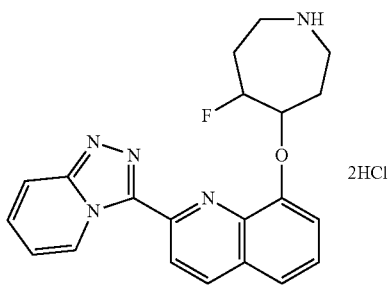 [SMILES: FC1CCNCCC1Oc1cccc2ccc(-c3nnc4ccccn34)nc12]

Stereoisomer #3 of 2-([1,2,4]triazolo[4,3-a]pyridin-3-yl)-8-(5-fluoroazepan-4-yloxy)quinoline dihydrochloride Step A: Preparation of Stereoisomer #3 of tert-butyl 4-(2-([1,2,4]triazolo[4,3-a]pyridin-3-yl)quinolin-8-yloxy)-5-fluoroazepane-1-carboxylate: The racemic material from Example 46 (Step D) was purified by Chiral HPLC OJ-H 85% MeOH/15% EtOH, to provide the third eluting peak as a single stereoisomer (99% ee, 99% de), designated as Stereoisomer #3.

Step B: Preparation of Stereoisomer #3 of 2-([1,2,4]triazolo[4,3-a]pyridin-3-yl)-8-(5-fluoroazepan-4-yloxy)quinoline dihydrochloride: Deprotection was performed as described in Example 47, step B. MS ESI (+) m/z 378.1 (M+1) detected. Specific rotation: $[\alpha]^{25}_D = -71°$ (c=0.95, MeOH).

Example 50

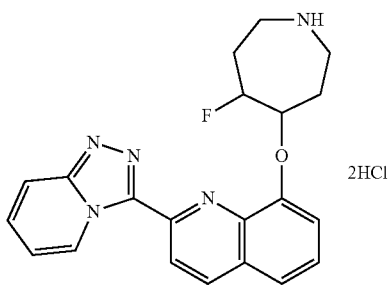 [SMILES: FC1CCNCCC1Oc1cccc2ccc(-c3nnc4ccccn34)nc12]

Stereoisomer #4 of 2-([1,2,4]triazolo[4,3-a]pyridin-3-yl)-8-(5-fluoroazepan-4-yloxy)quinoline dihydrochloride Step A: Preparation of Stereoisomer #4 of tert-butyl 4-(2-([1,2,4]triazolo[4,3-a]pyridin-3-yl)quinolin-8-yloxy)-5-fluoroazepane-1-carboxylate: The racemic material from Example 46 (Step D) was purified by Chiral HPLC OJ-H 85% MeOH/15% EtOH, to provide the fourth eluting peak as a single stereoisomer (99% ee, 60% de), designated as stereoisomer #4.

Step B: Preparation of Stereoisomer #4 of 2-([1,2,4]triazolo[4,3-a]pyridin-3-yl)-8-(5-fluoroazepan-4-yloxy)quinoline dihydrochloride: Deprotection was performed as described in Example 47, step B. MS ESI (+) m/z 378.1 (M+1) detected.

Example 51

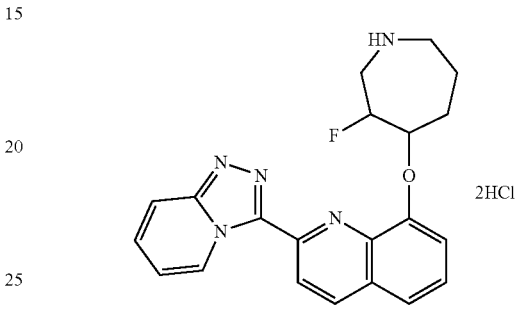

2-([1,2,4]triazolo[4,3-a]pyridin-3-yl)-8-(3-fluoroazepan-4-yloxy)quinoline dihydrochloride Step A: Preparation of 1-tert-butyl 4-ethyl 6-fluoro-5-oxoazepane-1,4-dicarboxylate: A solution of tert-butyl 3-fluoro-4-oxopiperidine-1-carboxylate (20.0 g, 92.1 mmol) in 1:1 (CH$_2$Cl$_2$:Et$_2$O, 250 mL) was cooled to –60° C. using an IPA/dry ice bath. In a separate flask was added BF$_3$-Etherate (12.8 mL, 101 mmol) and Et$_2$O (40 mL) which was cooled to 0° C., then ethyl 2-diazoacetate (12.6 mL, 120 mmol) was added. This mixture was added to the oxopiperidine solution and the reaction mixture was slowly warmed to ambient temperature over 2 hours. Water was added (100 mL) and the mixture was stirred at ambient temperature for 30 minutes. The phases were separated and the aqueous phase was extracted with EtOAc (100 mL) and the combined organic phases were washed with 1N KHSO$_4$, followed by brine and then dried over Na$_2$SO$_4$, filtered and concentrated. This provided the product as a thick, yellow oil (26 g).

Step B: Preparation of tert-butyl 3-fluoro-4-oxoazepane-1-carboxylate: The product from Step A was dissolved in DMSO (200 mL) and H$_2$O (8.29 g, 460 mmol) followed by addition of LiCl (19.5 g, 460 mmol). The solution was warmed to 125° C. and the mixture was stirred overnight. The mixture was cooled to ambient temperature and partitioned between EtOAc (2.5 L) and water:brine (1:1, 2.0 L). The mixture was filtered through activated charcoal over Celite, which was washed with EtOAc, forming visible layers. The organic layer was dried over Na$_2$SO$_4$, filtered and concentrated. The crude product was purified by column chromatography (10 to 80% EtOAc/hexanes) providing 4.5 g (21%) of the product as a thick pale orange oil.

Step C: Preparation of tert-butyl 3-fluoro-4-hydroxyazepane-1-carboxylate:

To a solution of the product from Step B (0.300 g, 1.30 mmol) in MeOH (6 mL) at 0° C. was added NaBH$_4$ (0.123 g, 3.24 mmol) in one portion, and the mixture was warmed to ambient temperature and stirred for 5.0 hours. The mixture was concentrated and the residue was taken up in EtOAc (20 mL) and a saturated aqueous NH₄Cl solution (5 mL) and water (5 mL). The layers were mixed and separated and the aqueous phase extracted with EtOAc (2×10 mL). The combined organic extracts were washed with brine and dried over Na₂SO₄, then filtered and concentrated. The crude product was purified by column chromatography (12% to 60% EtOAc/hexanes gradient) to provide 0.130 g (43%) of the major isomer as a colorless oil that solidified overnight to a white solid.

Step D: Preparation of tert-butyl 4-(2-([1,2,4]triazolo[4,3-a]pyridin-3-yl)quinolin-8-yloxy)-3-fluoroazepane-1-carboxylate: Prepared as described in Example 9 using tert-butyl 3-fluoro-4-hydroxyazepane-1-carboxylate in place of tert-butyl 4-hydroxypiperidine-1-carboxylate in Step A, substituting THF:Toluene (1:1) for THF and using DIAD in place of DEAD.

Step E: Preparation of 2-([1,2,4]triazolo[4,3-a]pyridin-3-yl)-8-(3-fluoroazepan-4-yloxy)quinoline dihydrochloride: To a solution of the product from Step D (0.10 g, 0.21 mmol) in CHCl₃ (2.1 mL) was added HCl (2.1 mL, 8.4 mmol, 4.0M in 1,4-Dioxane) and the reaction was stirred at ambient temperature for 5.0 hours. The resulting off-white suspension was directly filtered and the solid was washed with Et₂O and dried in vacuo. This provided 0.089 g (88%) of the desired product as an off-white solid. MS ESI (+) m/z 378.1 (M+1) detected.

Example 52

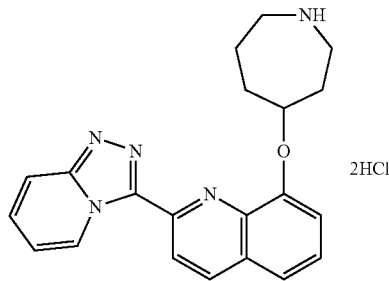 [SMILES: c1cc(OC2CCCNCC2)c2nc(-c3nnc4ccccn34)ccc2c1]

2-([1,2,4]triazolo[4,3-a]pyridin-3-yl)-8-(azepan-4-yloxy)quinoline dihydrochloride Step A: Preparation of tert-butyl 4-hydroxyazepane-1-carboxylate: A solution of tert-butyl 4-oxoazepane-1-carboxylate (0.60 g, 2.81 mmol), in MeOH (11 mL) was cooled to 0° C. NaBH₄ (0.266 g, 7.03 mmol) was added and the mixture was slowly warmed to ambient temperature where the reaction stirred overnight. The mixture was concentrated in vacuo and the residue was taken up in EtOAc (20 mL) and saturated aqueous NH₄Cl solution (20 mL). The layers were separated and the aqueous phase was extracted with EtOAc (2×10 mL). The combined organic extracts were washed with brine and dried over Na₂SO₄, then filtered and concentrated. The product was isolated as a thick colorless oil that solidified overnight to a white solid.

Step B: Preparation of tert-butyl 4-(2-([1,2,4]triazolo[4,3-a]pyridin-3-yl)quinolin-8-yloxy)azepane-1-carboxylate: Prepared as described in Example 9 using tert-butyl 4-hydroxyazepane-1-carboxylate in place of tert-butyl 4-hydroxypiperidine-1-carboxylate in Step A and substituting THF:Toluene (1:1) for THF and using DIAD in place of DEAD.

Step C: Preparation of 2-([1,2,4]triazolo[4,3-a]pyridin-3-yl)-8-(azepan-4-yloxy)quinoline dihydrochloride: To a solution of the product from Step B (0.40 g, 0.870 mmol) in CHCl₃ (9 mL) was added hydrogen chloride (7.62 mL, 30.5 mmol, 4.0 M in dioxane) and the reaction was stirred at ambient temperature for 5 hours. The resulting yellow solid was removed by direct filtration and the solid was washed with Et₂O and dried in vacuo to provide 0.296 g (72%) of the desired product as a yellow solid. MS ESI (+) m/z 360.1 (M+1) detected.

Example 53

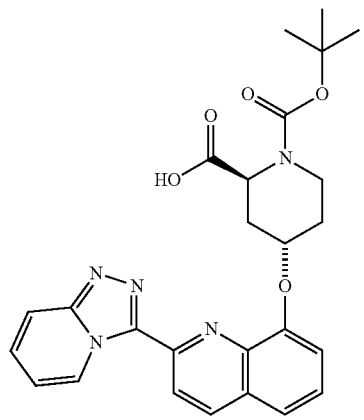

(2S,4S)-4-(2-([1,2,4]triazolo[4,3-a]pyridin-3-yl)quinolin-8-yloxy)-1-(tert-butoxycarbonyl)piperidine-2-carboxylic acid Step A: Preparation of (2S,4S)-di-tert-butyl 4-(2-([1,2,4]triazolo[4,3-a]pyridin-3-yl)quinolin-8-yloxy)piperidine-1,2-dicarboxylate: Prepared as described in Example 9 using di-tert-butyl (2S,4R)-4-hydroxy-1,2-piperidinedicarboxylate (prepared as described in J. Org. Chem. 2004, 69, 130) in place of tert-butyl 4-hydroxypiperidine-1-carboxylate in Step A and using DIAD in place of DEAD.

Step B: Preparation of (2S,4S)-4-(2-([1,2,4]triazolo[4,3-a]pyridin-3-yl)quinolin-8-yloxy)-1-piperidine-2-carboxylic acid: A solution of the product from Step A (1.3 g, 2.38 mmol) in TFA (6.42 mL, 83.4 mmol) was stirred at ambient temperature for 6 hours at which time the reaction was complete by HPLC. TFA was co-evaporated with hexanes and the residue was triturated with Et₂O and filtered. The solid was washed with Et₂O and dried in vacuo and taken on directly to the next step.

Step C: Preparation of (2S,4S)-4-(2-([1,2,4]triazolo[4,3-a]pyridin-3-yl)quinolin-8-yloxy)-1-(tert-butoxycarbonyl)piperidine-2-carboxylic acid: The product from Step B was then dissolved in THF (7 mL) and H₂O (3 mL) and was treated with NaOH (1.59 mL, 4.77 mmol, 3.0 M aqueous). Boc₂O (0.780 g, 3.57 mmol) was added and the reaction was stirred at ambient temperature overnight. THF was removed in vacuo and the residue was dissolved in water (20 mL) and Et₂O (10 mL). The layers were mixed and separated and the aqueous phase extracted with Et₂O (3×10 mL). The aqueous phase was adjusted to pH=2 with 1N KHSO₄. The acidic mixture was extracted with EtOAc (75 mL then 3×25 mL). The combined organic layers were washed with water and brine, and the combined aqueous phases were washed with EtOAc (50 mL). The combined organic layers were then dried over Na$_2$SO$_4$, filtered and concentrated to afford 1.06 g (70% pure, 63% yield) of the product. MS ESI (+) m/z 489.9 (M) detected.

Example 54

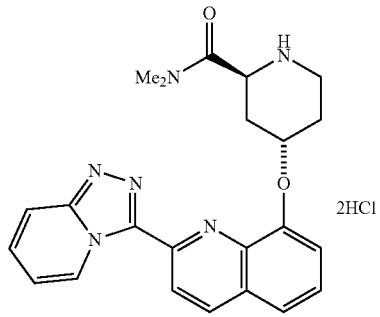

(2S,4S)-4-(2-([1,2,4]triazolo[4,3-a]pyridin-3-yl)quinolin-8-yloxy)-N,N-dimethylpiperidine-2-carboxamide dihydrochloride Step A: Preparation of (2S,4S)-tert-butyl 4-(2-([1,2,4]triazolo[4,3-a]pyridin-3-yl)quinolin-8-yloxy)-2-(dimethylcarbamoyl)piperidine-1-carboxylate: (2S,4S)-4-(2-([1,2,4]triazolo[4,3-a]pyridin-3-yl)quinolin-8-yloxy)-1-(tert-butoxycarbonyl)piperidine-2-carboxylic acid (Example 53; 0.100 g, 0.204 mmol), EDCI (0.0548 g, 0.286 mmol) and HOBT (0.0373 g, 0.276 mmol) were mixed in CH$_2$Cl$_2$ (2.5 mL) and the mixture was cooled to 0° C. Triethylamine (0.0712 mL, 0.511 mmol) was added and the mixture stirred for 15 minutes. Dimethylamine (0.153 mL, 0.306 mmol, 2.0M in THF) was added, and the mixture was warmed to ambient temperature and stirred for 5.0 hours. The mixture was diluted with EtOAc (20 mL) and washed with 1N KHSO$_4$ (2×10 mL), followed by saturated aqueous NaHCO$_3$, and brine. The organics were dried over MgSO$_4$, filtered and concentrated, then purified by column chromatography (1 to 5% MeOH/CH$_2$Cl$_2$) to afford 0.080 g (75%) of the desired product.

Step B: Preparation of (2S,4S)-4-(2-([1,2,4]triazolo[4,3-a]pyridin-3-yl)quinolin-8-yloxy)-N,N-dimethylpiperidine-2-carboxamide dihydrochloride: To the product from Step A (0.080 g, 0.155 mmol) was added chloroform (1.6 mL). To the resulting solution was added hydrogen chloride (0.387 mL, 1.55 mmol, 4.0 M in 1,4-dioxane) causing the solution to turn yellow. The mixture was stirred at ambient temperature for 3 hours. Additional hydrogen chloride (0.387 mL, 1.55 mmol, 4.0 M in 1,4-dioxane) was added and the reaction stirred at ambient temperature for another 3 hours. The mixture was diluted with diethyl ether (5 mL) and filtered. The product was washed with Et$_2$O and dried in vacuo to provide 0.068 g (86%) of the desired product as a yellow solid. MS ESI (+) m/z 417.1 (M+1) detected.

Example 55

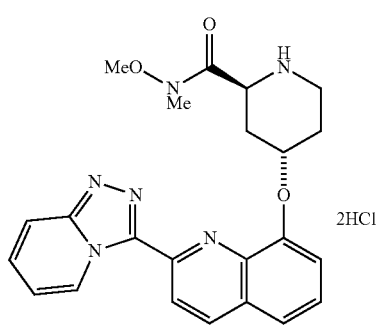

(2S,4S)-4-(2-([1,2,4]triazolo[4,3-a]pyridin-3-yl)quinolin-8-yloxy)-N-methoxy-N-methylpiperidine-2-carboxamide dihydrochloride Step A: Preparation of (2S,4S)-tert-butyl 4-(2-([1,2,4]triazolo[4,3-a]pyridin-3-yl)quinolin-8-yloxy)-2-(methoxy(methyl)carbamoyl)piperidine-1-carboxylate: (2S,4S)-4-(2-([1,2,4]triazolo[4,3-a]pyridin-3-yl)quinolin-8-yloxy)-1-(tert-butoxycarbonyl)piperidine-2-carboxylic acid (Example 53; 0.100 g, 0.204 mmol), EDCI (0.0548 g, 0.286 mmol) and HOBT (0.0359 g, 0.266 mmol) were mixed in CH$_2$Cl$_2$ (2.5 mL) and the mixture was cooled to 0° C. Triethylamine (0.0712 mL, 0.511 mmol) was added and the mixture was stirred for 15 minutes. Dimethyl hydroxylamine HCl (0.0299 g, 0.306 mmol) was added, and the mixture was warmed to ambient temperature and stirred for 4.5 hours. The mixture was diluted with EtOAc (20 mL) and washed with 1N KHSO$_4$ (2×10 mL), followed by a saturated aqueous NaHCO$_3$ solution and brine. The organic layer was dried over Na$_2$SO$_4$, filtered and concentrated. The crude material was purified by column chromatography (1 to 5% MeOH/CH$_2$Cl$_2$) to provide 0.076 g (70%) of the product as a white foam.

Step B: Preparation of (2S,4S)-4-(2-([1,2,4]triazolo[4,3-a]pyridin-3-yl)quinolin-8-yloxy)-N-methoxy-N-methylpiperidine-2-carboxamide dihydrochloride: To the product from Step A (0.032 g, 0.0601 mmol) was added CHCl$_3$ (0.600 mL) and HCl (0.451 mL, 1.80 mmol, 4.0M in dioxane). The mixture was stirred at ambient temperature for 9 hours, then diluted with Et$_2$O (5 mL) and filtered. The solid was washed with Et$_2$O and dried in vacuo. This provided 0.026 g (82%) of the desired product as a pale yellow solid. MS ESI (+) m/z 433.1 (M+1) detected.

Example 56

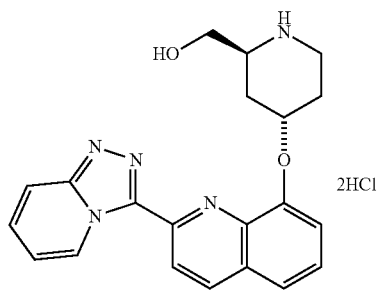

((2S,4S)-4-(2-([1,2,4]triazolo[4,3-a]pyridin-3-yl)quinolin-8-yloxy)piperidin-2-yl)methanol dihydrochloride Step A: Preparation of (2S,4S)-tert-butyl 4-(2-([1,2,4]triazolo[4,3-a]pyridin-3-yl)quinolin-8-yloxy)-2-(hydroxymethyl)piperidine-1-carboxylate: (2S,4S)-4-(2-([1,2,4]triazolo[4,3-a]pyridin-3-yl)quinolin-8-yloxy)-1-(tert-butoxycarbonyl)piperidine-2-carboxylic acid (Example 53; 0.250 g, 0.511 mmol) was dissolved in THF (5.0 mL) and the mixture was cooled to 0° C. BH$_3$—SMe$_2$ (0.242 mL, 2.55 mmol) was added and the mixture was warmed to ambient temperature and stirred for 27 hours. The reaction was quenched with MeOH (2 mL) and concentrated. The residue was taken up in EtOAc (30 mL), water (5 mL) and a saturated aqueous Na$_2$CO3 solution (5 mL). The layers were mixed and separated and the aqueous phase washed once with CH$_2$Cl$_2$ (10 mL). The combined organic phases were washed with brine, dried over Na$_2$SO$_4$, filtered and concentrated. During concentration a precipitate formed which was slurried in MeOH, isolated by filtration and washed with Et$_2$O to give 0.119 g (49%) of the desired product as a pale yellow solid.

Step B: Preparation of ((2S,4S)-4-(2-([1,2,4]triazolo[4,3-a]pyridin-3-yl)quinolin-8-yloxy)piperidin-2-yl)methanol dihydrochloride: The product from Step A (0.017 g, 0.036 mmol) was dissolved in CHCl$_3$ (1.0 mL). HCl (0.27 mL, 1.1 mmol, 4.0M in dioxane) was added. The reaction stirred at ambient temperature for 7 hours. The reaction was diluted with Et$_2$O (10 mL) and the mixture filtered. The solid was washed with Et$_2$O and dried in vacuo to afford 0.0098 g (55%) of the desired product as an off-white solid. MS ESI (+) m/z 376.1 (M+1) detected.

Example 57

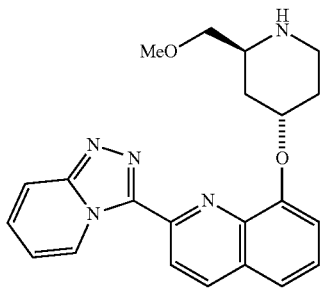

2-([1,2,4]triazolo[4,3-a]pyridin-3-yl)-8)-((2S,4S)-2-(methoxymethyl)piperidin-4-yloxy)quinoline Step A: Preparation of (2S,4S)-tert-butyl 4-(2-([1,2,4]triazolo[4,3-a]pyridin-3-yl)quinolin-8-yloxy)-2-(hydroxymethyl)piperidine-1-carboxylate: (2S,4S)-4-(2-([1,2,4] triazolo[4,3-a]pyridin-3-yl)quinolin-8-yloxy)-1-(tert-butoxycarbonyl)piperidine-2-carboxylic acid (Example 53; 0.250 g, 0.511 mmol) and THF (5.0 mL) was stirred for 10 minutes (until solution was complete) and cooled to 0° C. BH$_3$—SMe$_2$ (0.242 mL, 2.55 mmol) was added and the mixture was warmed to ambient temperature and for 48 hours. The reaction was carefully quenched with MeOH (1 mL) and concentrated. The residue was taken up in CH$_2$Cl$_2$ (20 mL), water (5 mL) and saturated aqueous Na$_2$CO$_3$ (5 mL). The layers were mixed and separated and the aqueous phase was washed with CH$_2$Cl$_2$ (10 mL). The combined organic phases were washed with brine, dried over Na$_2$SO$_4$, filtered and concentrated. The resulting solid was slurried in 25% CH$_2$Cl$_2$/Et$_2$O and filtered to provide 0.140 g (57%) of the desired product as a yellow solid.

Step B: Preparation of (2S,4S)-tert-butyl 4-(2-([1,2,4]triazolo[4,3-a]pyridin-3-yl)quinolin-8-yloxy)-2-(methoxymethyl)piperidine-1-carboxylate: The product from Step A (0.150 g, 0.315 mmol) was dissolved in dry DMF (2.1 mL) and the solution was cooled to 0° C. NaH (0.0159 g, 0.631 mmol) was added and the mixture was stirred at 0° C. for 1 hour. The reaction color went from yellow to a dark red/brown. MeI (0.197 mL, 3.15 mmol) was added and the mixture was warmed to ambient temperature and stirred for 2.0 hours during which the reaction color became lighter. The mixture was diluted with saturated aqueous NaHCO$_3$ (10 mL) and the mixture was extracted with CH$_2$Cl$_2$ (3×10 mL). The combined organic phases were washed with brine and dried over Na$_2$SO$_4$, then filtered and concentrated. The crude product was passed through a silica gel plug to provide the crude yellow product (0.280 g), which was slurried in 1:1 Et$_2$O:hexanes and then filtered to provide 0.075 g (48%) of the product as a pale yellow solid.

Step C: Preparation of 2-([1,2,4]triazolo[4,3-a]pyridin-3-yl)-8-((2S,4S)-2-(methoxymethyl)piperidin-4-yloxy)quinoline: The product from Step B (0.070 g, 0.14 mmol) was dissolved in CHCl$_3$ (1.4 mL). Then HCl (1.4 mL, 5.7 mmol, 4.0M in dioxane) was added and the mixture stirred at ambient temperature for 5.0 hours. The mixture was filtered directly and the solid washed with CH$_2$Cl$_2$ followed by Et$_2$O and dried. The crude solid was purified by preparative TLC (1 mm, 8% MeOH/DCM with 1% NH$_3$). This provided 0.031 g (56%) of the product as a pale orange solid. MS ESI (+) m/z 390.2 (M+1) detected.

Example 58

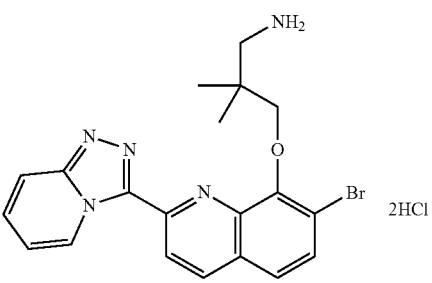 [SMILES: CC(C)(CN)COc1c(Br)ccc2ccc(-c3nnc4ccccn34)nc12]

3-(2-([1,2,4]triazolo[4,3-a]pyridin-3-yl)-7-bromo-quinolin-8-yloxy)-2,2-dimethylpropan-1-amine dihydrochloride Step A: Preparation of 7-bromo-2-methylquinolin-8-ol: To a 250 mL flask was added toluene (150 mL) and t-BuNH$_2$ (7.26 mL, 69.1 mmol). The solution was cooled to −25° C. and bromine (1.95 mL, 38.0 mmol) was added. The solution was cooled to −78° C. and 2-methylquinolin-8-ol (5.5 g, 34.6 mmol) was added as a CH$_2$Cl$_2$ solution (15 mL). The reaction mixture was gradually warmed to ambient temperature over 6 hours. The mixture was washed with water (50 mL) and treated with 3.0 M aqueous NaOH (250 mL). This provided copious amounts of precipitate, which went into solution after about 600 mL water were added. The layers were mixed and separated. The alkaline extract was carefully acidified with concentrated HCl(~50 mL). The solution was extracted with CH$_2$Cl$_2$ (4×200 mL), the combined extracts were washed with brine and dried over Na$_2$SO$_4$, filtered and concentrated. The original water wash was found to contain a significant amount of product, so 10 mL 1M HCl were added and the acidic solution was extracted with CH$_2$Cl$_2$ (2×75 mL) and these layers were also washed with brine, dried over Na$_2$SO$_4$, filtered and concentrated. The organic phases were combined to provide 5.01 g (60%) of the desired product as a red/brown solid.

Step B: Preparation of 7-bromo-8-(tert-butyldimethylsilyloxy)-2-methylquinoline: To the product from Step A (3.0 g, 12.6 mmol) was added imidazole (1.89 g, 27.7 mmol) and CH$_2$Cl$_2$ (40 mL). The solution was cooled to 0° C. and then tert-butylchlorodimethylsilane (2.09 g, 13.9 mmol) was added in one portion. The reaction was gradually warmed to ambient temperature over 1 hour then stirred overnight. The mixture was diluted with a saturated aqueous NH$_4$Cl solution (25 mL) and CH$_2$Cl$_2$ (40 mL). The layers were mixed and separated and the organic layer was washed with brine and dried over Na$_2$SO$_4$, filtered and concentrated. The crude product was purified by column chromatography (2 to 20% CH₂Cl₂/hexanes) to provide 3.36 g (76%) of the desired product as a white solid.

Step C: Preparation of 7-bromo-8-(tert-butyldimethylsilyloxy)quinoline-2-carbaldehyde: A slurry of SeO₂ (0.869 g, 7.83 mmol) and 1,4-dioxane (20 mL) was warmed to 80° C. and the product from Step B (2.3 g, 6.53 mmol) was added as a 1,4-dioxane solution (20 mL). The mixture was stirred at 80° C. for 32 hours and then cooled to ambient temperature and filtered through GF/F filter paper. The residual solid was washed with CH₂Cl₂, and the filtrate was concentrated and purified by passing through a silica gel plug, eluting with 50% CH₂Cl₂/hex to provide 2.14 g (89%) of the product as a yellow/orange solid.

Step D: Preparation of 7-bromo-8-(tert-butyldimethylsilyloxy)-2-((2-(pyridin-2-yl)hydrazono)methyl)quinoline: To the product from Step C (2.95 g, 8.05 mmol) was added EtOH (30 mL, anhydrous). To this solution was added 2-hydrazinylpyridine (0.967 g, 8.86 mmol). The mixture was stirred at ambient temperature for 24 hours. The resulting precipitate was isolated by vacuum filtration, washed with cold EtOH and then dried in vacuo to afford 2.98 g (73%) of the product.

Step E: Preparation of 2-([1,2,4]triazolo[4,3-a]pyridin-3-yl)-7-bromo-8-(tert-butyldimethylsilyloxy)quinoline: To the product from Step D (2.95 g, 6.45 mmol) was added CH₂Cl₂ (60 mL). Iodobenzene diacetate (2.28 g, 7.09 mmol) was added and the mixture stirred at ambient temperature overnight. The mixture was concentrated and the product purified directly by column chromatography (1 to 8% MeOH/CH₂Cl₂) to afford 2.87 g (88%) of the product.

Step F: Preparation of 2-([1,2,4]triazolo[4,3-a]pyridin-3-yl)-7-bromo quinolin-8-ol: To the product from Step E (2.8 g, 6.15 mmol) was added THF (60 mL). The solution was cooled to 0° C. then TBAF.3H₂O (2.33 g, 7.38 mmol) was added and the mixture was stirred for 1 hour. The mixture was then diluted with EtOAc (100 mL) and then washed with saturated aqueous NaHCO₃ (75 mL). The layers were separated and the aqueous phase washed with EtOAc (100 mL). The combined organic phases were washed with brine and dried over Na₂SO₄, filtered and concentrated. The crude mixture was triturated with MeOH and filtered. The solid was washed with Et₂O to provide 0.730 g (35%) of product.

Step G: Preparation of tert-butyl 3-(24 [1,2,4]triazolo[4,3-a]pyridin-3-yl)-7-bromoquinolin-8-yloxy)-2,2-dimethylpropylcarbamate: Prepared as described in Example 9 using tert-butyl 3-hydroxy-2,2-dimethylpropylcarbamate in place of tert-butyl 4-hydroxypiperidine-1-carboxylate in Step A. The crude product was used directly in the next step.

Step H: Preparation of 3-(24 [1,2,4]triazolo[4,3-a]pyridin-3-yl)-7-bromoquinolin-8-yloxy)-2,2-dimethylpropan-1-amine dihydrochloride: To the product from Step G (0.115 g, 0.143 mmol, isolated as a mixture with triphenylphosphine oxide) was added CHCl₃ (1.5 mL). To this solution was added HCl (1.43 mL, 5.72 mmol, 4.0M in dioxane) and the mixture was stirred at ambient temperature for 2.5 hours. The mixture was diluted with CH₂Cl₂ (2 mL) and filtered directly and the resulting solid was washed with CH₂Cl₂ (5 mL) and then with Et₂O. The solid was dried to provide 0.059 g (81%) of the desired product as the di-HCl salt free from triphenylphosphine oxide and as an off-white solid. MS ESI (+) m/z 426.1 (M+H) detected.

Example 59

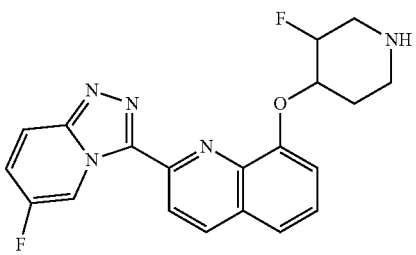 [SMILES: Fc1ccc2nnc(-c3ccc4cccc(OC5CCNCC5F)c4n3)n2c1]

2-(6-fluoro-[1,2,4]triazolo[4,3-a]pyridin-3-yl)-8-((cis)-3-fluoropiperidin-4-yloxy)quinoline Step A: Preparation of 5-fluoro-2-hydrazinylpyridine: 2-chloro-5-fluoropyridine (5.00 g, 38.01 mmol) was combined with hydrazine monohydrate (15 mL, 303.0 mmol) in a Teflon® lined reactor. The reaction was purged with argon gas and sealed, then heated to 200° C. overnight. Following overnight heating, the reaction mixture was evaporated to solids under reduced pressure, and then dissolved in water containing NaHCO₃. The mixture was transferred to a reparatory funnel, and extracted 4 times with EtOAc. The combined organic extracts were dried over Na₂SO₄, filtered and concentrated to residue under reduced pressure, followed by purification by flash column chromatography eluting with 5% MeOH 0.5% NH₄OH in DCM to give the desired 5-fluoro-2-hydrazinylpyridine (1.50 g, 31% yield). MS APCI (+) m/z 128.0 (M+1) detected.

Step B: Preparation of 8-(tert-butyldimethylsilyloxy)quinoline-2-carbaldehyde: A solution of 8-hydroxyquinoline-2-carbaldehyde (10.00 g, 57.75 mmol) and imidazole (8.649 g, 127.0 mmol) in DCM (290 mL, 57.75 mmol) was cooled to 0° C. on an ice bath. TBDMS-Cl (9.574 g, 63.52 mmol) was added and the reaction stirred overnight at ambient temperature. Water was added and the reaction transferred to a separatory funnel. The aqueous phase was extracted 3 times with DCM, the organics combined, followed by washes with water and brine. The combined organic layers were dried over Na₂SO₄, filtered and concentrated to residue under reduced pressure. The residue was purified by flash column chromatography, eluting with 25% EtOAc/Hexanes to give the product (12.2 g, 74% yield). MS APCI (+) m/z 288.1 (M+1) detected.

Step C: Preparation of 8-(tert-butyldimethylsilyloxy)-2-(6-fluoro[1,2,4]triazolo[4,3-a]pyridin-3-yl)quinoline: 8-(tert-butyldimethylsilyloxy)quinoline-2-carbaldehyde (1.39 g, 4.83 mmol) and 5-fluoro-2-hydrazinylpyridine (1.28 g, 6.04 mmol) were combined in DCM (12.1 mL, 4.83 mmol) at ambient temperature and stirred for 15 minutes. The mixture was cooled to 0° C. followed by addition of iodobenzene diacetate (IBD; 1.87 g, 5.80 mmol). The reaction was warmed to ambient temperature and stirred overnight. Additional IBD (0.8 equivalents, 4.64 mmol) was added and the reaction was allowed to stir at ambient temperature for 48 hours total. The mixture was transferred to a separatory funnel, diluting with water and DCM. The organic phase was washed with saturated aqueous Na₂SO₃, followed by back extraction of the aqueous phase 2 times with DCM. The organics were combined and washed with brine, dried over Na₂SO₄, filtered and concentrated to a residue under reduced pressure, followed by purification by flash column chromatography to give the product (1.08 g, 57% yield). MS APCI (+) m/z 395.3 (M+1) detected.

Step D: Preparation of 2-(6-fluoro-[1,2,4]triazolo[4,3-a]pyridin-3-yl)quinolin-8-ol: A solution of 8-(tert-butyldimethylsilyloxy)-2-(6-fluoro-[1,2,4]triazolo[4,3-a]pyridin-3-yl)quinoline (560 mg, 1.4195 mmol) in THF (10.13 mL, 1.267 mmol) was cooled to 0° C. in an ice bath. TBAF (1M in THF, 2.122 mL, 2.129 mmol) was added by syringe and the mixture stirred for 1 hour at 0° C. Water was added, followed by saturated aqueous NaHCO₃ solution. The mixture was transferred to a separatory funnel, diluting with EtOAc and water. The mixture was extracted with EtOAc, the combined organic layers were washed with brine, dried over Na₂SO₄, filtered and concentrated under reduced pressure. The residue was purified by flash column chromatography eluting with 10-15% MeOH 1% NH₄OH in EtOAc to give the product as a yellow film (35 mg, 9% yield). MS APCI (+) m/z 281.2 (M+1) detected.

Step E: Preparation of (cis)-tert-butyl 3-fluoro-4-(2-(6-fluoro-[1,2,4]triazolo[4,3-a]pyridin-3-yl)quinolin-8-yloxy)piperidine-1-carboxylate: A mixture of (trans)-tert-butyl 3-fluoro-4-(methylsulfonyloxy)piperidine-1-carboxylate (24 mg, 0.0807 mmol), 2-(6-fluoro-[1,2,4]triazolo[4,3-a]pyridin-3-yl)quinolin-8-ol (23.8 mg, 0.0850 mmol) and Cs₂CO₃ (55.4 mg, 0.170 mmol) in DMA (425 μl, 0.0850 mmol) was heated to 90° C. for 16 hours. The mixture was transferred to a reparatory funnel and diluted with EtOAc and water. The mixture was then extracted with EtOAc, and the combined organic layers were washed with brine, dried over Na₂SO₄, filtered and concentrated to a residue under reduced pressure to give the product without further purification (33 mg, 81% yield). MS APCI (+) m/z 481.9 (M+1) detected.

Step F: Preparation of 2-(6-fluoro-[1,2,4]triazolo[4,3-a]pyridin-3-yl)-8-((cis)-3-fluoropiperidin-4-yloxy)quinoline: (cis)-tert-butyl 3-fluoro-4-(2-(6-fluoro-[1,2,4]triazolo[4,3-a]pyridin-3-yl)quinolin-8-yloxy)piperidine-1-carboxylate (33 mg, 0.069 mmol) was dissolved in 2 mL DCM at ambient temperature. TFA (2 mL) was added and the mixture stirred at ambient temperature 1 hour. The reaction was evaporated under reduced pressure, and purified by preparative TLC eluting with 1:10 mixture of (0.5% NH₄OH in MeOH):DCM to give the product (4.5 mg, 17% yield). MS APCI (+) m/z 382.1 (M+1) detected.

Example 60

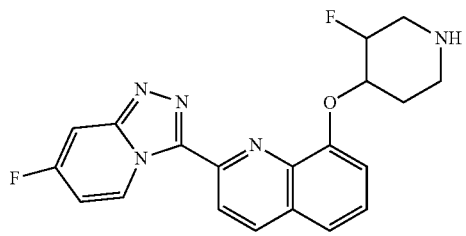 [SMILES: Fc1ccn2c(-c3ccc4cccc(OC5CCNCC5F)c4n3)nnc2c1]

cis-2-(7-fluoro-[1,2,4]triazolo[4,3-a]pyridin-3-yl)-8-3-fluoropiperidin-4-yloxy)quinoline Prepared as described in Example 59 using 4-fluoro-2-hydrazinylpyridine (as prepared in: *JOC*, 2005, 70: 2494) in place of 5-fluoro-2-hydrazinylpyridine. MS ESI (+) m/z 382.2 (M+1) detected.

Example 61

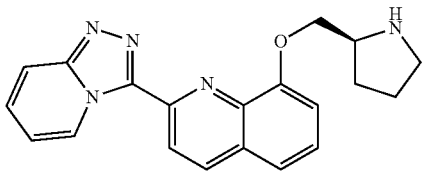 [SMILES: c1cc(OC[C@@H]2CCCN2)c2nc(-c3nnc4ccccn34)ccc2c1]

(S)-2-([1,2,4]triazolo[4,3-a]pyridin-3-yl)-8-(pyrrolidin-2-ylmethoxy)quinoline

Prepared as described in Example 25 using (S)-tert-butyl 2-((methylsulfonyloxy)methyl)pyrrolidine-1-carboxylate in place of (cis)-tert-butyl-3-fluoro-4-(methylsulfonyloxy)piperidine-1-carboxylate. Boc deprotection was achieved as described in Example 9, Step B. MS ESI (+) m/z 346.2 (M+1) detected.

Example 62

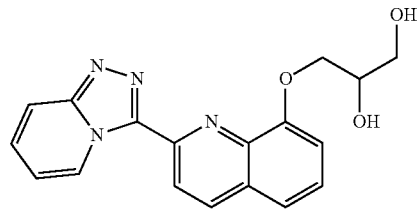 [SMILES: OCC(O)COc1cccc2ccc(-c3nnc4ccccn34)nc12]

3-(2-([1,2,4]triazolo[4,3-a]pyridin-3-yl)quinolin-8-yloxy)propane-1,2-diol

Prepared as described in Example 9, Step A, using (2,2-dimethyl-1,3-dioxolan-4-yl)methanol in place of tert-butyl 4-hydroxypiperidine-1-carboxylate. Ketal deprotection was achieved as described in Example 9, Step B, using aqueous HCl in place of TFA/DCM. MS ESI (+) m/z 337.1 (M+1) detected.

Example 63

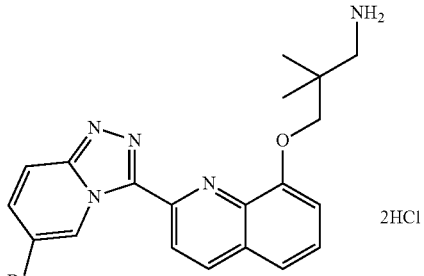

3-(2-(6-bromo-[1,2,4]triazolo[4,3-a]pyridin-3-yl)quinolin-8-yloxy)-2,2-dimethylpropan-1-amine dihydrochloride Step A: Preparation of 2-(6-bromo-[1,2,4]triazolo[4,3-a]pyridin-3-yl)-8-(tert-butyldimethylsilyloxy)-quinoline: Prepared as described in Example 1, Steps A-C, using 5-bromo-2-hydrazinylpyridine in place of 2-hydrazinylpyridine.

Step B: Preparation of 2-(6-bromo-[1,2,4]triazolo[4,3-a]pyridin-3-yl)quinolin-8-ol: Prepared as described in Example 1, Step D, using 2-(6-bromo-[1,2,4]triazolo[4,3-a]pyridin-3-yl)-8-(tert-butyldimethylsilyloxy)-quinoline in place of 2-([1,2,4]triazolo[4,3-a]pyridin-3-yl)-8-(tert-butyldimethylsilyloxy)-.

Step C: Preparation of tert-butyl 3-(2-(6-bromo-[1,2,4]triazolo[4,3-a]pyridin-3-yl)quinolin-8-yloxy)-2,2-dimethylpropylcarbamate: Prepared as described in Example 9, Step A, using tert-butyl 3-hydroxy-2,2-dimethylpropylcarbamate in place of tert-butyl-4-hydroxypiperidine-1-carboxylate and 2-(6-bromo-[1,2,4]triazolo[4,3-a]pyridin-3-yl)quinolin-8-ol in place of 2-([1,2,4]triazolo[4,3-a]pyridin-3-yl)quinolin-8-ol.

Step D: Preparation of 3-(2-(6-bromo-[1,2,4]triazolo[4,3-a]pyridin-3-yl)quinolin-8-yloxy)-2,2-dimethylpropan-1-amine dihydrochloride: To a solution of tert-butyl 3-(2-(6-bromo-[1,2,4]triazolo[4,3-a]pyridin-3-yl)quinolin-8-yloxy)-2,2-dimethylpropylcarbamate (0.108 g, 0.205 mmol) in 2 mL dichloromethane was added neat TFA (0.395 mL, 5.13 mmol). The reaction mixture was stirred at ambient temperature for 4 hours, after which it was concentrated. The residue was concentrated twice from dichloromethane/hexanes to give solids, which were dried in vacuo. The solids were dissolved in several drops of methanol and minimal dichloromethane, and this solution was added to a vigorously stirring solution of 20 mL ether and 1.5 mL 2M HCl/ether, causing precipitation. The solids were stirred 5 minutes, then isolated by filtration through a medium glass fitted funnel by pushing the solvent through the funnel with nitrogen pressure, rinsed twice with ether, twice with 1:1 dichloromethane:ether, twice with ether, and dried in vacuo to give the title compound (0.042 g, 0.0841 mmol, 41.0% yield) as a pale yellow powder. MS APCI (+) m/z 426/428 (M+1)(Br isotope) detected.

Example 64

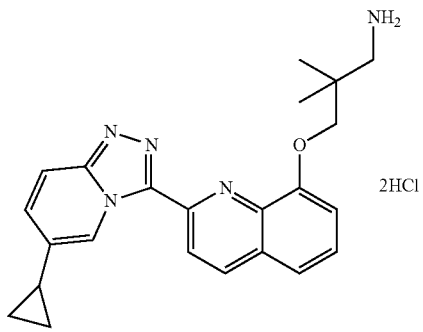 [SMILES: CC(C)(CN)COc1cccc2ccc(-c3nnc4ccc(C5CC5)cn34)nc12]

3-(2-(6-cyclopropyl-[1,2,4]triazolo[4,3-a]pyridin-3-yl)quinolin-8-yloxy)-2,2-dimethylpropan-1-amine dihydrochloride Step A: Preparation of 8-(tert-butyldimethylsilyloxy)-2-(6-cyclopropyl-[1,2,4]triazolo[4,3-a]pyridin-3-yl)quinoline: 2-(6-Bromo-[1,2,4]triazolo[4,3-a]pyridin-3-yl)-8-(tert-butyldimethylsilyloxy)quinoline (0.500 g, 1.10 mmol), cyclopropylboronic acid (0.123 g, 1.43 mmol), Pd(OAc)$_2$ (0.012 g, 0.0549 mmol), P(Cy)$_3$ (0.031 g, 0.110 mmol), and K$_3$PO$_4$ (0.699 g, 3.29 mmol) were combined with 5.5 mL toluene and 0.55 mL H$_2$O (both degassed with nitrogen 30 minutes prior to use). The mixture was sonicated and put on a 100° C. reaction block and stirred for 3 hours. The reaction mixture was cooled to ambient temperature, diluted with toluene, vacuum filtered through compressed Celite, rinsed with toluene, and the filtrate was concentrated. The crude material was purified on silica (5% to 60% ethyl acetate in dichloromethane) to give the title compound (0.159 g, 0.382 mmol, 34.8% yield) as a brown foam.

Step B: Preparation of 2-(6-cyclopropyl-[1,2,4]triazolo[4,3-a]pyridin-3-yl)quinolin-8-ol: To a 0° C. solution of 8-(tert-butyldimethylsilyloxy)-2-(6-cyclopropyl-[1,2,4]triazolo[4,3-a]pyridin-3-yl)quinoline (0.159 g, 0.382 mmol) in 4 mL THF was added solid TBAF hydrate (0.150 g, 0.573 mmol), causing the reaction mixture to turn cloudy. The reaction mixture was warmed to ambient temperature after 5 minutes and then stirred 17 hours, after which it was diluted with saturated NH$_4$Cl and water, causing solids to form. The solids were isolated by vacuum filtration through a Buchner funnel, rinsed with water, and air dried in vacuo to give the title compound (0.072 g, 0.238 mmol, 62.4% yield) as a light pink powder.

Step C: Preparation of tert-butyl 3-(2-(6-cyclopropyl-[1,2,4]triazolo[4,3-a]pyridin-3-yl)quinolin-8-yloxy)-2,2-dimethylpropylcarbamate: Prepared as described in Example 9, Step A, using tert-butyl 3-hydroxy-2,2-dimethylpropylcarbamate in place of tert-butyl-4-hydroxypiperidine-1-carboxylate and 2-(6-cyclopropyl-[1,2,4]triazolo[4,3-a]pyridin-3-yl)quinolin-8-ol in place of 2-([1,2,4]triazolo[4,3-a]pyridin-3-yl)quinolin-8-ol.

Step D: Preparation of 3-(2-(6-cyclopropyl-[1,2,4]triazolo[4,3-a]pyridin-3-yl)quinolin-8-yloxy)-2,2-dimethylpropan-1-amine dihydrochloride: Prepared as described in Example 63, Step D, using tert-butyl 3-(2-(6-cyclopropyl-[1,2,4]triazolo[4,3-a]pyridin-3-yl)quinolin-8-yloxy)-2,2-dimethylpropylcarbamate in place of tert-butyl 3-(2-(6-bromo-[1,2,4]triazolo[4,3-a]pyridin-3-yl)quinolin-8-yloxy)-2,2-dimethylpropyl-carbamate. MS APCI (+) m/z 388 (M+1) detected.

Example 65

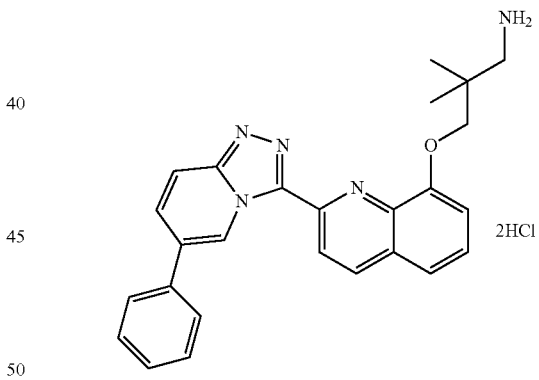

2,2-Dimethyl-3-(2-(6-phenyl-[1,2,4]triazolo[4,3-a]pyridin-3-yl)quinolin-8-yloxy)propan-1-amine dihydrochloride Step A: Preparation of 2-(6-phenyl-[1,2,4]triazolo[4,3-a]pyridin-3-yl)quinolin-8-ol: 2-(6-bromo-[1,2,4]triazolo[4,3-a]pyridin-3-yl)-8-(tert-butyldimethylsilyloxy)quinoline (0.500 g, 1.10 mmol), phenylboronic acid (0.167 g, 1.37 mmol), Pd(PPh$_3$)$_4$ (0.0634 g, 0.0549 mmol), and 2M aqueous Na$_2$CO$_3$ (2.74 mL, 5.49 mmol) (degassed with nitrogen 30 minutes prior to use) were combined with 7 mL dioxane (degassed with nitrogen 30 minutes prior to use), sonicated, and heated to 110° C. in a reaction block for 18 hours, during which the reaction went dry. The reaction mixture was cooled to ambient temperature, diluted with DMF, and the suspension was vacuum filtered through compressed Celite, rinsed with DMF, and the filtrate was concentrated. The crude material was purified on silica gel (1-20% methanol in dichloromethane gradient) to give the title compound (0.138 g, 0.408 mmol, 37.1% yield) as a brown solid.

Step B: Preparation of tert-butyl 2,2-dimethyl-3-(2-(6-phenyl-[1,2,4]triazolo[4,3-a]pyridin-3-yl)quinolin-8-yloxy)propylcarbamate: Prepared as described in Example 9, Step A, using tert-butyl 3-hydroxy-2,2-dimethylpropylcarbamate in place of tert-butyl-4-hydroxypiperidine-1-carboxylate and 2-(6-phenyl-[1,2,4]triazolo[4,3-a]pyridin-3-yl)quinolin-8-ol in place of 2-([1,2,4]triazolo[4,3-a]pyridine-3-yl)quinolin-8-ol.

Step C: Preparation of 2,2-dimethyl-3-(2-(6-phenyl-[1,2,4]triazolo[4,3-a]pyridin-3-yl)quinolin-8-yloxy)propan-1-amine dihydrochloride: Prepared as described in Example 63, Step D, using tert-butyl 2,2-dimethyl-3-(2-(6-phenyl-[1,2,4]triazolo[4,3-a]pyridin-3-yl)quinolin-8-yloxy)propylcarbamate in place of tert-butyl 3-(2-(6-bromo-[1,2,4]triazolo[4,3-a]pyridine-3-yl)quinolin-8-yloxy)-2,2-dimethylpropyl-carbamate. MS APCI (+) m/z 424 (M+1) detected.

Example 66

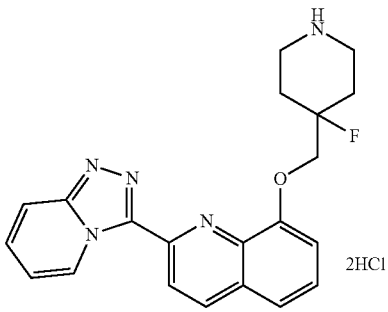 [SMILES: FC1(COc2cccc3ccc(-c4nnc5ccccn45)nc23)CCNCC1]

2-([1,2,4]triazolo[4,3-a]pyridin-3-yl)-8-((4-fluoropiperidin-4-yl)methoxy)quinoline dihydrochloride Step A: Preparation of tert-butyl 4-fluoro-4-(hydroxymethyl)piperidine-1-carboxylate: To a 0° C. solution of 1-tert-butyl 4-ethyl 4-fluoropiperidine-1,4-dicarboxylate (3.0 g, 10.90 mmol) in 55 mL THF was added 1M lithium aluminum hydride in THF (21.79 mL, 21.79 mmol). The reaction mixture was stirred at 0° C. for 3.5 hours, after which it was carefully quenched by the addition of 1:1 Na$_2$SO$_4$-10H$_2$O: Celite, diluted with THF, warmed to ambient temperature, and stirred vigorously for 2 hours. The slurry was vacuum filtered through GF/F paper on a Buchner funnel, rinsed with THF, and the filtrate was concentrated in vacuo to give the title compound (2.69 g) as a clear colorless oil, which was used without further purification.

Step B: Preparation of tert-butyl 4-fluoro-4-((methylsulfonyloxy)methyl)piperidine-1-carboxylate: To a 0° C. solution of tert-butyl 4-fluoro-4-(hydroxymethyl)piperidine-1-carboxylate (2.60 g, 11.1 mmol) and triethylamine (2.33 mL, 16.7 mmol) in 55 mL dichloromethane was added neat methanesulfonyl chloride (0.949 mL, 12.3 mmol) dropwise by syringe. The reaction mixture was slowly warmed to ambient temperature and stirred at ambient temperature for 17 hours. Saturated NaHCO$_3$ was added, the mixture was extracted with dichloromethane, and combined extracts were dried (Na$_2$SO$_4$), filtered, and concentrated. The crude was purified on silica gel (4:1 hexanes:ethyl acetate to 1:1 hexanes:ethyl acetate) to give the title compound (3.2 g, 92.2% yield) as a white powder.

Step C: Preparation of tert-butyl 4-42-([1,2,4]triazolo[4,3-a]pyridin-3-yl)quinolin-8-yloxy)methyl)-4-fluoropiperidine-1-carboxylate: Prepared as described in Example 23 using tert-butyl 4-fluoro-4-((methylsulfonyloxy)methyl)piperidine-1-carboxylate in place of neopentyl iodide. MS APCI (+) m/z 478 (M+1) detected.

Step D: Preparation of 2-([1,2,4]triazolo[4,3-a]pyridin-3-yl)-8-((4-fluoropiperidin-4-yl)methoxy)quinoline dihydrochloride: Prepared as described in Example 63, Step D, using tert-butyl 4-((2-([1,2,4]triazolo[4,3-a]pyridin-3-yl)quinolin-8-yloxy)methyl)-4-fluoropiperidine-1-carboxylate in place of tert-butyl 3-(2-(6-bromo-[1,2,4]triazolo[4,3-a]pyridine-3-yl)quinolin-8-yloxy)-2,2-dimethylpropyl-carbamate. MS APCI (+) m/z 378 (M+1) detected.

Example 67

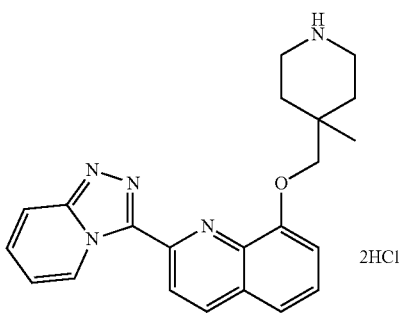 [SMILES: CC1(COc2cccc3ccc(-c4nnc5ccccn45)nc23)CCNCC1]

2-([1,2,4]triazolo[4,3-a]pyridin-3-yl)-8-((4-methylpiperidin-4-yl)methoxy)quinoline dihydrochloride Step A: Preparation of tert-butyl 4-((2-([1,2,4]triazolo[4,3-a]pyridin-3-yl)quinolin-8-yloxy)methyl)-4-methylpiperidine-1-carboxylate: Prepared according to the method of Example 66, Steps A-C, using 1-tert-butyl 4-ethyl 4-methylpiperidine-1,4-dicarboxylate in place of 1-tert-butyl 4-ethyl 4-fluoropiperidine-1,4-dicarboxylate. MS APCI (+) m/z 474 (M+1) detected.

Step B: Preparation of 2-([1,2,4]triazolo[4,3-a]pyridin-3-yl)-8-((4-methylpiperidin-4-yl)methoxy)quinoline dihydrochloride: Prepared according to the method of Example 63, Step D, using tert-butyl 4-((2-([1,2,4]triazolo[4,3-a]pyridin-3-yl)quinolin-8-yloxy)methyl)-4-methyl-piperidine-1-carboxylate in place of tert-butyl 3-(2-(6-bromo-[1,2,4]triazolo[4,3-a]pyridin-3-yl)quinolin-8-yloxy)-2,2-dimethylpropyl-carbamate. MS APCI (+) m/z 374 (M+1) detected.

Example 68

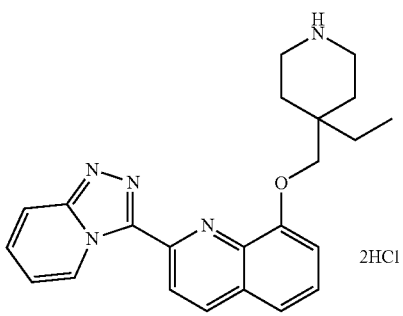 [SMILES: CCC1(COc2cccc3ccc(-c4nnc5ccccn45)nc23)CCNCC1]

2-([1,2,4]triazolo[4,3-a]pyridin-3-yl)-8-((4-ethylpiperidin-4-yl)methoxy)quinoline dihydrochloride Step A: Preparation of 1-tert-butyl 4-ethyl 4-ethylpiperidine-1,4-dicarboxylate: To a 0° C. solution of methyl piperidine-4-carboxylate (2.0 g, 14.0 mmol) in 35 mL THF was added 1M LHMDS in THF (27.9 mL, 27.9 mmol). The reaction mixture was stirred at 0° C. for 90 minutes, then neat iodoethane (3.91 mL, 48.9 mmol) was added slowly by syringe. The reaction mixture was stirred 10 minutes, warmed to ambient temperature, and stirred 18 hours. Saturated NH$_4$Cl was added, the mixture was extracted with ethyl acetate, and the combined extracts were dried (Na$_2$SO$_4$), filtered, and concentrated. The crude was purified on silica gel eluting with 10:1 hexanes:ethyl acetate to give the title compound (0.843 g, 3.11 mmol, 22.2% yield) as a clear, colorless oil.

Step B: Preparation of 2-([1,2,4]triazolo[4,3-a]pyridin-3-yl)-8-((4-ethylpiperidin-4-yl)methoxy)quinoline dihydrochloride: Prepared as described for Example 66 using 1-tert-butyl 4-ethyl 4-methylpiperidine-1,4-dicarboxylate in place of 1-tert-butyl 4-ethyl 4-fluoropiperidine-1,4-dicarboxylate. MS APCI (+) m/z 388 (M+1) detected.

Example 69

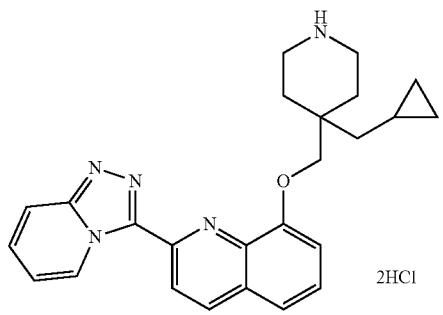 [SMILES: c1cc(OCC2(CC3CC3)CCNCC2)c2nc(-c3nnc4ccccn34)ccc2c1]

2-([1,2,4]triazolo[4,3-a]pyridin-3-yl)-8-44-(cyclopropylmethyl)piperidin-4-yl)methoxy)quinoline dihydrochloride Prepared as described for Example 68 using (bromomethyl)cyclopropane in place of iodoethane. MS APCI (+) m/z 414 (M+1) detected.

Example 70

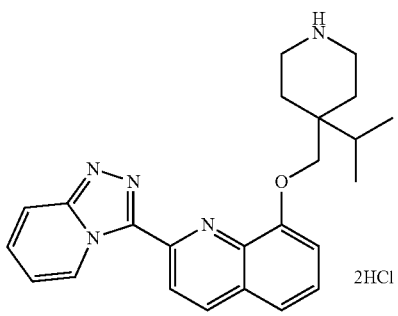 [SMILES: CC(C)C1(COc2cccc3ccc(-c4nnc5ccccn45)nc23)CCNCC1]

2-([1,2,4]triazolo[4,3-a]pyridin-3-yl)-8-((4-isopropylpiperidin-4-yl)methoxy)quinoline dihydrochloride Prepared as described for Example 68 using 2-iodopropane in place of iodoethane. MS APCI (+) m/z 402 (M+1) detected.

Example 71

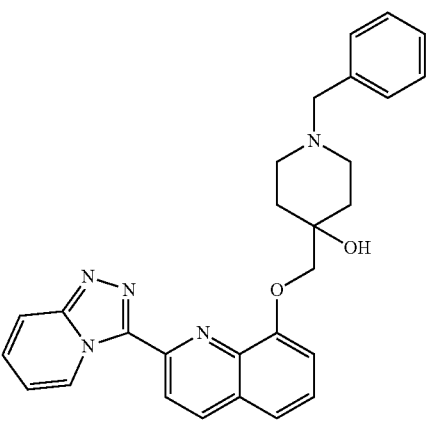 [SMILES: OC1(COc2cccc3ccc(-c4nnc5ccccn45)nc23)CCN(Cc2ccccc2)CC1]

4-((2-([1,2,4]triazolo[4,3-a]pyridin-3-yl)quinolin-8-yloxy)methyl)-1-benzylpiperidin-4-ol Prepared as described in Example 23 using 6-benzyl-1-oxa-6-azaspiro[2.5]octane in place of neopentyl iodide. MS APCI (+) m/z 466 (M+1) detected.

Example 72

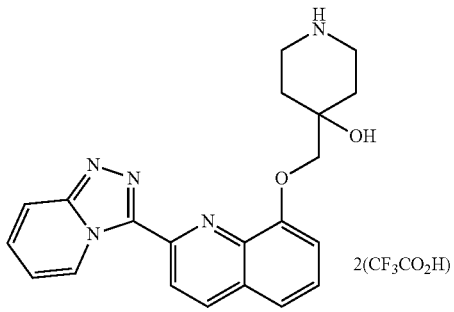 [SMILES: OC1(COc2cccc3ccc(-c4nnc5ccccn45)nc23)CCNCC1]

4-42-([1,2,4]triazolo[4,3-a]pyridin-3-yl)quinolin-8-yloxy)methyl)piperidin-4-ol bis(trifluoroacetate)

Step A: Preparation of tert-butyl 4-((2-([1,2,4]triazolo[4,3-a]pyridin-3-yl)quinolin-8-yloxy)methyl)-4-hydroxypiperidine-1-carboxylate: Prepared as described in Example 23 using tert-butyl 1-oxa-6-azaspiro[2.5]octane-6-carboxylate in place of neopentyl iodide.

Step B: Preparation of 4-((2-([1,2,4]triazolo[4,3-a]pyridin-3-yl)quinolin-8-yloxy)methyl)-piperidin-4-ol bis(trifluoroacetate): To a solution of tert-butyl 4-((2-([1,2,4]triazolo[4,3-a]pyridin-3-yl)quinolin-8-yloxy)methyl)-4-hydroxypiperidine-1-carboxylate (0.006 g, 0.013 mmol) in 0.15 mL dichloromethane was added neat TFA (0.029 mL, 0.37 mmol). The reaction mixture was stirred at ambient temperature for 5 hours, after which it was concentrated to dryness. The residue was dissolved in dichloromethane, and the resulting solution was added dropwise to vigorously stirring ether, causing precipitation. The resulting solids were isolated by filtration through a 0.2 micron nylon filter disc, rinsed with ether, and dried in vacuo to give the title compound (0.005 g, 65.7% yield) as a pale yellow powder. MS APCI (+) m/z 376 (M+1) detected.

situ with diisopropylethylamine) in place of neopentyl iodide. MS APCI (+) m/z 340 (M+1) detected.

Example 73

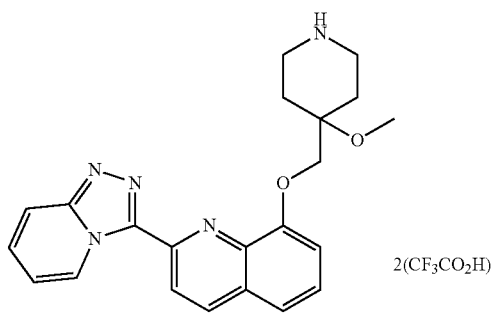 [SMILES: COC1(COc2cccc3ccc(-c4nnc5ccccn45)nc23)CCNCC1]

2-([1,2,4]triazolo[4,3-a]pyridin-3-yl)-8-((4-methoxypiperidin-4-yl)methoxy)quinoline bis(trifluoroacetate)

Step A: Preparation of tert-butyl 4-42-([1,2,4]triazolo[4,3-a]pyridin-3-yl)quinolin-8-yloxy)methyl)-4-methoxypiperidine-1-carboxylate: To a 0° C. suspension of tert-butyl 4-((2-([1,2,4]triazolo[4,3-a]pyridin-3-yl)quinolin-8-yloxy)methyl)-4-hydroxypiperidine-1-carboxylate (0.033 g, 0.069 mmol) in 2 mL DMF was added 60% NaH in mineral oil (0.0117 g, 0.486 mmol). The reaction mixture was warmed to ambient temperature and stirred 2 hours. Neat iodomethane (0.035 mL, 0.56 mmol) was added, and the reaction mixture was stirred for 21 hours. The reaction mixture was concentrated, and the residue was diluted with saturated NH₄Cl and extracted with dichloromethane. The combined extracts were dried (Na₂SO₄), filtered, and concentrated. The crude was purified by preparative TLC (0.5 mm plate, 9:1 dichloromethane:methanol) to give the title compound (0.016 g, 47.1% yield) as a yellow residue.

Step B: Preparation of 2-([1,2,4]triazolo[4,3-a]pyridin-3-yl)-8-((4-methoxypiperidin-4-yl)methoxy)quinoline bis(trifluoroacetate): Prepared as described for Example 72, Step B, using tert-butyl 4-((2-([1,2,4]triazolo[4,3-a]pyridin-3-yl) quinolin-8-yloxy)-methyl)-4-methoxypiperidine-1-carboxylate in place of tert-butyl 4-((2-([1,2,4]triazolo-[4,3-a]pyridin-3-yl)quinolin-8-yloxy)methyl)-4-hydroxypiperidine-1-carboxylate. MS APCI (+) m/z 390 (M+1) detected.

Example 74

2-([1,2,4]triazolo[4,3-a]pyridin-3-yl)-8-(pyridin-4-yloxy)quinoline

Prepared as described in Example 23 using 4-fluoropyridine hydrochloride (which was converted to the free base in

Example 75

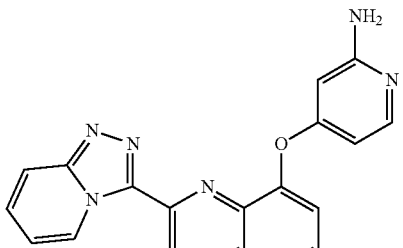

4-(2-([1,2,4]triazolo[4,3-a]pyridin-3-yl)quinolin-8-yloxy)pyridin-2-amine

Step A: Preparation of 2-([1,2,4]triazolo[4,3-a]pyridin-3-yl)-8-(2-chloropyridin-4-yloxy)quinoline: Prepared as described in Example 23 using 2-chloro-4-nitropyridine in place of neopentyl iodide. MS APCI (+) m/z 374 (M+1) detected.

Step B: Preparation of 4-(2-([1,2,4]triazolo[4,3-a]pyridin-3-yl)quinolin-8-yloxy)pyridin-2-amine: To a solution of 2-([1,2,4]triazolo[4,3-a]pyridin-3-yl)-8-(2-chloropyridin-4-yloxy)quinoline (0.105 g, 0.281 mmol) in 71 mL THF (degassed with nitrogen 30 minutes prior to use) was added sequentially XPHOS (0.0107 g, 0.0225 mmol), Pd₂ dba₃ (0.0103 g, 0.0112 mmol), and 1M LHMDS in THF (0.590 mL, 0.590 mmol) by syringe. The reaction mixture was heated to reflux and stirred for 3 hours. The reaction mixture was cooled to 0° C. and 1M aqueous HCl (1.40 mL, 1.40 mmol) was added, causing milky solids to form. The reaction mixture was stirred 30 minutes, then diluted with water and dichloromethane, and the aqueous layer was washed with dichloromethane. The aqueous layer was basified with 1M NaOH (pH>10), and the milky mixture was extracted with chloroform. The combined extracts were dried (Na₂SO₄), filtered, and concentrated. The crude was purified by preparative TLC (9:1 chloroform:6% NH₄OH in methanol) to give the title compound (0.027 g, 0.0762 mmol, 27.1% yield) as a yellow/orange powder. MS APCI (+) m/z 355 (M+1) detected.

Example 76

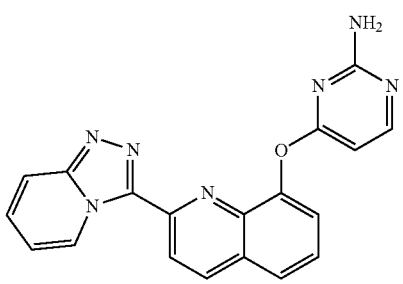 [SMILES: Nc1nccc(Oc2cccc3ccc(-c4nnc5ccccn45)nc23)n1]

4-(2-([1,2,4]triazolo[4,3-a]pyridin-3-yl)quinolin-8-yloxy)pyrimidin-2-amine

Step A: Preparation of 2-([1,2,4]triazolo[4,3-a]pyridin-3-yl)-8-(2-chloropyrimidin-4-yloxy)quinoline: Prepared as described in Example 23 using 2,4-dichloropyrimidine in place of neopentyl iodide. MS APCI (+) m/z 375 (M+1) detected.

Step B: Preparation of 4-(2-([1,2,4]triazolo[4,3-a]pyridin-3-yl)quinolin-8-yloxy)-pyrimidin-2-amine: Prepared as described in Example 75, Step B, using 2-([1,2,4]triazolo[4,3-a]pyridin-3-yl)-8-(2-chloropyrimidin-4-yloxy)quinoline in place of 2-([1,2,4]triazolo[4,3-a]pyridin-3-yl)-8-(2-chloropyridin-4-yloxy)quinoline. MS APCI (+) m/z 356 (M+1) detected.

Example 77

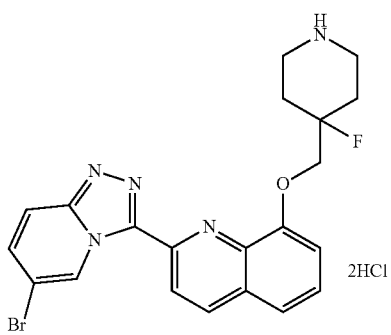 [SMILES: FC1(COc2cccc3ccc(-c4nnc5ccc(Br)cn45)nc23)CCNCC1]

2-(6-bromo-[1,2,4]triazolo[4,3-a]pyridin-3-yl)-8-((4-fluoropiperidin-4-yl)methoxy)-quinoline dihydrochloride Prepared as described in Example 66 using 2-(6-bromo-[1,2,4]triazolo[4,3-a]pyridin-3-yl)quinolin-8-ol in place of 2-([1,2,4]triazolo[4,3-a]pyridin-3-yl)quinolin-8-ol in Step C. MS APCI (+) m/z 456/458 (M+1) (Br isotope) detected.

Example 78

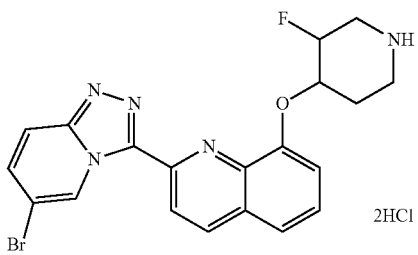 [SMILES: FC1CNCCC1Oc1cccc2ccc(-c3nnc4ccc(Br)cn34)nc12]

2-(6-bromo-[1,2,4]triazolo[4,3-a]pyridin-3-yl)-8-((cis)-3-fluoropiperidin-4-yloxy)quinoline dihydrochloride Prepared as described in Example 66 using (trans)-tert-butyl-3-fluoro-4-(methylsulfonyloxy)piperidine-1-carboxylate in place of tert-butyl 4-fluoro-4-((methylsulfonyloxy)methyl)piperidine-1-carboxylate and 2-(6-bromo-[1,2,4]triazolo[4,3-a]pyridin-3-yl)quinolin-8-ol in place of 2-([1,2,4]triazolo[4,3-a]pyridin-3-yl)quinolin-8-ol in Step C. MS APCI (+) m/z 442/444 (M+1) (Br isotope) detected.

Example 79

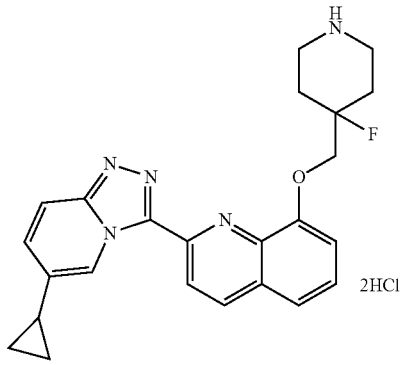 [SMILES: FC1(COc2cccc3ccc(-c4nnc5ccc(C6CC6)cn45)nc23)CCNCC1]

2-(6-cyclopropyl-[1,2,4]triazolo[4,3-a]pyridin-3-yl)-8-((4-fluoropiperidin-4-yl)methoxy)quinoline dihydrochloride Prepared as described in Example 66 using 2-(6-cyclopropyl-[1,2,4]triazolo[4,3-a]pyridin-3-yl)quinolin-8-ol in place of 2-([1,2,4]triazolo[4,3-a]pyridin-3-yl)quinolin-8-ol. MS APCI (+) m/z 418 (M+1) detected.

Example 80

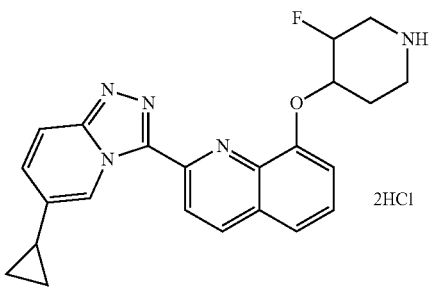 [SMILES: FC1CNCCC1Oc1cccc2ccc(-c3nnc4ccc(C5CC5)cn34)nc12]

2-(6-cyclopropyl-[1,2,4]triazolo[4,3-a]pyridin-3-yl)-8-((cis)-3-fluoropiperidin-4-yloxy)quinoline dihydrochloride Prepared as described in Example 66 using 2-(6-cyclopropyl-[1,2,4]triazolo[4,3-a]pyridin-3-yl)quinolin-8-ol in place of 2-([1,2,4]triazolo[4,3-a]pyridin-3-yl)quinolin-8-ol and (trans)-tert-butyl-3-fluoro-4-(methylsulfonyloxy)piperidine-1-carboxylate in place of tert-butyl 4-fluoro-4-((methylsulfonyloxy)methyl)piperidine-1-carboxylate in Step C. MS APCI (+) m/z 404 (M+1) detected.

Example 81

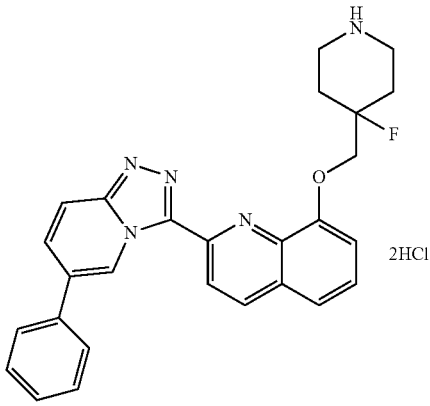 [SMILES: FC1(COc2cccc3ccc(-c4nnc5ccc(-c6ccccc6)cn45)nc23)CCNCC1]

8-((4-fluoropiperidin-4-yl)methoxy)-2-(6-phenyl-[1,2,4]triazolo[4,3-a]pyridin-3-yl)quinoline dihydrochloride Prepared as described in Example 66 using 2-(6-phenyl-[1,2,4]triazolo[4,3-a]pyridin-3-yl)quinolin-8-ol in place of 2-([1,2,4]triazolo[4,3-a]pyridin-3-yl)quinolin-8-ol in Step C. MS APCI (+) m/z 454 (M+1) detected.

Example 82

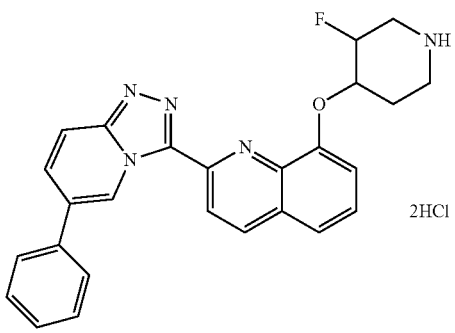 [SMILES: FC1CNCCC1Oc1cccc2ccc(-c3nnc4ccc(-c5ccccc5)cn34)nc12]

8-((cis)-3-fluoropiperidin-4-yloxy)-2-(6-phenyl-[1,2,4]triazolo[4,3-a]pyridin-3-yl)quinoline dihydrochloride Prepared as described in Example 66 using 2-(6-phenyl-[1,2,4]triazolo[4,3-a]pyridin-3-yl)quinolin-8-ol in place of 2-([1,2,4]triazolo[4,3-a]pyridin-3-yl)quinolin-8-ol and (trans)-tert-butyl-3-fluoro-4-(methylsulfonyloxy)piperidine-1-carboxylate in place of tert-butyl 4-fluoro-4-((methylsulfonyloxy)methyl)piperidine-1-carboxylate in Step C. MS APCI (+) m/z 440 (M+1) detected.

Example 83

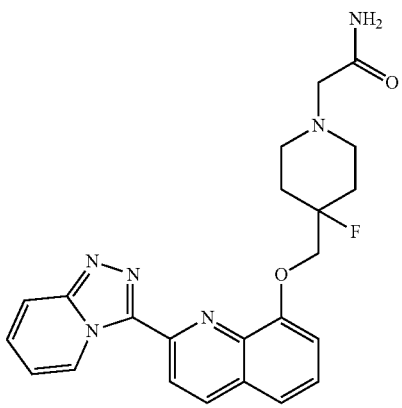 [SMILES: NC(=O)CN1CCC(F)(COc2cccc3ccc(-c4nnc5ccccn45)nc23)CC1]

2-(4-((2-([1,2,4]triazolo[4,3-a]pyridin-3-yl)quinolin-8-yloxy)methyl)-4-fluoropiperidin-1-yl)acetamide To a suspension of 2-([1,2,4]triazolo[4,3-a]pyridin-3-yl)-8-((4-fluoropiperidin-4-yl)methoxy)quinoline dihydrochloride (0.050 g, 0.111 mmol) and TEA (0.0619 mL, 0.444 mmol) in 0.4 mL THF, 0.3 mL dichloromethane, and 0.2 mL DMF was added 2-bromoacetamide (0.0184 g, 0.133 mmol). The reaction mixture was heated in a 40° C. reaction block and stirred 1 hour. The reaction mixture was cooled to ambient temperature, several drops of saturated NaHCO₃ were added, and the milky mixture was heated back to 40° C. and stirred another 3 hours. The reaction mixture was cooled to ambient temperature, diluted with water, and the resulting solids were collected by vacuum filtration through a 0.2 micron nylon filter disc, rinsed with water, air dried, then washed successively with ethyl acetate, dichloromethane, and ether, air dried, and dried in vacuo to give the title compound (0.014 g, 0.0322 mmol, 29.0% yield) as a white powder. MS APCI (+) m/z 435 (M+1) detected.

Example 84

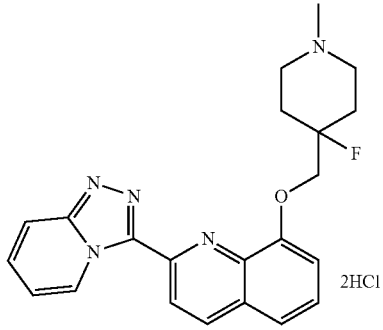 [SMILES: CN1CCC(F)(COc2cccc3ccc(-c4nnc5ccccn45)nc23)CC1]

2-([1,2,4]triazolo[4,3-a]pyridin-3-yl)-8-((4-fluoro-1-methylpiperidin-4-yl)methoxy)quinoline dihydrochloride To a suspension of 2-([1,2,4]triazolo[4,3-a]pyridin-3-yl)-8-((4-fluoropiperidin-4-yl)methoxy)quinoline dihydrochloride (0.050 g, 0.111 mmol) and triethylamine (0.0619 mL, 0.444 mmol) in 0.6 mL DCE and 0.3 mL DMF was added 37% formaldehyde in water (0.0413 mL, 0.555 mmol). After stirring at ambient temperature for 15 minutes, Na(OAc)₃BH (0.0471 g, 0.222 mmol) was added, and the reaction mixture was stirred at ambient temperature for 18 hours. Another 10 equivalents of 37% formaldehyde was added, followed by 10 equivalents of Na(OAc)₃BH. The reaction mixture was stirred another 6 hours, and saturated NaHCO₃ was added. The mixture was extracted with dichloromethane, and the combined extracts were dried (Na₂SO₄), filtered, and concentrated. The crude was purified by preparative TLC (1 mm plate, 6:1 dichloromethane: 6% NH₄OH in methanol). The resulting residue was dissolved in minimal dichloromethane, and this solution was added to a vigorously stirring solution of 1.5 mL 2M HCl/ether in 15 mL ether, causing precipitation. The solids were isolated by filtration through a medium glass fritted funnel by pushing the solvent through the frit with nitrogen pressure, rinsed with ether, dried under nitrogen pressure, and dried in vacuo to give the title compound (0.015 g, 0.0323 mmol, 29.1% yield) as a white powder. MS APCI (+) m/z 392 (M+1) detected.

zolo[4,3-a]pyridin-3-yl)-8-((4-methylpiperidin-4-yl)methoxy)quinoline dihydrochloride in place of 2-([1,2,4]triazolo[4,3-a]pyridin-3-yl)-8-((4-fluoropiperidin-4-yl)methoxy)quinoline dihydrochloride. MS APCI (+) m/z 418 (M+1) detected.

Example 85

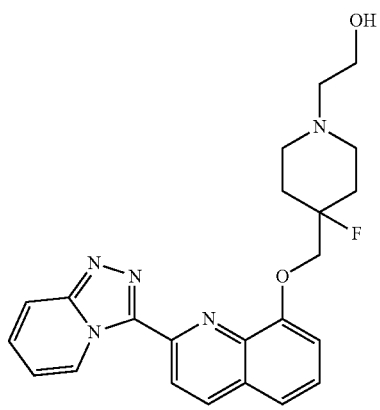 [SMILES: OCCN1CCC(F)(COc2cccc3ccc(-c4nnc5ccccn45)nc23)CC1]

2-(4-((2-([1,2,4]triazolo[4,3-a]pyridin-3-yl)quinolin-8-yloxy)methyl)-4-fluoropiperidin-1-yl)ethanol dihydrochloride Prepared as described in Example 84 using 2-hydroxyacetaldehyde in place of 37% formaldehyde. MS APCI (+) m/z 422 (M+1) detected.

Example 86

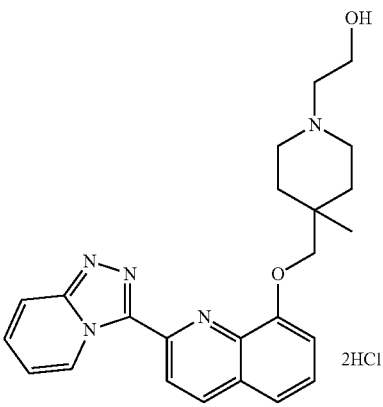 [SMILES: CC1(COc2cccc3ccc(-c4nnc5ccccn45)nc23)CCN(CCO)CC1]

2-(4-((2-([1,2,4]triazolo[4,3-a]pyridin-3-yl)quinolin-8-yloxy)methyl)-4-fluoropiperidin-1-yl)ethanol dihydrochloride Prepared as described in Example 84 using 2-hydroxyacetaldehyde in place of 37% formaldehyde and 2-([1,2,4]tria- Example 87

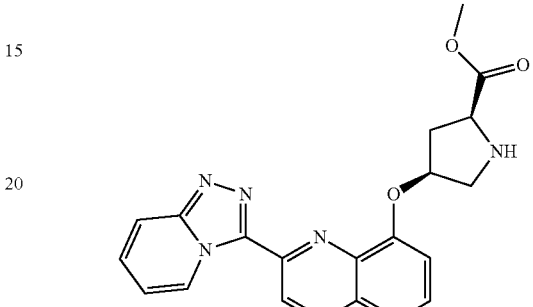

(2S,4S)-methyl 4-(2-([1,2,4]triazolo[4,3-a]pyridin-3-yl)quinolin-8-yloxy)pyrrolidine-2-carboxylate Prepared as described in Example 36 using (2S,4R)-1-tert-butyl 2-methyl 4-hydroxypyrrolidine-1,2-dicarboxylate in place (2S,4S)-1-tert-butyl 2-methyl 4-hydroxypiperidine-1,2-dicarboxylate. MS ESI (+) m/z 390.1 (M+1) detected.

Example 88

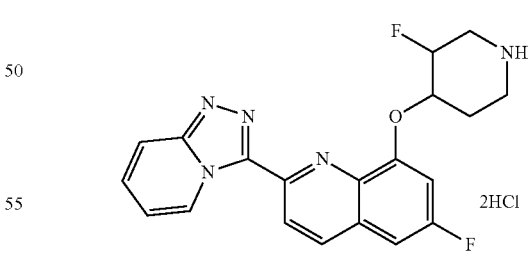

2-([1,2,4]triazolo[4,3-a]pyridin-3-yl)-6-fluoro-8-((cis)-3-fluoropiperidin-4-yloxy)quinoline Prepared as described in Example 26 using 2-([1,2,4]triazolo[4,3-a]pyridin-3-yl)-6-fluoroquinolin-8-ol in place of 2-([1,2,4]triazolo[4,3-a]pyridin-3-yl)-quinolin-8-ol. MS ESI (+) m/z 382.2 (M+1) detected.

Example 89

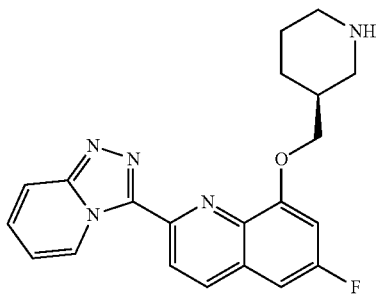 [SMILES: Fc1cc(OC[C@H]2CCCNC2)c2nc(-c3nnc4ccccn34)ccc2c1]

(S)-2-([1,2,4]triazolo[4,3-a]pyridin-3-yl)-6-fluoro-8-(piperidin-3-ylmethoxy)quinoline Prepared as described in Example 16 using (S)-tert-butyl 3-(hydroxymethyl)piperidine-1-carboxylate in place of tert-butyl 3-(hydroxymethyl)piperidine-1-carboxylate, and 2-([1,2,4]triazolo[4,3-a]pyridin-3-yl)-6-fluoroquinolin-8-ol in place of 2-([1,2,4]triazolo[4,3-a]pyridin-3-yl)-quinolin-8-ol. MS ESI (+) m/z 378.2 (M+1) detected.

Example 90

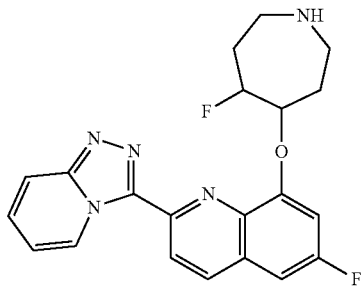 [SMILES: Fc1cc(OC2CCNCCC2F)c2nc(-c3nnc4ccccn34)ccc2c1]

Enantiomer 1 of cis-2-([1,2,4]triazolo[4,3-a]pyridin-3-yl)-6-fluoro-8-5-fluoroazepan-4-yloxy)quinoline Step A: Preparation of trans-tert-butyl 4-fluoro-5-hydroxyazepane-1-carboxylate: To a tert-butyl 4-fluoro-5-oxoazepane-1-carboxylate (20.0 g, 86.5 mmol) was dissolved in THF (430 mL) solution and the solution was cooled to −5° C. L-selectride (112 mL, 112 mmol, 1.0 M in THF) was added via syringe. The mixture was gradually warmed to ambient temperature over 3 hours and stirred for an additional 20 hours. The resulting cloudy mixture was diluted with 110 mL of MeOH which was followed by the addition of NaOH (355 mL, 355 mmol, 1.0M aqueous). The mixture was cooled in a water bath, and $H_2O_2$ (80.4 mL, 709 mmol, 30% aqueous) was added carefully via addition funnel over 30 minutes. The mixture was stirred vigorously for 1 hour, then diluted with water and extracted with EtOAc (3×200 mL). The combined organic layers were washed with water and 1N $KHSO_4$ (2×150 mL), and the combined aqueous phases were back-extracted with EtOAc (200 mL). The combined organic layers were washed with saturated aqueous $NaHCO_3$, then dried over $Na_2SO_4$, filtered and concentrated. The crude product was purified via column chromatography (15% to 60% EtOAc/hexanes) to provide the product as a thick colorless oil which slowly became a white solid (13.9 g, 69%; diastereomeric ratio (dr): ~7:1 trans:cis).

Step B: Preparation of trans-tert-butyl 4-fluoro-5-(4-nitrophenylsulfonyloxy)azepane-1-carboxylate: trans-tert-butyl 4-fluoro-5-hydroxyazepane-1-carboxylate (12.36 g, 52.98 mmol) was dissolved in $CH_2Cl_2$ (110 mL). The solution was cooled to 0° C., 4-nitrobenzene-1-sulfonyl chloride (14.09 g, 63.58 mmol) was added and the mixture was stirred for 10 minutes. $NEt_3$ (11.08 mL, 79.48 mmol) was added and the mixture was slowly warmed to ambient temperature over 1 hour and stirred for an additional 2 hours. The mixture was diluted with $CH_2Cl_2$ and washed with water followed by 1N $KHSO_4$ (2×50 mL), then with saturated aqueous $NaHCO_3$ (50 mL) and brine, and the combined organic layers were dried over $Na_2SO_4$, filtered and concentrated. The crude product was purified via column chromatography (10 to 70% MTBE/hexanes) to provide 18.4 g of the product (84%) as a single isomer and as a faint orange powder.

Step C: Preparation of cis-tert-butyl 4-(2-([1,2,4]triazolo[4,3-a]pyridin-3-yl)-6-fluoroquinolin-8-yloxy)-5-fluoroazepane-1-carboxylate: trans-tert-Butyl 4-fluoro-5-(4-nitrophenylsulfonyloxy)azepane-1-carboxylate (0.526 g, 1.26 mmol) and 2-([1,2,4]triazolo[4,3-a]pyridin-3-yl)-6-fluoroquinolin-8-ol (0.320 g, 1.14 mmol) were slurried in $CH_3CN$ (5.5 mL). To this mixture was added 2-tert-butyl-1,1,3,3-tetramethylguanidine (0.276 mL, 1.37 mmol) dropwise. The mixture was warmed to 40° C. and stirred overnight. The mixture was cooled to ambient temperature and diluted with water (10 mL) and stirred for 15 minutes, then filtered, and the solid was washed with water and hexanes and dried. This provided 0.460 g of the title compound (81%) as an off-white solid (>95% pure by HPLC). MS ESI (+) m/z 496.0 (M+1) detected.

Step D: Isolation of Enantiomer 1 of cis-tert-butyl 4-(2-([1,2,4]triazolo[4,3-a]pyridin-3-yl)-6-fluoroquinolin-8-yloxy)-5-fluoroazepane-1-carboxylate: Racemic cis-tert-butyl 4-(2-([1,2,4]triazolo[4,3-a]pyridin-3-yl)-6-fluoroquinolin-8-yloxy)-5-fluoro azepane-1-carboxylate was separated by chiral HPLC on a Prep Chiral OJ-H column using the following solvent mixture: 75% heptane, 20% EtOH, 3% MeOH, 2% acetonitrile, to provide the enantiomers as peak 1 (7.573 minutes) and peak 2 (8.373 minutes). Peak 1 was isolated to provide the title compound 99% ee, 99% de. MS ESI (+) m/z 496.0 (M+1) detected.

Step E: Preparation of Enantiomer 1 of cis-2-([1,2,4]triazolo[4,3-a]pyridin-3-yl)-6-fluoro-8-5-fluoroazepan-4-yloxy)quinoline: Enantiomer 1 of cis-tert-butyl 4-(2-([1,2,4]triazolo[4,3-a]pyridin-3-yl)-6-fluoroquinolin-8-yloxy)-5-fluoroazepane-1-carboxylate (0.119 g, 0.240 mmol) was dissolved in $CHCl_3$ (2.4 mL). HCl (2.40 mL, 9.61 mmol, 4.0 M dioxane) was added and the mixture was stirred at ambient temperature for 3 hours. The mixture was filtered through a polypropylene filter and washed with $CH_2Cl_2$ and $Et_2O$, then slurried in hexanes and dried carefully in vacuo to provide 0.095 g of the desired product as a white solid (85%). MS ESI (+) m/z 396.1 (M+1) detected. Specific rotation: $[\alpha]^{25}_D = -49.6°$ (c=0.95, MeOH).

Example 91

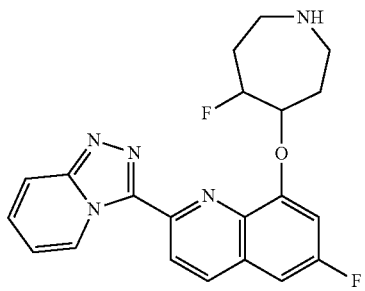 [SMILES: Fc1cc(OC2CCNCCC2F)c2nc(-c3nnc4ccccn34)ccc2c1]

Enantiomer 2 of trans-2-([1,2,4]triazolo[4,3-a]pyridin-3-yl)-6-fluoro-8-5-fluoroazepan-4-yloxy)quinoline Step A: Preparation of trans-tert-butyl 4-fluoro-5-hydroxyazepane-1-carboxylate: To a tert-butyl 4-fluoro-5-oxoazepane-1-carboxylate (20.0 g, 86.5 mmol) was dissolved in THF (430 mL) solution and the solution was cooled to −5° C. L-Selectride (112 mL, 112 mmol, 1.0 M in THF) was added via syringe. The mixture was gradually warmed to ambient temperature over 3 hours and stirred for an additional 20 hours. The resulting cloudy mixture was diluted with 110 mL of MeOH, followed by addition of NaOH (355 mL, 355 mmol, 1.0M aqueous). The mixture was cooled in a water bath and $H_2O_2$ (80.4 mL, 709 mmol, 30% aqueous) was added carefully via addition funnel over 30 minutes. The mixture was stirred vigorously for 1 hour. The mixture was diluted with water and extracted with EtOAc (3×200 mL). The combined organic layers were washed with water and 1N $KHSO_4$ (2×150 mL), and the combined aqueous phases were back extracted with EtOAc (200 mL). The combined organic layers were washed with saturated aqueous $NaHCO_3$, dried over $Na_2SO_4$, filtered and concentrated. The crude product was purified via column chromatography (15% to 60% EtOAc/hexanes) to provide the product as a thick colorless oil which slowly became a white solid (13.9 g, 69%; diastereomeric ratio (dr): ~7:1 trans:cis).

Step B: Preparation of cis-tert-butyl 4-fluoro-5-hydroxyazepane-1-carboxylate: trans-tert-butyl 4-fluoro-5-hydroxyazepane-1-carboxylate (25.00 g, 107.2 mmol) was dissolved in THF (1100 mL). To this solution was added 2-chloroacetic acid (15.19 g, 160.8 mmol) and $PPh_3$ (42.16 g, 160.8 mmol). The solution was cooled to 0° C. and DEAD (25.31 mL, 160.8 mmol) was added as a THF solution (250 mL). The reaction mixture was protected from light and stirred overnight as it slowly increased to ambient temperature. The THF was removed in vacuo and replaced with EtOAc. The solution was washed with saturated aqueous $NaHCO_3$, dried over $Na_2SO_4$, filtered and concentrated. The crude product was dissolved in dioxane (500 mL), and water was added (250 mL). A 1N NaOH solution was added until the pH reached ~10 (200 mL). The mixture was stirred for 1 hour and then quenched with 1N $KHSO_4$ (250 mL). The mixture was extracted with EtOAc (3×250 mL) and the combined organic phases were washed with saturated aqueous $NaHCO_3$, dried over $Na_2CO_3$, filtered and concentrated to a white paste. The paste was then slurried in 50% $Et_2O$/hexanes (200 mL) and filtered through qualitative paper. The resulting white solid was washed with 50% $Et_2O$/hexanes (3×200 mL) and the filtrate was concentrated. The crude residue was purified by column chromatography (10 to 40% Acetone/hexanes) to provide the product (22.4 g, 89%) as a thick colorless oil.

Step C: Preparation of cis-tert-butyl 4-fluoro-5-(4-nitrophenylsulfonyloxy)azepane-1-carboxylate: cis-tert-butyl 4-fluoro-5-hydroxyazepane-1-carboxylate (22.3 g, 95.59 mmol) was dissolved in $CH_2Cl_2$ (240 mL). The solution was cooled to 0° C., 4-nitrobenzene-1-sulfonyl chloride (25.42 g, 114.7 mmol) was added and the mixture was stirred for 30 minutes. $NEt_3$ (19.99 mL, 143.4 mmol) was added and the mixture was slowly warmed to ambient temperature over 2 hours and stirred overnight. The mixture was diluted with $CH_2Cl_2$ and washed with 1N $KHSO_4$ (2×100 mL) followed by washing with saturated aqueous $NaHCO_3$ (100 mL) and brine. The organic layer was dried over $Na_2SO_4$, filtered and concentrated. The crude orange solid was dissolved in minimal hot $CH_2Cl_2$ and hexanes were added with stirring until the solution became persistently cloudy. The warm mixture was cooled to ambient temperature and allowed to stand undisturbed for 1 hour. The solids were collected by filtration and the solid was successively washed with hexanes followed by 50% $Et_2O$/hexanes and finally with hexanes again to provide the clean cis isomer of the product as a pale yellow solid (27.05 g, 68%).

Step D: Preparation of trans-tert-butyl 4-(2-([1,2,4]triazolo[4,3-a]pyridin-3-yl)-6-fluoroquinolin-8-yloxy)-5-fluoroazepane-1-carboxylate: cis-tert-butyl 4-fluoro-5-(4-nitrophenylsulfonyloxy)azepane-1-carboxylate (0.484 g, 1.16 mmol) and 2-([1,2,4]triazolo[4,3-a]pyridin-3-yl)-6-fluoroquinolin-8-ol (0.300 g, 1.07 mmol) were slurried in $CH_3CN$ (5.0 mL). To this mixture was added 2-tert-butyl-1,1,3,3-tetramethylguanidine (0.259 mL, 1.28 mmol) dropwise. The dark solution was warmed to 40° C. and stirred overnight. The mixture was cooled to ambient temperature and diluted with water (10 mL) and stirred for 15 minutes, then filtered. The solid was washed with water and hexanes and dried in vacuo. The product was purified via column chromatography (10 to 50% Acetone/$CH_2Cl_2$) to provide the product as off-white solid. MS ESI (+) m/z 496.0 (M+1) detected.

Step E: Isolation of Enantiomer 2 of trans-tert-butyl 4-(2-[1,2,4]triazolo[4,3-a]pyridin-3-yl)-6-fluoroquinolin-8-yloxy)-5-fluoroazepane-1-carboxylate: Racemic trans tert-butyl 4-(2-([1,2,4]triazolo[4,3-a]pyridin-3-yl)-6-fluoroquinolin-8-yloxy)-5-fluoro azepane-1-carboxylate was separated by chiral HPLC on a Prep Chiral OJ-H column using the following solvent system: 20% EtOH and 80% hexanes, to provide the two enantiomers as peak 1 (9.715 minutes) and peak 2 (14.265 minutes). Peak 2 was isolated to provide the title compound with 98% ee and 99% de.

Step F: Enantiomer 2 of trans-2-([1,2,4]triazolo[4,3-a]pyridin-3-yl)-6-fluoro-8-5-fluoroazepan-4-yloxy)quinoline: Enantiomer 2 of trans-tert-butyl 4-(2-([1,2,4]triazolo[4,3-a]pyridin-3-yl)-6-fluoroquinolin-8-yloxy)-5-fluoroazepane-1-carboxylate (0.210 g, 0.424 mmol) was dissolved in $CHCl_3$ (4.3 mL). To this solution was added HCl (4.24 mL, 17.0 mmol, 4.0M Dioxane) and the mixture was stirred at ambient temperature for 3 hours. The mixture was filtered through a polypropylene filter and washed with $CH_2Cl_2$ and $Et_2O$, then slurried in hexanes and dried in vacuo to provide the desired product as white solid. MS ESI (+) m/z 396.1 (M+1) detected. Specific rotation: $[\alpha]^{25}_D = -77°$ (c=0.95, MeOH).

Example 92

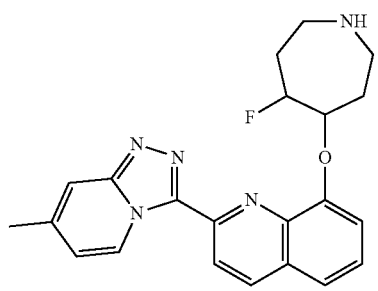 [SMILES: Cc1ccn2c(-c3ccc4cccc(OC5CCNCCC5F)c4n3)nnc2c1]

Enantiomer 1 of cis-8-5-fluoroazepan-4-yloxy)-2-(7-methyl-[1,2,4]triazolo[4,3-a]pyridin-3-yl)quinoline Step A: Preparation of 2-hydrazinyl-4-methylpyridine: 2-Chloro-4-methylpyridine (3.43 mL, 39.19 mmol) and hydrazine hydrate (19.07 mL, 391.9 mmol) were suspended together in a flask and heated to 150° C. for 72 hours. The mixture was concentrated in vacuo to an oil. The oil was taken up in EtOAc and the resulting solid was removed by vacuum filtration. The organic filtrate was washed with 40% aqueous NaOH (2×50 mL) and dried over $Na_2SO_4$, filtered and concentrated to provide the desired product (2.42 g, 54%) as a white solid.

Step B: Preparation of (E)-8-(tert-butyldimethylsilyloxy)-2-((2-(4-methylpyridin-2-yl)hydrazono)methyl)quinoline: 2-Hydrazinyl-4-methylpyridine (0.280 g, 2.27 mmol) and 8-(tert-butyldimethylsilyloxy)quinoline-2-carbaldehyde (0.653 g, 2.27 mmol) were suspended in EtOH (6 mL) and stirred overnight at ambient temperature. The resulting suspension was filtered and the solid was washed with cold EtOH and dried in vacuo to provide the title compound (0.720 g; 81%).

Step C: Preparation of 8-(tert-butyldimethylsilyloxy)-2-(7-methyl-[1,2,4]triazolo[4,3-a]pyridin-3-yl)quinoline: (E)-8-(tert-Butyldimethylsilyloxy)-2-((2-(4-methylpyridin-2-yl)hydrazono)methyl)quinoline (0.720 g, 1.83 mmol) was suspended in DCM (6 mL) at ambient temperature. Iodobenzene diacetate (0.650 g, 2.02 mmol) was added and the solution was allowed to stir at ambient temperature overnight. The mixture was concentrated to an orange oil and purified directly by column chromatography (20% EtOAc/DCM to 50% EtOAc/DCM) to provide the desired product (0.590 g, 82%).

Step D: Preparation of 247-methyl-[1,2,4]triazolo[4,3-a]pyridin-3-yl)quinolin-8-ol. 8-(tert-butyldimethylsilyloxy)-2-(7-methyl-[1,2,4]triazolo[4,3-a]pyridin-3-yl)quinoline (0.580 g, 1.49 mmol) was suspended in THF (2 mL) and the solution was cooled to 0° C. Tetrabutylammonium fluoride hydrate (0.582 g, 2.23 mmol) was added to the solution and the mixture stirred at 0° C. for 10 minutes, then warmed to ambient temperature and stirred for 4 hours. The mixture was diluted with a saturated aqueous $NH_4Cl$ solution and EtOAc. The resulting white solid was isolated by vacuum filtration and was combined with the organic layer which was concentrated. The solid thus obtained was slurried in $H_2O$ for 10 minutes and the solids isolated by vacuum filtration and dried to provide the title compound (0.320 g, 78%) as a white solid. MS ESI (+) m/z 277.1 (M+1) detected.

Step E: Preparation of cis-tert-butyl 4-fluoro-5-(2-(7-methyl-[1,2,4]triazolo[4,3-a]pyridin-3-yl)quinolin-8-yloxy)azepane-1-carboxylate: 2-(7-methyl-[1,2,4]triazolo[4,3-a]pyridin-3-yl)quinolin-8-ol (300 mg, 1.09 mmol) was suspended in $CH_3CN$ (5 mL) at ambient temperature, and trans-tert-butyl 4-fluoro-5-(4-nitrophenylsulfonyloxy)azepane-1-carboxylate (454 mg, 1.09 mmol) and 2-tert-butyl-1,1,3,3-tetramethylguanidine (263 µL, 1.30 mmol) were added. The dark solution was stirred at 40° C. overnight, then concentrated to a grey solid which was slurried in water for 10 minutes. The solid was filtered, washed and dried in vacuo to provide the desired product. MS ESI (+) m/z 492.3 (M+1) detected.

Step F: Isolation of Enantiomer 1 of cis-tert-butyl 4-fluoro-5-(2-(7-methyl-[1,2,4]triazolo[4,3-a]pyridin-3-yl)quinolin-8-yloxy)azepane-1-carboxylate: Racemic cis-tert-butyl 4-fluoro-5-(2-(7-methyl-[1,2,4]triazolo[4,3-a]pyridin-3-yl) quinolin-8-yloxy)azepane-1-carboxylate was separated by chiral HPLC on a Prep Chiral OJ-H column using the following solvent system: 90% hexanes, 10% EtOH, to provide the two enantiomers as peak 1 (7.397 minutes) and peak 2 (10.335 minutes). Peak 1 was collected to provide the title compound with 99% ee, 99% de.

Step G: Enantiomer 1 of cis-8-5-fluoroazepan-4-yloxy)-2-(7-methyl-[1,2,4]triazolo[4,3-a]pyridin-3-yl)quinoline: Enantiomer 1 of cis-tert-butyl 4-fluoro-5-(2-(7-methyl-[1,2,4]triazolo[4,3-a]pyridin-3-yl)quinolin-8-yloxy)azepane-1-carboxylate (0.161 g, 0.328 mmol) was dissolved in $CHCl_3$ (3 mL). To this solution was added HCl (6.55 mL, 13.1 mmol, 2.0M $Et_2O$) and the mixture was stirred at ambient temperature for 4 hours. The mixture was filtered through a polypropylene filter, washed with $CH_2Cl_2$ and $Et_2O$, slurried in hexanes, then dried carefully in vacuo to provide the desired product as a white solid. MS ESI (+) m/z 392.1 (M+1) detected. Specific rotation: $[\alpha]^{25}_D = -50°$ (c=1.0, MeOH).

Example 93

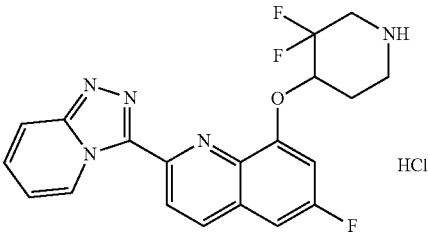 [SMILES: Fc1cc(OC2CCNCC2(F)F)c2nc(-c3nnc4ccccn34)ccc2c1 ; Cl]

2-([1,2,4]triazolo[4,3-a]pyridin-3-yl)-8-(3,3-difluoropiperidin-4-yloxy)-6-fluoroquinoline dihydrochloride Step 1A: Preparation of N-(2,4-difluorophenyl)cinnamamide: 2,4-difluoroaniline (9.0 g, 69.71 mmol) and pyridine (5.6 mL, 69.71 mmol) were dissolved in dichloromethane (45 mL) and the solution was cooled to 0° C. A solution of cinnamoyl chloride (13.04 g, 76.7 mmol) dissolved in dichloromethane (45 mL) was added dropwise, and after the addition the reaction was warmed to ambient temperature and stirred for 16 hours. The reaction was quenched with saturated $NaHCO_3$ and the layers were separated. The organic layer was washed with 1 M HCl then dried over $Na_2SO_4$ and concentrated in vacuo to provide a white solid. The solid was slurried in dichloromethane (150 mL), stirred for 30 minutes, and then hexanes (150 mL) were added. After stirring several minutes, the white solids were collected by filtration, washed with dichloromethane and air-dried to provide 13.5 g of the desired product. MS APCI (−) m/z 258.0 (M−1) detected.

Step 1B: Preparation of 6,8-difluoroquinolin-2-ol: Solid N-(2,4-difluorophenyl)cinnamamide (13.2 g, 50.7 mmol)

was pre-mixed with aluminum trichloride (20.29 g, 152.2 mmol) and the mixture was heated to 160° C. under gently flowing nitrogen gas for 80 minutes. The reaction was cooled and quenched with ice, and the resultant beige solid was collected by filtration, washed with water and air-dried to a light tan solid (9.89 g).

Step 1C: Preparation of 2-chloro-6,8-difluoro quinoline: 6,8-Difluoro quinolin-2-ol (9.89 g, 54.6 mmol) was slurried in 1,2-dichloroethane (550 mL) and treated with DMF (1 mL), and then 2M oxalyl chloride in $CH_2Cl_2$ (81.9 mL, 164 mmol) was added dropwise. The reaction was heated to 70° C. for 1 hour and then cooled and concentrated in vacuo. The residue was dissolved in $CHCl_3$ and washed with 50% saturated $NaHCO_3$. The aqueous layer (pH 8) was washed twice with $CHCl_3$ and the combined organics were dried over $Na_2SO_4$ and charcoal, filtered, and concentrated in vacuo to a brown solid. The solid was purified by recrystallization from hot hexanes and 1,2-dichloroethane (minimum volume). The solid was collected, washed with hexanes and air-dried to provide the desired product as an off-white solid (5.78 g).

Step 2: Preparation of [1,2,4]triazolo[4,3-a]pyridine: 2-Hydrazinylpyridine (5.06 g, 46.4 mmol) was treated with triethoxymethane (50.2 mL, 302 mmol) and the mixture was heated to reflux for 4 hours with nitrogen flowing over the top of the air condenser. The air condenser was replaced with a small distillation head and the low boiling solvents (75-80° C.) were removed from the system. Heating continued for 16 hours. The reaction was cooled to ambient temperature and concentrated in vacuo to a dark residue. The residue was chromatographed on $SiO_2$ eluting with a gradient of 6% $NH_4OH$ in MeOH/ethyl acetate. The desired product was isolated as a light orange solid (4.2 g). MS APCI (+) m/z 120.0 (M+1) detected.

Step 3: Preparation of 2-([1,2,4]triazolo[4,3-a]pyridin-3-yl)-6,8-difluoroquinoline: 2-Chloro-6,8-difluoroquinoline (0.025 g, 0.125 mmol) was combined with [1,2,4]triazolo[4,3-a]pyridine (0.016 g, 0.14 mmol), micronized $Cs_2CO_3$ (0.082 g, 0.25 mmol), and $PdCl_2(PPh_3)_2$ (0.0088 g, 0.013 mmol), and the solids were slurried in dioxane (1.25 mL). The reaction was degassed with argon (bubbled through the solution) then heated to reflux for 20 hours. The crude reaction mixture was chromatographed without workup on $SiO_2$ eluting with a gradient of 6% $NH_4OH$ in MeOH/ethyl acetate to provide the desired product as an orange solid (21 mg).

Step 4A: Preparation of 1-benzyl-3,3-difluoropiperidine-4,4-diol: Ethyl 1-benzyl-5,5-difluoro-4-oxopiperidine-3-carboxylate (6.00 g, 20.2 mmol; prepared as described in WO 2005/040120, p. 30) was dissolved in 3N HCl (60 mL) and heated to reflux for 16 hours. The reaction was cooled, adjusted to pH 8 with solid $NaHCO_3$, then extracted three times with ethyl acetate. The combined organics were washed with saturated NaCl, dried over $Na_2SO_4$ and concentrated in vacuo to a white solid (5.1 g). MS APCI (+) m/z 244.0 (M+1) detected.

Step 4B: Preparation of tert-butyl 3,3-difluoro-4,4-dihydroxypiperidine-1-carboxylate: 1-Benzyl-3,3-difluoropiperidine-4,4-diol (2.05 g, 8.43 mmol) was dissolved in 95% EtOH (40 mL) and treated with di-tert-butyl dicarbonate (3.68 g, 16.9 mmol) and 10% Pd on carbon (Degeussa type, 200 mg). The reaction was placed under a balloon of hydrogen gas and stirred for 12 hours. The reaction mixture was filtered through a nylon membrane, washed with ethanol and concentrated in vacuo to a colorless oil (4.05 g).

Step 4C: Preparation of tert-butyl 3,3-difluoro-4-hydroxypiperidine-1-carboxylate: tert-Butyl 3,3-difluoro-4,4-dihydroxypiperidine-1-carboxylate (3.10 g, 12.2 mmol) was dissolved in 95% EtOH (50 mL) and the solution was treated with sodium borohydride (2.32 g, 61.2 mmol) and stirred at ambient temperature for 3 hours. The reaction was treated dropwise with 3N HCl until vigorous gas evolution ceased, then stirred at ambient temperature for 20 minutes (pH of the mixture was 3-4 at this point). The reaction was neutralized with saturated $NaHCO_3$ and concentrated in vacuo. The residue was dissolved in ethyl acetate and water and the layers were separated. The aqueous layer was washed with ethyl acetate and the combined organic layers were washed with saturated NaCl, dried over $Na_2SO_4$ and concentrated in vacuo to provide the desired product as a white solid (1.39 g).

Step 5A: Preparation of tert-butyl 4-(2-([1,2,4]triazolo[4,3-a]pyridin-3-yl)-6-fluoroquinolin-8-yloxy)-3,3-difluoropiperidine-1-carboxylate: tert-Butyl 3,3-difluoro-4-hydroxypiperidine-1-carboxylate (0.0706 g, 0.298 mmol) was treated with 1 M KOtBu in THF (0.283 mL, 0.283 mmol) and stirred for 15 minutes. The solution was treated with 2-([1,2,4]triazolo[4,3-a]pyridin-3-yl)-6,8-difluoroquinoline (0.042 g, 0.149 mmol) and DMF (0.80 mL) then the mixture was stirred at ambient temperature for 16 hours. The mixture was directly chromatographed on $SiO_2$ eluting with a gradient of 2% $NH_4OH$ in isopropanol/ethyl acetate. The desired product was collected and concentrated to a colorless oil, (72 mg). MS APCI (+) m/z 500.0 (M+1) detected.

Step 5B: Preparation of 2-([1,2,4]triazolo[4,3-a]pyridin-3-yl)-8-(3,3-difluoropiperidin-4-yloxy)-6-fluoroquinoline dihydrochloride salt: tert-Butyl 4-(2-([1,2,4]triazolo[4,3-a]pyridin-3-yl)-6-fluoroquinolin-8-yloxy)-3,3-difluoropiperidine-1-carboxylate (0.072 g, 0.144 mmol) was dissolved in MeOH (0.72 mL) and treated with 4.0 M HCl in dioxane (0.360 mL, 1.44 mmol), then stirred at ambient temperature for 2 hours. The reaction mixture was concentrated in vacuo. The residue was taken up in MeOH and concentrated three times. The residue was chromatographed on $SiO_2$ eluting with a gradient of 2% $NH_4OH$ in isopropanol/methylene chloride. The desired product was dissolved in MeOH (2 mL), treated with 2.0 M HCl in ether (0.809 mL, 1.62 mmol) and concentrated in vacuo. The residue was again dissolve in MeOH and concentrated in vacuo several times, then placed under vacuum to give the desired product as a white solid (27.8 mg). MS APCI (+) m/z 400.3 (M+1) detected.

Example 94

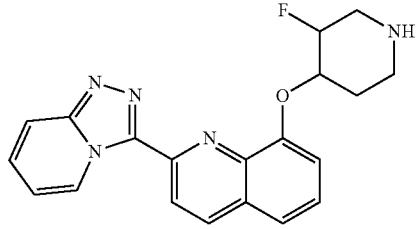

Enantiomer 1 of 2-([1,2,4]triazolo[4,3-a]pyridin-3-yl)-8-((cis)-3-fluoropiperidin-4-yloxy)quinoline dihydrochloride Step 1A: Preparation of N-(2-fluorophenyl)cinnamamide: Cinnamoyl chloride (89.2 g, 535 mmol) was dissolved in THF (170 mL) and added dropwise to a 0° C. solution of 2-fluoroaniline (54.1 g, 486 mmol) and pyridine (39.35 mL, 486.5 mmol) dissolved in THF (170 mL). The mixture was allowed to warm to ambient temperature after the addition and stirred for 15 hours. A solution of 2M HCl was added (1250 mL) and the mixture was stirred at ambient temperature for 8 hours, during which the initial oil solidified to a light pink solid. This material was collected by filtration, washed with several portions of water, and air-dried to provide the desired product (119.5 g).

Step 1B: Preparation of 8-fluoroquinolin-2-ol: N-(2-Fluorophenyl)cinnamamide (97.2 g, 403 mmol) was combined with $AlCl_3$ (161 g, 1209 mmol) and the solids were thoroughly mixed. The dry mixture was heated to 160° C. for 100 minutes. The reaction was cooled and quenched by addition of ice. A beige solid formed after complete dispersion of the dark solids and this was stirred overnight. The beige solid was filtered and air-dried overnight to provide the desired product as a free-flowing solid (69.8 g).

Step 1C: Preparation of 2-chloro-8-fluoroquinoline: 8-Fluoroquinolin-2-ol (35 g, 215 mmol) was slurried in 1,2-dichloroethane (875 mL) and treated with DMF (3 mL) then a solution of oxalyl chloride (2M in $CH_2Cl_2$) (322 mL, 644 mmol) was added dropwise. After the addition, the reaction was heated to 70° C. for 1 hour then cooled and concentrated in vacuo. The residue was dissolved in $CHCl_3$ and washed with 50% saturated $NaHCO_3$. The aqueous layer (pH 8) was washed twice with $CHCl_3$ and the combined organics were dried over $Na_2SO_4$, filtered and concentrated in vacuo to a brown solid (about 52 g). This crude solid was dissolved in methylene chloride and filtered through a plug of $SiO_2$ eluting with methylene chloride. The desired material was isolated as a light orange solid (32.9 g).

Step 2: Preparation of 2-([1,2,4]triazolo[4,3-a]pyridin-3-yl)-8-fluoro quinoline: 2-Chloro-8-fluoroquinoline (0.75 g, 4.13 mmol) was combined with [1,2,4]triazolo[4,3-a]pyridine (0.541 g, 4.54 mmol), micronized $Cs_2CO_3$ (2.69 g, 8.26 mmol), and $PdCl_2(PPh_3)_2$ (0.290 g, 0.413 mmol) then the mixture was slurried in dioxane (20 mL). The reaction was deoxygenated with argon and heated to reflux for 20 hours, then cooled, diluted with $CHCl_3$ and filtered through a pad of Celite®. The filtrate was concentrated onto $Na_2SO_4$ powder (15 g) and the mixture was chromatographed on $SiO_2$ eluting with a stepped gradient of 0-2% MeOH/ethyl acetate. The desired product was isolated as a cream-colored solid (1.12 g). MS APCI (+) m/z 265.3 (M+1) detected.

Step 3A: Preparation of benzyl 4-(trimethylsilyloxy)-5,6-dihydropyridine-1(2H)-carboxylate: To benzyl 4-oxopiperidine-1-carboxylate (152 g, 650 mmol) in DMF (650 mL) was added TMS-Cl (148 mL, 117 mmol) followed by triethylamine (326 mL, 234 mmol). The slurry was warmed to 80° C. for 16 hours, diluted with hexanes (1 L), washed 3 times with saturated $NaHCO_3$ solution, dried over $Na_2SO_4$, filtered and concentrated to obtain benzyl 4-(trimethylsilyloxy)-5,6-dihydropyridine-1(2H)-carboxylate, (199 g, 652 mmol) as a orange oil.

Step 3B: Preparation of benzyl 3-fluoro-4-oxopiperidine-1-carboxylate: Selectfluor® (181.2 g, 511.4 mmol) was added portion-wise (about 25 g portions) to a ice cold solution of benzyl 4-(trimethylsilyloxy)-5,6-dihydropyridine-1(2H)-carboxylate (142 g, 465 mmol) in $CH_3CN$ (2 L) over approximately 30 minutes. The ice bath was removed and the mixture was allowed to stand for 12 hours. The mixture was concentrated to a slurry, diluted with EtOAc and brine and the layers were separated. The brine phase was extracted once with EtOAc, and the combined organic phases were washed with saturated $NaHCO_3$ and brine, dried over $Na_2SO_4$, filtered and concentrated in vacuo to provide the desired product as a dark thick oil (112 g).

Step 3C: Preparation of cis-benzyl 3-fluoro-4-hydroxypiperidine-1-carboxylate: L-Selectride® (663 mL, 663 mmol) was added dropwise to an ice cold solution of benzyl 3-fluoro-4-oxopiperidine-1-carboxylate (138.9 g, 552.8 mmol) dissolved in anhydrous THF (421 mL). The ice bath was removed and the reaction was allowed to stand for 12 hours. The reaction mixture was carefully added (dropwise, via addition funnel) to a vigorously stirring mixture of 80 mL MeOH, 2 N NaOH (1400 mL) $H_2O_2$ (376 mL, 50%) in a large amount of ice, taking care to control the temperature rise. The mixture was stirred for 12 hours, then 2 L of EtOAc was added. The mixture was stirred an additional 1 hour. The layers were separated and the aqueous phase was extracted with EtOAc. The combined organic phases were dried over $Na_2SO_4$, filtered and concentrated in vacuo to an oil (112 g). The residue was purified by flash column chromatography (silica gel, eluting with a gradient of 30% EtOAc to 75% EtOAc in hexanes) to afford 38 g of the desired compound.

Step 3D: Preparation of non-racemic cis-benzyl 3-fluoro-4-hydroxypiperidine-1-carboxylate: A 32 g sample of the material of Step 3C was separated by chiral SFC separation (3 cm×15 cm Chiralpak AD-H column; mobile phase 22% Ethanol/$CO_2$, 100 bar; flow rate 100 mL/min; 50 mg/mL injections, 1.5 mL injection volume; 220 nM) to afford first eluting peak (Peak 1; 11.2 g, Rt 2.63 min) in >99% ee and second eluting peak (Peak 2; 11.8 g, Rt 4.01 min) in >99% ee.

Step 4A: Preparation of Enantiomer 1 of (cis)-benzyl 4-(2-[1,2,4]triazolo[4,3-a]pyridin-3-yl)quinolin-8-yloxy)-3-fluoropiperidine-1-carboxylate: Non-racemic (cis)-benzyl 3-fluoro-4-hydroxypiperidine-1-carboxylate (Peak 1 of Example 94, Step 3D; 0.288 g, 1.14 mmol) was treated with 1.0 M KOtBu in THF (1.10 mL, 1.10 mmol) and stirred at ambient temperature for 15 minutes. 2-([1,2,4]Triazolo[4,3-a]pyridin-3-yl)-8-fluoroquinoline (0.200 g, 0.757 mmol) was added as a solid, followed by the addition of DMF (3.3 mL), and the resultant mixture was stirred at ambient temperature for 40 hours. The crude reaction mixture was chromatographed on $SiO_2$ eluting with a gradient of (2% $NH_4OH$ in isopropanol)/methylene chloride. The desired product was isolated as a pale yellow solid (196 mg). MS APCI (+) m/z 498.2 (M+1) detected.

Step 4B: Preparation of Enantiomer 1 of 2-([1,2,4]triazolo[4,3-a]pyridin-3-yl)-8-((cis)-3-fluoropiperidin-4-yloxy)quinoline: Enantiomer 1 of (cis)-benzyl 4-(2-([1,2,4]triazolo[4,3-a]pyridin-3-yl)quinolin-8-yloxy)-3-fluoropiperidine-1-carboxylate (0.185 g, 0.372 mmol) was dissolved in dioxane (4.6 mL) and treated with 6 M hydrogen chloride (4.65 mL, 27.9 mmol) and the reaction mixture was heated at 100° C. for 2 hours. The reaction was cooled and carefully neutralized with solid $NaHCO_3$. The resulting aqueous layer (pH 8-9) was extracted four times with methylene chloride and the resulting organic layers were combined and dried over $Na_2SO_4$ then concentrated in vacuo. The residue was chromatographed on $SiO_2$ eluting with a gradient of 6% $NH_4OH$ in MeOH)/methylene chloride. The desired material was isolated as a colorless film (22 mg). MS APCI (+) m/z 364.1 (M+1) detected.

Step 4C: Preparation of the dihydrochloride salt of Enantiomer 1 of 2-([1,2,4]triazolo[4,3-a]pyridin-3-yl)-8-((cis)-3-fluoropiperidin-4-yloxy)quinoline: Non-racemic 2-([1,2,4]triazolo[4,3-a]pyridin-3-yl)-8-((cis)-3-fluoropiperidin-4-yloxy)quinoline (20 mg, 0.055 mmol) was dissolved in MeOH (2 mL) and treated with 4M HCl in dioxane (1 mL, 4 mmol). The mixture was stirred for 5 minutes then concentrated in vacuo. The residue was dissolved in fresh MeOH and concentrated in vacuo three times to a pale yellow solid (20.7 mg, 86%). Specific rotation: $[\alpha]^{20}_D$=+26° (c=0.45, 1:1 water/95% ethanol).

Example 95

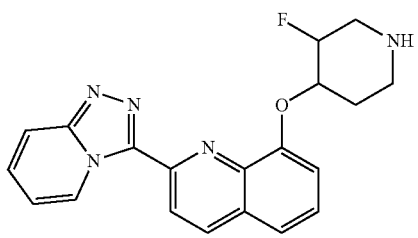 [SMILES: FC1CNCCC1Oc1cccc2ccc(-c3nnc4ccccn34)nc12]

Enantiomer 2 of 2-([1,2,4]triazolo[4,3-a]pyridin-3-yl)-8-((cis)-3-fluoropiperidin-4-yloxy)quinoline dihydrochloride Step 1: Preparation of Enantiomer 2 of 2-([1,2,4]triazolo[4,3-a]pyridin-3-yl)-8-((cis)-3-fluoropiperidin-4-yloxy)quinoline: Prepared according to the method of Example 94 using Peak 2 of non-racemic (cis)-benzyl 3-fluoro-4-hydroxypiperidine-1-carboxylate (Example 94, Step 3D) in place of Peak 1 of non-racemic (cis)-benzyl 3-fluoro-4-hydroxypiperidine-1-carboxylate (Example 94, Step 3D) in step 4A. MS APCI (+) m/z 364.1 (M+1) detected.

Step 2: Preparation of the dihydrochloride salt Enantiomer 2 of 2-([1,2,4]triazolo[4,3-a]pyridin-3-yl)-8-((cis)-3-fluoropiperidin-4-yloxy)quinoline: Prepared as described in Example 94 using non-racemic 2-([1,2,4]triazolo[4,3-a]pyridin-3-yl)-8-((cis)-3-fluoropiperidin-4-yloxy)quinoline in Step 4C. Specific rotation: $[\alpha]^{20}_D = -48°$ (c=0.46, 1:1 water/95% ethanol).

Example 96

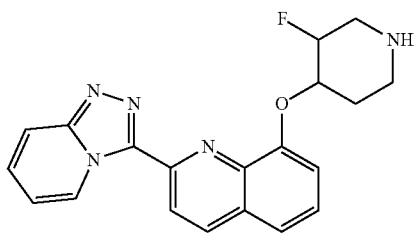 [SMILES: FC1CNCCC1Oc1cccc2ccc(-c3nnc4ccccn34)nc12]

Enantiomer 1 of 2-([1,2,4]triazolo[4,3-a]pyridin-3-yl)-8-((trans)-3-fluoropiperidin-4-yloxy)quinoline dihydrochloride Step 1A: Preparation of Enantiomer 1 of (trans)-benzyl 4-(benzoyloxy)-3-fluoropiperidine-1-carboxylate: Non-racemic (cis)-benzyl 3-fluoro-4-hydroxypiperidine-1-carboxylate (Peak 1 of Example 94, Step 3D; 0.306 g, 1.21 mmol) was treated with triphenylphosphine (0.475 g, 1.81 mmol) and benzoic acid (0.221 g, 1.81 mmol) and the solids were dissolved in THF (5 mL), then cooled to 0° C. The solution was treated dropwise with diisopropyl azodicarboxylate (0.357 mL, 1.81 mmol) dissolved in THF (1 mL). The solution was warmed to ambient temperature with a bath and stirred for 7 days, then concentrated in vacuo. The residue was dissolved in CH$_2$Cl$_2$ and washed with saturated NH$_4$Cl, water, 50% saturated NaHCO$_3$, dried over Na$_2$SO$_4$ and concentrated in vacuo to a colorless oil. The oil was chromatographed on SiO$_2$ eluting with 1:12 acetone/hexanes. The desired fraction was isolated to provide the desired product as a colorless oil (385 mg).

Step 1B: Preparation of Enantiomer 1 of (trans)-benzyl 3-fluoro-4-hydroxypiperidine-1-carboxylate: Enantiomer 1 of (trans)-benzyl 4-(benzoyloxy)-3-fluoropiperidine-1-carboxylate (6.50 g, 18.2 mmol) was dissolved in THF/MeOH/water (2:2:1, 50 mL) and treated with lithium hydroxide hydrate (1.53 g, 36.4 mmol), and the reaction was stirred at 50° C. for 2 hours. The reaction mixture was cooled, quenched with saturated NH$_4$Cl to pH 8, concentrated in vacuo and the aqueous layer (pH 8) was extracted with methylene chloride. The combined organic layer was dried over Na$_2$SO$_4$ and concentrated in vacuo to a colorless oil (295 mg). The crude material was chromatographed on SiO$_2$ eluting with 2:1 hexanes/ethyl acetate. The desired material was isolated as a colorless oil (3.7 g).

Step 2A: Preparation of Enantiomer 1 of (trans)-benzyl 4-(2-([1,2,4]triazolo[4,3-a]pyridin-3-yl)quinolin-8-yloxy)-3-fluoropiperidine-1-carboxylate: Non-racemic (trans)-benzyl 3-fluoro-4-hydroxypiperidine-1-carboxylate (0.192 g, 0.757 mmol) was treated with 1.0 M KOtBu in THF (0.757 mL, 0.757 mmol) and stirred at ambient temperature for 15 minutes. 2-([1,2,4]Triazolo[4,3-a]pyridin-3-yl)-8-fluoroquinoline (0.200 g, 0.757 mmol) was added along with DMF (2.25 mL) and the mixture was stirred at 50° C. for 15 hours. The reaction was cooled and chromatographed on SiO$_2$, eluting with a gradient of 2% NH$_4$OH in isopropanol/methylene chloride. After concentration in vacuo, the desired product was isolated as a beige solid (0.306 g). MS APCI (+) m/z 498.1 (M+1) detected.

Step 2B: Preparation of Enantiomer 1 of 2-([1,2,4]triazolo[4,3-a]pyridin-3-yl)-8-((trans)-3-fluoropiperidin-4-yloxy)quinoline: Non-racemic (trans)-benzyl 4-(2-([1,2,4]triazolo[4,3-a]pyridin-3-yl)quinolin-8-yloxy)-3-fluoropiperidine-1-carboxylate (0.304 g, 0.611 mmol) was dissolved in dioxane (7.6 mL) and treated with 6 M hydrogen chloride (7.64 mL, 45.8 mmol), and the reaction mixture was heated at 100° C. for 15 hours. The reaction was cooled and carefully neutralized with solid NaHCO$_3$. Additional water was added to dissolve the resulting NaCl as the neutralization proceeded. The resulting aqueous layer (pH 8-9) was extracted with methylene chloride and the combined organic layers were dried over Na$_2$SO$_4$ and concentrated in vacuo. The crude product was chromatographed on SiO$_2$ eluting with a gradient of 2% NH$_4$OH in isopropanol/methylene chloride. The desired product was isolated as a white foam (62.6 mg). MS APCI (+) m/z 364.2 (M+1) detected.

Step 2C: Preparation of the dihydrochloride salt of Enantiomer 1 of 2-([1,2,4]triazolo[4,3-a]pyridin-3-yl)-8-((trans)-3-fluoropiperidin-4-yloxy)quinoline: Prepared as described in Example 94 using non-racemic 2-([1,2,4]triazolo[4,3-a]pyridin-3-yl)-8-((trans)-3-fluoropiperidin-4-yloxy)quinoline in Step 4C. Specific rotation: $[\alpha]^{20}_D = -3.3°$ (c=0.45, 1:1 water/95% ethanol).

Example 97

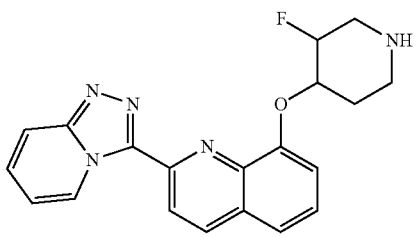 [SMILES: FC1CNCCC1Oc1cccc2ccc(-c3nnc4ccccn34)nc12]

Enantiomer 2 of 2-([1,2,4]triazolo[4,3-a]pyridin-3-yl)-8-((trans)-3-fluoropiperidin-4-yloxy)quinoline dihydrochloride Step 1: Preparation of Enantiomer 2 of 2-([1,2,4]triazolo[4,3-a]pyridin-3-yl)-8-((trans)-3-fluoropiperidin-4-yloxy)quinoline: Prepared according to the method of Example 96 using Peak 2 of non-racemic (cis)-benzyl 3-fluoro-4-hydroxypiperidine-1-carboxylate (Example 94, Step 3D) in place of Peak 1 non-racemic (cis)-benzyl 3-fluoro-4-hydroxypiperidine-1-carboxylate (Example 94, Step 3D) in step 1A. MS APCI (+) m/z 364.1 (M+1) detected.

Step 2: Preparation of the dihydrochloride salt of Enantiomer 2 of 2-k [1,2,4]triazolo[4,3-a]pyridin-3-yl)-8-((trans)-3-fluoropiperidin-4-yloxy)quinoline: Prepared as described in Example 94 using non-racemic 2-([1,2,4]triazolo[4,3-a]pyridin-3-yl)-8-((trans)-3-fluoropiperidin-4-yloxy)quinoline in Step 4C. Specific rotation: $[\alpha]^{20}_D = +2.7°$ (c=0.45, 1:1 water/95% ethanol).

Example 98

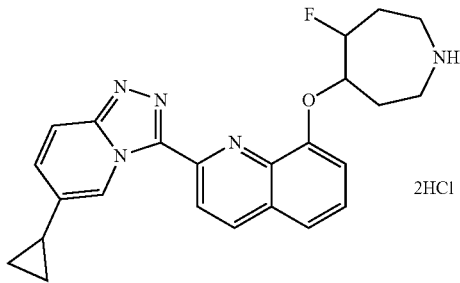 [SMILES: FC1CCNCCC1Oc1cccc2ccc(-c3nnc4ccc(C5CC5)cn34)nc12]

2-(6-cyclopropyl-[1,2,4]triazolo[4,3-a]pyridin-3-yl)-8-((trans)-5-fluoroazepan-4-yloxy)quinoline dihydrochloride Step A: Preparation of 2-(6-cyclopropyl-[1,2,4]triazolo[4,3-a]pyridin-3-yl)quinolin-8-ol: Prepared according to the method of Example 64, Steps A-B. MS APCI (+) m/z 303 (M+1) detected.

Step B: Preparation of trans-tert-butyl 4-(2-(6-cyclopropyl-[1,2,4]triazolo[4,3-a]pyridin-3-yl)quinolin-8-yloxy)-5-fluoroazepane-1-carboxylate: Prepared according to the method of Example 90 using cis-tert-butyl 4-fluoro-5-(4-nitrophenylsulfonyloxy)azepane-1-carboxylate in place of trans-tert-butyl 4-fluoro-5-(4-nitrophenylsulfonyloxy)azepane-1-carboxylate and 2-(6-cyclopropyl-[1,2,4]triazolo[4,3-a]pyridin-3-yl)quinolin-8-ol in place of 2-([1,2,4]triazolo[4,3-a]pyridin-3-yl)-6-fluoroquinolin-8-ol in Step C and running the reaction at 50° C.

Step C: Preparation of 2-(6-cyclopropyl-[1,2,4]triazolo[4,3-a]pyridin-3-yl)-8-((trans)-5-fluorozepan-4-yloxy)quinoline dihydrochloride: To a solution of trans-tert-butyl 4-(2-(6-cyclopropyl-[1,2,4]triazolo[4,3-a]pyridin-3-yl)quinolin-8-yloxy)-5-fluoroazepane-1-carboxylate (0.076 g, 0.147 mmol) in 1.5 mL DCM was added neat trifluoroacetic acid (0.339 mL, 4.40 mmol). The reaction mixture was stirred at ambient temperature for 90 minutes, then concentrated twice from DCM and dried in vacuo. The crude was dissolved in DCM, and a few drops of triethylamine and a few drops MeOH were added. The crude material was then purified by preparative TLC (eluting first with 9:1 DCM:6% NH$_4$OH in MeOH, then with 4:1 DCM:6% NH$_4$OH in MeOH). The product band was isolated, and the isolated material was dissolved in 1 mL DCM and a few drops of MeOH. This solution was added dropwise to a vigorously stirring solution of 1 mL 2M HCl/ether in 15 mL ether, causing a precipitate to form. The solids were isolated by filtration through a medium glass fritted funnel by pushing the solvent through with nitrogen pressure, rinsed with ether, dried under nitrogen pressure, and dried in vacuo to give the desired product as the dihydrochloride salt (0.036 g, 50.0% yield) as a white powder. MS APCI (+) m/z 418 (M+1) detected.

Example 99

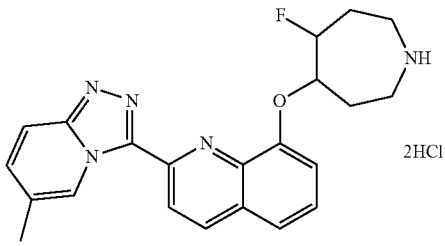 [SMILES: Cc1ccc2nnc(-c3ccc4cccc(OC5CCNCCC5F)c4n3)n2c1]

Enantiomer 1 of 8-((trans)-5-fluoroazepan-4-yloxy)-2-(6-methyl-[1,2,4]triazolo[4,3-a]pyridin-3-yl)quinoline dihydrochloride Step A: Preparation of (trans)-tert-butyl 4-(2-(6-bromo-[1,2,4]triazolo[4,3-a]pyridin-3-yl)quinolin-8-yloxy)-5-fluoroazepane-1-carboxylate. Prepared according to the method of Example 98, using 2-(6-bromo-[1,2,4]triazolo[4,3-a]pyridin-3-yl)quinolin-8-ol in place of 2-(6-cyclopropyl-[1,2,4]triazolo[4,3-a]pyridin-3-yl)quinolin-8-ol in Step A.

Step B: Preparation of enantiomer 1 of (trans)-tert-butyl 4-fluoro-5-(2-(6-methyl-[1,2,4]triazolo[4,3-a]pyridin-3-yl)quinolin-8-yloxy)azepane-1-carboxylate. To a solution of (trans)-tert-butyl 4-(2-(6-bromo-[1,2,4]triazolo[4,3-a]pyridin-3-yl)quinolin-8-yloxy)-5-fluoroazepane-1-carboxylate (0.125 g, 0.225 mmol) and Pd(PPh$_3$)$_4$ (0.0519 g, 0.0449 mmol) in 1.9 mL THF was added 2M methyl zinc chloride in THF (0.225 mL, 0.449 mmol) by syringe, and the reaction mixture was heated in an 80° C. reaction block. After 6 hours, the reaction mixture was cooled to ambient temperature and saturated NH$_4$Cl and water were added, causing a precipitate to form. The solids were isolated by vacuum filtration through qualitative filter paper, rinsed with water, air dried, and dried in vacuo. The crude was purified on silica gel (1-8% MeOH in DCM gradient) to give the racemic (trans)-product. The resulting mixture was separated by chiral HPLC using a Chiracell OJ-H column, 9.5% EtOH in hexanes, flow rate 16 mL/min to give Peak 1 trans-product (0.018 g, 16%, 99% ee) as a white solid, and Peak 2 trans-product (0.014 g, 13%, 92% ee) as a white solid.

Step C: Preparation of enantiomer 1 of 8-((trans)-5-fluoroazepan-4-yloxy)-2-(6-methyl-[1,2,4]triazolo[4,3-a]pyridin-3-yl)quinoline dihydrochloride. To a solution of Peak 1 trans-product from Step C (0.018 g, 0.0366 mmol) in 0.8 mL DCM was added neat trifluoroacetic acid (0.141 mL, 1.83 mmol). The reaction mixture was stirred at ambient temperature for 2 hours, then concentrated to dryness and dried in vacuo. The resulting residue was dissolved in 1.5 mL DCM and several drops MeOH, and this solution was added to a vigorously stirring solution of 1 mL 2M HCl/ether in 10 mL ether, causing a precipitate to form. The mixture was stirred 5 minutes, then concentrated to dryness and dried in vacuo. The solids were dissolved in 1 mL DCM and several drops MeOH, and this solution was added dropwise to a vigorously stirring solution of 10 mL ether, causing precipitation. The solids were isolated by filtration through a 0.2 micron nylon filter membrane by pushing the solvent through with nitrogen pressure, rinsed with ether, 1:1 ether/DCM, and again with ether, dried under nitrogen pressure, and dried in vacuo to give the corresponding trans-enantiomer 1 as the dihydrochloride salt (0.013 g, 76.5% yield) as a pale yellow powder. MS APCI (+) m/z 392 (M+1) detected.

Example 100

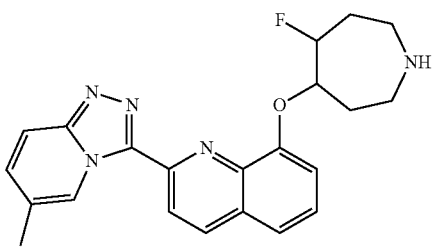 [SMILES: Cc1ccc2nnc(-c3ccc4cccc(OC5CCNCCC5F)c4n3)n2c1]

Enantiomer 2 of 8-((trans)-5-fluoroazepan-4-yloxy)-2-(6-methyl-[1,2,4]triazolo[4,3-a]pyridin-3-yl)quinoline Prepared according to the method of Example 99 using Peak 2 trans-product (from Step C) in place of Peak 1 trans-product in Step C. APCI (+) m/z 392 (M+1) detected.

Example 101

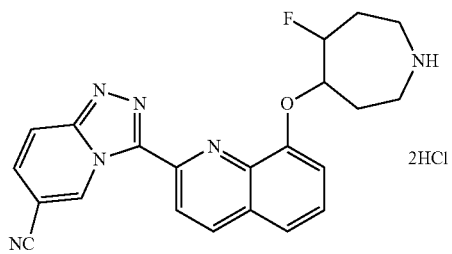 [SMILES: N#Cc1ccc2nnc(-c3ccc4cccc(OC5CCNCCC5F)c4n3)n2c1]

3-(8-((trans)-5-fluoroazepan-4-yloxy)quinolin-2-yl)-[1,2,4]triazolo[4,3-a]pyridine-6-carbonitrile dihydrochloride Step A: Preparation of 3-(8-(tert-butyldimethylsilyloxy)quinolin-2-yl)-[1,2,4]triazolo[4,3-a]pyridine-6-carbonitrile. Prepared according to the method of Example 98, Steps B-C, using 5-cyano-2-hydrazinylpyridine in place of 2-hydrazinylpyridine in Step B.

Step B: Preparation of 3-(8-hydroxyquinolin-2-yl)-[1,2,4]triazolo[4,3-a]pyridine-6-carbonitrile. Prepared according to the method of Example 64, using 3-(8-(tert-butyldimethylsi-lyloxy)quinolin-2-yl)-[1,2,4]triazolo[4,3-a]pyridine-6-carbonitrile in place of 8-(tert-butyldimethylsilyloxy)-2-(6-cyclopropyl-[1,2,4]triazolo[4,3-a]pyridin-3-yl)quinoline in Step B and rinsing the crude product with water, ethyl acetate, and ether.

Step C: Preparation of (trans)-tert-butyl 4-(2-(6-cyano-[1,2,4]triazolo[4,3-a]pyridin-3-yl)quinolin-8-yloxy)-5-fluoroazepane-1-carboxylate. Prepared according to the method of Example 90, using cis-tert-butyl 4-fluoro-5-(4-nitrophenylsulfonyloxy)azepane-1-carboxylate in place of trans-tert-butyl 4-fluoro-5-(4-nitrophenylsulfonyloxy)azepane-1-carboxylate and 3-(8-hydroxyquinolin-2-yl)-[1,2,4]triazolo[4,3-a]pyridine-6-carbonitrile in place of 2-([1,2,4]triazolo[4,3-a]pyridin-3-yl)-6-fluoroquinolin-8-ol in Step C and running the reaction at 50° C.

Step D: Preparation of 3-(8-((trans)-5-fluoroazepan-4-yloxy)quinolin-2-yl)-[1,2,4]triazolo[4,3-a]pyridine-6-carbonitrile dihydrochloride. Prepared according to the method of Example 99 using (trans)-tert-butyl 4-(2-(6-cyano-[1,2,4]triazolo[4,3-a]pyridin-3-yl)quinolin-8-yloxy)-5-fluoroazepane-1-carboxylate in place of Peak 1 trans-enantiomer in Step C to give the title compound as the dihydrochloride salt. MS APCI (+) m/z 403 (M+1) detected.

Example 102

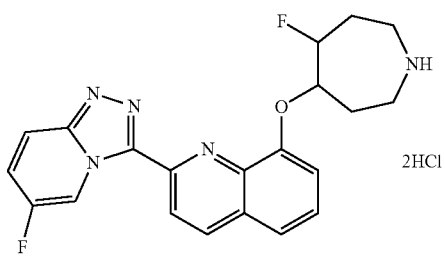 [SMILES: Fc1ccc2nnc(-c3ccc4cccc(OC5CCNCCC5F)c4n3)n2c1]

2-(6-fluoro-[1,2,4]triazolo[4,3-a]pyridin-3-yl)-8-((trans)-5-fluoroazepan-4-yloxy)quinoline dihydrochloride Prepared according to the method of Example 101, using 5-fluoro-2-hydrazinylpyridine in place of 5-cyano-2-hydrazinylpyridine in Step A to give the title compound as the dihydrochloride salt. MS APCI (+) m/z 396 (M+1) detected.

Example 103

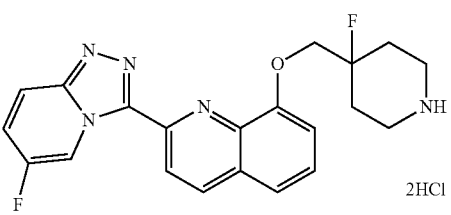 [SMILES: Fc1ccc2nnc(-c3ccc4cccc(OCC5(F)CCNCC5)c4n3)n2c1]

2-(6-fluoro-[1,2,4]triazolo[4,3-a]pyridin-3-yl)-8-((4-fluoropiperidin-4-yl)methoxy)quinoline dihydrochloride Prepared according to the method of Example 101 using 5-fluoro-2-hydrazinylpyridine in place of 5-cyano-2-hydrazinylpyridine in Step A and (4-fluoropiperidin-4-yl)methyl methanesulfonate in place of (cis)-tert-butyl 4-fluoro-5-(4- nitrophenylsulfonyloxy)azepane-1-carboxylate in Step C to give the title compound as the dihydrochloride salt. MS APCI (+) m/z 396 (M+1) detected.

Example 104

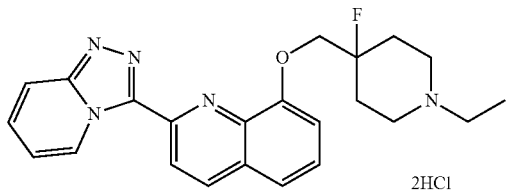 [SMILES: CCN1CCC(F)(COc2cccc3ccc(-c4nnc5ccccn45)nc23)CC1]

2-([1,2,4]triazolo[4,3-a]pyridin-3-yl)-8((1-ethyl-4-fluoropiperidin-4-yl)methoxy)quinoline dihydrochloride Prepared according to the method of Example 84 using acetaldehyde in place of 37% formaldehyde in water to give the title compound as the dihydrochloride salt. MS APCI (+) m/z 406 (M+1) detected.

Example 105

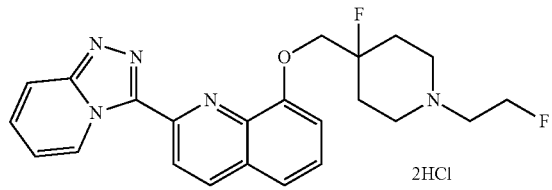 [SMILES: FCCN1CCC(F)(COc2cccc3ccc(-c4nnc5ccccn45)nc23)CC1]

2-([1,2,4]triazolo[4,3-a]pyridin-3-yl)-8-((4-fluoro-1-(2-fluoroethyl)piperidin-4-yl)methoxy)quinoline dihydrochloride To a suspension of 2-([1,2,4]triazolo[4,3-a]pyridin-3-yl)-8-((4-fluoropiperidin-4-yl)methoxy)quinoline dihydrochloride (Example 66; 0.070 g, 0.16 mmol) and 1-bromo-2-fluoroethane (0.16 g, 1.24 mmol) in 0.8 mL DMF was added DIEA (0.11 mL, 0.62 mmol). The reaction mixture was stirred at 80° C. for 5 days. The reaction mixture was concentrated, and the crude was purified twice by preparative TLC (1 mm plate, 9:1 DCM:MeOH). The resulting residue was dissolved in 0.8 mL DCM and added to a vigorously stirring solution of 1.5 mL 2M HCl/ether in 30 mL ether, causing precipitation. The mixture was concentrated and dried in vacuo. The resulting solids were dissolved in several drops MeOH and 1 mL DCM, and this solution was added to a vigorously stirring solution of ether, causing precipitation. The solids were isolated by filtration through a 0.2 micron nylon filter disc by pushing solvent through the filter with nitrogen pressure, rinsed with ether, 1:1 ether/DCM, and again with ether, dried under nitrogen pressure, then dried in vacuo to give the desired product as the dihydrochloride salt (0.020 g, 26% yield) as an off-white powder. MS APCI (+) m/z 424 (M+1) detected.

Example 106

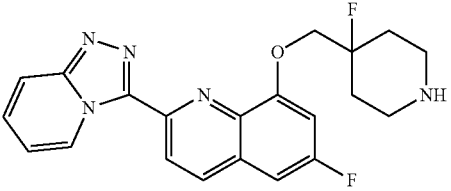 [SMILES: Fc1cc(OCC2(F)CCNCC2)c2nc(-c3nnc4ccccn34)ccc2c1]

2-([1,2,4]triazolo[4,3-a]pyridin-3-yl)-6-fluoro-8-((4-fluoropiperidin-4-yl)methoxy)quinoline dihydrochloride Prepared according to the method of Example 66 using 2-([1,2,4]triazolo[4,3-a]pyridin-3-yl)-6-fluoroquinolin-8-ol (Example 39, Step F) in place of 2-([1,2,4]triazolo[4,3-a]pyridin-3-yl)quinolin-8-ol in Step C. MS APCI (+) m/z 396 (M+1) detected.

Example 107

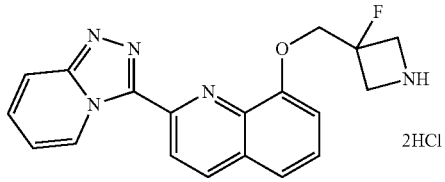 [SMILES: FC1(COc2cccc3ccc(-c4nnc5ccccn45)nc23)CNC1]

2-([1,2,4]triazolo[4,3-a]pyridin-3-yl)-8-((3-fluoroazetidin-3-yl)methoxy)quinoline dihydrochloride Step A: Preparation of tert-butyl 3-oxoazetidine-1-carboxylate. To a −78° C. solution of 2M oxalyl chloride (31.8 mL, 63.5 mmol) in 200 mL DCM was added DMSO (9.01 mL, 127 mmol), followed by the slow addition by addition funnel of a solution of tert-butyl 3-hydroxyazetidine-1-carboxylate (10.0 g, 57.7 mmol) in 200 mL DCM. The cloudy reaction mixture was stirred at −78° C. for 15 minutes, then a solution triethylamine (32.2 mL, 231 mmol) in 40 mL DCM was added slowly by addition funnel. The reaction mixture was stirred another 15 minutes, the bath was removed, and the reaction was allowed to warm to ambient temperature and stirred for 15 hours. Water and brine were added, and the mixture was extracted with DCM. The combined extracts were dried (Na$_2$SO$_4$), filtered and concentrated. The crude was purified on silica gel (3-20% ethyl acetate in hexanes gradient) to give the desired product (9.0 g, 91.1% yield) as a white solid.

Step B: Preparation of tert-butyl 3-methyleneazetidine-1-carboxylate. To a 0° C. mixture of KOtBu (5.90 g, 52.6 mmol) in 95 mL ether was added methyltriphenylphosphonium bromide (18.8 g, 52.6 mmol). The reaction mixture was warmed to ambient temperature and stirred 1.5 hours. A solution of tert-butyl 3-oxoazetidine-1-carboxylate (4.50 g, 26.3 mmol) in 10 mL ether was added. The reaction mixture was heated to reflux for 2 hours, then cooled to ambient temperature. Solids were removed by vacuum filtration through compressed Celite and rinsed with ether, and the filtrate was concentrated. The resulting residue was suspended in 1:1 hexanes:ethyl acetate, and the solids were removed by vacuum filtration through GF/F paper and rinsed with 1:1 hexanes:ethyl acetate. The filtrate was concentrated, and the resulting oil was purified on silica gel (5-20% ethyl acetate in hexanes gradient) to give the desired product (3.50 g, 78.7% yield) as a clear colorless oil.

Step C: Preparation of tert-butyl 1-oxa-5-azaspiro[2.3]hexane-5-carboxylate. To a 0° C. solution of tert-butyl 3-methyleneazetidine-1-carboxylate (3.50 g, 20.7 mmol) in 115 ml, CHCl$_3$ was added 77% mCPBA (13.9 g, 62.0 mmol) in 3 batches. Isopropyl alcohol (2 mL) was added. The reaction mixture was stirred for 10 minutes, then warmed to ambient temperature and stirred. After 19 hours, the milky reaction mixture was cooled to 0° C., 10 mL isopropyl alcohol was added (reaction mixture clarified), and another 1 equivalent of mCPBA was added. The reaction mixture was warmed to ambient temperature and stirred 2 hours, then another 1 equivalent mCPBA was added portionwise. After a total of 40 hours, the reaction mixture was cooled to 0° C., and 200 mL of 1:1 saturated Na$_2$S$_2$O$_3$/saturated NaHCO$_3$ was added slowly by pouring portionwise through ice (internal temperature was monitored; an initial 10° C. exotherm was observed). The mixture was stirred for 30 minutes, then extracted with CHCl$_3$, and combined extracts were dried (Na$_2$SO$_4$), filtered, and concentrated. The crude was purified on silica gel (5-50% ethyl acetate in hexanes gradient) to give the desired product (1.0 g, 26.1% yield) as a clear colorless oil.

Step D: Preparation of tert-butyl 3-42-([1,2,4]triazolo[4,3-a]pyridin-3-yl)quinolin-8-yloxy)methyl)-3-hydroxyazetidine-1-carboxylate. Prepared according to the method of Example 66 using tert-butyl 1-oxa-5-azaspiro[2.3]hexane-5-carboxylate in place of tert-butyl 4-fluoro-4-((methylsulfonyloxy)methyl)piperidine-1-carboxylate in Step C and running the reaction at 70° C.

Step E: Preparation of tert-butyl 3-((2-([1,2,4]triazolo[4,3-a]pyridin-3-yl)quinolin-8-yloxy)methyl)-3-fluoroazetidine-1-carboxylate. (NOTE: the reaction was run in a 10 mL plastic bottle) To a 0° C. cloudy solution of tert-butyl 3-42-([1,2,4]triazolo[4,3-a]pyridin-3-yl)quinolin-8-yloxy)methyl)-3-hydroxyazetidine-1-carboxylate (0.070 g, 0.156 mmol) in 2 mL DCM was added Deoxo-Fluor (0.0346 mL, 0.188 mmol). The reaction mixture was warmed to ambient temperature, and after 30 minutes, it was cooled back to 0° C., and another 2 equiv. of DeoxoFluor was added, and the reaction mixture continued to stir at 0° C. After a total of 3.5 hours, saturated NaHCO$_3$ was carefully added dropwise until the excess Deoxofluor was quenched. The mixture was extracted with DCM, and the combined extracts were dried (Na$_2$SO$_4$), filtered, and concentrated. The residue was purified by preparative TLC (2 mm plate, 9:1 DCM:MeOH) to give the desired product (0.0156 g, 22.2% yield) as a white foam.

Step F: Preparation of 2-([1,2,4]triazolo[4,3-a]pyridin-3-yl)-8-((3-fluoroazetidin-3-yl)methoxy)quinoline dihydrochloride. To a solution of tert-butyl 3-((2-([1,2,4]triazolo[4,3-a]pyridin-3-yl)quinolin-8-yloxy)methyl)-3-fluoroazetidine-1-carboxylate (0.016 g, 0.0356 mmol) in 1 mL DCM was added neat trifluoroacetic acid (0.137 mL, 1.78 mmol). The reaction mixture was stirred at ambient temperature for 1 hour, after which it was concentrated. The crude was purified on C18 reverse phase (10-40% acetonitrile in water gradient). The resulting solids were dissolved in 1 mL DCM plus several drops MeOH, and this solution was added to a vigorously stirring solution of 1 mL 2M HCl/ether in 15 mL ether, causing precipitation. The mixture was stirred for 5 minutes, then concentrated to dryness and dried in vacuo. The solids were dissolved in minimal MeOH/DCM, and this solution was added dropwise to 20 mL vigorously stirring ether, causing precipitation. The white solids were isolated by filtration through a 0.2 micron nylon filter disc by pushing solvent through with nitrogen pressure, rinsed with ether, dried under nitrogen pressure, and dried in vacuo to give the title compound as the dihydrochloride salt (0.002 g, 13%) as a white powder. MS APCI (+) m/z 350 (M+1) detected.

Example 108

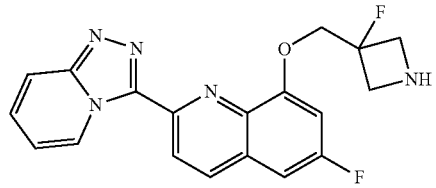 [SMILES: Fc1cc(OCC2(F)CNC2)c2nc(-c3nnc4ccccn34)ccc2c1]

2-([1,2,4]triazolo[4,3-a]pyridin-3-yl)-6-fluoro-8-((3-fluoro azetidin-3-yl)methoxy)quinoline Dihydrochloride Prepared as described for Example 107 using 2-([1,2,4]triazolo[4,3-a]pyridin-3-yl)-6-fluoroquinolin-8-ol (Example 39, Step F) in place of 2-([1,2,4]triazolo[4,3-a]pyridin-3-yl)quinolin-8-ol in Step D. MS APCI (+) m/z 368 (M+1) detected.

Example 109

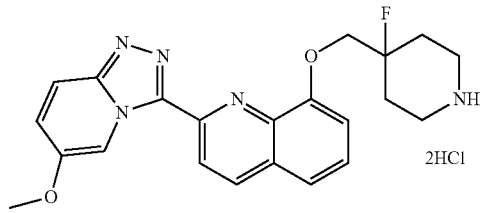 [SMILES: COc1ccc2nnc(-c3ccc4cccc(OCC5(F)CCNCC5)c4n3)n2c1]

8((4-fluoropiperidin-4-yl)methoxy)-2-(6-methoxy-[1,2,4]triazolo[4,3-a]pyridin-3-yl)quinoline dihydrochloride Step A: Preparation of 2-hydrazinyl-5-methoxypyridine. 2-bromo-5-methoxypyridine (4.90 g, 26.06 mmol) and anhydrous hydrazine (8.179 mL, 260.6 mmol) were combined and heated slowly to 140° C. in a sand bath and stirred for 24 hours. The reaction mixture was diluted with THF and concentrated three times. The resulting solids were suspended in 20 mL THF, stirred vigorously, and 100 mL ether was added. The resulting solids were cooled in a refrigerator for 2 hours, then isolated by filtration through a 0.4 micron nylon filter disc with nitrogen pressure, rinsed with ether, 1:1 ether:ethyl acetate, and ether, and dried in vacuo to give the desired product (>100%).

Step B: Preparation of 2-(6-methoxy-[1,2,4]triazolo[4,3-a]pyridin-3-yl)quinolin-8-ol. Prepared as described for Example 1, Steps A-D, using 2-hydrazinyl-5-methoxypyridine in place of 2-hydrazinylpyridine in Step B.

Step C: Preparation of 8-((4-fluoropiperidin-4-yl)methoxy)-2-(6-methoxy-[1,2,4]triazolo[4,3-a]pyridin-3-yl) quinoline dihydrochloride. Prepared according to the method of Example 66, Steps C-D, using 2-(6-methoxy-[1,2,4]triazolo[4,3-a]pyridin-3-yl)quinolin-8-ol in place of 2-([1,2,4]

triazolo[4,3-a]pyridin-3-yl)quinolin-8-ol in Step C to give the desired product. MS APCI (+) m/z 408 (M+1) detected.

Example 110

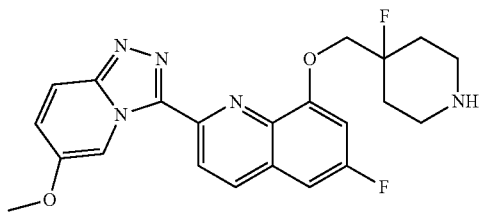 [SMILES: COc1ccc2nnc(-c3ccc4cc(F)cc(OCC5(F)CCNCC5)c4n3)n2c1]

6-fluoro-8-((4-fluoropiperidin-4-yl)methoxy)-2-(6-methoxy-[1,2,4]triazolo[4,3-a]pyridin-3-yl)quinoline dihydrochloride Prepared as described for Example 109 using 6-fluoro-2-(6-methoxy-[1,2,4]triazolo[4,3-a]pyridin-3-yl)quinolin-8-ol (Example 39, Step F) in place of 2-(6-methoxy-[1,2,4]triazolo[4,3-a]pyridin-3-yl)quinolin-8-ol in Step C. MS APCI (+) m/z 426 (M+1) detected.

Example 111

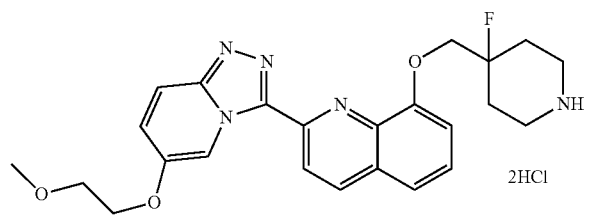 [SMILES: COCCOc1ccc2nnc(-c3ccc4cccc(OCC5(F)CCNCC5)c4n3)n2c1]

8((4-fluoropiperidin-4-yl)methoxy)-2-(7-(2-methoxyethoxy)-[1,2,4]triazolo[4,3-a]pyridin-3-yl)quinoline dihydrochloride Step A: Preparation of 2-fluoro-5-(2-methoxyethoxy)pyridine. To a 0° C. suspension of Cs$_2$CO$_3$ (18.73 g, 57.48 mmol) in 150 mL DMF was added 6-fluoropyridin-3-ol (5.0 g, 44.21 mmol). The cloudy brown mixture was stirred for 15 minutes, then 1-bromo-2-methoxyethane (6.232 mL, 66.32 mmol) was added. The reaction mixture was heated in a 110° C. sand bath and stirred for 17 hours, after which it was cooled to ambient temperature and the DMF was removed in vacuo. The resulting residue was combined with saturated NH$_4$Cl and the mixture was extracted with DCM. The combined extracts were dried (Na$_2$SO$_4$), filtered, and concentrated. The crude material was purified on silica gel (5-50% ethyl acetate in hexanes gradient) to give the desired product (7.00 g, 92.50% yield) as a clear, colorless oil.

Step B: Preparation of 8-((4-fluoropiperidin-4-yl)methoxy)-2-(7-(2-methoxyethoxy)-[1,2,4]triazolo[4,3-a]pyridin-3-yl)quinoline dihydrochloride. Prepared as described for Example 109 using 2-fluoro-5-(2-methoxyethoxy)pyridine in place of 2-bromo-5-methoxypyridine in Step A to give the desired product as the dihydrochloride salt. MS APCI (+) m/z 452 (M+1) detected.

Example 112

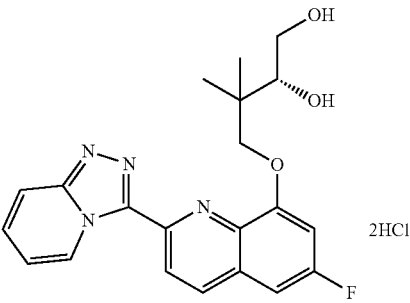 [SMILES: CC(C)(COc1cc(F)cc2ccc(-c3nnc4ccccn34)nc12)[C@@H](O)CO]

(R)-4-(2-([1,2,4]triazolo[4,3-a]pyridin-3-yl)-6-fluoroquinolin-8-yloxy)-3,3-dimethylbutane-1,2-diol dihydrochloride Step A: Preparation of (R)-3,3-dimethylbutane-1,2,4-triol: (R)-3-hydroxy-4,4-dimethyldihydrofuran-2(3H)-one (3.21 g, 24.7 mmol) was added to 30 mL THF and cooled to 0° C. Lithium aluminum hydride (24.7 mL, 24.7 mmol) was added slowly and the reaction was warmed to ambient temperature and heated for 6 hours at reflux, during which a heterogeneous mixture of white solids formed. The reaction was cooled to ambient temperature, and 1 mL water was added, followed by the addition of 1 mL of a 15% NaOH aqueous solution (w/v) and 3 mL of water, and the reaction was stirred overnight. The reaction was passed through Celite and filtered, rinsed with copious amounts of ethyl acetate, then dried over Na$_2$SO$_4$. The mixture was filtered, the filtrate was concentrated, and excess water was azeotroped with toluene-DCM (1-1). The residue was dried under high vacuum for 1 hour to yield 2.4 g of the desired product as a clear thick oil.

Step B: Preparation of (R)-2-(2,2-dimethyl-1,3-dioxolan-4-yl)-2-methylpropan-1-ol: (R)-3,3-dimethylbutane-1,2,4-triol (2.7 g, 20 mmol) and 4-methylbenzenesulfonic acid (0.017 g, 0.10 mmol) were added to 25 mL of acetone and catalytic 4-methylbenzenesulfonic acid (0.017 g, 0.10 mmol) and stirred overnight at ambient temperature. The solution was evaporated, and to the residue was added ethyl acetate. The organic layer was washed with aqueous Na$_2$CO$_3$, dried over MgSO$_4$ and filtered. The filtrate was concentrated to provide 1.7 g of the desired product as a clear oil.

Step C: Preparation of (R)-2-(2,2-dimethyl-1,3-dioxolan-4-yl)-2-methylpropyl 4-nitrobenzenesulfonate: (R)-2-(2,2-dimethyl-1,3-dioxolan-4-yl)-2-methylpropan-1-ol (0.823 g, 4.72 mmol) was added to 10 mL of DCM and cooled to 0° C. Triethylamine (0.982 mL, 7.09 mmol) and hypochlorous 4-nitrobenzenesulfonic anhydride (1.35 g, 5.67 mmol) were added and the solution was warmed to ambient temperature and stirred overnight. The solids were filtered off, and the filtrate was evaporated. The residue was purified on silica gel using hexane and ethyl acetate to yield 0.9 g of the desired product as a dark beige solid.

Step D: Preparation of (R)-2-([1,2,4]triazolo[4,3-a]pyridin-3-yl)-8-(2-(2,2-dimethyl-1,3-dioxolan-4-yl)-2-methylpropoxy)-6-fluoro quinoline: 2-([1,2,4]triazolo[4,3-a]pyridin-3-yl)-6-fluoroquinolin-8-ol (0.09 g, 0.34 mmol), (R)-2-(2,2-dimethyl-1,3-dioxolan-4-yl)-2-methylpropyl methanesulfonate (0.11 g, 0.45 mmol) and cesium carbonate (0.22 g, 0.69 mmol) were added to 1 to 2 mL of DMA and heated to 85° C. for 4-5 hours. The reaction was concentrated and treated with water and ethyl acetate. The reaction was extracted several times with ethyl acetate. The organic layer was dried over MgSO₄, filtered, and concentrated. The residue was purified on Silica gel using 2% NH₄OH in isopropyl acetate and DCM to provide 200 mgs of the desired product (85% pure).

Step E: Preparation of (R)-4-(2-([1,2,4]triazolo[4,3-a]pyridin-3-yl)-6-fluoroquinolin-8-yloxy)-3,3-dimethylbutane-1,2-diol dihydro chloride: (R)-2-([1,2,4]triazolo[4,3-a]pyridin-3-yl)-8-(2-(2,2-dimethyl-1,3-dioxolan-4-yl)-2-methylpropoxy)-6-fluoroquinoline (0.190 g, 0.435 mmol) was added to methanol saturated with HCl and stirred for 30 minutes. The solution was evaporated, DCM was added, and the material triturated and filtered to yield 140 mgs of the desired product as orange solid. MS ESI (+) m/z 397 (M+1) detected.

Example 113

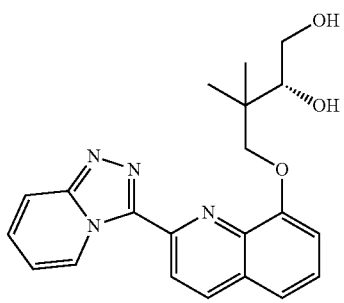 [SMILES: CC(C)(COc1cccc2ccc(-c3nnc4ccccn34)nc12)[C@@H](O)CO]

(R)-4-(2-([1,2,4]triazolo[4,3-a]pyridin-3-yl)quinolin-8-yloxy)-3,3-dimethylbutane-1,2-diol Step A: Preparation of (R)-2-([1,2,4]triazolo[4,3-a]pyridin-3-yl)-8-(2-(2,2-dimethyl-1,3-dioxolan-4-yl)-2-methylpropoxy)quinoline: 2-([1,2,4]triazolo[4,3-a]pyridin-3-yl)quinolin-8-ol (0.25 g, 0.95 mmol), (R)-2-(2,2-dimethyl-1,3-dioxolan-4-yl)-2-methylpropyl 4-nitrobenzenesulfonate (0.41 g, 1.1 mmol) and cesium carbonate (0.62 g, 1.9 mmol) were added to minimal amount of N,N-dimethylacetamide and heated to 85° C. The reaction was cooled, ethyl acetate was added and the mixture was sonicated. Solids were filtered off and the filtrate was dried over MgSO₄, filtered and evaporated. The crude material was purified on silica gel using isopropyl alcohol containing 2% NH₄OH and DCM to yield 30 mg of the desired product (90% pure. The crude material was used without further purification in the next step.

Step B: Preparation of (R)-4-(2-([1,2,4]triazolo[4,3-a]pyridin-3-yl)quinolin-8-yloxy)-3,3-dimethylbutane-1,2-diol: (R)-2-([1,2,4]triazolo[4,3-a]pyridin-3-yl)-8-(2-(2,2-dimethyl-1,3-dioxolan-4-yl)-2-methylpropoxy)quinoline (0.030 g, 0.072 mmol) was added to 1 N HCl in methanol and stirred for 30 minutes, then evaporated, co-evaporated once in methanol and triturated in DCM to isolate 23 mg of 95% pure desired product as a beige solid. MS ESI (+) m/z 379 (M+1) detected.

Example 114

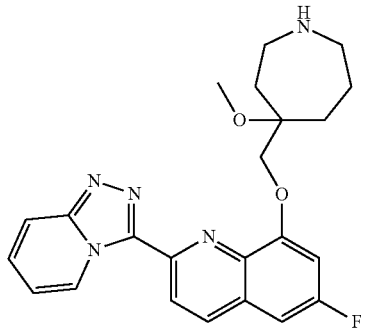 [SMILES: COC1(COc2cc(F)cc3ccc(-c4nnc5ccccn45)nc23)CCCNCC1]

2-([1,2,4]triazolo[4,3-a]pyridin-3-yl)-6-fluoro-8-((4-methoxyazepan-4-yl)methoxy)quinoline bis-trifluoroacetate Step A: Preparation of tert-butyl 4-((2-([1,2,4]triazolo[4,3-a]pyridin-3-yl)quinolin-8-yloxy)methyl)-4-hydroxyazepane-1-carboxylate: 2-([1,2,4]triazolo[4,3-a]pyridin-3-yl)-6-fluoroquinolin-8-ol (0.065 g, 0.25 mmol), cesium carbonate (0.16 g, 0.50 mmol) and tert-butyl 1-oxa-6-azaspiro[2.6]nonane-6-carboxylate (0.068 g, 0.30 mmol) were added to 1 mL of DMF and heated to 72° C. overnight. The reaction mixture was concentrated, and DCM was added to the residue. Solids were removed by filtration and the filtrate was purified on Silica gel using 6% NH₄OH in MeOH and DCM to yield 74 mg of the desired product as an off-white foam. MS ESI (+) m/z 490 (M+1) detected.

Step B: Preparation of tert-butyl 4-42-([1,2,4]triazolo[4,3-a]pyridin-3-yl)-6-fluoroquinolin-8-yloxy)methyl)-4-methoxyazepane-1-carboxylate: tert-butyl 4-((2-([1,2,4]triazolo[4,3-a]pyridin-3-yl)-6-fluoroquinolin-8-yloxy)methyl)-4-hydroxyazepane-1-carboxylate (0.060 g, 0.106 mmol) and sodium hydride (0.00468 g, 0.117 mmol) were added to 1 mL of DMF, then iodomethane (0.00732 mL, 0.117 mmol) was added and the reaction stirred for 1 hour at ambient temperature. The reaction mixture was concentrated, and DCM was added to the residue. Solids were removed by filtration and the filtrate was purified on Silica gel using 6% NH₄OH in MeOH and DCM to yield 32 mg of the desired product as a clear oil. MS ESI (+) m/z 522 (M+1) detected.

Step C: Preparation of 2-([1,2,4]triazolo [4,3-a]pyridin-3-yl)-6-fluoro-8-((4-methoxyazepan-4-yl)methoxy)quinoline: tert-butyl 4-((2-([1,2,4]triazolo[4,3-a]pyridin-3-yl)-6-fluoroquinolin-8-yloxy)methyl)-4-methoxyazepane-1-carboxylate (0.032 g, 0.061 mmol) was added to a mixture of trifluoroacetic acid and DCM (1:1) for 1 hour. The reaction was concentrated and co-evaporated several times with diethyl ether to yield 32 mgs of the desired product as a white solid. MS ESI (+) m/z 422 (M+1) detected.

Example 115

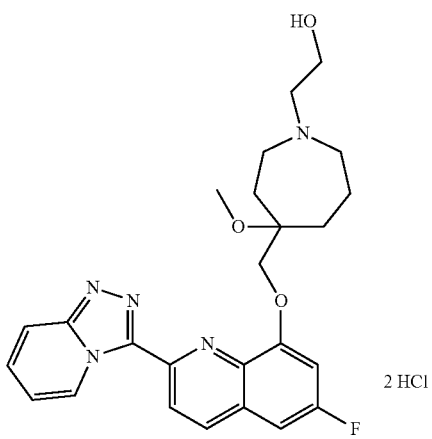 [SMILES: COC1(COc2cc(F)cc3ccc(-c4nnc5ccccn45)nc23)CCCN(CCO)CC1]

2-(4-42-([1,2,4]triazolo[4,3-a]pyridin-3-yl)-6-fluoro-quinolin-8-yloxy)methyl)-4-methoxyazepan-1-yl)ethanol dihydrochloride The free base of 2-([1,2,4]triazolo[4,3-a]pyridin-3-yl)-6-fluoro-8-((4-methoxyazepan-4-yl)methoxy)quinoline (prepared as described in Example 114, Step C) (0.006 g, 0.0142 mmol) was taken up in DMA and 2-bromoethanol (0.00402 mL, 0.0569 mmol) and N-isopropyl-N-methylpropan-2-amine (0.00899 mL, 0.0569 mmol) were added. The reaction mixture was stirred for 1 hour at 75° C., then cooled, evaporated, co-evaporated with DCM. HCl in diethyl ether was added, and the resulting solids were isolated and dried to yield 6 mg of the desired product as the dihydrochloride salt. MS ESI (+) m/z 466 (M+1) detected.

Example 116

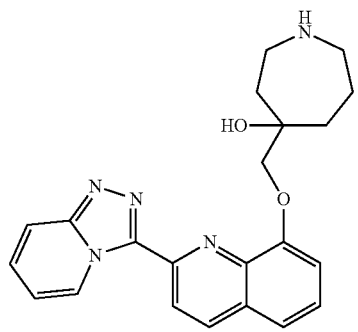 [SMILES: OC1(COc2cccc3ccc(-c4nnc5ccccn45)nc23)CCCNCC1]

4-((2-([1,2,4]triazolo[4,3-a]pyridin-3-yl)quinolin-8-yloxy)methyl)azepan-4-ol bis-trifluoroacetate Step A: Preparation of tert-butyl 4-42-([1,2,4]triazolo[4,3-a]pyridin-3-yl)quinolin-8-yloxy)methyl)-4-hydroxyazepane-1-carboxylate: 2-([1,2,4]triazolo[4,3-a]pyridin-3-yl)quinolin-8-ol (0.09 g, 0.34 mmol), tert-butyl 1-oxa-6-azaspiro[2.6]nonane-6-carboxylate (0.086 g, 0.38 mmol) and cesium carbonate (0.22 g, 0.69 mmol) were added to 1 mL of DMA in a sealed vial and heated to 70° C. overnight. The reaction was concentrated, and the residue was purified on Silica gel using 6% NH$_4$OH in MeOH and CHCl$_3$ to yield 56 mgs of 70% pure desired product (contaminated with starting phenol). MS ESI (+) m/z 490 (M+1) detected.

Step B: Preparation of 4-42-([1,2,4]triazolo[4,3-a]pyridin-3-yl)quinolin-8-yloxy)methyl)azepan-4-ol: tert-Butyl 4-((2-([1,2,4]triazolo[4,3-a]pyridin-3-yl)quinolin-8-yloxy)methyl)-4-hydroxyazepane-1-carboxylate (0.0039 g, 0.0080 mmol) was treated with a mixture of trifluoroacetic acid and DCM (1:1) for 1 hour. The reaction was concentrated to provide 4 mgs of the desired material as a solid. MS ESI (+) m/z 390 (M+1) detected.

Example 117

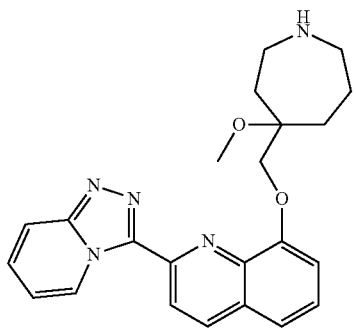 [SMILES: COC1(COc2cccc3ccc(-c4nnc5ccccn45)nc23)CCCNCC1]

2-([1,2,4]triazolo[4,3-a]pyridin-3-yl)-8-((4-methoxyazepan-4-yl)methoxy)quinoline dihydrochloride Step A: Preparation of tert-butyl 4-42-([1,2,4]triazolo[4,3-a]pyridin-3-yl)quinolin-8-yloxy)methyl)-4-hydroxyazepane-1-carboxylate: Prepared according to the procedure described in Example 116, Step A.

Step B: Preparation of tert-butyl 4-42-([1,2,4]triazolo[4,3-a]pyridin-3-yl)quinolin-8-yloxy)methyl)-4-methoxyazepane-1-carboxylate: tert-Butyl 4-((2-([1,2,4]triazolo[4,3-a]pyridin-3-yl)quinolin-8-yloxy)methyl)-4-hydroxyazepane-1-carboxylate (0.056 g, 0.114 mmol), iodomethane (0.00858 mL, 0.137 mmol) and sodium hydride (0.00915 g, 0.229 mmol) were added to DMF (1 mL) at ambient temperature and stirred for 2 hours. The reaction was concentrated and the residue was purified on Silica gel using methanol (containing 6% NH$_4$OH) and DCM, to yield 39 mg of the desired product (67% pure). MS ESI (+) m/z 504 (M+1) detected.

Step C: Preparation of 2-([1,2,4]triazolo[4,3-a]pyridin-3-yl)-8-((4-methoxyazepan-4-yl)methoxy)quinoline: tert-Butyl 4-((2-([1,2,4]triazolo[4,3-a]pyridin-3-yl)quinolin-8-yloxy)methyl)-4-methoxyazepane-1-carboxylate (0.040 g, 0.079 mmol) was added to a mixture of trifluoroacetic acid and DCM (1:1) for 30 minutes, and the reaction was concentrated. Ethyl acetate was added and the suspension was filtered through a Waters filter (to remove any errant silica gel), and the filtrate was concentrated. DCM was added followed by precipitation with HCl dissolved in diethyl ether, evaporated, co-evaporated in diethyl ether to yield 16 mgs of the desired product as a yellow solid (95% pure by LC). MS ESI (+) m/z 404 (M+1) detected.

Example 118

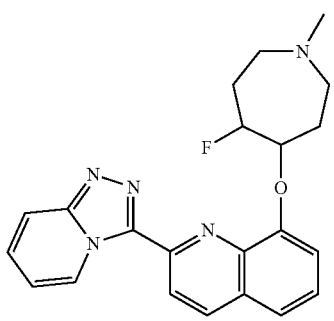 [SMILES: CN1CCC(F)C(Oc2cccc3ccc(-c4nnc5ccccn45)nc23)CC1]

Stereoisomers 1 and 2 of 2-([1,2,4]triazolo[4,3-a]pyridin-3-yl)-8-((trans)-5-fluoro-1-methylazepan-4-yloxy)quinoline Step A: Preparation of Stereoisomers 1 and 2 of 2-([1,2,4]triazolo[4,3-a]pyridin-3-yl)-8-((5-fluoroazepan-4-yloxy)quinoline: A mixture of cis and trans tert-butyl 4-(2-([1,2,4]triazolo[4,3-a]pyridin-3-yl)quinolin-8-yloxy)-5-fluoroazepane-1-carboxylate was prepared according to Example 46, Step E. The crude material was purified by column chromatography (Biotage SP1, 340G SNAP, 15% to 60% EtOAc/hexanes), and the first eluting material was collected to provide a racemic mixture of the Stereoisomers 1 and 2 as a thick colorless oil which slowly became a white solid.

Step B: Preparation of Stereoisomers 1 and 2 of 2-([1,2,4]triazolo[4,3-a]pyridin-3-yl)-8-((trans)-5-fluoro-1-methylazepan-4-yloxy)quinoline: A mixture of Stereoisomers 1 and 2 of 2-([1,2,4]triazolo[4,3-a]pyridin-3-yl)-8-((trans)-5-fluoroazepan-4-yloxy)quinoline (0.023 g, 0.0511 mmol) was slurried in $CH_2Cl_2$ (3 mL). A saturated aqueous $Na_2CO_3$ solution (5 mL) was added and the mixture was stirred at ambient temperature for 0.5 hours. The layers were separated and the aqueous phase was extracted with $CH_2Cl_2$. The combined organic layers were washed with brine and dried over $Na_2SO_4$, filtered and concentrated. The crude residue was treated with formic acid (0.289 mL, 7.66 mmol) and formaldehyde (0.0380 mL, 0.511 mmol). The mixture was stirred at 90° C. for 4 hours. The mixture was cooled to ambient temperature and carefully treated with a saturated aqueous $Na_2CO_3$ solution to adjust the mixture to about pH 11. The mixture was extracted with $CHCl_3$ and the combined organic phases were washed with brine and dried over $Na_2SO_4$, filtered and concentrated. The crude product was purified by Preparative TLC (0.5 mm, 10% MeOH/$CH_2Cl_2$ with 1% 7N $NH_3$/MeOH) to provide the desired product (0.011 g, 55%) as a white solid. MS ESI (+) m/z 392.1 (M+1) detected.

Example 119

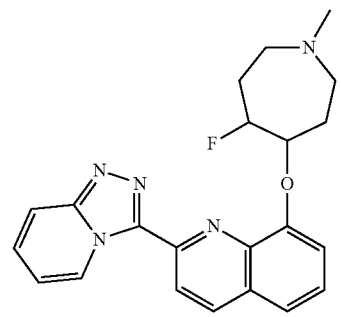 [SMILES: CN1CCC(F)C(Oc2cccc3ccc(-c4nnc5ccccn45)nc23)CC1]

Stereoisomers 3 and 4 of 2-([1,2,4]triazolo[4,3-a]pyridin-3-yl)-8-5-fluoro-1-methylazepan-4-yloxy)quinoline Step A: Preparation of Stereoisomers 3 and 4 of 2-([1,2,4]triazolo[4,3-a]pyridin-3-yl)-8-((5-fluoroazepan-4-yloxy)quinoline: A mixture of cis and trans tert-butyl 4-(2-([1,2,4]triazolo[4,3-a]pyridin-3-yl)quinolin-8-yloxy)-5-fluoroazepane-1-carboxylate was prepared according to Example 46, Step E. The crude material was purified by column chromatography (Biotage SP1, 340G SNAP, 15% to 60% EtOAc/hexanes), and the second eluting material was collected to provide a racemic mixture of the Stereoisomers 3 and 4 of isomers as a thick colorless oil which slowly became a white solid.

Step B: Preparation of Stereoisomers 3 and 4 of 2-([1,2,4]triazolo[4,3-a]pyridin-3-yl)-8-5-fluoro-1-methylazepan-4-yloxy)quinoline: A mixture of Stereoisomers 3 and 4 of tert-butyl 4-(2-([1,2,4]triazolo[4,3-a]pyridin-3-yl)quinolin-8-yloxy)-5-fluoroazepane-1-carboxylate (0.021 g, 0.0440 mmol) was dissolved in formic acid (0.332 mL, 8.80 mmol). Formaldehyde (0.0327 mL, 0.440 mmol, 37% aqueous) was added, and the mixture was stirred at 90° C. for 4 hours. The mixture was cooled to ambient temperature and treated with a saturated aqueous $Na_2CO_3$ solution to adjust the mixture to about pH 11. The mixture was extracted with $CHCl_3$ and the combined organic phases were washed with brine and dried over $Na_2SO_4$, filtered and concentrated. The crude product was purified by Preparative TLC (0.5 mm, 10% MeOH/$CH_2Cl_2$ with 1% 7N $NH_3$/MeOH) to provide the desired product (0.016 g, 93%) as a white solid. MS ESI (+) m/z 392.1 (M+1) detected.

Example 120

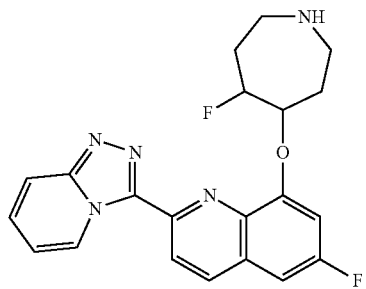 [SMILES: Fc1cc(OC2CCNCCC2F)c2nc(-c3nnc4ccccn34)ccc2c1]

Enantiomer 2 of 2-([1,2,4]triazolo[4,3-a]pyridin-3-yl)-6-fluoro-8-((cis)-5-fluoroazepan-4-yloxy)quinoline Enantiomer 2 of (cis)-tert-butyl 4-(2-([1,2,4]triazolo[4,3-a]pyridin-3-yl)-6-fluoroquinolin-8-yloxy)-5-fluoroazepane- 1-carboxylate (Example 90, Step D; 0.119 g, 0.240 mmol) was dissolved in CHCl₃ (2.4 mL). HCl (2.40 mL, 9.61 mmol, 4.0M Dioxane) was added and the mixture was stirred at ambient temperature for 3 hours. The mixture was filtered through a polypropylene filter and washed with CH₂Cl₂ and then Et₂O, then slurried in hexanes and dried carefully in vacuo to provide 0.095 g of the desired product as a white solid (85%). MS ESI (+) m/z 396.1 (M+1) detected.

Example 121

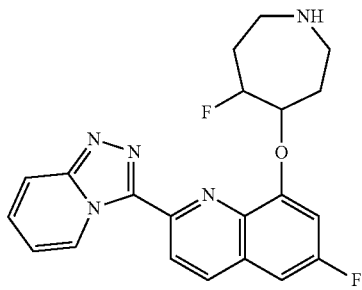 [SMILES: Fc1cc(OC2CCNCCC2F)c2nc(-c3nnc4ccccn34)ccc2c1]

2-([1,2,4]triazolo[4,3-a]pyridin-3-yl)-6-fluoro-8-(trans-5-fluoroazepan-4-yloxy)quinoline Enantiomer 1 of trans-tert-butyl 4-(2-([1,2,4]triazolo[4,3-a]pyridin-3-yl)-6-fluoroquinolin-8-yloxy)-5-fluoroazepane-1-carboxylate (Peak 1 from Example 91, Step E; 0.210 g, 0.424 mmol) was dissolved in CHCl₃ (4.3 mL). To this solution was added HCl (4.24 mL, 17.0 mmol, 4.0M Dioxane) and the mixture was stirred at ambient temperature for 3 hours. The mixture was filtered through a polypropylene filter and washed with CH₂Cl₂ and Et₂O, slurried in hexanes and then dried carefully in vacuo to provide the desired product as white solid. MS ESI (+) m/z 396.1 (M+1) detected.

Example 122

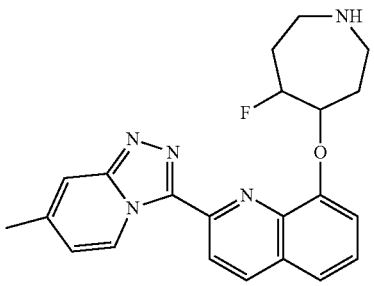 [SMILES: Cc1ccn2c(-c3ccc4cccc(OC5CCNCCC5F)c4n3)nnc2c1]

8-((cis-4,5)-5-fluoro azepan-4-yloxy)-2-(7-methyl-[1,2,4]triazolo[4,3-a]pyridin-3-yl)quinoline Enantiomer 2 of cis-tert-butyl 4-fluoro-5-(2-(7-methyl-[1,2,4]triazolo[4,3-a]pyridin-3-yl)quinolin-8-yloxy)azepane-1-carboxylate (Peak 2 from Example 92, Step F; 0.161 g, 0.328 mmol) was dissolved in CHCl₃ (3 mL). To this solution was added HCl (6.55 mL, 13.1 mmol, 2.0M Et₂O) and the mixture was stirred at ambient temperature for 4 hours. The mixture was then filtered through a polypropylene filter and washed with CH₂Cl₂ and then Et₂O and finally slurried in hexanes then dried carefully in vacuo to provide the desired product as a white solid. MS ESI (+) m/z 392.1 (M+1) detected.

Example 123

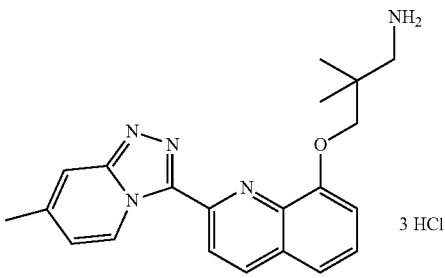 [SMILES: Cc1ccn2c(-c3ccc4cccc(OCC(C)(C)CN)c4n3)nnc2c1]

2,2-dimethyl-3-(2-(7-methyl-[1,2,4]triazolo[4,3-a]pyridin-3-yl)quinolin-8-yloxy)propan-1-amine trihydrochloride Step A: Preparation of (E/Z)-8-(tert-butyldimethylsilyloxy)-2-((2-(4-methylpyridin-2-yl)hydrazono)methyl)quinoline: A mixture of 8-(tert-butyldimethylsilyloxy)quinoline-2-carbaldehyde (6.11 g, 21.3 mmol) and 2-hydrazinyl-4-methylpyridine (2.62 g, 21.3 mmol) in ethanol (60 mL) was stirred at ambient temperature overnight. The resulting precipitate was filtered, washed with cold ethanol and dried in vacuo to provide 5.92 g (71%) of desired product as a beige-colored solid.

Step B: Preparation of 8-(tert-butyldimethylsilyloxy)-2-(7-methyl-[1,2,4]triazolo[4,3-a]pyridin-3-yl)quinoline: To a suspension of (E/Z)-8-(tert-butyldimethylsilyloxy)-2-42-(4-methylpyridin-2-yl)hydrazono)methyl)quinoline (5.92 g, 15.1 mmol) in dichloromethane (50 mL) was added iodosobenzene diacetate (5.34 g, 16.6 mmol). The mixture was stirred at ambient temperature overnight and then concentrated under reduced pressure. The residue was purified by silica gel chromatography eluting with 1:4 ethyl acetate/hexanes followed by 1:2 ethyl acetate/hexanes to provide 5.00 g (85%) of desired product.

Step C: Preparation of 2-(7-methyl-[1,2,4]triazolo[4,3-a]pyridin-3-yl)quinolin-8-ol: To a solution of 8-(tert-butyldimethylsilyloxy)-2-(7-methyl-[1,2,4]triazolo[4,3-a]pyridin-3-yl)quinoline (5.00 g, 12.8 mmol) in tetrahydrofuran (100 mL) at 0° C. was added tetrabutylammonium fluoride (19.2 mL, 1 M in tetrahydrofuran, 19.2 mmol). The reaction was stirred for 6 hours at ambient temperature and then diluted with saturated aqueous ammonium chloride. The mixture was concentrated under reduced pressure, triturated with water, filtered and air-dried to provide 3.50 g (99%) of desired product as a white solid.

Step D: Preparation of tert-butyl 2,2-dimethyl-3-(2-(7-methyl-[1,2,4]triazolo[4,3-a]pyridin-3-yl)quinolin-8-yloxy)propylcarbamate: A mixture of 2-(7-methyl-[1,2,4]triazolo[4,3-a]pyridin-3-yl)quinolin-8-ol (prepared according to Example 1; 50 mg, 0.18 mmol), 3-(tert-butoxycarbonylamino)-2,2-dimethylpropyl methanesulfonate (102 mg, 0.36 mmol) and cesium carbonate (118 mg, 0.36 mmol) in dimethylacetamide (2 mL) was heated to 50° C. overnight. The mixture was concentrated under reduced pressure and purified by successive silica gel chromatography, eluting with 1:9 methanol/dichloromethane and a gradient of dichloromethane to 1:9 methanol/dichloromethane. The residue was then purified by preparative thin layer chromatography eluting with 3:7 acetone/dichloromethane to provide 35 mg (42%) of desired product as a light yellow solid.

Step E: Preparation of 2,2-dimethyl-3-(2-(7-methyl-[1,2,4]triazolo[4,3-a]pyridin-3-yl)quinolin-8-yloxy)propan-1-amine trihydrochloride: A mixture of tert-butyl 2,2-dimethyl-3-(2-(7-methyl-[1,2,4]triazolo[4,3-a]pyridin-3-yl)quinolin-8-yloxy)propylcarbamate (35 mg, 0.076 mmol) and hydrochloric acid (4 M in dioxane, 0.57 mL, 2.3 mmol) in dichloromethane (0.5 mL) was stirred overnight. The reaction was concentrated under reduced pressure. The residue was evaporated from twice from toluene, once from hexanes, triturated with hexanes, filtered and dried in vacuo to provide 25 mg (70%) of desired product as the trihydrochloride salt. MS ESI (+) m/z 362 (M+1) detected.

Example 124

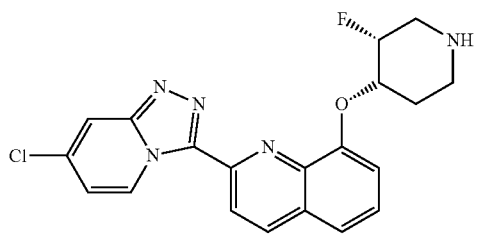

2-(7-chloro-[1,2,4]triazolo[4,3-a]pyridin-3-yl)-8-((3R,4S)-3-fluoropiperidin-4-yloxy)quinoline Prepared according to the method of Example 123 using 4-chloro-2-hydrazinylpyridine in place of 2-hydrazinyl-4-methylpyridine in Step A and (3R,4R)-tert-butyl-3-fluoro-4-(methylsulfonyloxy)piperidine-1-carboxylate in place of 3-(tert-butoxycarbonylamino)-2,2-dimethylpropyl methanesulfonate in Step D. MS ESI (+) m/z 398 (M+1) detected.

Example 125

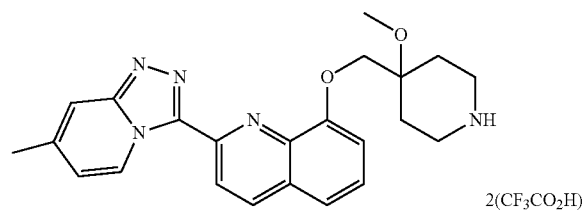 [SMILES: COC1(COc2cccc3ccc(-c4nnc5cc(C)ccn45)nc23)CCNCC1]

8((4-methoxypiperidin-4-yl)methoxy)-2-(7-methyl-[1,2,4]triazolo[4,3-a]pyridin-3-yl)quinoline di-trifluoroacetate Step A: Preparation of tert-butyl 4-hydroxy-4-42-(7-methyl-[1,2,4]triazolo[4,3-a]pyridin-3-yl)quinolin-8-yloxy)methyl)piperidine-1-carboxylate: A mixture of 2-(7-methyl-[1,2,4]triazolo[4,3-a]pyridin-3-yl)quinolin-8-ol (prepared according to Example 1; 20 mg, 0.72 mmol), tert-butyl-1-oxa-6-azaspiro[2.5]octane-6-carboxylate (178 mg, 0.83 mmol) and cesium carbonate (472 mg, 1.5 mmol) in dimethylacetamide (2.5 mL) was heated to 98° C. overnight. The mixture cooled to ambient temperature, filtered through celite and concentrated under reduced pressure. The residue was purified by silica gel chromatography with a gradient of dichloromethane to 1:9 methanol/dichloromethane to provide 170 mg (48%) of desired product.

Step B: Preparation of tert-butyl 4-methoxy-4-((2-(7-methyl-[1,2,4]triazolo[4,3-a]pyridin-3-yl)quinolin-8-yloxy)methyl)piperidine-1-carboxylate: A mixture of tert-butyl 4-hydroxy-4-((2-(7-methyl-[1,2,4]triazolo[4,3-a]pyridin-3-yl)quinolin-8-yloxy)methyl)piperidine-1-carboxylate (50 mg, 0.10 mmol) and sodium hydride (18 mg, 0.82 mmol) in dimethylformamide (1 mL) was stirred at ambient temperature for 15 minutes. Iodomethane (0.051 mL, 0.82 mmol) was added and the solution was stirred at ambient temperature overnight. The reaction was concentrated under reduced pressure. The residue was dissolved in dichloromethane and washed twice with saturated aqueous ammonium carbonate. The organic phase was dried over Na$_2$SO$_4$, filtered and concentrated under reduced pressure. The residue was triturated with hexanes and further purified by preparative thin layer chromatography with 1:9 methanol/dichloromethane to provide 25 mg (46%) of desired product.

Step C: Preparation of 8-((4-methoxypiperidin-4-yl)methoxy)-2-(7-methyl-[1,2,4]triazolo[4,3-a]pyridin-3-yl)quinoline di-trifluoroacetate: A mixture of tert-butyl 4-methoxy-4-((2-(7-methyl-[1,2,4]triazolo[4,3-a]pyridin-3-yl)quinolin-8-yloxy)methyl)piperidine-1-carboxylate (30 mg, 0.060 mmol) and trifluoroacetic acid (0.37 mL, 4.8 mmol) in dichloromethane (1 mL) was at ambient temperature for 30 minutes. The reaction was concentrated under reduced pressure. The residue was triturated with diethyl ether, filtered and dried in vacuo to provide 12 mg (52%) of desired product as the di-trifluoroacetate salt. MS ESI (+) m/z 404 (M+1) detected.

Example 126

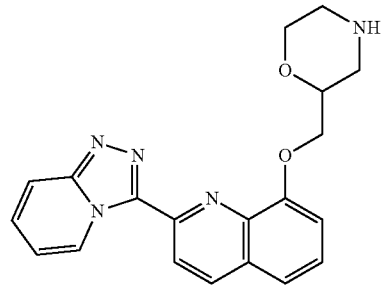 [SMILES: c1cc(OCC2CNCCO2)c2nc(-c3nnc4ccccn34)ccc2c1]

242-([1,2,4]triazolo[4,3-a]pyridin-3-yl)quinolin-8-yloxy)methyl)morpholine

Prepared according to the method of Example 16 using tert-butyl 2-(hydroxymethyl)morpholine-4-carboxylate in place of tert-butyl 3-(hydroxymethyl)piperidine-1-carboxylate. MS ESI (+) m/z 362.1 (M+1) detected.

Example 127

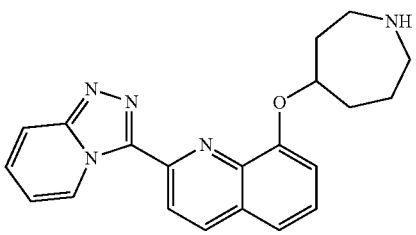 [SMILES: c1cc(OC2CCCNCC2)c2nc(-c3nnc4ccccn34)ccc2c1]

Enantiomer 1 of 2-([1,2,4]triazolo[4,3-a]pyridin-3-yl)-8-(azepan-4-yloxy)quinoline Prepared according to the procedure of Example 90, using 2-([1,2,4]triazolo[4,3-a]pyridin-3-yl)-8-(azepan-4-yloxy)quinoline (Example 52) as the starting material. Racemic-2-

([1,2,4]triazolo[4,3-a]pyridin-3-yl)-8-(azepan-4-yloxy)quinoline-1-carboxylate was separated by chiral HPLC on a Prep Chiral OJ-H column using the following solvent mixture: 75% heptane, 20% EtOH, 3% MeOH, 2% acetonitrile, to provide the enantiomers as peak 1 (7.32 minutes) and peak 2 (8.54 minutes). Peak 1 was isolated to provide the title compound 99% ee. MS ESI (+) m/z 360.1 (M+1) detected.

Example 128

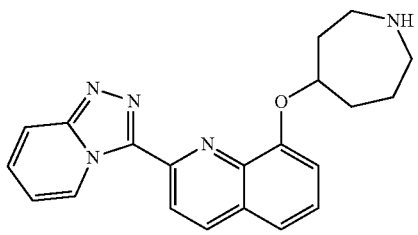 [SMILES: c1cc(OC2CCCNCC2)c2nc(-c3nnc4ccccn34)ccc2c1]

Enantiomer 2 of 2-([1,2,4]triazolo[4,3-a]pyridin-3-yl)-8-(azepan-4-yloxy)quinoline Prepared according to the procedure of Example 90, using 2-([1,2,4]triazolo[4,3-a]pyridin-3-yl)-8-(azepan-4-yloxy)quinoline (Example 52) as the starting material. Racemic-2-([1,2,4]triazolo[4,3-a]pyridin-3-yl)-8-(azepan-4-yloxy)quinoline-1-carboxylate was separated by chiral HPLC on a Prep Chiral OJ-H column using the following solvent mixture: 75% heptane, 20% EtOH, 3% MeOH, 2% acetonitrile, to provide the enantiomers as peak 1 (7.32 minutes) and peak 2 (8.54 minutes). Peak 2 was isolated to provide the title compound 98% ee. MS ESI (+) m/z 360.1 (M+1) detected.

Example 129

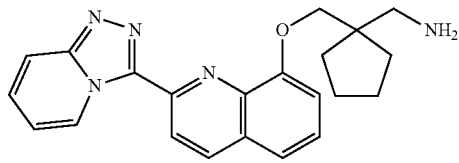 [SMILES: NCC1(COc2cccc3ccc(-c4nnc5ccccn45)nc23)CCCC1]

(1-((2-([1,2,4]triazolo[4,3-a]pyridin-3-yl)quinolin-8-yloxy)methyl)cyclopentyl)methanamine Prepared according to the method of Example 16 using tert-butyl (1-(hydroxymethyl)cyclopentyl)methylcarbamate in place of tert-butyl 3-(hydroxymethyl)piperidine-1-carboxylate. MS ESI (+) m/z 374.5 (M+1) detected.

Example 130

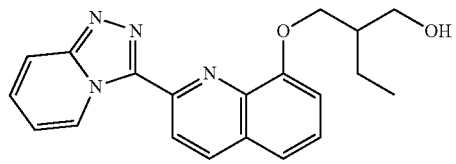 [SMILES: CCC(CO)COc1cccc2ccc(-c3nnc4ccccn34)nc12]

2-42-([1,2,4]triazolo[4,3-a]pyridin-3-yl)quinolin-8-yloxy)methyl)butan-1-ol

Prepared according to the method of Example 22, using 2-ethylpropane-1,3-diol in place of 1,1-bis(hydroxymethyl)cyclopropane. MS ESI (−) m/z 347.2 (M−1) detected.

Example 131

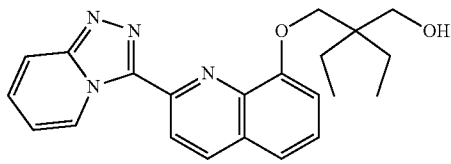 [SMILES: CCC(CC)(CO)COc1cccc2ccc(-c3nnc4ccccn34)nc12]

2-42-([1,2,4]triazolo[4,3-a]pyridin-3-yl)quinolin-8-yloxy)methyl)-2-ethylbutan-1-ol Prepared according to the method of Example 22, using 2,2-diethylpropane-1,3-diol in place of 1,1-bis(hydroxymethyl)cyclopropane. MS ESI (−) m/z 377.2 (M+1) detected.

Example 132

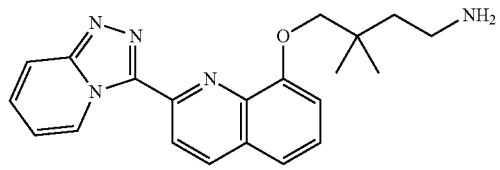 [SMILES: CC(C)(CCN)COc1cccc2ccc(-c3nnc4ccccn34)nc12]

4-(2-([1,2,4]triazolo[4,3-a]pyridin-3-yl)quinolin-8-yloxy)-3,3-dimethylbutan-1-amine Prepared according to the method of Example 18, using tert-butyl 4-hydroxy-3,3-dimethylbutylcarbamate in place of tert-butyl 3-hydroxy-2,2-dimethylpropylcarbamate.
MS ESI (+) m/z 362.3 (M+1) detected.

Example 133

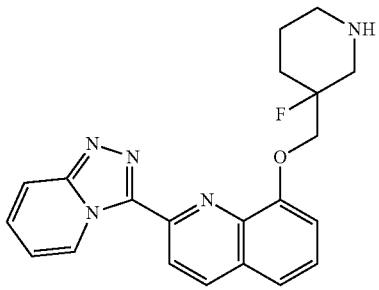 [SMILES: FC1(COc2cccc3ccc(-c4nnc5ccccn45)nc23)CCCNC1]

2-([1,2,4]triazolo[4,3-a]pyridin-3-yl)-8-((3-fluoropiperidin-3-yl)methoxy)quinoline Prepared according to the method of Example 16, using tert-butyl 3-fluoro-3-(hydroxymethyl)piperidine-1-carboxylate in place of using tert-butyl 2-(hydroxymethyl)morpholine-4-carboxylate. MS ESI (+) m/z 378.2 (M+1) detected.

Example 134

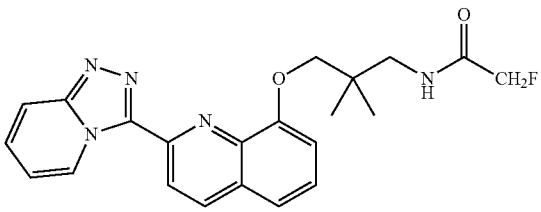

N-(3-(2-([1,2,4]triazolo[4,3-a]pyridin-3-yl)quinolin-8-yloxy)-2,2-dimethylpropyl)-2-fluoroacetamide 2-Fluoroacetyl chloride (12 mg, 0.13 mmol) was added to a stirred solution of 3-(2-([1,2,4]triazolo[4,3-a]pyridin-3-yl)quinolin-8-yloxy)-2,2-dimethylpropan-1-amine (prepared according to Example 18; 30 mg, 0.086 mmol) and diisopropylethyl amine (45 μL, 0.26 mmol) in DCM (2 mL) at 0° C. After 30 minutes, the reaction was quenched with saturated aqueous bicarbonate (5 mL), extracted into EtOAc, washed with water, dried over Na$_2$SO$_4$ followed by concentration in vacuo. The resulting oil was purified by flash column chromatography (silica gel), eluting with 100% EtOAc (Biotage) to give the desired product (12 mg, 0.029 mmol, 34% yield) as a white solid. MS ESI (+) m/z 408.2 (M+1) detected.

Example 135

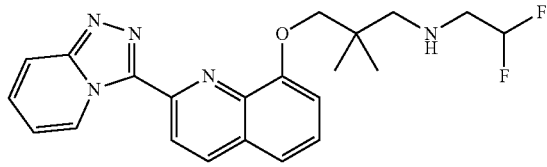 [SMILES: CC(C)(CNCC(F)F)COc1cccc2ccc(-c3nnc4ccccn34)nc12]

3-(2-([1,2,4]triazolo[4,3-a]pyridin-3-yl)quinolin-8-yloxy)-N-(2,2-difluoroethyl)-2,2-dimethylpropan-1-amine hydrochloride 2,2-diFluoroethyl trifluoromethanesulfonate (17 μL, 0.13 mmol) was added to a stirred solution of 3-(2-([1,2,4]triazolo[4,3-a]pyridin-3-yl)quinolin-8-yloxy)-2,2-dimethylpropan-1-amine (30 g, 0.086 mmol) and diisopropylethyl amine (39 μt 0.22 mmol) in dry THF/DMF (1 mL/1 mL) at ambient temperature. After stirring overnight, the reaction was diluted with EtOAc, washed with saturated aqueous bicarbonate, dried over Na$_2$SO$_4$, and concentrated in vacuo. The residue was purified by flash column chromatography (silica gel), eluting with 50% EtOAc/hexanes, affording the desired product (10 mg). MS ESI (+) m/z 412.2 (M+1) detected.

Example 136

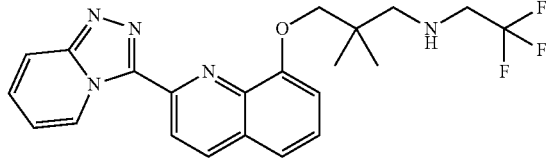 [SMILES: CC(C)(CNCC(F)(F)F)COc1cccc2ccc(-c3nnc4ccccn34)nc12]

3-(2-([1,2,4]triazolo[4,3-a]pyridin-3-yl)quinolin-8-yloxy)-2,2-dimethyl-N-(2,2,2-trifluoro ethyl)propan-1-amine Prepared according to the method of Example 135, using 2,2,2-trifluoroethyl trifluoromethanesulfonate in place of 2,2-difluoroethyl trifluoromethanesulfonate. MS ESI (+) m/z 430.2 (M+1) detected.

What is claimed is:
1. A compound of general Formula I:

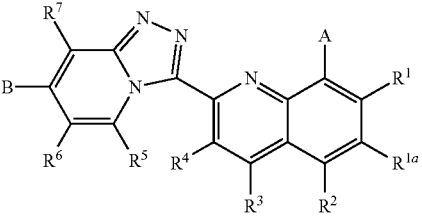

I or a pharmaceutically acceptable salt thereof, wherein:
A is OR$^{10}$ or NR$^{11}$R$^{12}$;
B is H, F, Cl, OR$^a$, (1-6C alkyl)NR$^b$R$^c$, (1-6C alkyl)OH, CH(OH)CH$_2$OH, or (1-4C alkyl);
R$^1$ is H, F, Cl, Br, Me, cyclopropyl or CN;
R$^{1a}$, R$^2$, R$^3$ and R$^4$ are independently H, F, Cl, Br, Me or CN;
R$^5$ and R$^7$ are independently H, F, Me or CN;
R$^6$ is H, F, Me, Br, CN, cyclopropyl, phenyl, MeO— or MeOCH$_2$CH$_2$O—;
R$^{10}$ is H, hetCyc$^1$, -(1-3C alkyl)hetCyc$^{1a}$, hetCyc$^2$, (CR$^{17}$R$^{18}$)$_p$(CR$^{13}$R$^{14}$)CH$_2$NR$^{15}$R$^{16}$, —(CR$^{17}$R$^{18}$)$_p$(CR$^{13}$R$^{14}$)CH$_2$OH, (1-6C alkyl), hetAr$^1$, (1-3C alkyl)hetAr$^{1a}$, or (3-7C)cycloalkyl substituted with NH$_2$, NH(1-6C alkyl) or N(1-6C alkyl)$_2$;
R$^{11}$ is H or (1-6C)alkyl;
R$^{12}$ is hetCyc$^3$, (1-6C alkyl)NR$^{15}$R$^{16}$, C(O)(1-6C alkyl)NR$^{15}$R$^{16}$, (1-6C alkyl)NHC(O)O(1-6C alkyl), or (4-7C) cycloalkyl optionally substituted with OH, NH$_2$, NH(1-6C alkyl) or N(1-6C alkyl)$_2$;
R$^{13}$ is H, (1-6C)alkyl, F or OH, and
R$^{14}$ is H, (1-6C)alkyl or F, or
R$^{13}$ and R$^{14}$ together with the carbon atom to which they are attached form a 3-6 membered carbocyclic ring;
each R$^{15}$, R$^{16}$, R$^{17}$ and R$^{18}$ is independently H or (1-6C) alkyl,
or each R$^{15}$, R$^{17}$ and R$^{18}$ is independently H or (1-6C)alkyl and R$^{16}$ is H, (1-6C)alkyl, C(=O)CH$_2$F, CH$_2$CHF$_2$ or CH$_2$CF$_3$;
or NR$^{15}$R$^{16}$ forms a 5-6 membered heterocyclic ring having a first ring heteroatom which is N and optionally having a second ring heteroatom selected from N and O;
hetCyc$^1$, hetCyc$^{1a}$, and hetCyc$^3$ are independently a 4-7 membered heterocycle having a ring nitrogen atom and optionally substituted with one or more R$^9$ groups, or
hetCyc$^1$ and hetCyc$^3$ are independently a 4-7 membered heterocycle having a ring nitrogen atom and optionally substituted with one or more R$^9$ groups, and hetCyc$^{1a}$ is selected from a morpholinyl and 4-7 membered azacyclic ring optionally substituted with one or more R$^9$ groups;
each R$^9$ is independently selected from halogen, (1-6C) alkyl, cyclopropylmethyl, benzyl, NR$^f$R$^g$, -(1-6C alkyl) NR$^h$R$^i$, OR$^j$, (1-6C alkyl)OR$^k$, (1-6C)fluoroalkyl, C(O) NR$^m$R$^n$, (1-6C alkyl)C(O)NR$^p$R$^q$, and C(O)O(1-6C alkyl);

hetCyc² is an 8-membered bridged heterocycle having a ring nitrogen atom;

hetAr¹ and hetAr¹ᵃ are independently a 5 or 6 membered heteroaryl having 1-2 ring nitrogen atoms and optionally substituted with one or more substituents independently selected from F, Cl, Br, Me, cyclopropyl, CN, NH₂, NH(1-6C alkyl) and N(1-6C alkyl)₂;

Rᵃ is H, (1-6C alkyl), -(1-6C alkyl)-O-(1-6C alkyl) or -(1-6C alkyl)-O-(3-6C cycloalkyl);

each Rᵇ, Rᶜ, Rᶠ, Rᵍ, Rʰ, Rⁱ, Rᵏ, Rᵐ, Rᵖ and Rᵠ is independently selected from H and (1-6C alkyl);

Rʲ is H, (1-6C alkyl) or cyclopropyl;

Rⁿ is H, (1-6C alkyl), —O(1-6C alkyl) or —O(3-6C cycloalkyl); and p is 0, 1 or 2.

2. A compound of claim 1, wherein:

A is OR¹⁰ or NR¹¹R¹²;

B is H, F, ORᵃ, (1-6C alkyl)NRᵇRᶜ, (1-6C alkyl)OH, CH(OH)CH₂OH or (1-4C alkyl);

R¹ is H, F, Cl, Br, Me, cyclopropyl or CN;

R¹ᵃ, R², R³ and R⁴ are independently H, F, Cl, Br, Me or CN;

R⁵ and R⁷ are independently H, F, Me or CN;

R⁶ is H, F, Me, Br, CN, cyclopropyl or phenyl;

R¹⁰ is H, hetCyc¹, -(1-3C alkyl)hetCyc¹ᵃ, hetCyc², —(CR¹⁷R¹⁸)ₚ(CR¹³R¹⁴)CH₂NR¹⁵R¹⁶, —(CR¹⁷R¹⁸)ₚ(CR¹³R¹⁴)CH₂OH, (1-6C alkyl), hetAr¹, (1-3C alkyl)hetAr¹ᵃ, or (3-7C)cycloalkyl substituted with NH₂, NH(1-6C alkyl) or N(1-6C alkyl)₂;

R¹¹ is H or (1-6C)alkyl;

R¹² is hetCyc³, (1-6C alkyl)NR¹⁵R¹⁶, C(O)(1-6C alkyl)NR¹⁵R¹⁶, (1-6C alkyl)NHC(O)O(1-6C alkyl), or (4-7C)cycloalkyl optionally substituted with OH, NH₂, NH(1-6C alkyl) or N(1-6C alkyl)₂;

R¹³ is H, (1-6C)alkyl, F or OH, and

R¹⁴ is H, (1-6C)alkyl or F, or

R¹³ and R¹⁴ together with the carbon atom to which they are attached form a 3-6 membered carbocyclic ring;

each R¹⁵, R¹⁶, R¹⁷ and R¹⁸ is independently H or (1-6C) alkyl, or NR¹⁵R¹⁶ forms a 5-6 membered heterocyclic ring having a first ring heteroatom which is N and optionally having a second ring heteroatom selected from N and O;

hetCyc¹, hetCyc¹ᵃ, and hetCyc³ are independently a 4-7 membered heterocycle having a ring nitrogen atom and optionally substituted with one or more R⁹ groups;

each R⁹ is independently selected from halogen, (1-6C) alkyl, cyclopropylmethyl, benzyl, NRʲRᵍ, -(1-6C alkyl)NRʰRⁱ, ORʲ, (1-6C alkyl)ORᵏ, (1-6C)fluoroalkyl, C(O)NRᵐRⁿ, (1-6C alkyl)C(O)NRᵖRᵠ, and C(O)O(1-6C alkyl);

hetCyc² is an 8-membered bridged heterocycle having a ring nitrogen atom;

hetAr¹ and hetAr¹ᵃ are independently a 5 or 6 membered heteroaryl having 1-2 ring nitrogen atoms and optionally substituted with one or more substituents independently selected from F, Cl, Br, Me, cyclopropyl, CN, NH₂, NH(1-6C alkyl) and N(1-6C alkyl)₂;

Rᵃ is H, (1-6C alkyl), -(1-6C alkyl)-O-(1-6C alkyl) or -(1-6C alkyl)-O-(3-6C cycloalkyl);

each Rᵇ, Rᶜ, Rᶠ, Rᵍ, Rʰ, Rⁱ, Rᵏ, Rᵐ, Rᵖ and Rᵠ is independently selected from H and (1-6C alkyl);

Rʲ is H, (1-6C alkyl) or cyclopropyl;

Rⁿ is H, (1-6C alkyl), —O(1-6C alkyl) or —O(3-6C cycloalkyl); and p is 0, 1 or 2.

3. The compound of claim 1, where B is H, F, ORᵃ, (1-6C alkyl)NRᵇRᶜ, (1-6C alkyl)OH, or CH(OH)CH₂OH.

4. The compound of claim 1, wherein A is OR¹⁰.

5. The compound of claim 4, wherein R¹⁰ is hetCyc¹, -(1-3C alkyl)hetCyc¹ᵃ or hetCyc², wherein hetCyc¹ and hetCyc¹ᵃ are optionally substituted with one or more R⁹ groups.

6. The compound of claim 5, wherein each R⁹ is independently selected from F, (1-6C)alkyl, C(O)O(1-6C)alkyl, (1-6C alkyl)ORᵏ, C(O)NᵐRⁿ, (1-6C alkyl)C(O)NRᵖRᵠ, and ORʲ.

7. The compound of claim 6, wherein hetCyc¹ and -(1-3C alkyl)hetCyc¹ᵃ are optionally substituted with one or two R⁹ groups independently selected from Me, Et, isopropyl, cyclopropylmethyl, F, OH, OMe, CH₂OH, CH₂CH₂OH, CH₂CH₂F, CH₂OMe, C(=O)OMe, C(=O)NH₂ and CH₂C(=O)NH₂.

8. The compound of claim 4, wherein R¹⁰ is —(CR¹⁷R¹⁸)ₚ(CR¹³R¹⁴) CH₂NR¹⁵R¹⁶.

9. The compound of claim 4, wherein R¹⁰ is —(CR¹⁷R¹⁸)ₚ(CR¹³R¹⁴)CH₂OH.

10. The compound of claim 4, wherein R¹⁰ is (1-6C alkyl).

11. The compound of claim 4, wherein R¹⁰ is (3-7C)cycloalkyl substituted with NH₂, NH(1-6C alkyl) or N(1-6C alkyl)₂.

12. The compound of claim 4, wherein R¹⁰ is hetAr¹ or (1-3C alkyl)hetAr¹ᵃ.

13. The compound of claim 1, wherein A is NR¹¹R¹².

14. The compound of claim 13, wherein R¹² is hetCyc³ optionally substituted with one or more R⁹ groups.

15. The compound of claim 14, wherein each R⁹ is independently selected from (1-6C) alkyl.

16. The compound of claim 13, wherein R¹² is (4-7C) cycloalkyl optionally substituted with OH, NH₂, NH(1-6C alkyl) or N(1-6C alkyl)₂.

17. The compound of claim 13, wherein R¹² is (1-6C alkyl)NR¹⁵R¹⁶, C(O)(1-6C alkyl)NR¹⁵R¹⁶ or (1-6 C alkyl)NHC(O)(1-6C alkyl).

18. The compound of claim 1, wherein B is H.

19. The compound of claim 1, wherein B is ORᵃ.

20. The compound of claim 19, wherein B is selected from OMe, —OCH₂CH₂OMe and —OCH₂CH₂O(cyclopropyl).

21. The compound of claim 1 wherein B is F.

22. The compound of claim 1, wherein B is (1-6C alkyl)NRᵇRᶜ.

23. The compound of claim 1, wherein B is (1-6C alkyl) OH.

24. The compound of claim 1, wherein B is CH(OH)CH₂OH.

25. The compound of claim 1, wherein B is (1-4C alkyl).

26. The compound of claim 1, wherein B is Cl.

27. The compound of claim 1, wherein each of R¹, R², R³, R⁵ and R⁷ is hydrogen.

28. A pharmaceutical composition, which comprises a compound of Formula I of claim 1, or a pharmaceutically acceptable salt thereof, and a pharmaceutically acceptable diluent or carrier.

29. A process for the preparation a compound of claim 1, which comprises:

(a) for a compound of Formula I wherein A is NR¹¹R¹², coupling a corresponding compound having the formula II

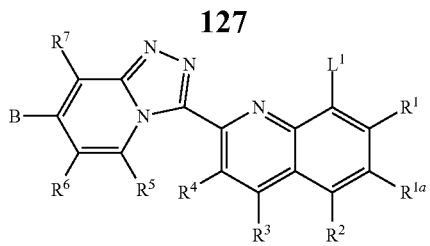

wherein $L^1$ represents a leaving atom or group, with a compound having the formula $HNR^{11}R^{12}$, using a palladium (II) catalyst and a ligand in the presence of a base; or (b) reacting a compound of Formula III

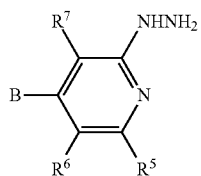

with a compound having the Formula IV

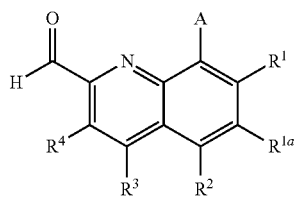

in the presence of an organo hypervalent iodine reagent; or (c) for a compound of Formula I wherein A is $OR^{10}$, coupling a corresponding compound having the Formula V

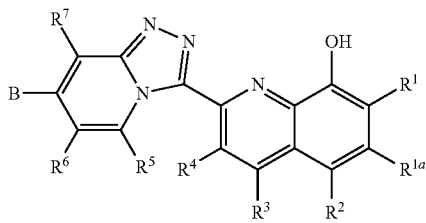

with a compound having the formula $HO-R^{10}$ in the presence of a coupling agent and triphenylphosphine in a suitable solvent; or (d) for a compound of Formula I wherein B is $(CH_2)NR^bR^c$, reacting a corresponding compound having the Formula VI

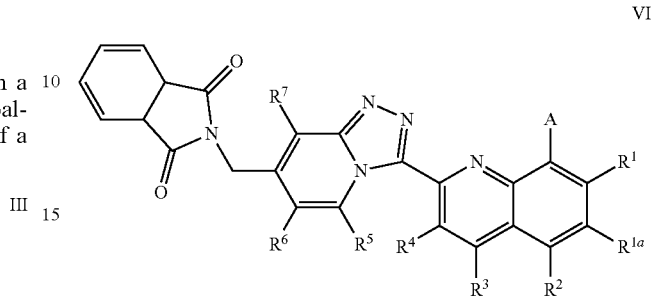

with hydrazine; or (e) for a compound of Formula I where B is $OR^a$, reacting a corresponding compound having the Formula VII

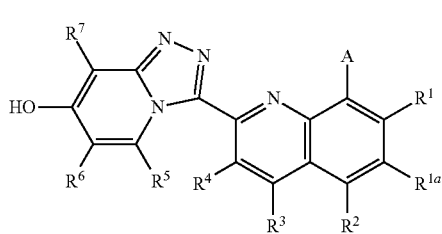

with a compound of the formula $R^a$-$L^2$, wherein $L^2$ represents a leaving atom or group, in the presence of a base; and removing any protecting group or groups and, if desired, forming a salt.

* * * * *

UNITED STATES PATENT AND TRADEMARK OFFICE
CERTIFICATE OF CORRECTION

| | | |
|---|---|---|
| PATENT NO. | : 8,575,145 B2 | Page 1 of 1 |
| APPLICATION NO. | : 13/059902 | |
| DATED | : November 5, 2013 | |
| INVENTOR(S) | : Allen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 338 days.

Signed and Sealed this
Thirty-first Day of March, 2015

Michelle K. Lee
*Director of the United States Patent and Trademark Office*